(12) United States Patent
Meyers et al.

(10) Patent No.: US 7,282,360 B2
(45) Date of Patent: Oct. 16, 2007

(54) HUMAN PROTEIN KINASE, PHOSPHATASE, AND PROTEASE FAMILY MEMBERS AND USES THEREOF

(75) Inventors: Rachel E. Meyers, Newton, MA (US); Peter J. Olandt, Newton, MA (US); Rosana Kapeller-Libermann, Chestnut Hill, MA (US); Rory A. J. Curtis, Framingham, MA (US); Mark Williamson, Saugus, MA (US); Nadine Weich, Brookline, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/636,948

(22) Filed: Dec. 11, 2006

(65) Prior Publication Data

US 2007/0099274 A1 May 3, 2007

Related U.S. Application Data

(60) Division of application No. 11/151,601, filed on Jun. 13, 2005, now Pat. No. 7,198,930, which is a division of application No. 10/170,789, filed on Jun. 13, 2002, now Pat. No. 7,070,947, and a continuation-in-part of application No. 10/045,367, filed on Nov. 7, 2001, now abandoned, and a continuation-in-part of application No. 09/961,721, filed on Sep. 24, 2001, now abandoned, and a continuation-in-part of application No. 09/934,406, filed on Aug. 21, 2001, now abandoned, and a continuation-in-part of application No. 09/882,166, filed on Jun. 15, 2001, now abandoned, and a continuation-in-part of application No. 09/861,801, filed on May 21, 2001, now abandoned, and a continuation-in-part of application No. 09/829,671, filed on Apr. 10, 2001, now abandoned, and a continuation-in-part of application No. 09/801,267, filed on Mar. 6, 2001, now abandoned, and a continuation-in-part of application No. 09/801,275, filed on Mar. 6, 2001, now abandoned, which is a continuation-in-part of application No. 09/797,039, filed on Feb. 28, 2001, now Pat. No. 6,730,491.

(60) Provisional application No. 60/246,561, filed on Nov. 7, 2000, provisional application No. 60/235,023, filed on Sep. 25, 2000, provisional application No. 60/226,740, filed on Aug. 21, 2000, provisional application No. 60/212,078, filed on Jun. 15, 2000, provisional application No. 60/205,508, filed on May 19, 2000, provisional application No. 60/197,508, filed on Apr. 18, 2000, provisional application No. 60/187,454, filed on Mar. 7, 2000, provisional application No. 60/187,420, filed on Mar. 7, 2000, provisional application No. 60/186,061, filed on Feb. 29, 2000.

(51) Int. Cl.
*C12N 9/20* (2006.01)
*C12N 15/00* (2006.01)
*C12N 1/20* (2006.01)
*C12Q 1/68* (2006.01)
*C07H 21/04* (2006.01)

(52) U.S. Cl. .............. 435/194; 435/320.1; 435/252.3; 435/6; 536/23.2

(58) Field of Classification Search ............... 435/194, 435/6, 252.3, 320.1; 536/23.2
See application file for complete search history.

(56) References Cited

U.S. PATENT DOCUMENTS 6,476,210 B2 * 11/2002 Turner et al. ............ 536/23.2
2004/0034888 A1  2/2004 Liu et al.

FOREIGN PATENT DOCUMENTS

WO    WO 00/73469 A2   12/2000

* cited by examiner

*Primary Examiner*—Maryam Monshipouri

(57) ABSTRACT

The invention provides isolated nucleic acids molecules, designated 53070, 15985, 26583, 21953, m32404, 14089, and 23436 nucleic acid molecules, which encode novel human protein kinase family members, serine/threonine protein kinase family members, serine/threonine phosphatase family members, prolyl oligopeptidase family members, trypsin family members, trypsin serine protease family members, and ubiquitin protease family members. The invention also provides antisense nucleic acid molecules, recombinant expression vectors containing 53070, 15985, 26583, 21953, m32404, 14089, or 23436 nucleic acid molecules, host cells into which the expression vectors have been introduced, and nonhuman transgenic animals in which a 53070, 15985, 26583, 21953, m32404, 14089, or 23436 gene has been introduced or disrupted. The invention still further provides isolated 53070, 15985, 26583, 21953, m32404, 14089, or 23436 proteins, fusion proteins, antigenic peptides and anti-53070, 15985, 26583, 21953, m32404, 14089, or 23436 antibodies. Diagnostic methods utilizing compositions of the invention are also provided.

15 Claims, 35 Drawing Sheets pkinase: domain 1 of 1, from 12 to 272: score 256.9, E = 2.8e-73

```
Begin SEQ ID NO:17        *->yellekIgEgsfGkVykakhk.tgkivAvKilkkesls........1
                             y l+  lGeGs++kV+ a+ + + vA+Ki+++++ + + ++
53070 (SEQ ID NO:15)   12 YLLGINLGEGSYAKVKSAYSErlKFNVAIKIIDRKKAPadflekflP 58 rEiqilkrlsHpNIvrllgvfedtddhlylvmEymegGdLfdylrrmgpl
                          rEi+il++l+H I++ +++fe +++++y++ymE++  GdL+++++ +g+l
53070                 59  REIEILAMLNHCSIIKTYEIFETSHGKVYIVMELAVQGDLLELIKTRGAL 108 sekeakkialQilrGleYLHsngivHRDLKpeNILldengtvKiaDFGLA
                          e+ea+k ++Q+   +++Y+H+  +vHRDLK +N+Lid++ ++K++DF ++
53070                 109 HEDEARKKFHQLSLAIKYCHDLDVHRDLKCDNLLLDKDFNIKLSDFSFS 158 rll.......eklttfvGTpwYmmAPEvileg.rgysskvDvWSlGviL
                          +          +++++    +tf+G+p Y  APEv  l+g  ++  D+WSlGviL
53070                 159 KRClrddsgrmALSKTFCGSPAYA-APEV-LQGiPYQPKVYDIWSLGVIL 206 yElltggplfpgadlpaftggdevdqliifvlklPfsdelpktridplee
                          y +++g                         P++d         +++++
53070                 207 YIMVCG------------------------SMPYDD------SNIKK 223 lfrikkr...rlplpsncSeelkdLlkcLnkDPskRpGsatakeilnhp
                          ++ri+k+++ ++p+   +++  e+kdL+  +L++D ++R+    + eil h
53070                 224 MLRIQKEhrvNFPRSKHLTGECKDLIYHMLQPDVNRRL---HIDEILSHC 270 wf<-*   End SEQ ID NO:17
                          w+
53070                 271 WM   272  (SEQ ID NO:15)
```

FIGURE 2 serkin_6: domain 1 of 1, from 12 to 272: score 296.6, E = 3.1e-85

```
Begin SEQ ID NO:18         *->YellkklGkGaFGkVylardkktgrlvAiKvik..........eril
                              Y l+ lG+G+++kV+ a+ + + vAiK+i++++ + + ++ +
53070 (SEQ ID NO:15)  12   YLLGINLGEGSYAKVKSAYSERLKFNVAIKIIDrkkapadfleKFLP    58 rEikiLkk dHPNIVkLydvfed..dklylVmByceGdlGdlfdllkkrg
                           rEi+iL + +H   I+k y+++fe+++k+y++VmE++ +  GdL++l+k rg
53070                 59   REIEILAMlNHCSIIKTYEIFETshGKVYIVMELAVQ--GDLLELIKTRG  106 rrglrkvlsE.earfyfrQilsaLeYlHsqgIiHRDLKPeNilLds..hv
                                l+E+ear+ f+Q+ +a++Y+H++ ++HRDLK +N+LLd++ ++
53070                107   A------LHEdEARKKFHQLSLAIKYCHDLDVVHRDLKCDNLLLDKdfNI  150

KlaDFGlArql..........ttfvGTpeYmAPEvl...gYgkpavDiW
                           Kl+DF ++++   ++++++  ++tf+G+p Y APEvl++ +Y ++ DiW
53070                151   KLSDFSFSKRClrddsgrmalsKTFCGSPAYAAPEVLqgiPYQPKVYDIW 200

SlGcilyEltGkpPFp..qldlifkkig..........SpeakdLik
                           SlG+ily+++G  P+++++++++ ++++ + +++++ + e+kdLi
53070                201   SLGVILYIMVCGSMPYDdsNIKKMLRIQkehrvnfprskhlTGECKDLIY 250 klLvkdPekRlta.eaLededikaHPff<-* End SEQ ID NO:18
                           ++L+ d ++Rl ++e+L    H ++
53070                251   HMLQPDVNRRLHIdEILS------HCWM        272 (SEQ ID NO:15)
```

FIGURE 3 pkinase: domain 1 of 1, from 394 to 651: score 321.4, E = 1e-92

```
                *->yelleklGeGsfGkVykakhk.tgkivAvKilkkesls......lrE
                   y+++++G G+f++V+++++++tgk++A+Ki++k +   ++++   +E
15985      394     YKIGKVIGDNFAVVKECIDRsTGKEFALKIIDKAKCCgkehliENE  440 iqilkrlsHpNIvrllgvfedtddhlylvmEymegGdLfdylrrngplse
                   ++il+lr++HpNI+ l + +e t ++l lvmE++ gGdLfd +++ ++++e
15985      441     VSILRRVKHPNIIMLVEEME-TATELFLVMELVKGGDLFDAITSSTKYTE  489 keakkialQilrGleYLHsngivHRDLKpeNILlden....gtvKiaDFG
                   ++   +++ +++l YLH+ +ivHRD+KpeN+L+ e ++++ +K++DFG
15985      490     RDGSAMVYNLANALRYLHGLSIVHRDIKPENLLVCEYpdgtKSLKLGDFG  539

LArll.ekLttfvGTpwYmmAPEvilegrgysskvDvWSlGviLyElltg
                   LA+++++l+t++GTp+Y+ APE+ +  +gY+ kvD+W+ Gvi y ll+g
15985      540     LATVVeGPLYTVCGTPTYV-APEI-IAETGYGLKVDIWAAGVITYILLCG  587 gplfpgadlpaftggdevdqliifvlklPfsdelpktridpleelfrikk
                   +Pf+ e+   ++d +++++++k+;
15985      588     --------------------------FPPFRSEN-NLQEDLFDQILAGKL  610 r.rlplpsncSeelkdLlkkcLnkDPskRpGsatakeilnhpwf<-*    (SEQ ID NO:23)
                   + + p ++n+ +++k+L++++ + R   ta +il hpw+
15985      611     EfPAPYWDNITDSAKELISQMLQVNVEARC---TAGQILSHPWV       651
```

FIGURE 5 doubl_11: domain 1 of 2, from 67 to 158: score 155.7, E = 8.2e-43

```
              *->slvkpkrirvyRNGDrffkGvrlvvnrkrqfksFeaLLqdlTelklv
                 s++k+k+ r+yRNGDr+fkG ++++++r f+SF+alL +lT+ +l+
15985   67    SEKKAKRARFYRNGDRYFKGLVFAISSDR-FRSFDALLIELTR-SLS  111 vkldlpfaVRklyTldGgkkvtsldeledgDgvVasgteEkFkkvdYg<
              +++lp++VR++YT+dG++kvtsldel +g ++YV++++e +F+kvdY+
15985   112   DNVNLPQGVRTIYTIDGSRKVTSLDELLEG-ESYVCASNE-PFRKVDYT  158

-*             (SEQ ID NO:24)
15985    -                (SEQ ID NO:21)
```

FIGURE 6A doubl_11: domain 2 of 2, from 192 to 280: score 135.7, E = 8.3e-37

```
              *->slvkpkrirvyRNGDrffkGvrlvvnrkrqfksFeaLLqdlTelklv
                 ++ kpk ++v+R+G++++k+vr+++n+k+ ++SFe++L+d+Te +
15985   192   DFIKPKLVTVIRSGVKPRKAVRILLNKKT-AHSFEQVLTDITE---A  234 vkldlpfaVRklyTldGgkkvtsldeledgDgvVasgteEkFkkvdYg<
              +kld++ +V++l TldG k++vt+l++++++D+v++a+g e.kF+++++
15985   235   IKLDSG-VVKRLCTLDG-KQVTCLQDFFGDDDVFIACGPE-KFRYAQDD  280

-*             (SEQ ID NO:24)
15985    -                (SEQ ID NO:21)
```

FIGURE 6B serkin_6: domain 1 of 1, from 394 to 651: score 350.3, E = 2.1e-101

```
            *->YellkklglGkGaFGkVylardkktgrlvAiKvik........erilrE
               Y+++k++G G F++V+ ++d++tg+++A+K+i++ + +++ i++E
15985    394   YKIGKVIGDGNFAVVKECIDRSTGKEFALKIIDkakccgkeHLIENE    440 ikiLkk.dHPNIVKLydvfed.dklylVmEyceGdlGdLfdllkkrgrrg
               ++iL++ +HPNI+ L + +e+ ++l+lVmE++ G GdLfd + +   +
15985    441   VSILRRvKHPNIIMLVEEMETaTELFLVMELVKG--GDLFDAITSSTK--   486 lrkvlsE.earfyfrQilsaLeYLhsgqIiHRDLKPeNiLLds........h
               ++E++    +++   +++aL YLH + I+HRD+KPeN+L+++ +++++
15985    487   ----YTERDGSAMVYNLANALRYLHGLSIVHRDIKPENLLVCEypdgtkS    532 vKladDFGlArql....ttfvGTpeYmAPEvl...gYgkpavDiwS1Gcil
               +Kl+DFGlA++++++ +t++GTp Y+APE++ ++gYg +vDiW+ G+i
15985    533   LKLIGDFGLATVVegplYTVCGTPTYVAPEIIaetGYGL-KVDIWAAGVIT   581 yEl1tGkpPFp...qldlifkkig...........SpeakdLikkl
               y+ll+G pPF+++++ ++ +f++i+ ++ + + ++++++ +++ak+Li+++
15985    582   YILLCGFPPFRsennLQEDLFDQILagklefpapywdniTDSAKELISQM   631

LvkdPekRlta.eaLededeldikaHPff<-*        (SEQ ID NO:25)
               L+++ e R ta+++L          HP++
15985    632   LQVNVEARCTAGQILS------HPWV              651    (SEQ ID NO:21)
```

FIGURE 7

```
Identities = 192/254 (75%), Positives = 218/254 (85%)
Query:   42 NGLIPSPAHSAHCSFYRTRTLQALSSEKKAKKARFYRNGDRYFKGLVFAISSDRFRSFDA 101
            NGL PSP HSAHCSFYRTRTLQ LS+EKKAKK RFYRNGDRYFKG+V+A+S DRFRSFDA
Sbjct:   23 NGL-PSPTHSAHCSFYRTRTLQTLSNEKKAKKVRFYRNGDRYFKGIVYAVSPDRFRSFDA 81

Query:  102 LLIELTRSLSDNVNLPQGVRTIYTIDGSRKVTSLDELLEGESYVCASNEPFRKVDYTKNI 161
            LL +LTR+LSDN+NLPQGVR IYTIDGSRK+ S+DEL EGESYVC S+ PF+KV+YTKN+
Sbjct:   82 LLADLTRTLSDNINLPQGVRYIYTIDGSRKIGSMDELEEGESYVCGSDNPFKKVEYTKNV 141

Query:  162 NPNWSVNIKGGTS----RALXXXXXXXXXXXXXXXDFIKPKLVTVIRSGVKPRKAVRILLN 217
            NPNWSVN+K    +    ++L                DF++PKLVT+IRSGVKPRKAVR+LLN
Sbjct:  142 NPNWSVNVKTTANMKAPQSLATSNGAPSQARENKDFVRPKLVTIIRSGVKPRKAVRVLLN 201

Query:  218 KKTAHSFEQVLTDITEAIKLDSGVVKRLCTLDGKQVTCLQDFFGDDDVFIACGPEKFRYA 277
            KKTAHSFEQVLTDIT+AIKLD+GVVK+L TLDGKQVTCL DFFGDDDVFIACGPEKFRYA
Sbjct:  202 KKTAHSFEQVLTDITDAIKLDTGVVKKLYTLDGKQVTCLHDFFGDDDVFIACGPEKFRYA 261

Query:  278 QDDFVLDHSECRVL 291
            QDDF LD +ECRV+
Sbjct:  262 QDDFSLDENECRVM 275
```

FIGURE 8

```
PP2C: domain 1 of 1, from 173 to 461: score 261.3, E = 1.3e-74
            *->ldvgvsrmqgwrksmeDahialknlnsssgkdswsffavfDGhgGs
               1  ++++ + r +++ ++++++ ++ s++ s+ +f  +++ +
     26583  173  LLEIENAVESGRALLPILQWHKHPNDYF-SKEASKLYFNSLRTYWQE 218 qaakyagkhlhk.tilaerksfpegdpwEmklsdledalkesfleadtde
            +   +g++ +++ + a++  f+ +d+      d +   ++++ ++++++
     26583  219  LIDLNTGESTDIdVKEALINAFKRLDN------DISLEAQVGDPNSFLNY 262 elrsaeasaankvltkedlssGsTAvvalirgnkLyVANvGDSRavLcrn
            +++                + sG+TA+va+++g +L+VAN+GDSRa+L+ +
     26583  263  LVLR---------------VAFSGATACVAHVDGVDLHVANTGDSRAMLGVQ 299 gnaikw.avtLteDHkPsnedEreRIeaaGGfvsrvs...ngRvnGvLav
            +++++W+avtL++DH+++ne+E+eR++ ++++ + +s  +++R++G L++
     26583  300  EEDGSWsAVTLSNDHNAQNERELERLKLEHPKSEAKSvvkQDRLLGLLMP 349

SRAfGDfelKpgsklgpeas.l.e.a.ny.eyiks.pe.....qlVtaeP
            RAfGD+++K+  +l+++ +++++++ n++ey+k+ p++ +++++ taeP
     26583  350  FRAFGDVKFKWSIDLQKRVIeSgPdQlNDnEYTKFiPPnyhtpPYLTAEP 399 dvtsstdltpdkDeFliLAcDGLWDvvsdqevvdivrselsdgnksaedp
            +vt +++l+p+ D+Fl+LA+DGLW++++ q+vv iv + l+ +      +
     26583  400  EVT-YHRLRPQ-DKFLVLATDGLWETMHRQDVVRIVGEYLTGM------H 441 meaaeklvdeaiargaeDni<-*
            ++   ++  + + g ++
     26583  442  HQQPIAVGGYKVTLGQMHGL      461
```

FIGURE 10A

```
PP2C_4: domain 1 of 1, from 99 to 523: score 338.5, E = 7.6e-98
              *->es.sgknlglryglgessmqgwrkpmEDahvirp.......ffgvfD
                 +   gkn +++ g+ +s++ +++  p+ED+ ++ +  ++++ + gVfD
       26583  99 PEfDGKNVSSILGF-DSNQLPANAPIEDRRSAATClqtrgmLLGVFD 144

GHGGseaakflsknlheilaeelsfdkdeslkene.e.lk.d.ep.....
                 GH+G ++++ +s++l+ ++a +l +++ ++ en+ e+++ + ++ + ++
       26583 145 GHAGCACSQAVSERLFYYIAVSLLPHETLLEIENAvEsGRaLlPIlqwnk 194

..................ess.e.r.ln.gdksledveealrkaFlrtd
                 ++++    +++ ++   ++ +++++e  +ln+g++++ dv+eal++aF+r+d
       26583 195 hpndyfskeaskIyfnslrTYWqElIdLNtGESTDIDVKEALINAFKRLD 244 eei....................sTAvvalirgnklyvANvGDSRa
                 ++i+ + + +++++  +     +  +++TA+va++g +l+vAN+GDSRa
       26583 245 NDIsleaqvgdpnsflnylvlrvafsgATACVAHVDGVDLHVANTGDSRA 294 vLcrngkd.swegvrtysavqLteDHkpanedEreRieaaGGevepidre
                 +L+ +  +d+sw       sav L++DH++ ne+E+eR++ ++++ e +++
       26583 295 MLGVQEEDgSW------SAVTLSNDHNAQNERELERLKLEHPKSE--AKS 336 fvsngggvvwRvnGvvisLavsRalGDfelKk.ked.e.lie.....en.
                 +v ++    R++G   L++ Ra+GD+++K+++++++++ie++++++n+
       26583 337 VVKQD-----RLLGL---LMPFRAFGDVKFKWsIDLqKrVIEsgpdqLNd 378 rlyekfdprlpgkepyvsaePevtvvelsqtlvptedddfliLASDGLWD
                 ++y+kf  p+ ++++py++aePevt+++l       +++d+fl+LA+DGLW+
       26583 379 NEYTKFIPPNYHTPPYLTAEPEVTYHRL------RPQDKFLVLATDGLWE 422 vlsnqeavdivrkhlrkgddk.evksaaqela.r.a.d....s.......
                 +  q++v iv + l+++++++++++  ++++ +++++ ++++++ ++
       26583 423 TMHRQDVVRIVGEYLTGMHHQqPIAVGGYKVTlGqMhGllteRrtkmssv 472

.........l.r..skkhndpkeaaklLvdlAl.........kDNiTvvv
                 ++++  ++l r+ +++++      +++L +++  +++ +  +D+iT++v
       26583 473 fedqnaathLiRhaVGNNEFGTVDHERLSKMLSlpeelarmyRDDITIIV 522 v<-*
                 v
       26583 523 V   523
```

FIGURE 10B

Prolyl Oligopeptidase Domain from 672 to 744: score 38.1, E = 1.6e-10

```
      *-> vasllnhrGggiyAvvdiRGgGeyGqkwheagtrrlkkmefnDfiaAA
          ++++l +G +++v d RG+    G k+  a +   ++ e++D+++
  672   RLNTLASLGYVVVVIDNRGSCHRGLKFEGAFKYKMGQIEIDDQVEGL 718 eylskl.GytspkriaifGgSnGGlL    <-*
          +yl +   +  +  +r+ i G+S+GG+L
  719   QYLASRyDFIDLDRVGIHGWSYGGYL 744
```

```
DPP IV   ------------------------------------MKTPWKVLLGLLG---AAALVT  19
21953    MAAAMETEQLGVEIFETADCEENIESQDRPKLEPFYVERYSWSQLKKLLADTRKYHGYMM  60
                                              .*.  **

DPP IV   IITVPVLLNKGTDDATADSRKTYTLTDYLKNTYRLKLY-----SLRWISDHEYLYKQEN  74
21953    AKAPHDFMFVKRNDPDGPHSDRIYYLAMSGENRENTLFYSEIPKTINRAAVLMLSWKPLL 120
          :: *  .   *:          .* :*   :*    :*: . :*

DPP IV   NILVFNAEYGNSS----VFLENSTFDEFGHSINDYSISPDGQFILLEYNYVKQWRHSYTA 130
21953    DLFQATLDYGMYSREEELLRERKRIGTVGIASYDYHQGS-GTFLFQAGSGIYHVKDGGPQ 179
          :  .  :   *.      :. :.*  *   ..**     *::* .  * : : :

DPP IV   SYDIYDLNKRQLITEERIPNNTQWVTWSPVG-HKLAYVWNNDIYVKIEPNLPSYRITWTG 189
21953    GFTQQPLRPN--LVETSCPNIRMDPKLCPADPDWIAFIHSNDIWISNIVTRBERRLTYVH 237
          .:    *  :. *:  :*   * *     .  *:*:::*** *.  . * ***:*

DPP IV   -----KEDIIYNGITDWVYEEEVFSAYSALWWS------PNGTFLAYAQFNDTEVPLIE 237
21953    NELANMEEDARSAGVATFVLQEE-FDRYSGYWWCPKAETTPSGGKILRILYEENDESEVE 296
              :*:    .. :* *:*:  *.**. *  .          *:: * *::: .:

DPP IV   YSFYSDESLQYPKTVRVPYPKAGAVNPTVKFFV--VNTDSLSSVTNATSIQITAPASMLI 295
21953    IIHVTSPMLETRRADSFRYPKTGTANPKVTFKMSEIMIDAEGRIIDVIDKELIQPPEILP 356
          : .:   *: . *. **** .*.** ** *    ::     .    *  :.   : *

DPP IV   G-DHYLCDVTWATQER---------------------ISLQWLRRIQNYS 323
21953    EGVEYIARAGWTPEGKYAWSILLDRSQTRLQIVLISPELFIPVEDDVMERQRLIESVPDS 416
          .  :  .  .**  ::                     .* * :   .

DPP IV   VMDICDYDESSGRWN------CLVARQHIEMSTTGWVGRFRPSEPHFTLDGNSFY--KII 375
21953    VTPLIYEETTDIWINIHDIFHVFPQSHEEEIEFIFASECKTGFRHLYKITSILKESKYK 476
          *  :   :  .  :*        *.* ::    :. .*. ::  .  : *:.
```

FIGURE 14A

```
DPP IV    SNEEGYRHICYFQIDKKDCTFITKGTWEVIG-----IEALTSDYLYYISNEYKGMPGGRN    430
21953     RSSGGLPAPSDFKCPIKEEIAITSGEWEVLGRHGSNIQVDEVRRLVYFEGTKD-SPLEHH    535
          .  * .  *:   ** * ***:*         * :.     *  :: .    .  ::

DPP IV    LYKIQLSDYTKVTCLSCELNPERCQYYSVSFSKEAKYYQLRCSGPGLPLYTLHSSVNDKG    490
21953     LYVVSYVNPGEVTRLTDRGYSHSCCISQHCDFFISKYSNQKNP-HCVSLYKLSSPEDDPT    594
          ** :: .  : .***.      :: : . :   ::**.*        : **.*.  *.  :*

DPP IV    LRVLEDNSALDKMLQNVQ--MPSKKLDFIILNETKFWYQMILPPHFDKSKKYPLLLDVYA    548
21953     CKTKEFWATILDSAGPLPDYTPPEIFSFESTTGFTLYGMLYKPHDLQPGKKYPTVLFIYG    654
          : * *  *::: :   ::          ::  .. *  * *  ****  .**** :*:*

DPP IV    GPCSQKADTVFR--LNWATYLASTENIIVASFDGRGSGYQGDKIMHAINRRLGTFEVEDQ    606
21953     GPQVQLVNNRFKGVKYFRLNTLASLGYVVVVIDNRGSCHRGLKFPEGAFKYKMGQIEIDDQ    714
          **  * .:. *:   ::     ***  *.   * *** :* * :*  ***: :.  :**

DPP IV    IEAARQFS-KMGFVDNKRIAIWGWSYGGYVTSMVLGSGSGVFKCGIAVAPVSRWEYYDSV    665
21953     VEGLQYLASRYDFIDLDRVGIHGWSYGGYLSLMALMQRSDIFRVAIAGAPVTLWIFYDTG    774
          :*.:*::: :  *:* : .. ***.*** *:: *::*** :* .*** ** ** :**..

DPP IV    YTERYMGLPTPEDNLDHYRNSTVMSRAENFKQVEYLLIHGTADDNVHFQQSAQISKALVD    725
21953     YTERYMGHPDQNEQGYYLGSVAMQAEKFPSEPNRLLLLHGFLDENVHFAHTSILLSFLVR    834
          *******    :  :   ..*.* :*:*:* *  * ::** ***** ::::: . :  *

DPP IV    VGVDFQAMWYTDEDHGIASSTAHQHIYTHMSHFIKQCFSLP------    766
21953     AGKPYDLQIYPQERHSIRVPESGEHYELHLLHYLQENLGSRIAALKVI    882
          .* ::: *   : .  :  . . *   :*   :::: : : .  ::
```

FIGURE 14B

Alignments of top-scoring domains:
trypsin: domain 1 of 2, from 45 to 268: score 150.2, E = 7.2e-47

```
               *->pgsfgsPwqvslqvrsgggsrkhfCGGsLisenwVLTAAHCvsgaas
                  pg++  Pwq+s+ + +      h+C+GsL+ + wVLTAAHC++   a
m32404   45    PGEW--PWQASVRRQG-----VHICSGSLVADTWVLTAAHCFEKMAT   84 apassvrVSlsvrlGehnlsltegteqkfdvkktiivHpnynpdtldnga
               a  ss++V    +lG+  + ++ + + + v+     + yn     ++
m32404   85    AELSSWSV----VLGSLKQEGQSPGAEEVGVAA-LQLPKAYNHYSQG---   126

YdnDiAllkLkspgvtlgdtvrpicLpsassdlpvGttctvsGwGrrptk
               D+AL1+L   p                ++cLp++      +p G++c+++Gw  + t
m32404   127   --SDLALLQLTHP----TVQTTLCLPQPTYHFPFGASCWATGWDQN-TS   168 nlglsdtLqevvvpvvsretCrsaye.yggt....dDkvefvtdnmiCag
               +             tL+ + ++++sr tC++ y +    +     ++m+C g
m32404   169   DVS--RTLRNLRLRLISRPTCNCLYNrLHQRllsnP-----ARPGMLCGG   211 al.ggkdaCqGDSGGGPLvcsdgnrdgrwelvGivSwGsygCargnkPGvy
               a++g  +++CqGDSGGP++c+  +  g w  vGi+S+  ++Ca+  +P
m32404   212   AQPGEQGPCQGDSGGPVMCREPD--GHWVQVGIISFT-SKCAQEDTPVLL   258 trVssyldWI<-*  (SEQ ID NO:45)
               t +    W+
m32404   259   TDMAVHSSWL     268
```

FIGURE 16A trypsin: domain 2 of 2, from 311 to 520: score 111.2, E = 1.9e-34

```
         *->sfgsPwqvslqvrsgggsrkhfCGGsLisenwVLTAAHCvsgaaasap
            ++ Pw + l    +        k+ CGG+L+se  VLTAAHC+ g  +
m32404 311  QW--PWDARLKHHG----KLACGGALVSEVVVLTAAHCFIG--RQT  348 assvrVSlsvrlGehnlsltegteqkfdvkktiivHpnynpdtldngaYd
         ++++V      lG+       +e +      k+   i H y    +  +
m32404 349 LEEWSV----GLGA----GPEEW----GLKQ-LILHGAYTHPEGG----  380 nDiALlkLkspgvtlgdtvrpiclpsassdlpvGttctvsGwGrrptknl
         +D+A l L++p vtlg+   rp+cLp a+   lp+G +++v G +
m32404 381 YDVAFLLAQP-VTLGPGLRPLCLPYADHHLPDGEHGWVLGLTQ--KAGI  427 glsdtIqevvvpvvsretCrsayeyggt...dDkvefvtdnmiCagalgg
         +              q+v v+v++   C++++   +g++++  +  ++m+C++  g
m32404 428 N----YPQTVPVTVLGPMACSRQHAAPGGtgiP----ILPGMVCTTVVGE  469 kdaCgDSGGPLvcsdgnrdgrwelvGivSwGsygCargnkPGvytrVss
           C G SG PLv++       g+w+lvG +S+G + C +  kP+v++  s
m32404 470 PPHCEGLSGAPLVHEIR---GTWFLVGLHSFG-DTCQSSAKPAVFAALSA  515 yldWI<-*  (SEQ ID NO:46)
         y dWI
m32404 516 YEDWI
         520
```

FIGURE 16B

Alignments of top-scoring domains:
trypsin_2: domain 1 of 2, from 38 to 268: score 164.6, E = 1.6e-45

```
              *->RIVGGseakigsfPWqvsLq......CGGSLIsprwVLTAAHC.....
                 G  + +g++PWq+s++++++ + C GSL+++ wVLTAAHC    +
m32404   38   PQEG--NTLPGEWPWQASVRrggvhiCSGSLVADTWVLTAAHCfekm  82 rVrlGshdlssgeeteggprldspggqvikVskiievHpnYn
                 +   ++ V+lGs+ +                   spg++ ++V+       Yn
m32404   83   ataelsswSVVLGSLKQEGQ----------SPGAEEVGVAALQ-LPKAYN 121

....NDIALLkLkepvtlsdsntvrPiclPssneiktsegntvpaGttc
                 + +++ D+ALL+L+ p        +    ++clP++        +++p G+ c
m32404  122   hysggSDLALLQLTHP----T--VQTTLCLPQP-------TYHFPFGASC 158 tVsGWGrtsegpeesggggslpdvLqevnvpivsnetCr..........
              +++GW    ++         +++L+ ++ ++s+ tC+   +++ +++    +
m32404  159   WATGWDQNTS---------DVSRTLRNLRLRLISRPTCNclynrlhqrlls 200

.....MlCAGyleggntpgGkDaCqGDSGGPLvc........vLvGiVSW
                 ++ +++MlC G +       g +++CqGDSGGP +c++++++++v+vGi+S+
m32404  201   nparpgMLCGGAQP-----GEQGPCQGDSGGPVMCrepdghwVQVGIISF 245

GssslygCarpnkPGVYTrVssyldWI<-* (SEQ ID NO:47)
                 s    Ca+ + P GVYT+ + + +W
m32404  246   TS----KCAQEDTPVLLTDMAVHSSWL 268
```

FIGURE 17A trypsin_2: domain 2 of 2, from 300 to 520: score 110.2, E = 3.9e-29

```
                *-->RIVGGseakigsfPWqvsLq......CGGSLIsprwVLTAAHC....
                   R G + + ++PW + L ++++ CGG+L+s+  VLTAAHC   ++
m32404    300   RSAGPQAGALSQWPWDARLKhhgklaCGGALVSEVVVLTAAHCfigr    346

......rVrlGshdlssgeeteggprldspggqvikVskiievHpnYn..
                ++          V lG+             + +++ i H Y ++
m32404    347   qtleewSVGLGAGP--------------EEWGLKQLI-LHGAYThp      377

...NDIALLkLkepvtlsdsntvrPiclPssneiktsegntvpaGttctV
                ++++D+A L L++pvtl++         rP+clP        + ++p+G  ++V
m32404    378   eggYDVAFLLLAQPVTLGP--GLRPLCLPYA-------DHHLPDGEHGWV   418 sGWGrtsegpeesgggslpdvLqevnvpivsnetCr..............
                G  ++   +g +p++   v v+++  C++++  +++++ +
m32404    419   LG--LTQK-----AGINYPQT---VPVTVLGPMACSrqhaapggtgipil   458

..MlCAGyleggntpgGkDaCqGDSGGPLvc......vLvGiVSWGsssl
                ++M+C+        g   C+G SG PLv++ +++++LvG+ S+G
m32404    459   pgMVCTTVV-----GEPPHCEGLSGAPLVHeirgtwFLVGLHSFG----    498 ygCarpnkPGVYTrVssyldWI<-* (SEQ ID NO:47)
                + C + kP+V++  s+y dWI                    52
m32404    499   DTCQSSAKPAVFAALSAYEDWI
```

FIGURE 17B trypsin: domain 1 of 1, from 41 to 234: score 122.5, E = 4.6e-38

```
        *->CGGsLisenwWLTAAHCvsgaasapassvrVSlsvrlGe.hnlslte
           C G+Li++  wV+TAAHC              ++rV       +lG +    ++e
14089  41  CAGVLIHPLWVITAAHCNLP------KLRV-----ILGVtIPADSNE   76 gteqkfdvkktiivHpnynpdtldngaYdnDiAllkLkspgvtlgdtvrp
           q++  +k   i Hp+++    +d    +Di+L+kIk+   ++l+d+v+
14089  77  KHLQVIGYEK-MIHHPHFSVTSID-----HDIMLIKLKTE-AELNDYVKL  119 icLpsassdlpvGttctvsGwGrrptknlg...lsdtLqevvvpvvsret
           ++Lp         + + +t+c+vs w +      + +d+Lq+v+++v+s  +
14089 120  ANLPY--QTISENTMCSVSTWSY---NVCDiykEPDSLQTVNISVISKPQ  164

Crsaye.yggtdDkvefvtdnmiCagal.ggkdaCqGDSGGPLvcsdgnr
           Cr ay +y+        +t+nm+C+g   +g + +C+  S  P++c++
14089 165  CRDAYKTYN-------ITENMLCVGIVpGRRQPCKEVSAAPAICNGM--  204 dgrwelvGivSwGsygCargnkPGvytrVssyldwI<-*          (SEQ ID NO:54)
           1+Gi S+  +gC + G+y+++++y +WI
14089 205  -----LQGILSFA-DGCVLRADVGIYAKIFYYIPWI              234
```

FIGURE 19A trypsin_2: domain 1 of 1, from 24 to 234: score 143.5, E = 3.7e-39

```
        *->RIVGGseakigsfPWqvsLq.....CGGSLIsprwVLTAAHC.....
           +++      P+ v L ++   +C G+LI+p wV+TAAHC+ ++
14089   24 ----VSSTP---PYLVYLKsdylpCAGVLIHPLWVITAAHCnlpkl  62 rVrlgshdlssgeeteggprldspggqvikVskiievHpnYn.....NDI
           rV+lG +     ++e+          qvi+ +k i  Hp+++ ++ ++DI
14089   63 RVILGVTIPADSNEKHL----------QVIGYEKMI-HHPHFSvtsidHDI 102

ALLkkepvtlsdsntvrPiclPssneiktsegntvpaGttctVsGWGrt
           +L+kLk+ ++l+d   +v+ + LP +           t+ ++t+c Vs W +
14089  103 MLIKLKTEAELND--YVKLANLPYQ----------TISENTMCSVSTWSYN 141 segpeesgggslpdvLqevnvpivsnetCr........MlCAGyleg
            +  pd Lq vn+ ++s+ +Cr+ +++++  +++MlC+G
14089  142 VC----DIYKEPDSLQTVNISVISKPQCRdayktynitenMLCVGIVP- 185 gntpgGkDaCqGDSGGPLvc..vLvGiVSWGssslygCarpnkPGVYTrv
           g + +C+   S  P +c++  L+Gi S+     +gC   +    G+Y+++
14089  186 ----GRRQPCKEVSAAPAICngMLQGILSFA----DGCVLRADVGIYAKI 227 ssyldWI<-*     (SEQ ID NO:55)
           +y++WI
14089  228 FYYIPWI  234
```

FIGURE 19B

>46 p99.2 (489) TRYP(11) TRY1(8) MCT1(8) // PROTEASE SERINE PRECURSOR SIGNAL HYDROLASE ZYMOGEN GLYCOPROTEIN FAMILY MULTIGENE FACTOR
Length = 266

Score = 199 (75.1 bits), Expect 2.6e-16, P = 2.6e-16
Identities = 62/191 (32%), Positives = 97/191 (50%)

```
Query:  72 ADSNEKHLQVIGYEKMIHHPHF--SVTSIDHDIMLIKLK-----TEAEINDYVKLANLPY 124
           +++ E    QVI   K+I HP++  S ++ D+DI L+KL      T +  +D V+   LP
Sbjct:  76 SNNEEGSEQVISVSKVIVHPNYYNSSSTYDNDIALLKLSSPVSFTSSAFSDNVQPICLPS 135

Query: 125 --QTISE--NTMCSVSTWSYNVCDIYKE--PDSLQTVNISVISKPQCRDAYKTYN----I 174
            +T +     T  C+VS W         PD+LQ VNI +IS  +C+ +Y +      I
Sbjct: 136 SNETEPKPPGTTCTVSGWGRTSSSGSSSSYPDTLQQVNIPIISNEECKSSYYSNGNKSTI 195

Query: 175 TENMLCVGIVP-GRRQPCKEVSAAPAIC----NG--MLQGILSF-ADGCVLRADV----GI 223
           T+NM+C G     G +    C + S P +C       NG    +L  GI+S+ + GC   A   G+
Sbjct: 196 TDNMICAGYYSEGGKDSCQGDSGGPLVCKDQKNGNWVLVGIVSWGSSGCGCPAQPNKPGV 255

Query: 224 YAKIFYYIPWI 234
           Y ++  Y+ WI
Sbjct: 256 YTRVSSYLDWI 266   (SEQ ID NO:56)
```

FIGURE 20A

Score = 106 (42.4 bits), Expect 0.00057, P = 0.00057
Identities = 31/81 (38%), Positives = 45/81 (55%)

```
Query:  41 CAGVLIHPLMWVITAAHC------NLPKLRVILGV--TIPADSNEKHL-QVIGYEKMIHH 90
            C G LI+  WV+TAAHC        +   +V LG  T   +NE+   QVI   K+I H
Sbjct:  35 CGGSLINEQWVLTAAHCFQNNGSSTSSYQVTLGEHNTSENSNNEEGSEQVISVSKVIVH 94

Query:  91 PHF--SVTSIDHDIMLIKLKT 109
            P++  S  ++ D+DI L+KL +
Sbjct:  95 PNYYNSSSTYDNDIALLKLSS 115  (SEQ ID NO:57)
```

FIGURE 20B

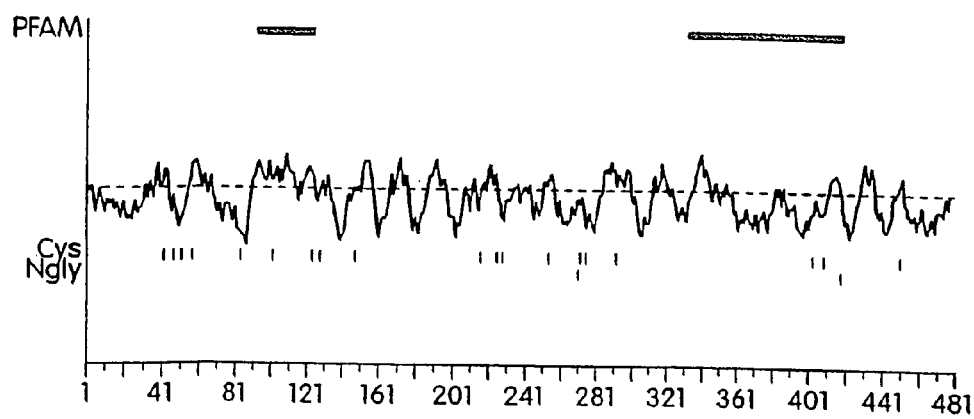

>23436
MAPRLQLEKAAWRWAETVRPEEVSQEHIETAYRIWLEPCIRGVCRRNCKCNPNCLVGIGE
HIWLGEIDENSFHNIDDFNCERRKKNSFVGLTNLGATCYVNTFLQVWFLNLELRQALYLC
PSTCSDYMLGDGIQEEKDYEPQTICEHLQYLFALLQNSNRRYIDPSGFVKALGLDTCQQQ
DAQEFSKLFMSLLEDTLSKQKNPDVRNIVQQQFCGEYAYVTVCNQCGRESKLLSKFYELE
LNIQCHKQLTDCISEFLKEEKLEGDNRYFCENCQSKQNATRKIRLLSLPCTLNLQLMRFV
FDRQTGHKKKLNTYIGFSEILDMEPYVEHKGGSYVYELSAVLIHRCVSAYSGHYIAHVKD
PQSGEWYKFNDEDIEKMEGKKLQLGIEEDLAEPSKSQTRKFKCGKGTHCSRNAYMLVYRL
QTQEKPNTTVQVPAFLQELVDRDNSKFEEWCIEMAEMRKQSVDKGKAKHEEVKELYQRLP
AGAGL

FIGURE 21

```
UCH-1: domain 1 of 1, from 89 to 120: score 31.6, E = 8.6e-06
              *->tGLiNlGNTCYmNSvLQcLfsipplrdyIldi<-*
                 +GL NlG+TCY N  LQ++f + +lr++l+ +
      23436  89  VGLTNLGATCYVNTFLQVWFLNLELRQALYLC   120
```

FIGURE 22A

```
UCH-2: domain 1 of 1, from 332 to 420: score 77.3, E = 3.3e-19
              *->gpgkYeLyaVvvHsGsslsgGHYtayvkken...WykFDDdkVsrvt
                 g+++YeL aV++H G s+++GHY+a+vk++ +++WykF+D+ ++ ++
      23436  332 GSYVYELSAVLIHRGVSAYSGHYIAHVKDPQsgeWYKFNDEDIEKME 378 eeevlkesgg................esgdtssAYiLfYer<-*
                 + + ++ ++  +++++++++++ +++    + +AY+L+Y+
      23436  379 GKKLQLGIEEdlaepsksqtrkpkcgkGTHCSRNAYMLVYRL    420
```

FIGURE 22B

HUMAN PROTEIN KINASE, PHOSPHATASE, AND PROTEASE FAMILY MEMBERS AND USES THEREOF

RELATED APPLICATIONS

The present application is a divisional of U.S. application Ser. No. 11/151,601, filed Jun. 13, 2005, now U.S. Pat. Ser. No. 7,198,930, which is a divisional of U.S. application Ser. No. 10/170,789, filed Jun. 13, 2002, now U.S. Pat. Ser. No. 7,070,947, which is a continuation-in-part of U.S. application Ser. No. 09/797,039, filed Feb. 28, 2001, now U.S. Pat. Ser. No. 6,730,491, which claims the benefit of U.S. Provisional Application Ser. No. 60/186,061, filed Feb. 29, 2000 (abandoned). U.S. application Ser. No. 10/170,789 is also a continuation-in-part of U.S. application Ser. No. 09/882,166, filed Jun. 15, 2001 (abandoned), which claims the benefit of U.S. Provisional Application Ser. No. 60/212,078, filed Jun. 15, 2000 (abandoned). U.S. application Ser. No. 10/170,789 is also a continuation-in-part of U.S. application Ser. No. 09/934,406, filed Aug. 21, 2001 (abandoned), which claims the benefit of U.S. Provisional Application Ser. No. 60/226,740, filed Aug. 21, 2000 (abandoned). U.S. application Ser. No. 10/170,789 is also a continuation-in-part of U.S. application Ser. No. 09/861,801, filed May 21, 2001 (abandoned), which claims the benefit of U.S. Provisional Application Ser. No. 60/205,508, filed May 19, 2000 (abandoned). U.S. application Ser. No. 10/170,789 is also a continuation-in-part of U.S. application Ser. No. 09/801,267, filed Mar. 6, 2001, (abandoned), which claims the benefit of U.S. Provisional Application Ser. No. 60/187,454, filed Mar. 7,2000 (abandoned). U.S. application Ser. No. 10/170,789 is also a continuation-in-pan of U.S. application Ser. No. 09/829,671, filed Apr. 10, 2001 (abandoned), which claims the benefit of U.S. Provisional Application Ser. No. 60/197,508, filed Apr. 18, 2000 (abandoned). U.S. application Ser. No. 10/170,789 is also a continuation-in-pan of U.S. application Ser. No. 09/961,721, filed Sep. 24, 2001 (abandoned), which claims the benefit of U.S. Provisional Application Ser. No. 60/235,023, filed Sep. 25, 2000 (abandoned). U.S. application Ser. No. 10/170,789 is also a continuation-in-part of U.S. application Ser. No. 10/045,367, filed Nov. 7, 2001 (abandoned), which claims the benefit of U.S. Provisional Application Ser. No. 60/246,561, filed Nov. 7, 2000 (abandoned). U.S. application Ser. No. 10/170,789 is also a continuation-in-part of U.S. application Ser. No. 09/801,275, filed Mar. 6, 2001 (abandoned), which claims the benefit of U.S. Provisional Application Ser. No. 60/187,420, filed Mar. 7, 2000 (abandoned), the contents of each of which are incorporated herein by reference.

The contents of the Sequence Listing are submitted herewith on compact disc in duplicate. Each duplicate disc has a copy of the file "sequence listing.txt" which is incorporated herein by this reference. This file is 140 kilobytes and was created on Jun. 8, 2005. The compact disc copies were created on Dec. 8, 2006.

BACKGROUND OF THE INVENTION

The invention provides isolated polypeptide molecules and nucleic acid molecules encoded the polypeptide molecules, designated 53070, 15985, 26583, 21953, m32404, 14089, and 23436 molecules, which encode novel kinase family molecules, phosphatase family members, and protease family members, including prolyl oligopeptidases, serine proteases, and ubiquitin carboxy terminal hydrolases.

SUMMARY OF THE INVENTION

The present invention is based, in part, on the discovery of novel protein kinase, serine/threonine protein kinase, serine/threonine phosphatase, prolyl oligopeptidase, trypsin, serine protease, and ubiquitin carboxy-terminal hydrolase family members, referred to herein as "53070, 15985, 26583, 21953, m32404, 14089, and 23436". The nucleotide sequences of cDNAs encoding 53070, 15985, 26583, 21953, m32404, 14089, and 23436 are recited in SEQ ID NO: 1, 7, 14, 19, 24, 33, and 40, respectively, and the amino acid sequences of 53070, 15985, 26583, 21953, m32404, 14089, and 23436 polypeptides are recited in SEQ ID NO:2, 8, 15, 20, 25, 34, and 41, respectively. In addition, the nucleotide sequences of the coding regions are recited in SEQ ID NO: 3, 9, 16, 21, 26, 35, and 42, respectively.

Accordingly, in one aspect, the invention features a nucleic acid molecule that encodes a 53070 protein or polypeptide, e.g., a biologically active portion of the 53070, 15985, 26583, 21953, m32404, 14089, or 23436 protein. In a preferred embodiment the isolated nucleic acid molecule encodes a polypeptide having the amino acid sequence of SEQ ID NO:2, 8, 15, 20, 25, 34, and 41. In other embodiments, the invention provides isolated 53070, 15985, 26583, 21953, m32404, 14089, or 23436 nucleic acid molecules having the nucleotide sequence shown in SEQ ID NO:1, 3, 7, 9, 14, 16, 19, 21, 24, 26, 33, 35, 40, or 42. In still other embodiments, the invention provides nucleic acid molecules that are substantially identical (e.g., naturally occurring allelic variants) to the nucleotide sequence shown in SEQ ID NO:1, 3, 7, 9, 14, 16, 19, 21, 24, 26, 33, 35, 40, or 42. In other embodiments, the invention provides a nucleic acid molecule which hybridizes under a stringency condition described herein to a nucleic acid molecule comprising the nucleotide sequence of SEQ ID NO:1, 3, 7, 9, 14, 16, 19, 21, 24, 26, 33, 35, 40, or 42, wherein the nucleic acid encodes a full length 53070, 15985, 26583, 21953, m32404, 14089, or 23436 protein or an active fragment thereof.

In a related aspect, the invention further provides nucleic acid constructs that include a 53070, 15985, 26583, 21953, m32404, 14089, or 23436 nucleic acid molecule described herein. In certain embodiments, the nucleic acid molecules of the invention are operatively linked to native or heterologous regulatory sequences. Also included, are vectors and host cells containing the 53070, 15985, 26583, 21953, m32404, 14089, or 23436 nucleic acid molecules of the invention e.g., vectors and host cells suitable for producing 53070, 15985, 26583, 21953, m32404, 14089, or 23436 nucleic acid molecules and polypeptides.

In another related aspect, the invention provides nucleic acid fragments suitable as primers or hybridization probes for the detection of 53070-, 15985-, 26583-, 21953-, m32404-, 14089-, or 23436-encoding nucleic acids.

In still another related aspect, isolated nucleic acid molecules that are antisense to a 53070, 15985, 26583, 21953, m32404, 14089, or 23436 encoding nucleic acid molecule are provided.

In another aspect, the invention features, 53070, 15985, 26583, 21953, m32404, 14089, and 23436 polypeptides, and biologically active or antigenic fragments thereof that are useful, e.g., as reagents or targets in assays applicable to treatment and diagnosis of 53070-, 15985-, 26583-, 21953-, m32404-, 14089-, or 23436-mediated or -related disorders. In another embodiment, the invention provides 53070, 15985, 26583, 21953, m32404, 14089, and 23436 polypeptides having a 53070, 15985, 26583, 21953, m32404, 14089, or 23436 activity, respectively. Preferred polypeptides are 53070 proteins including at least one protein kinase domain, e.g., a serine/threonine kinase domain, and, preferably, having a 53070 activity, e.g., a 53070 activity as described herein.

Preferred polypeptides are 15985 proteins including at least one protein kinase domain and at least one, preferably two doublecortin repeats, and, preferably, having a 15985 activity, e.g., a 15985 activity as described herein.

Preferred polypeptides are 26583 proteins including at least one phosphatase catalytic domain, and, preferably, having a 26583 activity, e.g., a 26583 activity as described herein.

Preferred polypeptides are 21953 proteins including at least one prolyl oligopeptidase domain, and, preferably, having a 21953 activity, e.g., a 21953 activity as described herein.

Preferred polypeptides are m32404 proteins including at least one trypsin domain, e.g., polypeptides including m32404 amino acids from about 35 to 268 or polypeptides including m32404 amino acids from about 300-520, and, preferably, having an m32404 activity, e.g., an m32404 activity as described herein.

Preferred polypeptides are 14089 proteins including at least one trypsin domain, and, preferably, having a 14089 activity, e.g., a 14089 activity as described herein.

Preferred polypeptides are 23436 polypeptides including at least one ubiquitin carboxy-terminal hydrolase domain, and, preferably, having a 23436 activity, e.g., a 23436 de-ubiquitinating activity as described herein.

In other embodiments, the invention provides 53070, 15985, 26583, 21953, m32404, 14089, and 23436 polypeptides, e.g., a 53070, 15985, 26583, 21953, m32404, 14089, or 23436 polypeptide having the amino acid sequence shown in SEQ ID NO:2, 8, 15, 20, 25, 34, or 41 an amino acid sequence that is substantially identical to the amino acid sequence shown in SEQ ID NO:2, 8, 15, 20, 25, 34, and 41; or an amino acid sequence encoded by a nucleic acid molecule having a nucleotide sequence which hybridizes under a stringency condition described herein to a nucleic acid molecule comprising the nucleotide sequence of SEQ ID NO: 1, 3, 7, 9, 14, 16, 19, 21, 24, 26, 33, 35, 40, or 42, wherein the nucleic acid encodes a full length 53070, 15985, 26583, 21953, m32404, 14089, or 23436 protein or an active fragment thereof.

In a related aspect, the invention further provides nucleic acid constructs which include a 15985, 21953, m32404, or 23436 nucleic acid molecule described herein.

In a related aspect, the invention provides 53070, 15985, 26583, 21953, m32404, 14089, or 23436 polypeptides or fragments operatively linked to non-53070, 15985, 26583, 21953, m32404, 14089, or 23436 polypeptides to form fusion proteins.

In another aspect, the invention provides a method of evaluating a sample. The method includes: providing a sample; detecting a 21953 polypeptide or nucleic acid in the sample; and, optionally, comparing the level of expressed 21953 molecules to a reference sample. For example, an increased level of 21953 molecules can be an indication that the sample includes cells transiting from the GI cell cycle phase to S phase. In other examples, the level of 21953 molecules can be an indication that a sample includes a proliferating cell, e.g., a proliferating lung, breast, ovary, or colon cell; or a heart cell, a prostate cell, a vascular cell (e.g., a smooth muscle or an endothelial cell), or a brain cell.

In another aspect, the invention features antibodies and antigen-binding fragments thereof, that react with, or more preferably specifically bind 53070, 15985, 26583, 21953, m32404, 14089, or 23436 polypeptides or fragments thereof, e.g., the protein kinase domain of a 53070 polypeptide, the C-terminal non-kinase domain of a 53070 polypeptide, an epitope that includes a phosphorylated amino acid residue, an extracellular domain of a 15985 polypeptide, trypsin domain of an m32404 polypeptide, a trypsin domain of a 14089 polypeptide, or ubiquitin carboxy-terminal hydrolase domain. In one embodiment, the antibodies or antigen-binding fragment thereof competitively inhibit the binding of a second antibody to a 53070 or 15985 polypeptide or a fragment thereof, e.g., the protein kinase domain of 53070, the C-terminal non-kinase domain of 53070, an epitope that includes a phosphorylated amino acid residue, or an extracellular domain of a 15985 polypeptide.

In another aspect, the invention provides methods of screening for compounds that modulate the expression or activity of the 53070, 15985, 26583, 21953, m32404, 14089, or 23436 polypeptides or nucleic acids. In a preferred embodiment, a screened compound alters the de-ubiquitinating activity of the 23436 polypeptide.

In still another aspect, the invention provides a method for modulating 53070, 15985, 26583, 21953, m32404, 14089, or 23436 polypeptide or nucleic acid expression or activity, e.g. using the screened compounds. In certain embodiments, the methods involve treatment of conditions related to aberrant activity or expression of the 53070, 15985, 26583, 21953, m32404, 14089, or 23436 polypeptides or nucleic acids, such as conditions involving aberrant or deficient cellular proliferation or differentiation; cell migration; conditions involving cholesterol biosynthesis, mitochondrial dysfunction, or aberrant cellular proliferation of a 26583 expressing cell, e.g., a lung cell, a breast cell, a colon cell, a liver cell, or a brain cell; e.g., a cancer (e.g. a cancer of the lung, breast, ovary, prostate, or colon), or conditions or disorders of the cardiovascular (including vascular, e.g., a smooth muscle or an endothelial cell), neuronal, or reproductive (e.g., prostatic) systems; as well as conditions involving the immune response, and the blood clotting system, or tumor invasion or metastasis; conditions involving aberrant or deficient proteolytic cleavage; or proliferation or cellular differentiation of a hematopoietic cell (e.g., a hematopoietic or an erythroid disorder).

In one embodiment, a method for inhibiting abnormal phosphorylation in a cell or a subject is provided. In other embodiments, a method for enhancing phosphorylation in a cell or a subject is provided. The method includes contacting a cell, or administering to a subject, a modulator of 53070 polypeptide or nucleic acid activity or expression, to thereby modulate, e.g., inhibit or enhance, the phosphorylation state in the cell or subject.

The invention also provides assays for determining the activity of or the presence or absence of 15985 polypeptides or nucleic acid molecules in a biological sample, including for disease diagnosis.

In yet another aspect, the invention provides methods for inhibiting the proliferation or inducing the killing, of a 15985-expressing cell, e.g., a hyperproliferative 15985-expressing cell. The method includes contacting the cell with an agent, e.g., a compound, (e.g., a compound identified using the methods described herein) that modulates the activity, or expression, of the 15985 polypeptide or nucleic acid. In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol. In a preferred embodiment, the cell is a hyperproliferative cell, e.g., a cell found in a solid tumor, a soft tissue tumor, or a metastatic lesion. In other embodiments, the hyperproliferative cell is an ovarian or a lung tumor cell.

In still another aspect, the invention features a method of modulating (e.g., enhancing or inhibiting) the proliferation, survival, and/or differentiation of a cell, e.g., a 26583-expressing cell, e.g., a lung cell, a breast cell, a colon cell, a liver cell, or a brain cell. The method includes contacting the cell with an agent that modulates the activity or expression of a 26583 polypeptide or nucleic acid, in an amount effective to modulate the proliferation and/or differentiation of the cell.

In a preferred embodiment, the 26583 polypeptide has an amino acid sequence identical to, or substantially identical to, SEQ ID NO:15. In other embodiments, the 26583 polypeptide is a fragment of at least 15, 20, 50, 100, 150, 200, 213, 250, or more contiguous amino acids of SEQ ID NO:15. In a preferred embodiment, the 26583 polypeptide is a fragment of at least 213 contiguous amino a In a preferred embodiment, the 26583 nucleic acid has a nucleotide sequence identical to, or substantially identical to, SEQ ID NO:14 or 16. In other embodiments, the 26583 nucleic acid is a fragment of at least 50, 100, 150, 200, 250, 300, 350, 400, 450, 500, or more contiguous nucleotides of SEQ ID NO:14 or 16.

In a preferred embodiment, the agent modulates (e.g., increases or decreases) 26583 protein phosphatase activity, e.g., serine/threonine phosphatase activity.

In a preferred embodiment, the agent modulates (e.g., increases or decreases) expression of the 26583 nucleic acid by, e.g., modulating transcription, mRNA stability, etc.

In a preferred embodiment, the cell, e.g., the 26583-expressing cell, is a lung cell, a breast cell, a colon cell, a liver cell, or a brain cell, e.g., a neuron or glial cell.

In a preferred embodiment, the cell, e.g., the 26583-expressing cell, is a tumor cell, e.g., a lung, breast, colon, liver, or brain tumor cell.

In a preferred embodiment, the cell, e.g., the 26583-expressing cell, is further contacted with a protein, e.g., a cytokine or a hormone. Exemplary proteins include, but are not limited to, G-CSF, GM-CSF, stem cell factor, interleukin-3 (IL-3), IL-4, Flt-3 ligand, thrombopoietin, and erythropoietin. The protein contacting step can occur before, at the same time, or after the agent is contacted. The protein contacting step can be effected in vitro or ex vivo. For example, the cell, e.g., the 26583-expressing cell is obtained from a subject, e.g., a patient, and contacted with the protein ex vivo. The treated cell can be re-introduced into the subject. Alternatively, the protein contacting step can occur in vivo.

In a preferred embodiment, the agent and the 26583-polypeptide or nucleic acid are contacted in vitro or ex vivo.

In a preferred embodiment, the contacting step is effected in vivo in a subject, e.g., as part of a therapeutic or prophylactic protocol. Preferably, the subject is a human, e.g., a patient with a metabolic disorder, e.g., a mitochondrial related disorder or a cholesterol biosynthesis related disorder, or a patient with a cell proliferation or differentiation disorder, e.g., a tumor. For example, the subject can be a cancer patient, e.g., a patient with a lung, breast, colon, liver, or brain tumor. The subject can also be a patient with diabetes mellitus or a neurodegenerative disorder (e.g., Parkinson's, Huntington's, or Alzheimer's disease). In other embodiments, the subject is a non-human animal, e.g., an experimental animal.

The contacting step(s) can be repeated.

In a preferred embodiment, the agent decreases the proliferation and/or enhances the differentiation of the cell, e.g., the 26583-expressing cell, e.g., the lung, breast, colon, liver, or brain cell. Such agents can be used to treat or prevent cancers, e.g., liver, breast, brain, colon, or lung carcinomas.

In yet another aspect, the invention features a method of treating or preventing a disorder, e.g., a metabolic disorder, e.g., a mitochondrial related disorder or a cholesterol biosynthesis related disorder; or a cellular proliferation and/or differentiation disorder, in a subject. The method includes administering to the subject an effective amount of an agent that modulates the activity or expression of a 26583 polypeptide or nucleic acid such that the disorder is ameliorated or prevented.

In a preferred embodiment, the 26583 polypeptide has an amino acid sequence identical to, or substantially identical to, SEQ ID NO:15. In other embodiments, the 26583 polypeptide is a fragment of at least 15, 20, 50, 100, 150, or more contiguous amino acids of SEQ ID NO:15. In a preferred embodiment, the 26583 polypeptide is a fragment of at least 213 contiguous amino acids of SEQ ID NO:15.

In a preferred embodiment, the 26583 nucleic acid has a nucleotide sequence identical to, or substantially identical to, SEQ ID NO:14 or 16. In other embodiments, the 26583 nucleic acid is a fragment of at least 50, 100, 150, 200, 250, 300, 350, 400, 450, 500, or more contiguous nucleotides of SEQ ID NO:14 or 16.

In a preferred embodiment, the agent modulates (e.g., increases or decreases) protein phosphatase activity.

In a preferred embodiment, the agent modulates (e.g., increases or decreases) expression of the 26583 nucleic acid by, e.g., modulating transcription, mRNA stability, etc.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense, a ribozyme, or a triple helix molecule, or an 26583 nucleic acid, or any combination thereof.

In a preferred embodiment, the agent is administered in combination with a cytotoxic agent.

In a preferred embodiment, the subject is a human, e.g., a patient with a metabolic disorder, e.g., a mitochondrial related disorder or a cholesterol biosynthesis related disorder, e.g., hypo- or hypercholesterolemia, diabetes mellitus, or a neurodegenerative disorder (e.g., Parkinson's, Huntington's, or Alzheimer's disease). The subject can also be a patient with a cell proliferation or differentiation disorder, e.g., a tumor, e.g., a patient with a lung, breast, colon, liver, or brain tumor. In other embodiments, the subject is a non-human animal, e.g., an experimental animal.

In a preferred embodiment, the agent decreases the proliferation and/or enhances the differentiation of the cell, e.g., the 26583-expressing cell, e.g., the lung, breast, colon, liver, or brain cell. Such agents can be used to treat or prevent cancers, e.g., liver, breast, brain, colon, or lung carcinomas.

In a preferred embodiment, the disorder is a metabolic disorder, e.g., a cholesterol synthesis disorder, e.g., hypo- or hypercholesterolemia; or a mitochondrial related disorder, e.g., diabetes mellitus, or Parkinson's, Huntington's, or Alzheimer's disease.

In a preferred embodiment, the disorder is a cancer, e.g., a lung, breast, colon, liver, or brain cancer.

In a preferred embodiment, the method further includes administering an effective amount of a protein, e.g., a cytokine or a hormone, to the subject. Exemplary proteins include, but are not limited to, G-CSF, GM-CSF, stem cell factor, interleukin-3 (IL-3), IL-4, Flt-3 ligand, thrombopoietin, and erythropoietin. The protein can be administered before, at the same time or after, administration of the agent.

The administration of the agent and/or protein can be repeated.

In still another aspect, the invention features a method for evaluating the efficacy of a treatment of a disorder, in a subject. The method includes treating a subject with a protocol under evaluation; assessing the expression of a 26583 nucleic acid or 26583 polypeptide, such that a change in the level of 26583 nucleic acid or 26583 polypeptide after treatment, relative to the level before treatment, is indicative of the efficacy of the treatment of the disorder.

In a preferred embodiment, the disorder is a metabolic disorder, e.g., a cholesterol synthesis disorder, e.g., hypo- or hypercholesterolemia; or a mitochondrial related disorder, e.g., diabetes mellitus, or Parkinson's, Huntington's, or Alzheimer's disease. In a preferred embodiment, the disorder is a cancer, e.g., a lung, breast, colon, liver, or brain cancer. In a preferred embodiment, the subject is a human. In a preferred embodiment, the subject is an experimental animal, e.g., an animal model for a metabolic disorder or cancer.

In a preferred embodiment, the method can further include treating the subject with a protein, e.g., a cytokine or a hormone. Exemplary proteins include, but are not limited to, G-CSF, GM-CSF, stem cell factor, interleukin-3 (IL-3), IL-4, Flt-3 ligand, thrombopoietin, and erythropoietin.

The invention also features a method of diagnosing a disorder, e.g., a metabolic disorder or a cell proliferation/differentiation disorder, e.g., cancer, in a subject. The method includes evaluating the expression or activity of a 26583 nucleic acid or a 26583 polypeptide, such that, a difference in the level of 26583 nucleic acid or 26583 polypeptide relative to a normal subject or a cohort of normal subjects is indicative of the disorder.

In a preferred embodiment, the evaluating step occurs in vivo. For example, by administering to the subject a detectably labeled agent that interacts with the 26583 nucleic acid or polypeptide, such that a signal is generated relative to the level of activity or expression of the 26583 nucleic acid or polypeptide.

In a preferred embodiment, the disorder is a metabolic disorder, e.g., a cholesterol synthesis disorder, e.g., hypo- or hypercholesterolemia; or a mitochondrial related disorder, e.g., diabetes mellitus, or Parkinson's, Huntington's, or Alzheimer's disease. In a preferred embodiment, the disorder is a cancer, e.g., a lung, breast, colon, liver, or brain cancer.

The invention also provides assays for determining the activity of or the presence or absence of 26583 polypeptides or nucleic acid molecules in a biological sample, including for disease diagnosis.

In further aspect, the invention provides assays for determining the presence or absence of a genetic alteration in a 26583 polypeptide or nucleic acid molecule, including for disease diagnosis.

In yet another aspect, the invention features a method for identifying an agent, e.g., a compound, which modulates the activity of a 26583 polypeptide, e.g., a 26583 polypeptide as described herein, or the expression of a 26583 nucleic acid, e.g., a 26583 nucleic acid as described herein, including contacting the 26583 polypeptide or nucleic acid with a test agent (e.g., a test compound); and determining the effect of the test compound on the activity of the polypeptide or nucleic acid to thereby identify a compound which modulates the activity of the polypeptide or nucleic acid.

In a preferred embodiment, the activity of the 26583 polypeptide is a protein phosphatase activity.

In a preferred embodiment, the activity of the 26583 polypeptide is proliferation, differentiation, and/or survival of a cell, e.g., a 26583-expressing cell, e.g., a lung, breast, colon, liver, or brain cell.

In yet another aspect, the invention features a method of treating or preventing a hematopoietic disorder, e.g., an erythroid-associated disorder, in a subject. The method includes administering to the subject an effective amount of an agent that modulates the activity or expression of a 23436 polypeptide or nucleic acid such that the hematopoietic disorder is ameliorated or prevented. In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In another aspect, the invention features a method of modulating a hematopoietic disorder, e.g., an erythroid-associated disorder or a disorder of erythropoiesis, comprising contacting a hematopoietic cell, e.g., a blood cell, such as an erythroid cell or erythroid-precursor, with a agent that increases or decreases the activity or expression of a 23436 polypeptide or nucleic acid, thereby (a) ameliorating or preventing the hematopoietic disorder and/or (b) modulating the differentiation of the hematopoietic cell, e.g., the blood cell.

The invention also provides assays for determining the activity of or the presence or absence of 23436 polypeptides or nucleic acid molecules in a biological sample, including for disease diagnosis.

In one embodiment, the modulator of the 53070, 15985, 26583, 21953, m32404, 14089, or 23436 is an agent as described herein.

In yet another aspect, the invention provides methods for modulating, e.g., inhibiting or increasing, the activity or expression of a 53070-, 15985-, 26583-, 21953-, m32404-, 14089-, or 23436-expressing cell, e.g., a hyper-proliferative 53070-, 15985-, 26583-, 21953-, m32404-, 14089-, or 23436-expressing cell. The method includes contacting the cell with an agent, e.g., a compound (e.g., a compound identified using the methods described herein) that modulates the activity, or expression, of the 53070, 15985, 26583, 21953, m32404, 14089, or 23436 polypeptide or nucleic acid.

Preferably, the methods inhibit the proliferation or induce the killing of a 53070-, 15985-, 26583-, 21953-, m32404-, 14089-, or 23436-expressing cell, e.g., a hyper-proliferative 53070-, 15985-, 26583-, 21953-, m32404-, 14089-, or 23436-expressing cell.

In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol.

In a preferred embodiment, the cell is a hyperproliferative cell, e.g., a cell found in a solid tumor, a soft tissue tumor, or a metastatic lesion. For example, the 21953-expressing cell is a lung, breast, ovary, prostate, or colon cell. In a preferred embodiment, the cell is lung cell.

In other embodiments, the 21953-expressing cell is a neural cell (e.g., a neuronal or a glial cell), a vascular cell (e.g., smooth muscle or an endothelial cell), a heart cell, a prostatic cell, or an immune cell. Preferably, the tumor is a sarcoma, a carcinoma, or an adenocarcinoma. Preferably, the m32404-expressing hyperproliferative cell is found in a cancerous or pre-cancerous tissue, e.g., a cancerous or pre-cancerous tissue where an m32404 polypeptide or nucleic acid is expressed, e.g., breast, ovarian, colon, liver, lung, kidney, or brain cancer. Most preferably, the m32404-expressing hyperproliferative cell is found in a tumor from the breast, ovary, colon, liver and lung.

In a preferred embodiment, the agent, e.g., the compound, is an inhibitor of a 53070, 15985, 26583, 21953, m32404, 14089, or 23436 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion). In another preferred embodiment, the agent, e.g., compound, is an inhibitor of a 53070, 15985, 26583, 21953, m32404, 14089, or 23436 nucleic acid, e.g., an antisense, a ribozyme, or a triple helix molecule. The inhibitor can also be a protease inhibitor or a derivative thereof, or a peptidomimetic, e.g., a phosphonate analog of a peptide substrate such as a prolyl peptide substrate. In another preferred embodiment, the compound is an inhibitor of a 21953 nucleic acid, e.g., an antisense, a ribozyme, or a triple helix molecule. The inhibitor can also be a trypsin inhibitor or a derivative thereof, or a peptidomimetic, e.g., a phosphonate analog of a peptide substrate.

In another embodiment, the agent, e.g., the compound, is administered in combination with a cytotoxic agent. Examples of cytotoxic agents include anti -microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another embodiment, the agent, e.g., compound, is an activator of a 53070, 15985, 26583, 21953, m32404, 14089, or 23436 polypeptide. Preferably, the activator is chosen from a peptide, a phosphopeptide, a small organic molecule, a small inorganic molecule and an antibody. In yet another embodiment, the compound stimulates the expression of a 53070, 15985, 26583, 21953, m32404, 14089, or 23436 nucleic acid.

In another aspect, the invention features methods for treating or preventing a disorder characterized by aberrant cellular proliferation or differentiation of a 53070-, 15985-, 26583-, m32404-, 14089-, or 23436-expressing cell, in a subject. Preferably, the method includes comprising administering to the subject (e.g., a mammal, e.g., a human) an effective amount of a compound (e.g., a compound identified using the methods described herein) that modulates the activity, or expression, of the 53070, 15985, 26583, 21953, m32404, 14089, or 23436 polypeptide or nucleic acid. In a preferred embodiment, the disorder is a cancerous or pre-cancerous condition, e.g. in the case of 21953, relating to proliferation of a lung, breast, ovary, prostate, or colon cell. In another preferred embodiment, the disorder is an immune, a neuronal, cardiovascular, reproductive disorder, e.g., a disorder relating to aberrant processing of a polypeptide hormone. Preferably, the cancer is found in a tissue where an m32404 polypeptide or nucleic acid is expressed, e.g., breast, ovarian, colon, liver, lung, kidney, or brain cancer. Most preferably, the cancer is found in the breast, ovary, colon, liver and lung.

In another aspect, the invention provides methods of diagnosing or staging a disorder, e.g., proliferative disorder. The method includes: (i) identifying a subject having, or at risk of having, the disorder; (ii) obtaining a sample of a tissue or cell affected with the disorder; (iii) contacting said sample or a control sample with a labeled agent specific for a 15985 polypeptide or nucleic acid, e.g., a probe or a primer, under conditions that allow interaction of the labeled agent and the 15985 nucleic acid, e.g., cDNA, mRNA, or 15985 protein to occur, and (iv) detecting formation of a complex. A statistically significant increase in the formation of the complex between the labeled agent with respect to a reference, e.g., a control sample, is indicative of the disorder or the stage of the disorder. The level of 15985 nucleic acid or polypeptide expression can be detected by any method described herein. Preferably, the labeled agent is directly or indirectly labeled with a detectable substance to facilitate detection of the bound or unbound binding agent. Suitable detectable substances include various enzymes, prosthetic groups, fluorescent materials, luminescent materials and radioactive materials.

In a further aspect, the invention provides methods for evaluating the efficacy of a treatment of a disorder, e.g., a proliferative disorder or a differentiation disorder (e.g. in the case of 21953, lung cancer, or a neuronal disorder). The method includes: treating a subject, e.g., a patient or an animal, with a protocol under evaluation (e.g., treating a subject with one or more of: chemotherapy, radiation, and/or a compound identified using the methods described herein); and evaluating the expression of a 53070, 15985, 26583, 21953, m32404, 14089, or 23436 nucleic acid or polypeptide before and after treatment. A change, e.g., a decrease or increase, in the level of a 53070, 15985, 26583, 21953, m32404, 14089, or 23436 nucleic acid (e.g., mRNA) or polypeptide after treatment, relative to the level of expression before treatment, is indicative of the efficacy of the treatment of the disorder. The level of 53070, 15985, 26583, 21953, m32404, 14089, or 23436 nucleic acid or polypeptide expression can be detected by any method described herein.

The invention also provides assays for determining the activity of or the presence or absence of m32404 polypeptides or nucleic acid molecules in a biological sample, including for disease diagnosis. Preferably, the biological sample includes a cancerous or pre-cancerous cell or tissue. For example, the cancerous tissue can be a solid tumor, a soft tissue tumor, or a metastatic lesion. Preferably, the cancerous tissue is a sarcoma, a carcinoma, or an adenocarcinoma. Preferably, the cancerous tissue is from the breast, ovarian, colon, lung, liver, kidney, or brain.

In a further aspect the invention provides assays for determining the presence or absence of a genetic alteration in an m32404 polypeptide or nucleic acid molecule in a sample, for, e.g., disease diagnosis. Preferably, the sample includes a cancer cell or tissue. For example, the cancer can be a solid tumor, a soft tissue tumor, or a metastatic lesion. Preferably, the cancer is a sarcoma, a carcinoma, or an adenocarcinoma. Preferably, the cancer is a breast, ovarian, colon, lung, liver, kidney, or brain cancer.

In a still further aspect, the invention provides methods for evaluating the efficacy of a treatment of a disorder, e.g., proliferative disorder, e.g., cancer (e.g., breast, ovarian, colon, liver or lung cancer). The method includes: treating a subject, e.g., a patient or an animal, with a protocol under evaluation (e.g., treating a subject with one or more of: chemotherapy, radiation, and/or a compound identified using the methods described herein); and evaluating the expression of an m32404 nucleic acid or polypeptide before and after treatment. A change, e.g., a decrease or increase, in the level of an m32404 nucleic acid (e.g., mRNA) or polypeptide after treatment, relative to the level of expression before treatment, is indicative of the efficacy of the treatment of the disorder.

In a preferred embodiment, the disorder is a cancer of the breast, ovary, colon, lung, or liver. The level of m32404 nucleic acid or polypeptide expression can be detected by any method described herein.

In a preferred embodiment, the evaluating step includes obtaining a sample (e.g., a tissue sample, e.g., a biopsy, or a fluid sample) from the subject, before and after treatment and comparing the level of expressing of a 53070, 15985, 26583, 21953, m32404, 14089, or 23436 nucleic acid (e.g., mRNA) or polypeptide before and after treatment.

In another aspect, the invention provides methods for evaluating the efficacy of a therapeutic or prophylactic agent (e.g., an anti-neoplastic agent). The method includes: contacting a sample with an agent (e.g., a compound identified using the methods described herein, a cytotoxic agent) and, evaluating the expression of 53070, 15985, 26583, 21953, m32404, 14089, or 23436 nucleic acid or polypeptide in the sample before and after the contacting step. A change, e.g., a decrease or increase, in the level of 53070, 15985, 26583, 21953, m32404, 14089, or 23436 nucleic acid (e.g., mRNA) or polypeptide in the sample obtained after the contacting step, relative to the level of expression in the sample before the contacting step, is indicative of the efficacy of the agent. The level of 53070, 15985, 26583, 21953, m32404, 14089, or 23436 nucleic acid or polypeptide expression can be detected by any method described herein. In a preferred embodiment, the sample includes cells obtained from a cancerous tissue. The cancerous tissue can include, for example in the case of 21953, cells of lung, breast, ovary, prostate, or colon. In a preferred embodiment, the sample includes cells obtained from a cancerous tissue where an m32404 polypeptide or nucleic acid is obtained, e.g., a cancer of the breast, ovary, colon, lung, or liver.

The invention also provides assays for determining the activity of or the presence or absence of 14089 polypeptides or nucleic acid molecules in a biological sample, including for disease diagnosis.

In further aspect, the invention provides assays for determining the presence or absence of a genetic alteration in a 53070, 15985, 26583, 21953, m32404, 14089, or 23436 polypeptide or nucleic acid molecule, including for disease diagnosis, or, in the case of 23436, a disease susceptibility (e.g., susceptibility to prostate cancer and/or brain cancer).

In a still further aspect, the 21953 invention features a method of processing a polypeptide hormone precursor, e.g., in vitro.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 53070, 15985, 26583, 21953, m32404, 14089, or 23436 molecule. In one embodiment, the capture probe is a nucleic acid, e.g., a probe complementary to a 53070, 15985, 26583, 21953, m32404, 14089, or 23436 nucleic acid sequence. In another embodiment, the capture probe is a polypeptide, e.g., an antibody specific for 53070, 15985, 26583, 21953, m32404, 14089, or 23436 polypeptides. Also featured is a method of analyzing a sample by contacting the sample to the aforementioned array and detecting binding of the sample to the array.

Other features and advantages of the invention will be apparent from the following detailed description, and from the claims.

BRIEF DESCRIPTION OF THE DRAWINGS

FIG. 2 depicts an alignment of the protein kinase domain of human 53070 with a consensus amino acid sequence derived from a hidden Markov model (HMM) from PFAM. The upper sequence is the consensus amino acid sequence (SEQ ID NO:4), while the lower amino acid sequence corresponds to amino acids 12 to 272 of SEQ ID NO:2.

FIG. 3 depicts an alignment of the serine/threonine protein kinase domain of human 53070 with a consensus amino acid sequence derived from a hidden Markov model (HMM) from SMART. The upper sequence is the consensus amino acid sequence (SEQ ID NO:5), while the lower amino acid sequence corresponds to amino acids 12 to 272 of SEQ ID NO:2.

FIG. 5 depicts an alignment of the protein kinase domain of human 15985 with a consensus amino acid sequence derived from a hidden Markov model (HMM) from PFAM. The upper sequence is the consensus amino acid sequence (SEQ ID NO:10), while the lower amino acid sequence corresponds to amino acids 394 to 651 of SEQ ID NO:8.

FIGS. 6A-6B depicts an alignment of the doublecortin repeats of human 15985 with a consensus amino acid sequence derived from a hidden Markov model (HMM) from SMART. A. The upper sequence is the consensus amino acid sequence (SEQ ID NO:11), while the lower amino acid sequence corresponds to the first doublecortin repeat of human 15985, amino acids 67 to 158 of SEQ ID NO:8. B. The upper sequence is the consensus amino acid sequence (SEQ ID NO:11), while the lower amino acid sequence corresponds to the second doublecortin repeat of human 15985, amino acids 192 to 280 of SEQ ID NO:8.

FIG. 7 depicts an alignment of the protein kinase domain of human 15985 with a consensus amino acid sequence for serine/threonine protein kinases derived from a hidden Markov model (HMM) from SMART. The upper sequence is the consensus amino acid sequence (SEQ ID NO:12), while the lower amino acid sequence corresponds to the protein kinase domain of human 15985, amino acids 394 to 651 of SEQ ID NO:8.

FIG. 8 depicts an alignment of the doublecortin repeats of human 15985 with a consensus amino acid sequence derived from a ProDom family PD024506 (ProDomain Release 2000.1). The lower sequence is the consensus amino acid sequence (SEQ ID NO:13), while the upper amino acid sequence corresponds to the doublecortin repeats of human 15985, amino acids 42 to 291 of SEQ ID NO:8.

FIGS. 10A-10B depict alignments of human 26583 amino acid sequence with a consensus amino acid sequence derived from protein phosphatase 2C (PP2C) (FIG. 10A) and protein phosphatase 2C_4 (PP2C_4) (FIG. 10B). In FIG. 10A, the upper sequence is the consensus amino acid sequence (SEQ ID NO:17) for PP2C, while the lower amino acid sequence corresponds to amino acids 173 to 461 of SEQ ID NO:15. In FIG. 10B, the upper sequence is the consensus amino acid sequence (SEQ ID NO:18) for PP2C_4, while the lower amino acid sequence corresponds to amino acids 99 to 522 of SEQ ID NO:15.

FIG. 13 depicts an alignment of the prolyl oligopeptidase domain of human 21953 with a consensus amino acid sequence derived from a hidden Markov model for prolyl oligopeptidase domains. The upper sequence is the consensus amino acid sequence (SEQ ID NO:22), while the lower amino acid sequence corresponds to amino acids 672 to 744 of SEQ ID NO:20.

FIGS. 14A-14B depict an alignment of human dipeptidyl peptidase IV (Accession Number P48147) (upper line, SEQ ID NO:23), to the 21953 amino acid sequence. The * symbol indicates identities, and the: or. symbols indicate similarities. The alignment was generated by ClustalW (Thompson et al. (1994) Nucleic Acids Res. 22:4673-4680).

FIGS. 16A-16B depict alignments of the trypsin domains of human m32404 with a consensus amino acid sequence derived from a hidden Markov model (HMM) from PFAM. The upper sequence is the consensus amino acid sequence (SEQ ID NO:27), while the lower amino acid sequence corresponds to amino acids 45 to 268 of SEQ ID NO:25 (FIG. 16A) or upper sequence is the consensus amino acid sequence (SEQ ID NO:28), while the lower amino acid sequence corresponds to to amino acids 311 to 520 of SEQ ID NO:25 (FIG. 16B).

FIGS. 17A-17B depict alignments of the trypsin domains of human m32404 with a consensus amino acid sequence for a model trypsin domain from SMART. The upper sequence is the consensus amino acid sequence (SEQ ID NO:29), while the lower amino acid sequence corresponds to amino acids 38 to 268 of SEQ ID NO:25 (FIG. 17A) or to amino acids 300 to 520 of SEQ ID NO:25 (FIG. 17B).

FIGS. 19A-19B depict alignments of the trypsin domain of human 14089 with a consensus amino acid sequence derived from a hidden Markov model (HMM) from PFAM (3A) and SMART (3B). The upper sequences are the consensus amino acid sequences (SEQ ID NO:36 and SEQ ID NO:37), while the lower amino acid sequence corresponds to amino acids 41 to 234 of SEQ ID NO:34 and amino acids 24 to 234 of SEQ ID NO:34 (FIGS. 19A and 19B, respectively).

FIGS. 20A-20B depict a BLAST alignment of the serine protease zymogen domain of human 14089 with a consensus amino acid sequence derived from ProDomain No. 46 (Release 1999.2; see also ProDom family PD00000046 (ProDomain Release 2000.1). FIG. 20A: The lower sequence is the consensus amino acid sequence (SEQ ID NO:38), while the upper amino acid sequence corresponds to the serine protease zymogen domain of human 14089, about amino acids 72 to 234 of SEQ ID NO:34. FIG. 20B: The lower sequence is the consensus amino acid sequence (SEQ ID NO:39), while the upper amino acid sequence corresponds to the serine protease zymogen domain of human 14089, about amino acids 41 to 109 of SEQ ID NO:34.

FIG. 21 depicts a hydropathy plot of human 23436. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 23436 are indicated. Polypeptides of the invention include fragments which include: all or part of a hydrophobic sequence, i.e., a sequence above the dashed line, e.g., the sequence from about amino acid 103 to 114, from about 285 to 297, and from about 413 to 420 of SEQ ID NO:41; all or part of a hydrophilic sequence, i.e., a sequence below the dashed line, e.g., the sequence of from about amino acid 76 to 87, from about 138 to 143, and from about 458 to 478 of SEQ ID NO:41; a sequence which includes a Cys, or a glycosylation site.

FIGS. 22A-22B depict alignment of the ubiquitin carboxy-terminal hydrolase (family 2) domain of human 23436 with consensus amino acid sequences derived from a hidden Markov model (H) from PFAM. The consensus sequence for the ubiquitin carboxy-terminal hydrolase (family 2) domain comprises two non-contiguous segments, UCH-1 and UCH-2. FIG. 22A depicts the alignment of human 23436 with the UCH-1 segment of the ubiquitin carboxy-terminal hydrolase (family 2) domain. The upper sequence is the consensus amino acid sequence (SEQ ID NO:43), while the lower amino acid sequence corresponds to amino acids 89 to 120 of SEQ ID NO:41. FIG. 22B depicts the alignment of human 23436 with the UCH-2 segment of the ubiquitin carboxy-terminal hydrolase (family 2) domain. The upper sequence is the consensus amino acid sequence (SEQ ID NO:44), while the lower amino acid sequence corresponds to amino acids 332 to 420 of SEQ ID NO:41.

DETAILED DESCRIPTION OF THE INVENTION

Figure 1:
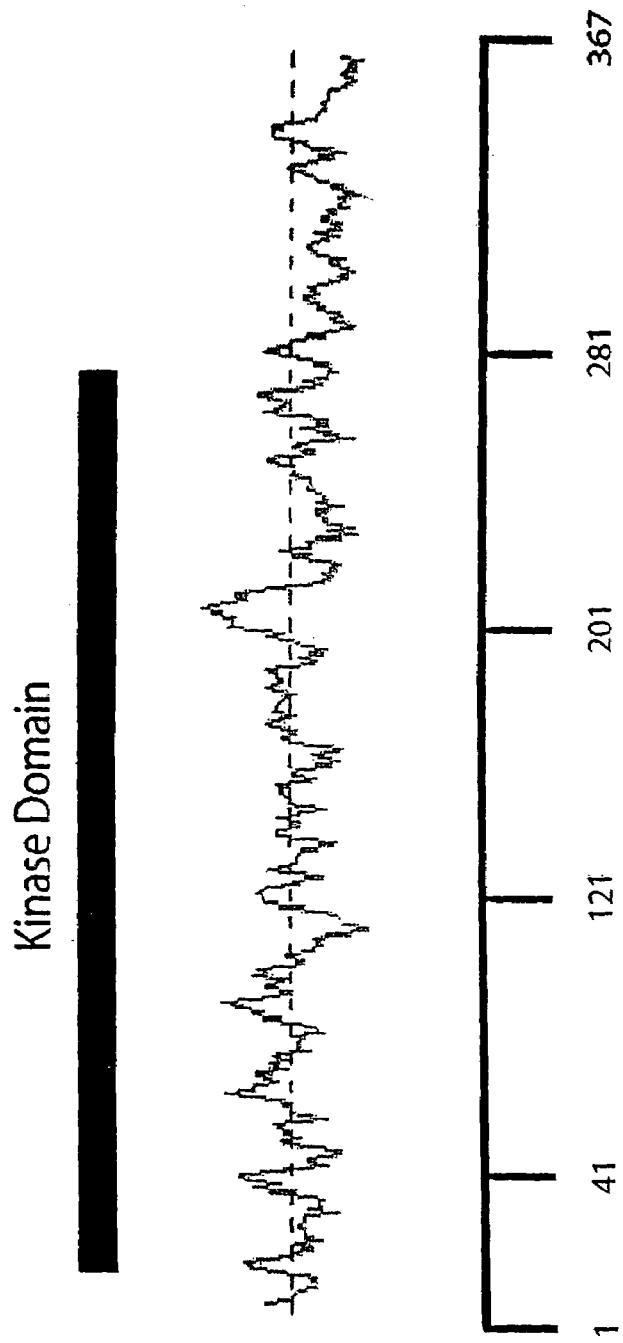
FIG. 1 depicts a hydropathy plot of human 53070. Relative hydrophobic residues are shown above the dashed horizontal line, and relative hydrophilic residues are below the dashed horizontal line. Numbers corresponding to positions in the amino acid sequence of human 53070 are indicated. Polypeptides of the invention include fragments which include: all or part of a hydrophobic sequence, i.e., a sequence above the dashed line, e.g., the sequence from about amino acid 63 to 73, from about 86 to 102, and from about 199 to 216 of SEQ ID NO:2; all or part of a hydrophilic sequence, i.e., a sequence below the dashed line, e.g., the sequence of from about amino acid 103 to 119, from about 226 to 247, and from about 301 to 329 of SEQ ID NO:2.

Phosphate tightly associated with protein has been known since the late nineteenth century. The occurrence of phosphorylated proteins implies the existence of one or more protein kinases capable of phosphorylating amino acid residues on proteins, and also of protein phosphatases capable of hydrolyzing phosphorylated amino acid residues on proteins.

Protein kinases play critical roles in the regulation of biochemical and morphological changes associated with cellular growth and division (D'Urso, G. et al. (1990) Science 250: 786-791; Birchmeier. C. et al. (1993) Bioessays 15: 185-189). They serve as growth factor receptors and signal transducers and have been implicated in cellular transformation and malignancy (Hunter, T. et al. (1992) Cell 70: 375-387; Posada, J. et al. (1992) Mol. Biol. Cell 3: 583-592; Hunter, T. et al. (1994) Cell 79: 573-582). For example, protein kinases have been shown to participate in the transmission of signals from growth-factor receptors (Sturgill, T. W. et al. (1988) Nature 344: 715-718; Gomez, N. et al. (1991) Nature 353: 170-173), control of entry of cells into mitosis (Nurse, P. (1990) Nature 344: 503-508; Maller, J. L. (1991) Curr. Opin. Cell Biol. 3: 269-275) and regulation of actin bundling (Husain-Chishti, A. et al. (1988) Nature 334: 718-721).

Protein kinases can be divided into two main groups based on either amino acid sequence similarity or specificity for either serine/threonine or tyrosine residues. A small number of dual-specificity kinases are structurally like the serine/threonine-specific group. Within the broad classification, kinases can be further sub-divided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks, S. K. et al. (1988) Science 241: 42-52).

The human 53070 sequence (see SEQ ID NO:1), which is approximately 1704 nucleotides long including untranslated regions, contains a predicted methionine-initiated coding sequence of about 1104 nucleotides, including the termination codon. The coding sequence encodes a 367 amino acid protein (see SEQ ID NO:2).

Human 53070 contains the following regions or other structural features:

a protein kinase domain (PFAM accession number PF00069) located at about amino acid residues 12 to 272 of SEQ ID NO:2;

thirteen highly conserved amino acid residues typically present in members of the protein kinase family, including a glycine residue located at about amino acid residue 19 of SEQ ID NO:2, a glycine residue located at about amino acid residue 21 of SEQ ID NO:2, a valine residue located at about amino acid residue 26 of SEQ ID NO:2, a lysine residue located at about amino acid residue 41 of SEQ ID NO:2, a glutamic acid residue located at about amino acid residue 60 of SEQ ID NO:2, an aspartic acid residue located at about amino acid residue 136 of SEQ ID NO:2, an asparagine residue located at about amino acid residue 141 of SEQ ID NO:2, an aspartic acid residue located at about amino acid residue 154 of SEQ ID NO:2, a phenylalanine residue located at about amino acid residue 155 of SEQ ID NO:2, a glutamic acid residue located at about amino acid residue 185 of SEQ ID NO:2, an aspartic acid residue located at about amino acid residue 198 of SEQ ID NO:2, a glycine residue located at about amino acid residue 203 of SEQ ID NO:2, and an arginine residue located at about amino acid residue 260 of SEQ ID NO:2;

one serine/threonine active site signature motif (PS00108), located at about amino acid residues 132 to 144;

five predicted Protein Kinase C phosphorylation sites (PS00005) located at about amino acid residues 31 to 33, 158 to 160, 166 to 168, 290 to 292, and 304 to 306 of SEQ ID NO:2;

three predicted Casein Kinase II phosphorylation sites (PS00006) located at about amino acid residues 310 to 313, 326 to 329, and 349 to 352 of SEQ ID NO:2; and one predicted N-myristylation sites (PS00008) from about amino acid residues 15 to 20 of SEQ ID NO:2.

For general information regarding PFAM identifiers, PS prefix and PF prefix domain identification numbers, refer to: Sonnhammer et al. (1997) *Protein* 28:405-420;

The 53070 protein contains a significant number of structural characteristics in common with members of the protein kinase family, and in particular the serine/threonine protein kinase subfamily. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Protein kinase family members are characterized by a common fold, which includes a small lobe associated primarily with binding ATP and a large lobe associated primarily with binding substrate peptides and catalyzing the transfer of phosphate from ATP to substrate. Bases on sequence similarity, the kinase domain has been divided into eleven distinct regions, or subdomains, and within these eleven subdomains there are a large number of amino acid residues that are considered "invariant", or highly conserved, amongst members of the protein kinase family. As used herein, an amino acid is "invariant" if it is present in the equivalent position, as determined by a sequence alignment, in 95% or more of the members of family. For example, in subdomain 1 of kinase domain family members there are two invariant glycine residues and an invariant valine residue; in subdomain 2 there is an invariant lysine residue; in subdomain 3 there is an invariant glutamic acid residue; in subdomain 6 there is an invariant aspartic acid residue and an invariant asparagine residue; in subdomain 7 there are three invariant residues adjacent to one another, consisting of the sequence aspartic acid, phenylalanine, and glycine; in subdomain 8 there is an invariant glutamic acid residue; in subdomain 9 there is an invariant aspartic acid residue and an invariant glycine; and in subdomain 11 there is an invariant arginine residue. An alignment of protein kinase family members that includes a description of the eleven subdomains and the invariant residues found within each subdomain can be found in Hanks et al. (1988), *Science* 241:42-52, the contents of which are incorporated herein by reference.

Structural analyses of the kinase domains of several different proteins have been performed, and the function of the invariant amino acid residues can be assigned accordingly. The invariant glycines of subdomain 1 are part of a loop that anchors the Θ-phosphate of ATP, while the invariant valine of subdomain 1 forms part of the adenine binding pocket. The invariant lysine of subdomain 2 also helps the kinase domain bind ATP by interacting with both the I- and Θ-phosphate groups of ATP. The invariant aspartic acid residue of subdomain 6 catalyzes the transfer of the K-phosphate group of ATP to the substrate. The invariant aspartic acid residue in subdomain 7 binds to a magnesium ion which is required for the catalytic activity of the kinase domain. And finally, the invariant aspartic acid of subdomain 9 stabilizes the position of the catalytic loop, located in subdomain 7. A more extensive description of the structures of protein kinase domains and the function of the invariant residues can be found in Taylor and Radzio-Andzelm (1994), *Structure* 2:345-55, the contents of which are incorporated herein by reference.

A 53070 polypeptide can include a "protein kinase domain" or regions homologous with a "protein kinase domain".

As used herein, the term "protein kinase domain" includes an amino acid sequence of about 225 to 350 amino acid residues in length and having a bit score for the alignment of the sequence to the protein kinase domain profile (PFAM HMM) of at least 150. Preferably, a protein kinase domain includes an amino acid sequence of about 225 to 350 amino acid residues in length and having a bit score for the alignment of the sequence to the serine/threonine kinase domain profile (SMART HMM) of at least 150. Even more preferably, a protein kinase domain includes at least about 230 to 325 amino acids, more preferably about 235 to 300 amino acid residues, or about 240 to 280 amino acids and has a bit score for the alignment of the sequence to the serine/threonine protein kinase domain (SMART HMM) of at least 200, 250, 280, or greater. The protein kinase domain (HMM) has been assigned the PFAM identifier PF00069, and the serine/threonine protein kinase domain (HMM) has been given the SMART identifier S_TKc. An alignment of the protein kinase domain (amino acids 12 to 272 of SEQ ID NO:2) of human 53070 with the PFAM consensus amino acid sequence (SEQ ID NO:4) derived from a hidden Markov model is depicted in FIG. 2, and with the SMART serine/threonine protein kinase domain consensus amino acid sequence (SEQ ID NO:5) derived from a hidden Markov model is depicted in FIG. 3.

In a preferred embodiment, a 53070 polypeptide or protein has a "protein kinase domain" or a region which includes at least about 230 to 325 more preferably about 235 to 300, or 240 to 280 amino acid residues and has at least about 85%, 90%, 95%, 99%, or 100% homology with a "protein kinase domain," e.g., the protein kinase domain of human 53070 (e.g., residues 12 to 272 of SEQ ID NO:2).

To identify the presence of a "protein kinase domain" in a 53070 protein sequence, and make the determination that a polypeptide or protein of interest has a particular profile, the amino acid sequence of the protein can be searched against the PFAM database of HMMs (e.g., the PFAM database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the PFAM database can be found in Sonhammer et al. (1997) *Proteins* 28(3): 405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235: 1501-1531; and Stultz et al. (1993) *Protein Sci.* 2:305-314, the contents of which are incorporated herein by reference. A search was performed against the HMM database resulting in the identification of a "protein kinase domain" in the amino acid sequence of human 53070 at about residues 12 to 272 of SEQ ID NO:2 (see FIG. 2).

To identify the presence of a "serine/threonine protein kinase domain" in a 53070 protein sequence, the amino acid sequence of the protein can be searched against a SMART database (Simple Modular Architecture Research Tool) of HMMs as described in Schultz et al. (1998), *Proc. Natl. Acad. Sci. USA* 95:5857 and Schultz et al. (200) *Nucl. Acids Res* 28:231. The database contains domains identified by profiling with the hidden Markov models of the HMMer2 search program (R. Durbin et al. (1998) *Biological sequence analysis: probabilistic models of proteins and nucleic acids.* Cambridge University Press). The database also is extensively annotated and monitored by experts to enhance accuracy. A search was performed against the HMM database resulting in the identification of a "serine/threonine protein kinase domain" in the amino acid sequence of human 53070 at about residues 12 to 272 of SEQ ID NO:2 (see FIG. 3).

In one embodiment, a 53070 protein includes at least one, preferably two, three, four, five, six, seven, eight, nine, ten, eleven, twelve, or even more preferably thirteen of the invariant residues present in protein kinase family members, selected form the group consisting of a glycine residue located at about amino acid residue 19 of SEQ ID NO:2, a glycine residue located at about amino acid residue 21 of SEQ ID NO:2, a valine residue located at about amino acid residue 26 of SEQ ID NO:2, a lysine residue located at about amino acid residue 41 of SEQ ID NO:2, a glutamic acid residue located at about amino acid residue 60 of SEQ ID NO:2, an aspartic acid residue located at about amino acid residue 136 of SEQ ID NO:2, an asparagine residue located at about amino acid residue 141 of SEQ ID NO:2, an aspartic acid residue located at about amino acid residue 154 of SEQ ID NO:2, a phenylalanine residue located at about amino acid residue 155 of SEQ ID NO:2, a glutamic acid residue located at about amino acid residue 185 of SEQ ID NO:2, an aspartic acid residue located at about amino acid residue 198 of SEQ ID NO:2, a glycine residue located at about amino acid residue 203 of SEQ ID NO:2, and an arginine residue located at about amino acid residue 260 of SEQ ID NO:2.

In one embodiment, a 53070 protein includes at least one serine/threonine protein kinase active-site signature motif (PS00108), located at about amino acid residues 132 to 144 of SEQ ID NO:2. As used herein, the term "serine/threonine protein kinase active-site signature motif" includes a sequence of at least 8 amino acid residues defined by the sequence: [LIVMFYC]-X-[HY]-X-D-[LIVMFY]-K-X-X-N-[LIVMFYCT]-[LIVMFYCT]-[LIVNFYCT] (SEQ ID NO:6). A serine/threonine protein kinase active-site signature motif, as defined, can be involved in the enzymatic transfer of a phosphate moiety from ATP to an appropriate acceptor molecule, e.g., a serine or threonine residue in a substrate molecule. More preferably, a serine/threonine protein kinase active-site signature motif includes 10 or, even more preferably, 13 amino acid residues. Serine/threonine protein kinase active-site signature motifs have been given the PROSITE identifier PS00108.

A 53070 family member can include at least one protein kinase domain. Furthermore, a 53070 family member can include at least one serine/threonine protein kinase active-site signature motif (PS00108); at least one, two, three, four, preferably five predicted protein kinase C phosphorylation sites (PS00005); at least one, two, preferably three predicted casein kinase II phosphorylation sites (PS00006); and at least one predicted N-myristylation sites (PS00008).

As the 53070 polypeptides of the invention may modulate 53070-mediated activities, they may be useful as of for developing novel diagnostic and therapeutic agents for 53070-mediated or related disorders, as described below.

As used herein, a "53070 activity", "biological activity of 53070" or "functional activity of 53070", refers to an activity exerted by a 53070 protein, polypeptide or nucleic acid molecule. For example, a 53070 activity can be an activity exerted by 53070 in a physiological milieu on, e.g., a 53070-responsive cell or on a 53070 substrate, e.g., a protein substrate. A 53070 activity can be determined in vivo or in vitro. In one embodiment, a 53070 activity is a direct activity, such as an association with a 53070 target molecule. A "target molecule" or "binding partner" is a molecule with which a 53070 protein binds or interacts in nature. In an exemplary embodiment, 53070 is a protein kinase, e.g., a serine/threonine protein kinase.

As used herein, the term "protein kinase" includes a protein or polypeptide that is capable of modulating its own phosphorylation state or the phosphorylation state of another protein or polypeptide. Protein kinases can have a specificity for (i.e., a specificity to phosphorylate) serine/threonine residues, tyrosine residues, or both serine/threonine and tyrosine residues. Specificity of a protein kinase for phosphorylation of either tyrosine or serine/threonine can be predicted by the sequence of two of the subdomains (VIb and VIII) in which different residues are conserved in each class (as described in, for example, Hanks et al. (1988) Science 241:42-52) the contents of which are incorporated herein by reference). Preferably, the protein kinase of the invention is a serine/threonine protein kinase.

A 53070 activity can also be an indirect activity, e.g., a cellular signaling activity mediated by interaction of the 53070 protein with a 53070 substrate. Protein kinases play a role in signaling pathways associated with cellular growth. For example, protein kinases are involved in the regulation of signal transmission from cellular receptors, e.g., growth-factor receptors; entry of cells into mitosis; and the regulation of cytoskeleton function, e.g., actin bundling. The features of the 53070 molecules of the present invention can provide similar biological activities as protein kinase family members. For example, the 53070 proteins of the present invention can have one or more of the following activities: (1) the ability to bind to at least one nucleoside tri-phosphate, e.g., ATP; (2) the ability to auto-phosphorylate; (3) the ability to phosphorylate other proteins; (4) the ability to phosphorylate serine or threonine residues on other proteins; (5) the ability to to alter the activity or sub-cellular localization of a substrate molecule via phosphorylation; (6) the ability to regulate the transmission of signals from cellular receptors, e.g., growth factor receptors or adhesion receptors; (7) the ability to modulate the entry of a cell into mitosis; (8) the ability to regulate the process of cell death; (9) the ability to regulate cell differentiation; (10) the ability to regulate cell growth; (11) the ability to regulate actin or tubulin dynamics; and/or (12) the ability to regulate cell shape and motility.

Inhibition or over stimulation of the activity of protein kinases involved in signaling pathways associated with cellular growth or differentiation can lead to perturbed cellular growth or function, which can in turn lead to cellular growth and/or differentiation related disorders. As used herein, a "cellular growth and/or differentiation disorder" includes a disorder, disease, or condition characterized by a deregulation, e.g., an upregulation or a downregulation, of cellular growth and/or abnormal cellular behavior. Cellular growth deregulation may be due to a deregulation of cellular proliferation, cell cycle progression, cellular differentiation and/or cellular hypertrophy.

Thus, the 53070 molecules can act as novel diagnostic targets and therapeutic agents for controlling one or more of cellular proliferative and/or differentiative disorders, disorders associated with bone metabolism, immune disorders (e.g., inflammatory disorders), cardiovascular disorders, liver disorders, viral diseases, pain or metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The 53070 nucleic acid and protein of the invention can be used to treat and/or diagnose a variety of immune disorders. Examples of hematopoieitic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

The 53070 molecules of the invention may be used to treat, prevent, and/or diagnose reproductive disorders, e.g., prostatic or testicular disorders. As used herein, "a prostate disorder" refers to an abnormal condition occurring in the male pelvic region characterized by, e.g., male sexual dysfunction and/or urinary symptoms. This disorder may be manifested in the form of genitourinary inflammation (e.g., inflammation of smooth muscle cells) as in several common diseases of the prostate including prostatitis, benign prostatic hyperplasia and cancer, e.g., adenocarcinoma or carcinoma, of the prostate.

15985

Protein kinases are a large, diverse protein family. Prominent among protein kinases in eukaryotes, are serine/threonine protein kinases. These enzymes transfer a phosphate from ATP to the hydroxyl of a serine or threonine side chain, where the phosphate can remain stably attached. Serine/threonine protein kinases, also called serine protein kinases, are frequently utilized in signalling cascades as the activity of these enzymes can be finely regulated by stimuli. A common stimulus is phosphorylation of the serine protein kinase itself. Hence, signalling pathways, such as the MAP protein kinase cascade, can contain multiple proteins kinases which sequentially activate. This design has the advantages of regulation, sensitivity, and amplification. Kinase cascades can be activated locally, for example, near a signalling receptor on a discrete region of the plasma membrane. An ultimate target of protein kinases is the cytoskeleton and its associated proteins, as it is often the object of signalling cascades to alter cell morphology, or cell movement.

One important cytokeletal protein is doublecortin. Doublecortin coassembles with microtubules in neurons of the brain. Doublecortin was observed in vitro to stimulate the polymerization of microtubules (Gleeson et al. (1999) *Neuron* 23:257-271). Moreover, doublecortin colocalizes with microtubules in neurons that are migrating in the central and peripheral nervous system during embryonic and postnatal development (Gleeson, supra.). Remarkably, defects in gene for doublecortin are the cause of X-linked lissencephaly, also called Double Cortex Syndrome (Gleeson et al. (1998) *Cell* 92:63-72). Patients with this disorder have severe mental retardation, and intractable epilepsy. As result of the failure of almost all cortical neurons to migrate completely to their destination, the cerebral cortex is malformed, literally "smooth brain" as a result. The doublecortin protein appears to be critical to the neuronal migration process.

A feature of the doublecortin protein is two copies of a short repeats of approximately 80 amino acids. Mutations in affected individuals cluster in these repeats (Gleeson et al. (1999) *Ann. Neurol.* 45:146-153; Sapir et al. (2000) *Hum. Mol. Genet.* 9:703-712). These repeats in isolation can modulate the properties of microtubules (Sapir, supra.). Interestingly, another human protein, KIAA0369, has two copies of these noted doublecortin repeats. KIAA0369 also contains a CAM kinase-like serine protein kinase domain. KIAA0369 is highly expressed in the fetal and adult brain (Sossey-Alaoui and Srivastava (1999) *Genomics* 56:121-126) and may function in a calcium signaling pathway controlling neuronal migration in the brain (see GenBank entry GI:6225242).

The human 15985 sequence (see SEQ ID NO:7), which is approximately 3552 nucleotides long including untranslated regions, contains a predicted methionine-initiated coding sequence of about 2301 nucleotides, including the termination codon. The coding sequence encodes a 766 amino acid protein (see SEQ ID NO:8).

Human 15985 contains the following regions or other structural features.

a protein kinase domain (PFAM Accession Number PF00069) located at about amino acid residues 394 to 651 of SEQ ID NO:8;

a serine/threonine kinase active-site signature (Prosite PS00108) located at about amino acid residues 511 to 523 of SEQ ID NO:8;

two doublecortin repeats located at about amino acid residues 67 to 158, and 192 to 280 of SEQ ID NO:8;

four predicted N-glycosylation sites (PS00001) at about amino acids 164 to 167, 363 to 366, 619 to 622, and 681 to 684 of SEQ ID NO:8;

nineteen predicted Protein Kinase C phosphorylation sites (PS00005) at about amino acids 3 to 5, 23 to 25, 67 to 69, 93 to 95, 129 to 131, 173 to 175, 182 to 184, 312 to 314, 331 to 333, 334 to 336, 357 to 349, 416 to 418, 484 to 486, 488 to 490, 532 to 534, 623 to 625, 666 to 668, 710 to 712, and 760 to 762 of SEQ ID NO:8;

eleven predicted Casein Kinase II phosphorylation sites (PS00006) located at about amino acids 109 to 122, 133 to 136, 389 to 392,416 to 419, 461 to 464, 488 to 491, 542 to 545, 623 to 626, 693 to 696, 724 to 727, and 739 to 742 of SEQ ID NO:8;

one predicted cAMP/cGMP-dependent protein kinase phosphorylation sites (PS00004) located at about amino acids 130 to 133 of SEQ ID NO:8; and ten predicted N-myristylation sites (PS00008) from about amino acids 22 to 27, 32 to 37, 86 to 91, 172 to 177, 323 to 328, 346 to 351, 378 to 383, 643 to 648, 699 to 704, and 754 to 759 of SEQ ID NO:8.

For general information regarding PFAM identifiers, PS prefix and PF prefix domain identification numbers, refer to Sonnhammer et al. (1997) *Protein* 28:405-420.

The 15985 protein contains a significant number of structural characteristics in common with members of the protein kinase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Protein kinases have a catalytic protein kinase domain, which contains both α-helical and β-stranded structures. In general, the domain has a smaller amino-terminal lobe whose primarily function is to bind ATP, whereas the larger carboxy-terminal lobe functions to recognize and bind peptide substrates, and contributes catalytic side chains for phosphoryl transfer. One hallmark of serine protein kinases is the active site signature, Prosite PS00108, [LIVMFYC]-X-[HY]-D-[LIVMFY]-K-X-X-N-[LIVMFYCT](3) wherein X represents any amino acid and the number in parentheses indicates the number of consecutive positions with a given profile of amino acids.

Protein kinases play a role in signaling pathways associated with cellular growth. For example, protein kinases are involved in the regulation of signal transmission from cellular receptors, e.g., growth-factor receptors; entry of cells into mitosis; and the regulation of cytoskeleton function, e.g., actin bundling. Thus, the molecules of the present invention may be involved in: 1) the regulation of transmission of signals from cellular receptors, e.g., cell growth factor receptors; 2) the modulation of the entry of cells, e.g., precursor cells, into mitosis; 3) the modulation of cellular differentiation; 4) the modulation of cell death; and 5) the regulation of cytoskeleton function, e.g., actin bundling.

Inhibition or over stimulation of the activity of protein kinases involved in signaling pathways associated with cellular growth can lead to perturbed cellular growth, which can in turn lead to cellular growth related disorders. As used herein, a "cellular growth related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma.

A 15985 polypeptide can include a "protein kinase domain" or regions homologous with a "protein kinase domain".

As used herein, the term "protein kinase domain" includes an amino acid sequence of about 200 to 500 amino acid residues in length and having a bit score for the alignment of the sequence to the protein kinase domain profile (Pfam HMM) of at least 300. Preferably, a protein kinase domain includes at least about 200 to 500 amino acids, more preferably about 210 to 400 amino acid residues, or about 230 to 280 amino acids and has a bit score for the alignment of the sequence to the protein kinase domain (HMM) of at least 345 or greater. The protein kinase domain (HMM) has been assigned the PFAM Accession Number PF00069. An alignment of the protein kinase domain (amino acids 394 to 651 of SEQ ID NO:8) of human 15985 with a consensus amino acid sequence (SEQ ID NO:10) derived from a hidden Markov model is depicted in FIG. 5.

In a preferred embodiment 15985 polypeptide or protein has a "protein kinase domain" or a region which includes at least about 200 to 500 more preferably about 200 to 400 or 230 to 280 amino acid residues and has at least about 50%, 60%, 70% 80% 90% 95%, 99%, or 100% homology with a "protein kinase domain," e.g., the protein kinase domain of human 15985 (e.g., residues 394 to 651 of SEQ ID NO:8). In addition, a 15985 polypeptide preferably includes a serine protein kinase active site signature, e.g., the amino acid sequence from about residues 511 to 523 of SEQ ID NO:8, including a highly conserved aspartic acid, lysine, and asparagine at amino acids 515, 517, and 520 of SEQ ID NO:8, respectively.

To identify the presence of a "protein kinase" domain in a 15985 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of a "protein kinase" domain in the amino acid sequence of human 15985 at about residues 394 to 651 of SEQ ID NO:8 (see FIG. 5).

A doublecortin repeats family of proteins is characterized by a common fold, as typified by the doublecortin and the KIAA0367 proteins. These repeats can modulate the activity and properties of microtubules, especially microtubules in neuronal cells. A 15985 polypeptide can include at least one, preferably two "doublecortin repeats" or regions homologous with a "doublecortin repeat".

As used herein, the term "doublecortin repeat" includes an amino acid sequence of about 50 to 120 amino acid residues in length and having a bit score for the alignment of the sequence to the doublecortin repeat (HMM) of at least 250. Preferably, a doublecortin repeat includes at least about 50 to 120 amino acids, more preferably about 60 to 100 amino acid residues, or about 75 to 90 amino acids and has a bit score for the alignment of the sequence to the doublecortin repeat (HMM) of at least 280 or greater. An alignment of the doublecortin repeats (amino acids 67 to 158 and 192 to 280 of SEQ ID NO:8) of human 15985 with a consensus amino acid sequence derived from a hidden Markov model is depicted in FIGS. 6A-6B.

In a preferred embodiment 15985 polypeptide or protein has a "doublecortin repeat" or a region which includes at least about 50 to 120 more preferably about 60 to 100 or 75 to 90 amino acid residues and has at least about 70% 80% 90% 95%, 99%, or 100% homology with a "doublecortin repeat," e.g., the doublecortin repeats of human 15985 (e.g., residues 67 to 158 and 192 to 280 of SEQ ID NO:8).

To identify the presence of a "doublecortin repeat" in a 15985 protein sequence, and make the determination that a polypeptide or protein of interest has a particular profile, the amino acid sequence of the protein can be searched against a database of HMMs (e.g., the SMART database, Washington University School of Medicine) as described above. A search was performed against the SMART database resulting in the identification of "doublecortin repeats" in the amino acid sequence of human 15985 at about residues 67 to 158 and 192 to 280 of SEQ ID NO:8 (see FIG. 4).

A 15985 family member can include at least one protein kinase domain; and at least one, preferably two "doublecortin repeats." Furthermore, a 15985 family member can include at least one, two, three, four, five, six, seven, eight, nine, ten, eleven, twelve, thirteen, fourteen, fifteen, sixteen, seventeen, eighteen, and preferably nineteen predicted protein kinase C phosphorylation sites (PS00005); at least one, two, three, four, five, six, seven, eight, nine, ten, and preferably eleven predicted casein kinase II phosphorylation sites (PS00006); at least one predicted cAMP/cGMP-dependent protein kinase phosphorylation site (PS00004); at least one, two, three, four, five, six, seven, eight, nine, preferably ten predicted N-myristylation sites (PS00008), at least one, two, three, preferably four predicted N-glycosylation sites (PS000001); at least one protein kinase ATP-binding region signature (PS00107),: and at least one serine/threonine protein kinase active-site signature (PS00108).

As the 15985 polypeptides of the invention may modulate 15985-mediated activities, they may be useful as of for developing novel diagnostic and therapeutic agents for 15985-mediated or related disorders, as described below.

As used herein, a "15985 activity", "biological activity of 15985" or "functional activity of 15985", refers to an activity exerted by a 15985 protein, polypeptide or nucleic acid molecule. For example, a 15985 activity can be an activity exerted by 15985 in a physiological milieu on, e.g., a 15985-responsive cell or on a 15985 substrate, e.g., a protein substrate. A 15985 activity can be determined in vivo or in vitro. In one embodiment, a 15985 activity is a direct activity, such as an association with a 15985 target molecule. A "target molecule" or "binding partner" is a molecule with which a 15985 protein binds or interacts in nature. In an exemplary embodiment, 15985 is a microtubule binding protein A 15985 activity can also be an indirect activity, e.g., a cellular signaling activity mediated by interaction of the 15985 protein with a 15985 receptor. The features of the 15985 molecules of the present invention can provide similar biological activities as protein kinase family members. For example, the 15985 proteins of the present invention can have one or more of the following activities: (1) the ability to bind a cytoskeletal protein, e.g., a microtubule; (2) the ability to stimulate microtubule polymerization; (3) the ability to phosphorylate a protein substrates, e.g., a protein having a serine and/or threonine residue; (4) the ability to bind to a nucleotide, e.g., an ATP molecule; (5) the ability to modulate cellular migration, e.g., neuronal cell migration; (6) the ability to modulate neural development and/or maintenance; (7) the ability to regulate the transmission of signals from cellular receptors, e.g., cell growth factor receptors; 8) the ability to modulate the entry of cells, e.g., precursor cells, into mitosis; 9) the ability to modulate cellular differentiation; and/or 10) the ability to modulate cell death.

Based on the above-described sequence similarities, the 15985 molecules of the present invention are predicted regulate cell migration, e.g., neuronal cell migration, inflammation, and cellular growth and differentiation, e.g., cancer. Thus, the 15985 molecules can act as novel diagnostic targets and therapeutic agents for controlling such disorders that can include neurological and hematopoietic disorders, as well as cancer.

15985 mRNA is expressed in tumors from the ovary and lung (Example 7), as well as breast cancer cell lines (e.g., SkBr3 cells). Lower levels of expression are detected in cardiovascular tissues and the brain (Example 7). Accordingly, molecules of the invention may serve as tools to diagnose and/or treat disorders involving aberrant activities of those cells in which they are expressed disorders of the lung, breast or ovaries, e.g., cancers, e.g., ovarian, breast, or lung cancers, as well as cardiovascular or neurological disorders.

The 15985 molecules can act as novel diagnostic targets and therapeutic agents for controlling one or more of cellular proliferative and/or differentiative disorders, disorders associated with bone metabolism, immune disorders (e.g., inflammatory disorders), cardiovascular disorders, liver disorders, viral diseases, pain or metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Additional examples of proliferative disorders include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of neurological disorders include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, *Varicalla-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

The 15985 nucleic acid and protein of the invention can be used to treat and/or diagnose a variety of immune disorders. Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

15985 is expressed at relatively high levels in normal vein tissue. Thus, aberrant expression and/or activity of 15985 molecules may mediate disorders involving the blood vessels. Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

As used herein, disorders involving the heart, or "cardiovascular disease" or a "cardiovascular disorder" includes a disease or disorder which affects the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. A cardiovascular disorder includes, but is not limited to disorders such as arteriosclerosis, atherosclerosis, cardiac hypertrophy, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, including but not limited to, valvular degeneration caused by calcification, rheumatic heart disease, endocarditis, or complications of artificial valves; atrial fibrillation, long-QT syndrome, congestive heart failure, sinus node dysfunction, angina, heart failure, hypertension, atrial fibrillation, atrial flutter, pericardial disease, including but not limited to, pericardial effusion and pericarditis; cardiomyopathies, e.g., dilated cardiomyopathy or idiopathic cardiomyopathy, myocardial infarction, coronary artery disease, coronary artery spasm, ischemic disease, arrhythmia, sudden cardiac death, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). A cardiovasular disease or disorder also can include an endothelial cell disorder.

15985 mRNA is expressed at relatively high levels in ovary tumor and normal ovary tissue. Thus, aberrant expression and/or activity of 15985 molecules may mediate disorders involving ovary tissue, e.g. disorders involving the ovary. Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

As 15985 mRNA is expressed in lung tissue, and therefore aberrant expression and/or activity of 15985 molecules may mediate disorders involving this tissue, e.g. disorders involving the lung. Examples of disorders of the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

26583

Protein phosphatases are enzymes that reverse the actions of protein kinases by cleaving phosphate from serine, threonine, and/or tyrosine residues in proteins. The protein phosphatases are divided into three groups according to catalytic function: (1) protein phosphatases that dephosphorylate serine and threonine residues; (2) protein phosphatases which dephosphorylate tyrosine residues; and (3) protein phosphatases which dephosphorylate serine, threonine and tyrosine residues.

Serine/threonine protein phosphatases are associated with the regulation of cholesterol biosynthesis, glycogen metabolism, muscle contractility, calcium ion channels, protein synthesis, regulation of the G2 to M transition of the cell cycle, regulation of glycolysis (6-phosphofructo-2-kinase and pyruvate kinase), glycogenolysis (phosphorylase kinase subunit), gluconeogenesis (fructose-2,6-bisphosphatase and pyruvate kinase), amino-acid degradation (phenylalanine hydroxylase), lipid metabolism (acetyl-CoA carboxylase), catecholamine synthesis (tyrosine hydroxylase) and protein synthesis (elongation factor 2).

Protein tyrosine phosphatases (PTPs) are a family of intracellular and integral membrane phosphatases that dephosphorylate tyrosine residues in proteins. PTPs have been identified in mammals, Drosophila and Schiz. pombe and are implicated in the control of normal and neoplastic growth and proliferation.

Generally, the balance of protein phosphorylation in a cell depends on the level of protein kinase and protein phosphatase activity. Protein phosphorylation is important for the regulation of numerous metabolic processes such as cholesterol biosynthesis and has been associated with cell cycle progression and transformation of cells. Thus, protein phosphatases can serve as positive or negative regulators of metabolic function as well as cell growth and differentiation. Given the important biological roles and properties of phosphatases, there exists a need for the identification of novel genes encoding such proteins as well as for the discovery of modulators of such molecules for use in regulating a variety of normal and/or pathological cellular processes.

The human 26583 sequence (SEQ ID NO:14), which is approximately 2838 nucleotides long including untranslated regions, contains a predicted methionine-initiated coding sequence of about 1613 nucleotides (nucleotides 462 to 2075 of SEQ ID NO:14; SEQ ID NO:16). The coding sequence encodes a 537 amino acid protein (SEQ ID NO:15).

Human 26583 contains the following regions or other structural features: a predicted serine/threonine catalytic domain at residues 172-461; a predicted serine/threonine catalytic domain at residues 99-523; one predicted N-glycosylation site (PS00001) from about amino acids 105 to 108; five predicted Protein Kinase C sites (PS00005) from about amino acids 95 to 97, 156 to 158, 182 to 184, 211 to 213 and 463 to 465 of SEQ ID NO:15; five predicted Casein Kinase II phosphorylation sites (PS00006) from about amino acids 172 to 175, 228 to 231, 371 to 374, 471 to 474 and 505 to 508 of SEQ ID NO:15; seven predicted N-myristoylation sites (PS00008) from about amino acids 137 to 142, 148 to 153, 271 to 276, 303 to 308, 419 to 424, 456 to 461 and 531 to 536 of SEQ ID NO:15; one amidation site (PS00009) at about amino acids 67 to 70 of SEQ ID NO:15; and one protein phosphatase 2C signature (PS01037) from about amino acids 139 to 147 of SEQ ID NO:15.

For general information regarding PFAM identifiers, PS prefix and PF prefix domain identification numbers, refer to Sonnhammer et al. (1997) Protein 28:405-420.

The 26583 protein contains a significant number of structural characteristics in common with members of the serine/threonine phosphatase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

A 26583 polypeptide of the invention can include a "serine/threonine phosphatase catalytic domain" or regions homologous with a "serine/threonine phosphatase catalytic domain." As used herein, the term "serine/threonine phosphatase catalytic domain" refers to an amino acid sequence having about 200 to 450, preferably about 150 to 350, more preferably about 100 to 300, and even more preferably about 288 amino acid residues.

Based on structural similarities, members of the serine/threonine phosphatase family have been classified into various subfamilies, including four major types of protein phosphatase catalytic subunits that dephosphorylate serine and threonine residues. These enzymes are termed protein phosphatases 1, 2A, 2B, and 2C (PP1, PP2A, PP2B and PP2C, the human genome symbols being PPP1, PPP2, PPP3 and PPM1 respectively). Protein phosphatase PP1 appears to have pleiotropic actions in the regulation of glycogen metabolism, muscle contractility, calcium ion channels, protein synthesis and cell division. Protein phosphatase 2A (PP2A) dephosphorylates enzymes involved in the regulation of glycolysis (6-phosphofructo-2-kinase and pyruvate kinase), glycogenolysis (phosphorylase kinase subunit), gluconeogenesis (fructose-2,6-bisphosphatase and pyruvate kinase), amino-acid degradation (phenylalanine hydroxylase), lipid metabolism (acetyl-CoA carboxylase), catecholamine synthesis (tyrosine hydroxylase) and protein synthesis (elongation factor 2). The catalytic subunit has also been identified as a negative regulator of the dephosphorylation and activation of p34cdc2 protein kinase in *Xenopus* and *S. pombe* and therefore as a suppressor of the G2 to M transition of the cell cycle. Protein phosphatase 2B (PP2B) is particularly abundant in brain where it comprises up to 1% of total protein. The physiological roles of PP2B may be to allow extracellular signals that act via $Ca^{2+}$ to attenuate those that act through cyclic AMP. PP2B may be involved in the regulation of ion channels in both neuronal and non-neuronal cells. Protein phosphatase 4 (PP4) is required in late G1 of the cell cycle for progression into S phase in yeast.

Protein phosphatase 2C (PP2C) may play a role in the regulation of cholesterol biosynthesis, as PP2C possesses high activity against hydroxymethylglutaryl-CoA reductase kinase, which inactivates HMG-CoA reductase, the rate-limiting enzyme of this pathway. Protein phosphatase 2C (PP2C) is a monomeric enzyme of about 42 Kd that shows broad substrate specificity and is dependent on divalent cations (mainly manganese and magnesium) for its activity. At least three isozymes are known in mammals: PP2C-alpha, -beta and -gamma. In yeast, there are at least four PP2C homologs: phosphatase PTC1 that has weak tyrosine phosphatase activity in addition to its activity on serines, phosphatases PTC2 and PTC3. Isozymes of PP2C are also known from *Arabidopsis thaliana* (ABI1, PPH1), *Caenorhabditis elegans* (FEM-2, F42G9.1, T23F11.1), *Leishmania chagasi* and *Paramecium tetraurelia*. In *Arabidopsis thaliana*, the kinase associated protein phosphatase (KAPP) is an enzyme that dephosphorylates the Ser/Thr receptor-like kinase RLK5 and which contains a C-terminal PP2C domain. In addition, PP2C appears to be significantly similar to the catalytic subunit of pyruvate dehydrogenase phosphatase (EC 3.1.3.43) (PDPC) that catalyzes dephosphorylation and concomitant reactivation of the alpha subunit of the E1 component of the pyruvate dehydrogenase complex. PDPC is a mitochondrial enzyme and, like PP2C, is magnesium-dependent.

In addition, protein serine/threonine phosphatases may play a role in signaling pathways associated with cellular growth. For example, protein serine/threonine phosphatases can be involved in the regulation of signal transmission from cellular receptors, e.g., growth-factor receptors; entry of cells into mitosis. Thus, the 26583 molecules of the present invention may be involved in: (1) catalyzing the removal of a phosphate group attached to a tyrosine residue in a protein; (2) the regulation of transmission of signals from cellular receptors; (3) modulation of cellular growth signaling mechanisms; (4) modulation of cell proliferation or growth; (5) modulation of cell differentiation; (6) modulation of cell survival; (7) modulation of transformation; (8) modulation of apoptosis of a cell (e.g., a cancer cell); (9) modulation of cholesterol biosynthesis; (10) modulation of glycogen metabolism; (11) modulation of muscle contractility; (12) modulation of calcium ion channel activity; (13) modulation of glycolysis, glycogenolysis, or gluconeogenesis; (14) modulation of amino-acid degradation; (15) modulation of lipid metabolism; and/or (16) modulation of catecholamine synthesis.

In a preferred embodiment, a 26583 polypeptide or protein has a "serine/threonine phosphatase catalytic domain" refers to an amino acid sequence having 200 to 450, preferably about 150 to 350, more preferably about 100 to 300, and even more preferably about 288 amino acid residues and has at least about 70% 80% 90% 95%, 99%, or 100% homology with a "serine/threonine phosphatase catalytic domain," e.g., the serine/threonine phosphatase catalytic domain of human 26583.

Thus, a 26583 molecule of the present invention can be identified based on the presence of a "serine/threonine phosphatase catalytic domain" in the protein or corresponding nucleic acid molecule. Preferably, a serine/threonine phosphatase catalytic domain includes a protein domain having an amino acid sequence of about 200 to 500 amino acid residues and having a bit score for the alignment of the sequence to the fibroblast growth factor domain (HMM) of at least 150. Preferably, a "serine/threonine phosphatase catalytic domain" refers to an amino acid sequence having about 200 to 500, preferably about 250 to 400, more preferably about 250 to 350 amino acid residues and has a bit score for the alignment of the sequence to a serine/threonine phosphatase catalytic domain (HMM) of at least 100, 200, 250 or greater. An alignment of the serine/threonine phosphatase of human 26583 (SEQ ID NO:15) with a consensus amino acid sequence derived from a hidden Markov model is depicted in FIGS. 10A-10B.

To identify the presence of a "serine/threonine phosphatase catalytic domain" in a 26583 protein sequence and to make the determination that a polypeptide or protein of interest has a particular profile, the amino acid sequence of the protein can be searched against a database of HMMs using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of an amino acid sequence of human 26583 that is homologous to a sequence contained in PP2C at about residues 172 to 461 of SEQ ID NO:15 (see FIG. 10A). The search further identified an amino acid sequence of human 26583 that is homologous to a sequence contained in PP2C_4 at about residues 99 to 523 of SEQ ID NO:15 (see FIG. 10B).

As the 26583 polypeptides of the invention may modulate 26583-mediated activities, they may be useful as of for developing novel diagnostic and therapeutic agents for 26583-mediated or related disorders, as described below. As used herein, "26583 activity," "biological activity of 26583" or "functional activity of 26583," refers to an activity exerted by a 26583 protein, polypeptide or nucleic acid molecule on e.g., a 26583-responsive cell or on a 26583 substrate, e.g., a protein substrate, as determined in vivo or in vitro. In one embodiment, a 26583 activity is a direct activity, such as an association with a 26583 target molecule. A "target molecule" or "binding partner" is a molecule with which a 26583 protein binds or interacts with in nature, e.g., a protein containing one or more serine/threonine residues. A 26583 activity also can be an indirect activity, e.g., a cellular signaling activity mediated by interaction of the 26583 protein with a 26583 receptor (e.g., a receptor that is a protein serine/threonine kinase). For example, a 26583 protein of the present invention can have one or more of the following activities: (1) removal of phosphate moieties from phospho-serine/threonine residues in proteins; (2) the regulation of transmission of signals from cellular receptors; (3) modulation of cellular growth signaling mechanisms; (4) modulation of cell proliferation; (5) modulation of cell differentiation; (6) modulation of transformation; (7) modulation of apoptosis (e.g., a cancer cell); (8) modulation of cholesterol biosynthesis; (9) modulation of glycogen metabolism; (10) modulation of muscle contractility; (11) modulation of calcium ion channel activity; (12) modulation of glycolysis, glycogenolysis and gluconeogenesis; (13) modulation of amino-acid degradation; (14) modulation of lipid metabolism; and/or (15) modulation of catecholamine synthesis.

As used herein, the term "cellular growth signaling mechanism" includes the ability to interact with, e.g., bind to, and remove a phospho-serine/threonine residue present in a protein, e.g., a serine or threonine phosphorylated protein and modulate, e.g., inhibit, one or more of: (1) induction of receptor dimerization, (2) serine/threonine kinase activation, (3) phosphorylation of signaling molecules, and/or (4) induction gene expression; thereby regulating one or more of: (5) cell proliferation, (6) cell differentiation, (7) cell survival, (8) oncogenic transformation, (9) migration, and/or (10) apoptosis, of a cell (e.g., a cancer cell), (11) modulation of cholesterol biosynthesis, (12) modulation of glycogen metabolism, (13) modulation of muscle contractility, (14) modulation of calcium ion channel activity, (15) modulation of glycolysis, glycogenolysis and gluconeogenesis, (16) modulation of amino-acid degradation, (17) modulation of lipid metabolism and/or (18) modulation of catecholamine synthesis.

Based on the above-described sequence similarities, a 26583 molecule of the present invention is predicted to have similar biological activities as serine/threonine phosphatase family members. Thus, the 26583 molecules can act as novel diagnostic targets and therapeutic agents for controlling cellular proliferative disorders or metabolic disorders such as those associated with cholesterol biosynthesis or mitochondrial dysfunction.

As used herein, a "cholesterol biosynthesis-associated disorder" includes any disorder wherein the regulation of cholesterol biosynthesis is affected by the presence or absence of a 25583 activity of the invention. For example, the 26583 protein of the present invention contains sequence homology to PP2C (see FIG. 10A). PP2C possesses high activity against hydroxymethylglutaryl-CoA reductase kinase, which inactivates HMG-CoA reductase, the rate-limiting enzyme of the cholesterol biosynthetic pathway. Thus, the present invention provides a means for diagnosing and/or treating a cholesterol biosynthesis-associated disorder such as, for example, hypo- or hypercholesterolemia.

As previously noted, the 26583 protein of the present invention contains sequence homology to PP2C (see FIG. 10A). PP2C appears to be significantly similar to the catalytic subunit of pyruvate dehydrogenase phosphatase (EC 3.1.3.43) (PDPC) that catalyzes dephosphorylation and concomitant reactivation of the alpha subunit of the E1 component of the pyruvate dehydrogenase complex. PDPC is a mitochondrial enzyme and, like PP2C, is magnesium-dependent. Thus, the present invention is additionally useful as a means for diagnosing and/or treating disorders associated with mitochondria. As used herein, a "mitochondrial-associated disorder" includes any disorder related to the function or dysfunction of mitochondria. For example, diabetes mellitus has been associated with deficient mitochondrial oxidative phosphorylation. Also, mitochondrial dysfunction has been implicated in neuro-degenerative disorders, such as Parkinson's, Huntington's and Alzheimer's diseases.

In addition, the 26583 molecules of the invention are useful for diagnosing and/or treating cellular proliferative disorders. As used herein, a "cellular proliferative disorder" includes a disorder, disease, or condition characterized by a deregulated, e.g., up-regulated or down-regulated, growth response. As used herein, a "cellular differentiative disorder" includes a disorder, disease, or condition characterized by aberrant cellular differentiation. As used herein, metastatic refers to the ability of a tumor cell to form implants at a site distant from the original tumor. Thus, the 26583 molecules can act as novel diagnostic targets and therapeutic agents for controlling cellular proliferative and/or differentiative disorders.

Based on the above-described sequence similarities, the 26583 molecules of the present invention are predicted to have similar biological activities as serine/threonine phosphatase family members. Thus, the 26583 molecules can act as novel diagnostic targets and therapeutic agents for controlling one or more of cellular proliferative and/or differentiative disorders, disorders associated with bone metabolism, immune or hematopoietic disorders, cardiovascular disorders, liver disorders, viral diseases, pain or metabolic disorders such as hypo- or hypercholesterolemia, or disorders associated with mitochondrial dysfunction.

Figure 11:
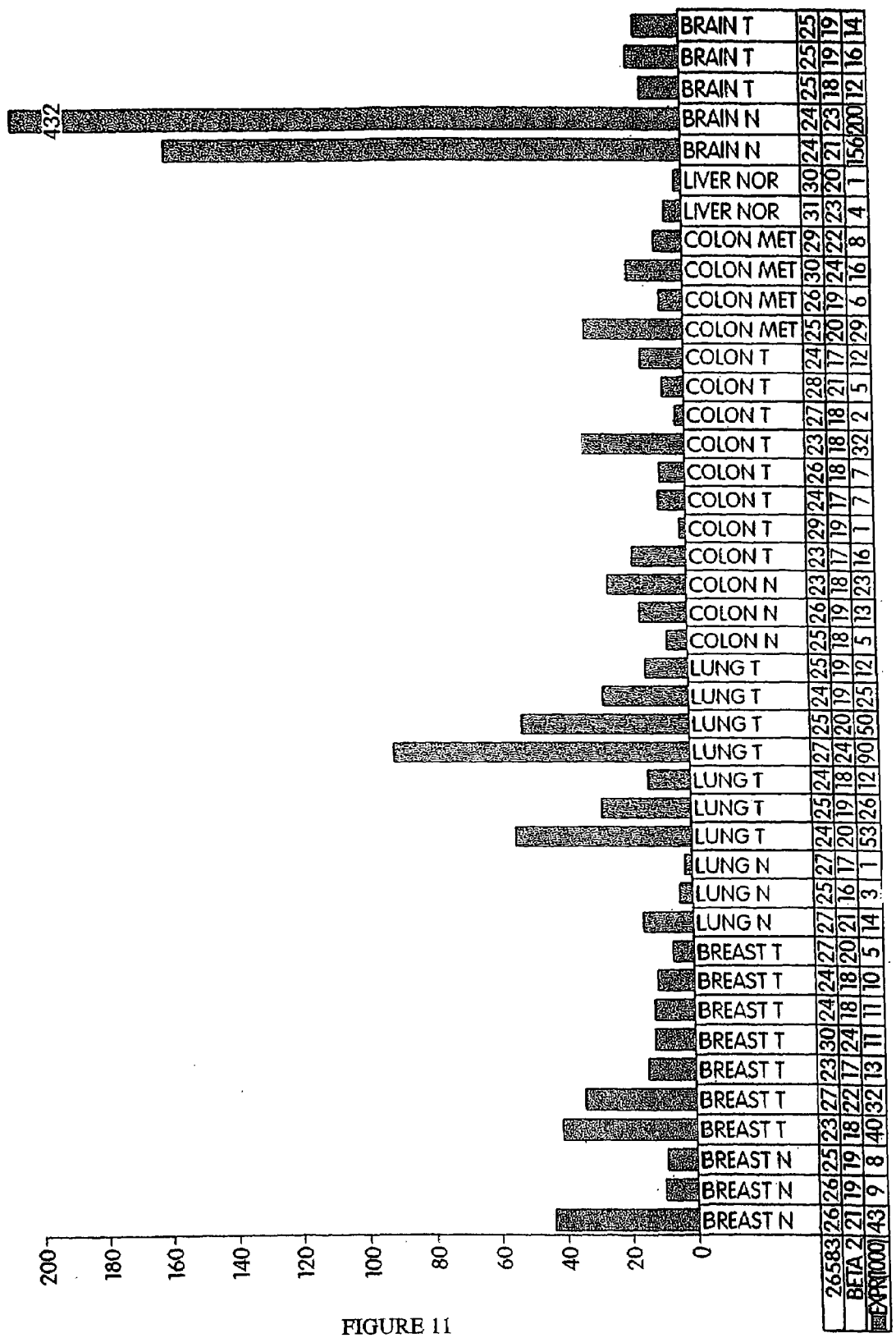
FIG. 11 shows a bar graph depicting relative 26583 mRNA expression as determined by TaqMan assays on mRNA derived from the following tissue samples. Columns are numbered at five-column intervals at the bottom of the Figure (i.e., columns 1-42), and correspond to the following: columns 1-3, normal breast; columns 4-10, breast tumor; columns 11-13, normal lung; columns 14-20, lung tumor; columns 21-23, normal colon; columns 24-31, colon tumor; columns 32-35, colon metastases; columns 36-37, normal liver; columns 38-39, normal brain; columns 40-42, brain tumor.
Figure 12:
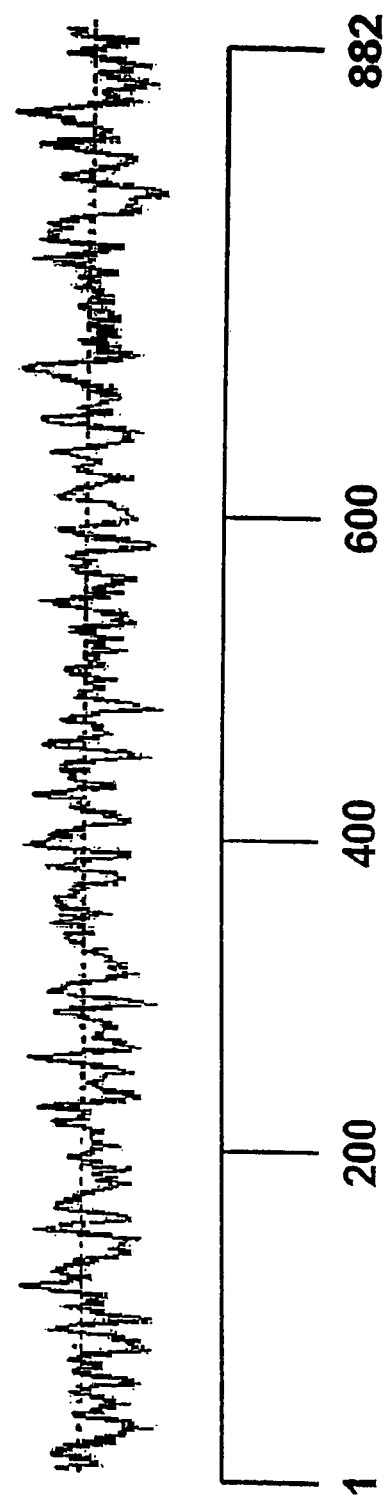
FIG. 12 depicts a hydropathy plot of human 21953. Relative hydrophobic residues are shown above the dashed horizontal line, and relative hydrophilic residues are below the dashed horizontal line. Numbers corresponding to positions in the amino acid sequence of human 21953 are indicated.

In addition, the 26583 molecules of the invention may modulate physiological and pathological processes in the cells or tissues where they are expressed. For example, Taq Man studies described herein show expression of 26583 in normal human breast, lung, colon, liver, and brain tissue (FIG. 11). 26583 expression can be modulated in samples of tumor tissue compared to normal tissue. For example, 26583 expression in brain tumor samples can be significantly higher than in normal brain tissue samples; and 26583 expression in lung tumor tissue can be higher than in normal lung tissue (FIG. 11).

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer," "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The 26583 nucleic acid and protein of the invention can be used to treat and/or diagnose a variety of proliferative disorders. Such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Aberrant expression and/or activity of 26583 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 26583 molecules effects in bone cells, e.g., osteoclasts and osteoblasts, that may in turn result in bone formation and degeneration. For example, 26583 molecules may support different activities of bone resorbing osteoclasts, such as the stimulation of differentiation of monocytes and mononuclear phagocytes into osteoclasts. Accordingly, 26583 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions,leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, Al-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as, for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 26583 molecules may play an important role in the etiology of certain viral diseases, including, but not limited to, Hepatitis B, Hepatitis C, and Herpes Simplex Virus (HSV). Modulators of 26583 activity could be used to control viral diseases. The modulators can be used in the treatment and/or diagnosis of viral infected tissue or virus-associated tissue fibrosis, especially liver and liver fibrosis. Also, 26583 modulators can be used in the treatment and/or diagnosis of virus-associated carcinoma, especially hepatocellular cancer.

Additionally, 26583 may play an important role in the regulation of metabolism or pain disorders. Diseases of metabolic imbalance include, but are not limited to, obesity, anorexia nervosa, cachexia, lipid disorders or diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with muscoloskeletal disorders, e.g., joint pain; tooth pain; headaches; pain associated with surgery; pain related to irritable bowel syndrome; or chest pain.

21953

Prolyl oligopeptidases are a distinct sub-group of endopeptidases that degrade a variety of proline-containing peptides by cleaving the peptide bond at the carboxyl side of proline residues. The natural substrates of prolyl oligopeptidases include many biologically active peptides such as peptide messenger molecules. For example, they are involved in the metabolism of peptide hormones and neuropeptides. Prolyl oligopeptidases have few naturally occurring inhibitors and their distinctive specificity prevents them from interacting with β-macroglobulin, unlike the great majority of endopeptidases. The specificity of an oligopeptidase depends on the three dimensional structure of its active site, which includes a putative catalytic triad, which contains aspartate, serine and histidine residues.

Examples of known prolyl oligopeptidases include human prolyl oligopeptidase (Yoshimoto et al. Genebank AB020018), mouse prolyl oligopeptidase (Ishino et al., *J. Biochem.* 123 (3), 540-545 (1998)), pig prolyl oligopeptidase (Rennix et al., *Biochemistry*, 30:2195-2203, 1991), rat dipeptidyl-peptidase IV (Ognata et al., *J. Biol. Chem,* 264: 3596-3601, 1989), *F. meningosepticum* prolyl oligopeptidase (Yoshimoto et al., *J. Biochem.* 110:873-878, 1991), and *E. coli* protease II (Kanatani et al., *J. Biochemistry* (Tokyo), 110: 315-320, 1991).

Prolyl oligopeptidases also control the activity of other peptides present in body fluids such as bradykinin and angiotensin. Bradykinin is a very potent vasodilator that increases the permeability of post capillary venules and acts on endothelial cells to activate phospholipase A2. Angiotensin causes contraction of vascular smooth muscle, raising blood pressure and stimulating aldosterone release from the adrenal glands. Other members of the prolyl oligopeptidase family mediate the degradation of neuropeptides such as substance P, thyrotropin releasing hormone, hippocampal cholinergic neurostimulating peptide (HCNP), neuropeptide Y (NPY), and neuropeptides derived from pro-opiomelanocortin (POMC) and neurohypophyseal hormones.

The human 21953 sequence (see SEQ ID NO:19), which is approximately 3143 nucleotides long, including untranslated regions, contains a predicted methionine-initiated coding sequence of about 2649 nucleotides, including the termination codon. The coding sequence encodes a 882 amino acid protein (see SEQ ID NO:20).

Human 21953 contains the following regions or other structural features: a predicted prolyl oligopeptidase domain (PFAM Accession PF00326) located at about amino acids 672-744 of SEQ ID NO:20; two predicted cAMP phosphorylation sites and cGMP-dependent protein kinase phosphorylation domains (Prosite Accession PS00004) located at about amino acid residues 231 to 234 of SEQ ID NO:20 and about amino acid residues 476-479 of SEQ ID NO:20; ten predicted Protein Kinase C sites (PS00005) at about amino acids 52 to 54, 80 to 82, 115 to 117, 307 to 309, 312 to 314, 326 to 328, 551 to 553, 594 to 596, 776 to 778, and 850 to 852 of SEQ ID NO:20; 11 predicted Casein Kinase II sites (PS00006) located at about amino 133 to 136, 227 to 230, 293 to 296, 412 to 415, 443 to 446, 499 to 502, 530 to 533, 587 to 590, 603 to 606, 615 to 618, and 723 to 726 of SEQ ID NO:20; five predicted tyrosine phosphorylation sites (PS00007) at about amino acids 29 to 36, 47 to 55, 308 to 315, 549 to 555, and 837 to 844 of SEQ ID NO:20; four predicted N-myristylation sites (PS00008) from about amino 176 to 181, 741 to 746, 762 to 767 and 873 to 878 of SEQ ID NO:20 and one predicted amidation site (PS00009) from about amino acid 642 to 645 of SEQ ID NO:20.

For general information regarding PFAM identifiers, PS prefix and PF prefix domain identification numbers, refer to Sonnhammer et al. (1997) *Protein* 28:405-420.

The 21953 polypeptide contains a significant number of structural characteristics in common with members of the human prolyl oligopeptidase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Polypeptide of the prolyl oligopeptidase family such as a 21953 polypeptide typically include an N-terminal seven-blade β-propeller domain and a C-terminal α/β hydrolase domain. The N-terminal seven-blade β-propeller domain can include a "DPP IV N-terminal domain" or regions homologous with a "DPP IV N-terminal domain." The C-terminal α/β hydrolase domain, e.g., the C-terminal region of a 21953 polypeptide, can include a "prolyl oligopeptidase domain" or regions homologous with a "prolyl oligopeptidase domain". The "prolyl oligopeptidase domain" can include a catalytic active site, which generally occurs at the C-terminal region of the polypeptide chain, which is involved in the hydrolysis of proline-containing peptide bonds. A prolyl oligopeptidase can be soluble. An alignment of human dipeptidyl peptidase IV (Accession Number P48147) to the 21953 amino acid sequence is depicted in FIGS. 14A-14B.

As used herein, the term "prolyl oligopeptidase domain" includes an amino acid sequence of at least about 60 amino acid residues in length and having a bit score for the alignment of the sequence to the Pfam Hidden Markov Model (HHM) PF00326 of at least 10. Preferably, a prolyl oligopeptidase domain includes at least about 30 to 180 amino acids, more preferably about 50 to 140 amino acid residues, or about 60 to 80 amino acids and has a bit score for the alignment of the sequence to the prolyl oligopeptidase domain (HMM) of at least 10, 20, 30 or greater. An alignment of the prolyl oligopeptidase domain (amino acids 672 to 744 of SEQ ID NO:20) of human 21953 with a consensus amino acid sequence derived from a hidden Markov model is depicted in FIGS. 14A-14B. In a preferred embodiment, a human 21953 polypeptide has a serine peptidase active site, e.g., an active site that is nearly identical to the Prosite signature PDOC00587. The active site can have a conserved catalytic triad with a conserved serine, e.g., a serine residue located at about amino acid 739 of SEQ ID NO:20, a conserved aspartic acid, e.g., an aspartic acid residue located at about amino acid 817 of SEQ ID NO:20, and a conserved histidine, e.g., a histidine residue located at about amino acid 849 of SEQ ID NO:20.

In a preferred embodiment 21953 polypeptide or protein has a "prolyl oligopeptidase domain" or a region which includes at least about 30-300, more preferably about 50-150, or 60-80 amino acid residues and has at least about 50%, 60%, 70% 80% 90% 95%, 99%, or 100% homology with a "prolyl oligopeptidase domain," e.g., the prolyl oligopeptidase domain of human 21953 (e.g., residues 672-744 of SEQ ID NO:20).

To identify the presence of a "prolyl oligopeptidase" domain in a 21953 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28(3): 405-420 and a detailed description of HMMs can be found, for example, in Gribskov et al. (1990) Meth. Enzymol. 183:146-159; Gribskov et al. (1987) Proc. Natl. Acad. Sci. USA 84:4355-4358; Krogh et al. (1994) J. Mol. Biol. 235: 1501-1531; and Stultz et al. (1993) Protein Sci. 2:305-314, the contents of which are incorporated herein by reference. A search was performed against the HMM database resulting in the identification of a "prolyl oligopeptidase domain" domain in the amino acid sequence of human 21953 at about residues 672-744 of SEQ ID NO:20 (see FIG. 13).

In a preferred embodiment, a 21953 polypeptide includes an N-terminal seven-blade β-propeller domain, e.g., residues about 88 to 663 of SEQ ID NO:20. The amino acid sequence of this region can be aligned to the HMM profile for DPP IV N-terminal domain or the human DPP IV amino acid sequence (P27487). As used herein, the term "DPP IV N-terminal domain" refers to an amino acid sequence at least 60% identical to residues about 88 to 663 of SEQ ID NO:20.

A 21953 family member can include a prolyl oligopeptidase domain and may also include a cAMP phosphorylation site and cGMP-dependent protein kinase phosphorylation domain, a predicted Protein Kinase C site, a predicted Casein Kinase II site, a predicted tyrosine phosphorylation site, a predicted N-myristylation site, and an amidation site.

As the 21953 polypeptides of the invention may modulate 21953-mediated activities, e.g., a dipeptidyl peptidase activity such as a prolyl oligopeptidase activity, they may be useful for developing novel diagnostic and therapeutic agents for 21953-mediated or related disorders, as described below. The 21953 polypeptide of the invention are highly expressed in tumors, for example in breast and lung tumors. Further, 21953 polypeptide expression is increased at the G1-S phase transition of the mammalian cell cycle. Additional expression data for 21953 polypeptides are described below and in the Figures. Generally, increased prolyl oligopeptidase activity has been detected in human prostate, lung, and sigmoid tumors relative to healthy normal tissue. Such increased activity can result from 21953 increased expression.

As used herein, a "21953 activity", "biological activity of 21953" or "functional activity of 21953", refers to an activity exerted by a 21953 protein, polypeptide or nucleic acid molecule on, e.g., a 21953-responsive cell or on a 21953 substrate, e.g., a oligopeptide substrate, as determined in vivo or in vitro. In one embodiment, a 21953 activity is a direct activity, such as an association with a 21953 target molecule. A "target molecule" or "binding partner" is a molecule with which a 21953 protein binds or interacts in nature. For example, the 21953 proteins of the present invention can have one or more of the following activities: (1) hydrolyzing peptide bonds at the carboxyl side of proline residues; (2) mediating degradation of proline-containing peptides, e.g., a prolyl endopeptidases activity; (3) processing of peptide factors (e.g., peptide hormones, chemokines, cytokines, neuropeptides, and vasoactive peptides); (4) processing N-terminal dipeptides of unmodified N-termini wherein the penultimate residue is proline; (5) modulating cell proliferation and/or modulating cell differentiation (e.g., of a lung, breast, lymphoid, or colon cell); (6) modulating the regulation of transmission of intracellular signals, e.g., during immunological processes; (7) modulating metabolism of neurotransmitters or neuropeptides; (8) modulating neurodegeneration; or (9) modulating follicular development.

As used herein, a "dipetidyl peptidase activity" refers to a catalytic activity that accelerates the scission of a peptide bond between an amino acid sequence of less than four amino acids and the remainder of the polypeptide. Preferably, the cleaved peptide is a dipeptide having two amino acids. The catalytic activity can be mediated by the side chain of a serine amino acid and surrounding residues in the active site.

As used herein, a "prolyl endopeptidases activity" refers to a catalytic activity that accelerates the scission of a peptide bond adjacent to a proline amino acid in a peptide or polypeptide chain. This catalytic activity has been detected, for example, in primary human lung tumors, squamous cell lung carcinomas, and lung adenocarcinomas. For example, squamous cell lung carcinomas and lung adenocarcinomas showed significantly higher levels of prolyl endopeptidases activity relative to normal lung parenchyma.

In accordance with the above-described sequence similarities and observed polypeptide expression pattern, the 21953 molecules of the present invention can have similar biological activities as related prolyl oligopeptidase family members. Members of the prolyl oligopeptidase family can play an important role in the metabolism of a variety of proline containing peptides by cleaving prolyl bonds. These peptides can be less than about 200, 150, 100, or 50 residues in length. Prolyl oligopeptidases are involved, e.g., alone or together with other factors, in the regulation, e.g., processing, activation, or degradation of biological factors, e.g., peptide hormones (such as growth hormone, insulin, prolactin, adrenocorticotropic hormone, placental lactogen, calcitonin, parathyroid hormone, and thyroid stimulating hormone); chemokines; cytokines; neuropeptides; and vasoactive peptides.

As the 21953 mRNA is highly expressed, for example, in cancerous tissues (e.g., lung and breast tumors), as well as normal cardiovascular, neural, and prostatic tissues, the molecules of the invention can be used to treat, prevent and/or diagnose disorders involving aberrant activity of 21953-expressing cells. Accordingly, the 21953 molecules can act as novel diagnostic targets and therapeutic agents for controlling disorders associated with the aberrant activity or degradation of peptide hormones, e.g., disorders associated with cell differentiation and proliferation (e.g., a cancer of the lung, breast, ovary, and colon tissues), immune function (e.g., T cell activities, e.g., lymphomas, leukemias, and immune disorders), reproductive, neurological and cardiovascular function.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Examples of cellular proliferative and/or differentiative disorders include cancer, e.g., carcinoma, sarcoma, or metastatic disorders. The 21953 molecules can act as novel diagnostic targets and therapeutic agents for controlling lung cancer, breast cancer, ovarian cancer, colon cancer, metastasis of such cancers and the like. A metastatic tumor can arise from a multitude of primary tumor types, including but not limited to those of lung, breast, liver, colon and ovarian origin.

Examples of cellular proliferative and/or differentiative disorders of the lung include, but are not limited to, squamous cell lung carcinomas, small cell lung carcinoma, lung adenocarcinomas, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The 21953 nucleic acid and protein of the invention can be used to treat and/or diagnose a variety of immune disorders, e.g., as a result of aberrant 21953 activity in T cells. Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of neuronal disorders include, but are not limited to disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

The term "vascular disorder" includes disorders involving aberrant activity (e.g., proliferation, metabolism, angiogenesis, vascularization) of blood vessel-associated cells, e.g., smooth muscle or endothelial cells. Examples of such disorders include but are not limited to hypertension (e.g., arterial hypertension), vascular restenosis, ischemic disease (e.g., atherosclerosis), tumorigenesis, tumor metastasis, diabetic retinopathy, endometriosis, Grave's disease. Aberrant vascular activity may also affect cardiovascular function, and thus the molecules of the invention can be used to treat, prevent and/or diagnose cardiovascular disorders. Examples of cardiovascular disorders, include but are not limited to, heart failure, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

As used herein, "a prostate disorder" refers to an abnormal condition occurring in the male pelvic region characterized by, e.g., male sexual dysfunction and/or urinary symptoms. This disorder may be manifested in the form of genitourinary inflammation (e.g., inflammation of smooth muscle cells) as in several common diseases of the prostate including prostatitis, benign prostatic hyperplasia and cancer, e.g., adenocarcinoma or carcinoma, of the prostate.

The 21953 nucleic acid and protein of the invention can be used to treat and/or diagnose a variety of conditions, in addition to the ones described above (see "Methods of Treatment" for additional examples).

The presence of 21953 RNA or protein can also be used to identify a cell or tissue, or other biological sample, as being derived from breast, T-cell, kidney, liver, and aorta, or being of human origin. Expression can also be used to diagnose or stage a disorder, e.g., a cancer (e.g., a cancer of the lung or breast), or a breast, lymphoid, lung, ovarian, or liver disorder. Expression can be determined by evaluating RNA, e.g., by hybridization of a 21953 specific probe, or with a 21953 specific antibody.

m32404

Four major classes of proteases are known and are designated by the principal functional group in their active site: serine, thiol, carboxyl, and metallo. Serine proteases are characterized by the presence of a unique serine residue that functions as a nucleophile to cleave peptide bonds. In some cases, the serine forms covalent adducts with substrates and inhibitors. The serine functions with two other principal residues of the active site, a histidine, and an acid, frequently aspartic acid. Together these three residues compose the catalytic triad which is a signature of the family. Serine proteases are divided into two major evolutionary families. One family is represented by the bacterial protease subtilisin. The other family is the trypsin-chymotrypsin family and includes chymotrypsin, trypsin, and elastase. Members of the trypsin-chymotrypsin serine protease family are involved in a range of diverse cellular functions including, cell motility, cell growth and differentiation, hormone production, organogenesis, extracellular matrix regulation, blood clotting, and complementation activation.

While the various serine proteases catalyze this reaction in very similar ways, they differ in their preference for the amino acid side chains immediately C-terminal to the cleave site. Trypsin cleaves bonds only after lysine and arginine residues, whereas chymotrypsin cleaves bonds after large hydrophobic residues. Some members of the trypsin serine protease family play critical roles in a variety of important biological events including regulating cell proliferation, tumor growth, tumor invasion, metastasis, development, and tissue remodeling.

Figure 15:
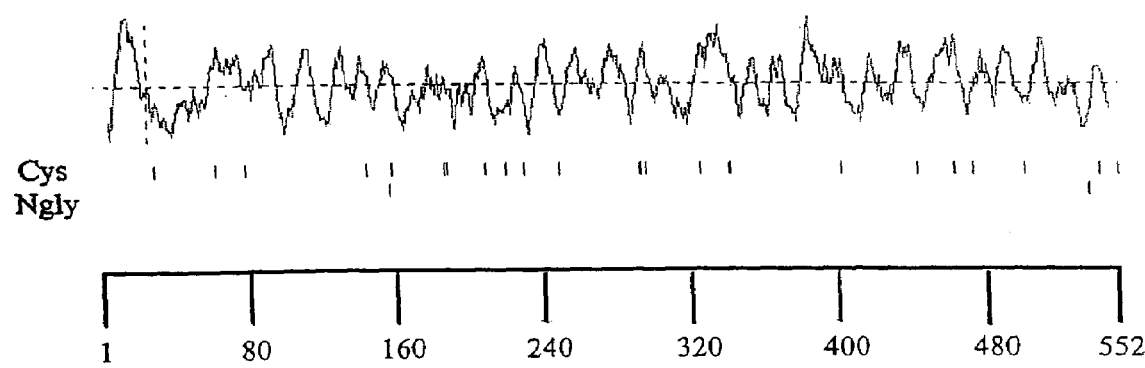
FIG. 15 depicts a hydropathy plot of human m32404. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human m32404 are indicated. Polypeptides of the invention include fragments which include: all or part of a hydrophobic sequence, i.e., a sequence above the dashed line, e.g., the sequence from about amino acid 320 to 340, and from about 450-470, of SEQ ID NO:25; all or part of a hydrophilic sequence, i.e., a sequence below the dashed line, e.g., the sequence from about amino acid 30 to 60 of SEQ ID NO:25; a sequence which includes a Cys, or a glycosylation site.

The human m32404 sequence (see SEQ ID NO:24), which is approximately 2219 nucleotides long including untranslated regions, contains a predicted methionine-initiated coding sequence of about 1659 nucleotides, including the termination codon. The coding sequence encodes a 552 amino acid protein (SEQ ID NO:25). The human m32404 protein of SEQ ID NO:25 and FIG. 15 includes an amino-terminal hydrophobic amino acid sequence, consistent with a signal sequence, of about 23 amino acids (from amino acid 1 to about amino acid 23 of SEQ ID NO:25), which upon cleavage results in the production of a mature protein form. This mature protein form is approximately 529 amino acid residues in length (from about amino acid 24 to amino acid 552 of SEQ ID NO:25).

Human m32404 contains the following regions or other structural features:

two trypsin domains (PFAM Accession PF00089) located at about amino acid residues 45 to 268 and 311 to 520 of SEQ ID NO:25, which include trypsin histidine and serine active sites located at about amino acids 73-78 and 337-342, and 218-229, respectively, of SEQ ID NO:25;

eight predicted Protein Kinase C phosphorylation sites (PS00005) at about amino acids 4 to 6, 53 to 55, 96 to 98, 173 to 175, 246 to 248, 298 to 300, 422 to 424, and 504 to 506 of SEQ ID NO:25;

six predicted Casein Kinase II phosphorylation sites (PS00006) located at about amino acid 161 to 164, 348 to 351, 375 to 378, 496 to 499, 514 to 517, and 521 to 524 of SEQ ID NO:25;

two predicted N-glycosylation sites (PS00001) from about amino acid 166 to 169 and 545 to 548 of SEQ ID NO:25; and nine predicted N-myristylation sites (PS00008) from about amino 20 to 25, 58 to 63, 64 to 69, 101 to 106, 126 to 131, 206 to 211, 297 to 302, 328 to 333, and 460 to 465 of SEQ ID NO:25.

For general information regarding PFAM identifiers, PS prefix and PF prefix domain identification numbers, refer to Sonnhammer et al. (1997) *Protein* 28:405-420.

The m32404 polypeptide contains a significant number of structural characteristics in common with members of the trypsin serine protease family (Rawlings and Barret (1993) *Biochem J.* 290: 205-218, and *Meth. Enzymol.* (1994) 244: 19-61, the contents of which are hereby incorporated by reference in their entirety). Based on the presence of the histidine-aspartate-serine catalytic triad, the m32404 polypeptide appears to be a member of the serine protease clan SA (Rawlings and Barret supra). The clan SA includes the trypsin-chymotrypsin family (S1), the α-lytic endopeptidase family (S2), and the Togavirus endopeptidase family (S3).

The m32404 polypeptide seems to belong to the trypsin-chymotrypsin family (S1). The prototype of this family is chymotrypsin and the 3D structure of some of its members has been resolved. The trypsin-chymotrypsin family (S1) includes such members as: trypsin (forms I, II, III, IV, Va and Vb); trypsin-like enzyme; hepsin; TMPRSS2; venombin; cercarial elastase; brachyurin; Factor C; Proclotting enzyme; easter gene product; snake gene product; stubble gene product; Vitellin-degrading endopeptidase; hypodermin C; Serine proteases 1 and 2; achelase; chymotrypsin (forms A, B, II, and 2); Proteinase RVV-V (forms α and γ); flavoboxin; venombin A; Crotalase; enteropeptidase; acrosin; ancrod; seminin; semenogelase; tissue kallikrein; renal kallikrein; submandibular kallikrein; 7S nerve growth factor (chains α and γ); epidermal growth factor-binding protein (forms 1, 2, and 3); tonin; arginine esterase; pancreatic elastase I; pancreatic elastase II (forms A and B); pancreatic endopeptidase E (forms A and B); leukocyte elastase; medullasin; azurocidin; cathepsin G; proteinase 3 (myeloblastin); chymase (forms I and II); γ-renin; tryptase (forms 1, 2, and 3); granzyme A; natural killer cell protease 1; gilatoxin; granzymes B, C, D, E, F, G and Y; carboxypeptidase A complex component III; complement factors D, B, I; complement components C1r, C1s, and C2; calcium-dependent serine protease; hypodermin A, B, and C; haptoglobin (forms 1 and 2); haptoglobin-related protein; plasmin; apolipoprotein (a); hepatocyte growth factor; medullasin; thrombin; t-plasminogen activator; u-plasminogen activator; salivary plasminogen activator; plasma kallikrein; coagulation factors VII, IX, X, XI, and XII; and proteins C and Z, as well as as-yet unidentified members.

Accordingly, the m32404 polypeptide contains a significant number of structural characteristics in common with members of the S1 family of the SA clan of serine-type proteases (also referred to herein as "trypsin-chymotrypsin" or "trypsin" family members). The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, a "trypsin-chymotrypsin family member" typically contains a catalytic unit which is generally a polypeptide sequence of about 100 to about 300 amino acids, more preferably about 150 to about 250 amino acid residues, even more preferably about 200 to about 230 amino acid residues, although some members have N-terminal extensions of unrelated peptide segments. The catalytic unit almost always forms the C-terminal portion of the enzyme. These proteases typically cleave arginine or lysine residues in a target protein.

Trypsin-chymotrypsin family members preferably have at least one trypsin domain, comprising at least one histidine active site residue, and at least one serine active site residue. Trypsin-chymotrypsin family members can also include an aspartate residue within the trypsin domain. These three residues act as a "catalytic triad," with serine as nucleophile, aspartate as electrophile, and histidine as base. The serine nucleophile typically occurs in a signature motif characterized by Prosite Motif PS00135 (also PDOC00124): G-[DE]-S-G-[GS]. Typically, a trypsin domain additionally includes an activation and cleavage site, Arg-Ile-Val-Gly-Gly (or "RIVGG"; SEQ ID NO:30), which is present just N-terminal to the serine protease domain.

m32404 polypeptides contain structural features similar to trypsin-chymotrypsin family members. For example, each of the two trypsin domains of the m32404 polypeptide has a conserved histidine residue present at about amino acid 77 and 341 of SEQ ID NO:25. The histidine base typically occurs in a signature motif characterized by Prosite Motif PS00134 (also PDOC00124): [LIVM]-[ST]-A-[STAG]-H-C. An m32404 polypeptide also contains the sequence LTAAHC (SEQ ID NO:31), which matches PS00134, at about amino acids 73 to 78 and 337 to 342 of SEQ ID NO:25.

In addition, the m32404 polypeptide includes the sequence GDSGG (SEQ ID NO:32), which matches PS00135, at about amino acids 222 to 226 of SEQ ID NO:25. The serine active site is located at amino acid 224 of SEQ ID NO:25. The trypsin domains of the m32404 polypeptide additionally include eleven conserved cysteines, which are present at about amino acids 62, 187, 209, 220, 249, 326, 342, 443, 463, 473, 501 of SEQ ID NO:25.

Trypsin-chymotrypsin family members occasionally function intracellularly, but more generally, they act extracellularly. Examples of such extracellular activity include release or activation of growth factors, degradation of extracellular matrix, coagulation, fibrinolysis, zymogen and growth hormone activation, and complement activation. Trypsin-chymotrypsin family members have been implicated in modulating tumor invasion and growth by, for example, releasing or activating growth factors and/or digesting extracellular matrix components.

An m32404 polypeptide includes at least one and preferably two "trypsin domains" or at least one and preferably two regions homologous with a "trypsin domain."

As used herein, the term "trypsin domain" (or a "trypsin-chymotrypsin" domain) refers to a protein domain having an amino acid sequence of from about 50 to about 350 amino acid residues and having a bit score for the alignment of the sequence to the trypsin domain (HMM) of at least 60. Preferably, a trypsin domain includes at least about 100 to about 300 amino acids, more preferably about 150 to about 250 amino acid residues, more preferably about 200 to about 230 amino acids and has a bit score for the alignment of the sequence to the trypsin domain (HMM) of at least 80, preferably at least 90, more preferably at least 100, and most preferably 110 or greater. The trypsin domain (HMM) has been assigned the PFAM Accession (PF00089). Alignments of two trypsin domains (from about amino acids 45 to 268 and from about amino acids 311 to 520 of SEQ ID NO:25) of human m32404 with a consensus amino acid sequence derived from a hidden Markov model (PFAM) are depicted in FIGS. 16A and 16B. Alignments of the two trypsin domains (from about amino acids 38 to about 268 and from about amino acids 300 to 520 of SEQ ID NO:25) of human m32404 with a consensus amino acid sequence derived from another hidden Markov model (SMART) are depicted in FIGS. 17A and 17B.

In a preferred embodiment, an m32404 polypeptide or protein has a "trypsin" domain or a region which includes at least about 100 to about 300 amino acids, more preferably about 150 to about 250 amino acid residues, or about 210 to about 235 amino acid residues and has at least about 70%, 80%, 90%, 95%, 99%, or 100% homology with a "trypsin domain," e.g., either trypsin domain of human m32404 (e.g., residues about 45 to 268 and 311 to 520 of SEQ ID NO:25). Preferably, the trypsin domain includes at least one histidine active site residue, and at least one serine active site residue. The trypsin domain can also include an aspartate residue, thus forming a catalytic triad, with serine as nucleophile, aspartate as electrophile, and histidine as base.

To identify the presence of a "trypsin" domain in an m32404 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28(3):405-420 and a detailed description of HMMs can be found, for example, in Gribskov et al. (1990) Meth. Enzymol. 183:146-159; Gribskov et al. (1987) Proc. Natl. Acad. Sci. USA 84:4355-4358; Krogh et al. (1994) J. Mol. Biol. 235:1501-1531; and Stultz et al. (1993) Protein Sci. 2:305-314, the contents of which are incorporated herein by reference. A search was performed against the PFAM HMM database resulting in the identification of two "trypsin domains" in the amino acid sequence of human m32404 from about residues 45 to 268 and 311 to 520 of SEQ ID NO:25 with a bit score of 254 (see FIGS. 16A-16B).

To identify the presence of a "trypsin" domain in an m32404 protein sequence, and make the determination that a polypeptide or protein of interest has a particular profile, the amino acid sequence of the protein can also be searched against a SMART database (Simple Modular Architecture Research Tool) of HMMs as described in Schultz et al. (1998), Proc. Natl. Acad. Sci. USA 95:5857 and Schultz et al. (200) Nucl. Acids Res 28:231. The database contains domains identified by profiling with the hidden Markov models of the HMMer2 search program (R. Durbin et al. (1998) Biological sequence analysis: probabilistic models of proteins and nucleic acids. Cambridge University Press). The database also is extensively annotated and monitored by experts to enhance accuracy. A search was performed against the HMM database resulting in the identification of two "trypsin" domains in the amino acid sequence of human m32404 at about residues 38 to 268 and 300 to 520 of SEQ ID NO:25 (see 3A-3B).

An m32404 family member can include one or more of a trypsin domain, a signal peptide domain, an N-glycosylation site, a protein kinase C phosphorylation site, a casein kinase II phosphorylation site, or an N-myristoylation site.

As used herein, a "signal peptide" or "signal sequence" refers to a peptide of about 15 to 30, preferably about 20 to 25, more preferably, 23 amino acid residues in length which occurs at the N-terminus of secretory and integral membrane proteins and which contains a majority of hydrophobic amino acid residues. For example, a signal sequence contains at least about 15 to 25 amino acid residues, preferably about 20 to 25 amino acid residues, more preferably about 23 amino acid residues, and has at least about 40-70%, preferably about 50-65%, and more preferably about 55-60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, an m32404 protein contains a signal sequence of about amino acids 1 to 23 of SEQ ID NO:25. The "signal sequence" is cleaved during processing of the mature protein. The mature m32404 protein corresponds to amino acids 24 to 552 of SEQ ID NO:25.

As the m32404 polypeptides of the invention may modulate m32404-mediated activities, they may be useful as of for developing novel diagnostic and therapeutic agents for m32404-mediated or related disorders, as described below.

As used herein, a "m32404 activity," "biological activity of m32404" or "functional activity of m32404," refers to an activity exerted by an m32404 protein, polypeptide or nucleic acid molecule on e.g., an m32404-responsive cell or on an m32404 substrate, e.g., a protein substrate, as determined in vivo or in vitro. In one embodiment, an m32404 activity is a direct activity, such as an association with an m32404 target molecule. A "target molecule" or "binding partner" is a molecule with which an m32404 protein binds or interacts in nature. An m32404 activity can also be an indirect activity, e.g., a cellular signaling activity mediated by interaction of the m32404 protein with an m32404 receptor. For example, the m32404 proteins of the present invention can have one or more of the following activities: (1) modulate (e.g., stimulate or inhibit) cellular proliferation (2) modulate cell differentiation; (3) modulate tumorigenesis and/or tumor invasion; (4) alter extracellular matrix composition; (5) catalyze polypeptide growth factor activation and/or release; (6) regulate the blood clotting cascade; (7) catalyze proteolytic cleavage of a substrate, e.g., a protein substrate (e.g., cleavage at an arginine or lysine residue); (8) catalyze the proteolytic activation of signaling molecules, e.g., other proteases, growth factor activation or release; or (9) regulate of cell motility or attachment.

Based on the above-described sequence similarities, the m32404 molecules of the present invention are predicted to have similar biological activities as other trypsin family members, such as hepsin proteases. Hepsin proteases are overexpressed in ovarian tumors and hepatoma cells (Tanimoto, H. et al. (1997) Cancer Res. 57:2884-2887). Further in vitro studies have shown inhibition of hepatoma cell proliferation using hepsin inhibitors (Torres-Rosado, A. et al. (1993) Proc. Natl. Acad. Sci. USA 90: 7181-7185). Accordingly, m32404 molecules are predicted to have peptidase activity, and are predicted to regulate cell proliferation and differentiation, to regulate coagulation (such as in blood clotting), regulate organogenesis, control hormone production, and/or modulate complement activation. Thus, the m32404 molecules can serve as novel diagnostic targets and therapeutic agents for controlling cell proliferation and differentiation disorders, coagulation disorders, hormonal disorders, fertilization disorders, and disorders of organogenesis and cell signaling.

The polypeptides and nucleic acids of the invention can also be used to treat, prevent, and/or diagnose cancers and neoplastic conditions in addition to the ones described above. As used herein, the terms "cancer," "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Examples of cellular proliferative and/or differentiative disorders include cancer, e.g., carcinoma, sarcoma, or metastatic disorders. The m32404 molecules can act as novel diagnostic targets and therapeutic agents for controlling breast cancer, ovarian cancer, colon cancer, lung cancer, metastasis of such cancers and the like. A metastatic tumor can arise from a multitude of primary tumor types, including but not limited to those of breast, lung, liver, colon and ovarian origin.

Examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

14089

The human 14089 sequence (see SEQ ID NO:33), which is approximately 957 nucleotides long including untranslated regions, contains a predicted methionine-initiated coding sequence of about 726 nucleotides, including the termination codon (nucleotides indicated as coding of SEQ ID NO:33; SEQ ID NO:35). The coding sequence encodes a 241 amino acid protein (SEQ ID NO:34). The human 14089 protein of SEQ ID NO:34 includes an amino-terminal hydrophobic amino acid sequence, consistent with a signal sequence, of about 18 amino acids (from amino acid 1 to about amino acid 18 of SEQ ID NO:34), which upon cleavage results in the production of a mature protein. This mature protein form is approximately 222 amino acid residues in length (from about amino acid 19 to amino acid 241 of SEQ ID NO:34).

Human 14089 contains the following regions or other structural features:

a trypsin domain (PFAM Accession Number PF00089) located at about amino acid residues 24 to 234 or 41 to 234 of SEQ ID NO:34 (according to SMART and PFAM, respectively);

four predicted Casein Kinase II phosphorylation sites (PS00006) located at about amino acids 96 to 99, 109 to 112, 126 to 129, and 210 to 213 of SEQ ID NO:34;

three predicted N-glycosylation sites (PS00001) from about amino acids 11 to 14, 156 to 159, and 173 to 176 of SEQ ID NO:34;

two predicted N-myristylation sites (PS00008) from about amino acids 182 to 187 and 203 to 208 of SEQ ID NO:34;

one predicted amidation site (PS00009) from about amino acids 185 to 188 of SEQ ID NO:34;

one predicted tyrosine kinase phosphorylation site (PS00007) from about amino acids 108 to 116 of SEQ ID NO:34; or one predicted serine protease, histidine active site (PS00134) from about amino acids 52 to 57 of SEQ ID NO:34.

For general information regarding PFAM identifiers, PS prefix and PF prefix domain identification numbers, refer to Sonnhammer et al. (1997) *Protein* 28:405-420.

The 14089 polypeptide contains a significant number of structural characteristics in common with members of the trypsin serine protease family (Rawlings and Barret (1993) *Biochem J.* 290: 205-218, and *Meth. Enzymol.* (1994) 244: 19-61, the contents of which are hereby incorporated by reference in their entirety). Based on the presence of the histidine-aspartate-serine catalytic triad, the 14089 polypeptide appears to be a member of the serine protease clan SA (Rawlings and Barret, supra). The clan SA includes the trypsin-chymotrypsin family (S1), the α-lytic endopeptidase family (S2), and the Togavirus endopeptidase family (S3).

The 14089 polypeptide seems to belong to the trypsin-chymotrypsin family (S1). The prototype of this family is chymotrypsin and the 3D structure of some of its members has been resolved. The trypsin-chymotrypsin family (S1) includes such members as: trypsin (forms I, II, III, IV, Va and Vb); trypsin-like enzyme; hepsin; venombin; cercarial elastase; brachyurin; Factor C; Proclotting enzyme; easter gene product; snake gene product; stubble gene product; Vitellin-degrading endopeptidase; hypodermin C; Serine proteases 1 and 2; achelase; chymotrypsin (forms A, B, II, and 2); Proteinase RVV-V (forms α and γ); flavoboxin; venombin A; Crotalase; enteropeptidase; acrosin; ancrod; seminin; semenogelase; tissue kallikrein; renal kallikrein; submandibular kallikrein; 7S nerve growth factor (chains α and γ); epidermal growth factor-binding protein (forms 1, 2, and 3); tonin; arginine esterase; pancreatic elastase I; pancreatic elastase II (forms A and B); pancreatic endopeptidase E (forms A and B); leukocyte elastase; medullasin; azurocidin; cathepsin G; proteinase 3 (myeloblastin); chymase (forms I and II); γ-renin; tryptase (forms 1, 2, and 3); granzyme A; natural killer cell protease 1; gilatoxin; granzymes B, C, D, E, F, G and Y; carboxypeptidase A complex component III; complement factors D, B, I; complement components C1r, C1s, and C2; calcium-dependent serine protease; hypodermin A, B, and C; haptoglobin (forms 1 and 2); haptoglobin-related protein; plasmin; apolipoprotein (a); hepatocyte growth factor; medullasin; thrombin; t-plasminogen activator; u-plasminogen activator; salivary plasminogen activator; plasma kallikrein; coagulation factors VII, IX, X, XI, and XII; and proteins C and Z, as well as as-yet unidentified members.

The 14089 polypeptides can be homologous to the mouse bodenin gene (GenBank Accession No. AJ001373). The mouse bodenin gene is expressed in region of the brain such as the basal ganglia, thalamus, cerebral cortex, and may play a role in the developing and mature central nervous system. See, Faisst and Gruss, (1998) *Dev. Dyn.* 212:293-303.

Accordingly, the 14089 polypeptide contains a significant number of structural characteristics in common with members of the SI family of the SA clan of serine-type proteases (also referred to herein as "trypsin-chymotrypsin" or "trypsin" family members). The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, a "trypsin-chymotrypsin family member" typically contains a catalytic unit that is generally a polypeptide sequence of about 100 to about 300 amino acids, more preferably about 150 to about 250, or about 170 to about 230 amino acid residues, although some members have N-terminal extensions of unrelated peptide segments. The catalytic unit typically forms the C-terminal portion of the enzyme. These proteases typically cleave arginine or lysine residues in a target protein.

Trypsin-chymotrypsin family members preferably have at least one trypsin domain, comprising at least one histidine active site residue, and at least one serine active site residue. Trypsin-chymotrypsin family members can also include an aspartate residue within the trypsin domain. These three residues act as a "catalytic triad", with serine as nucleophile, aspartate as electrophile, and histidine as base.

14089 polypeptides contain structural features similar to trypsin-chymotrypsin family members. For example, the trypsin domain of the 14089 polypeptide has a conserved histidine residue present at about amino acid 56 of SEQ ID NO:34, and a serine active site located at amino acid 195 of SEQ ID NO:34. The trypsin domain of the 14089 polypeptide additionally includes eight conserved cysteines, which are present at about amino acids 40, 57, 133, 143, 165, 180, 191, 201, and 215 of SEQ ID NO:34. Eight of these cysteines can form disulfide bonds together in an intramolecular context. Preferably, the disulfide bonds are formed between residues about 40 and 57, 133 and 201, 165 and 180, 191 and 215 of SEQ ID NO:34.

In addition, the 14089 polypeptide includes an active site serine at about residue 195 of SEQ ID NO:34. The histidine base typically occurs in a signature motif characterized by Prosite Motif PS00134: [LIVM]-[ST]-A-[STAG]-H-C. A 14089 polypeptide also contains the sequence ITAAHC, which matches PS00134, at about amino acids 52 to 57 of SEQ ID NO:34.

Trypsin-chymotrypsin family members occasionally function intracellularly, but more generally, they act extracellularly. Examples of such extracellular activity include release or activation of growth factors, degradation of extracellular matrix, coagulation, fibrinolysis, zymogen and growth hormone activation, and complement activation. Trypsin-chymotrypsin family members have been implicated in modulating tumor invasion and growth by, for example, releasing or activating growth factors and/or digesting extracellular matrix components. A 14089 polypeptide can include a signal sequence, located at residues about 1 to 18 of SEQ ID NO:34, which directs the polypeptide to the extracellular milieu.

A 14089 polypeptide includes at least one "trypsin domain" or at least one region homologous with a "trypsin domain". As used herein, the term "trypsin domain" (or a "trypsin-chymotrypsin" domain) refers to a protein domain having an amino acid sequence of from about 50 to about 350 amino acid residues and having a bit score for the alignment of the sequence to the trypsin domain (HMM) of at least 70. Preferably, a trypsin domain includes at least about 100 to about 300 amino acids, more preferably about 150 to about 250, or about 170 to about 220 amino acid residues and has a bit score for the alignment of the sequence to the trypsin domain (HMM) of at least 100, preferably at least 110, more preferably at least 120 or greater. The trypsin domain (HMM) has been assigned the PFAM Accession (PF00089). An alignment of the trypsin domain (from about amino acids 41 to 234 of SEQ ID NO:34) of human 14089 with a consensus amino acid sequence derived from a hidden Markov model (PFAM) is depicted in FIG. 19A. An alignment of the trypsin domain (from about amino acids 24 to about 234 of SEQ ID NO:34) of human 14089 with a consensus amino acid sequence derived from another hidden Markov model (SMART) is depicted in FIG. 19B.

In a preferred embodiment, a 14089 polypeptide or protein has a "trypsin" domain or a region which includes at least about 100 to about 300 amino acids, more preferably about 150 to about 250, or about 170 to about 220 amino acid residues and has at least about 70%, 80%, 90%, 95%, 99%, or 100% homology with a "trypsin domain," e.g., the trypsin domain of human 14089 (e.g., about residues 224 to 234 or 241 to 234 of SEQ ID NO:34). Preferably, the trypsin domain includes at least one histidine active site residue, and at least one serine active site residue. The trypsin domain can also include an aspartate residue, thus forming a catalytic triad, with serine as nucleophile, aspartate as electrophile, and histidine as base.

Figure 18:
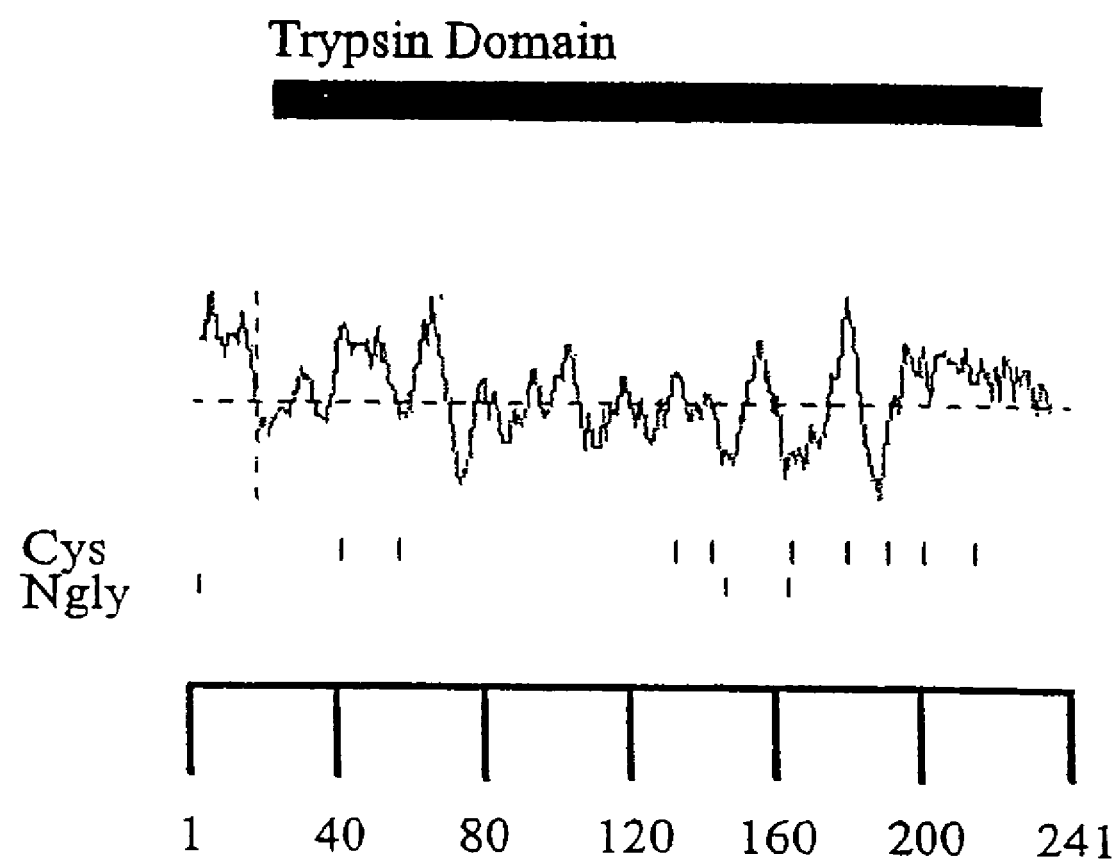
FIG. 18 depicts a hydropathy plot of human 14089. Relative hydrophobic residues are shown above the dashed horizontal line, and relative hydrophilic residues are below the dashed horizontal line. Cysteine (cys) residues are noted by short vertical lines just below the hydropathy trace. The numbers corresponding to the amino acid sequence of human 14089 are indicated. Polypeptides of the invention include fragments that include: all or part of a hydrophobic sequence, i.e., a sequence above the dashed line, e.g., the sequence from about amino acid 35 to 55, from about 58 to 70, and from about 175 to 184 of SEQ ID NO:34; all or part of a hydrophilic sequence, i.e., a sequence below the dashed line, e.g., the sequence of from about amino acid 71 to 79, from about 161 to 171, and from about 185 to 192 of SEQ ID NO:34; a sequence which includes a Cys, or a glycosylation site.
Figure 23:
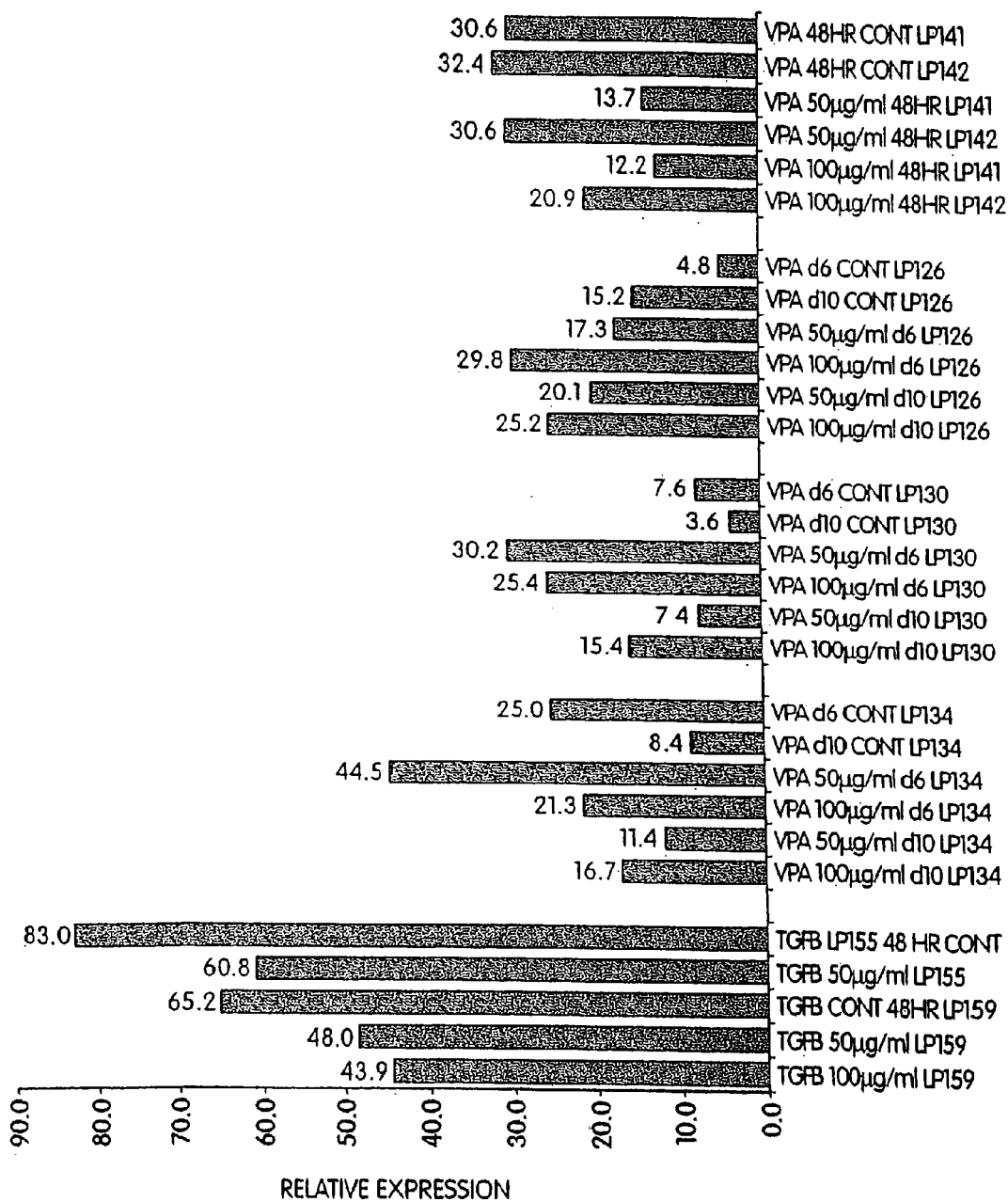
FIG. 23 is a bar graph depicting relative 23436 mRNA expression as determined by TaqMan assays on mRNA derived from human hematological cell lines treated for various times with transforming growth factor-β (TGF-β) and VPA. Erythroid lineage precursors have elevated 23436 expression levels. Expression is reduced by TGF-β treatment.
Figure 24:
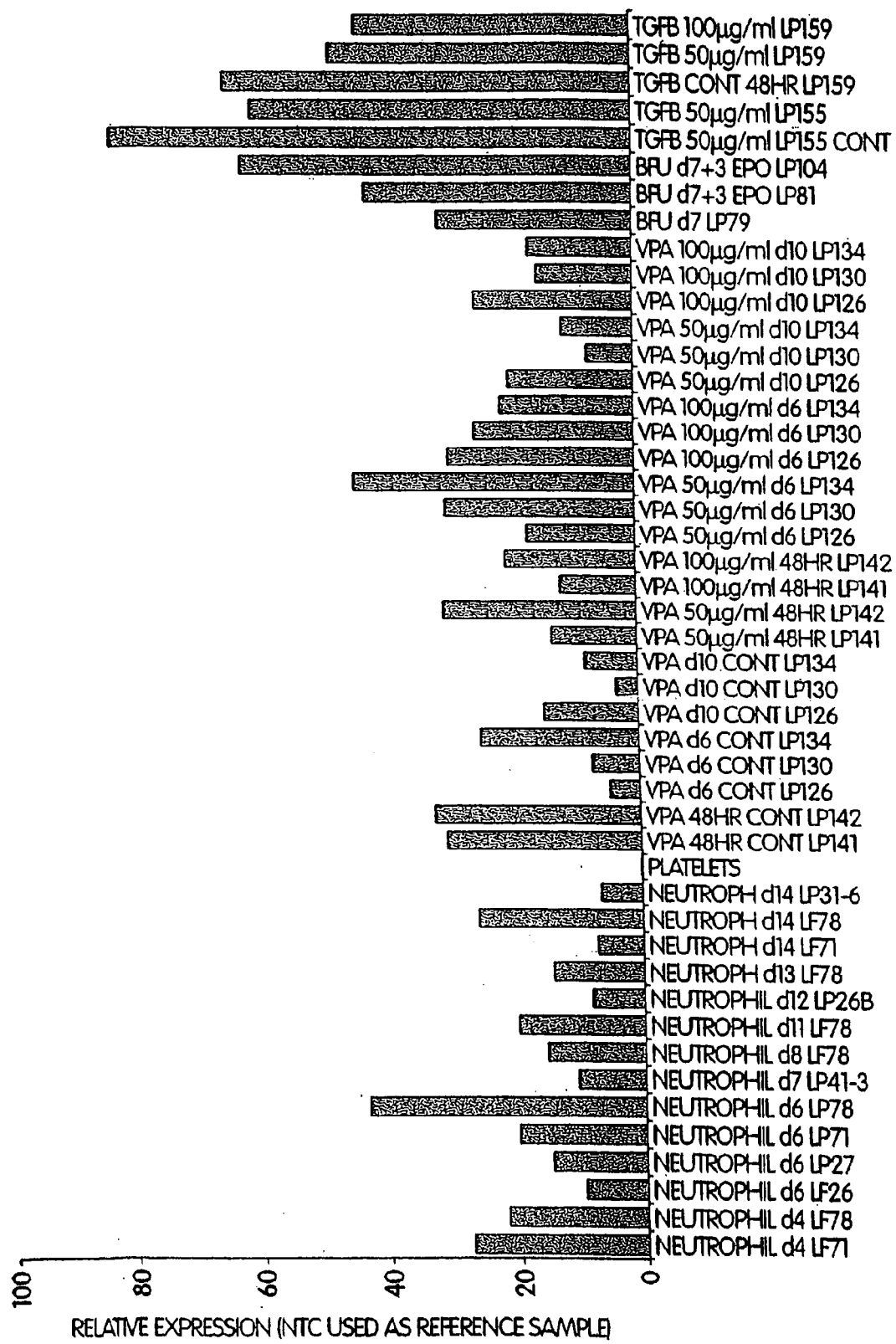
FIG. 24 is a bar graph depicting relative 23436 mRNA expression as determined by TaqMan assays on mRNA derived from human hematological cells including neutrophils, platelets, blood forming units (BFU), and TGFβ-treated hematopoietic precursors. BFUs treated with erythropoietin (EPO) have elevated 23436 expression levels.

To identify the presence of a "trypsin" domain in a 14089 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the PFAM HMM database resulting in the identification of a "trypsin domain" in the amino acid sequence of human 14089 at about residues 41 to 234 of SEQ ID NO:34 with a bit score of 122.5 (see FIGS. 18 and 20A-20B).

To identify the presence of a "trypsin" domain in a 14089 protein sequence, the amino acid sequence of the protein can also be searched against a SMART database (Simple Modular Architecture Research Tool) of HMMs as described in Schultz et al. (1998), *Proc. Natl. Acad. Sci. USA* 95:5857 and Schultz et al. (200) *Nucl. Acids Res* 28:231. The database contains domains identified by profiling with the hidden Markov models of the HMMer2 search program (R. Durbin et al. (1998) *Biological sequence analysis: probabilistic models of proteins and nucleic acids*. Cambridge University Press). The database also is extensively annotated and monitored by experts to enhance accuracy. A search was performed against the HMM database resulting in the identification of a "serine protease" domain in the amino acid sequence of human 14089 at about residues 24 to 234 of SEQ ID NO:34 (see FIG. 18).

The sequence of interest can also be characterized using the ProDom database. To perform this analysis, the amino acid sequence of the protein is searched against a database of domains, e.g., the ProDom database (Corpet et al. (1999), *Nucl. Acids Res.* 27:263-267) The ProDom protein domain database consists of an automatic compilation of homologous domains. Current versions of ProDom are built using recursive PSI-BLAST searches (Altschul SF et al. (1997) *Nucleic Acids Res.* 25:3389-3402; Gouzy et al. (1999) *Computers and Chemistry* 23:333-340.) of the SWISS-PROT 38 and TREMBL protein databases. The database automatically generates a consensus sequence for each domain. A BLAST search was performed against the HMM database resulting in the identification of a "protease serine precursor signal hydrolase zymogen glycoprotein family multigene factor" domain in the amino acid sequence of human 14089 at about residues 76 to 266 of SEQ ID NO:34 (see FIGS. 20A-20B).

A 14089 family member can include at least one trypsin domain and at least one serine protease, typsin family, histidine active site. Furthermore, a 14089 family member can include at least one, two, three, and preferably four predicted casein kinase II phosphorylation sites (PS00006); at least one, and preferably two predicted N-myristoylation sites (PS00008); at least one predicted tyrosine kinase phosphorylation site (PS00007); at least one amidation site (PS00009); and at least one or two, and preferably three N-glycosylation sites (PS00001).

As the 14089 polypeptides of the invention may modulate 14089-mediated activities, they may be useful as of for developing novel diagnostic and therapeutic agents for 14089-mediated or related disorders, as described below.

As used herein, a "14089 activity", "biological activity of 14089" or "functional activity of 14089", refers to an activity exerted by a 14089 protein, polypeptide or nucleic acid molecule on e.g., a 14089-responsive cell or on a 14089 substrate, e.g., a protein substrate, as determined in vivo or in vitro. In one embodiment, a 14089 activity is a direct activity, such as an association with a 14089 target molecule. A "target molecule" or "binding partner" is a molecule with which a 14089 protein binds or interacts in nature, e.g., a substrate for proteolytic cleavage. A 14089 activity can also be an indirect activity, e.g., a cellular signaling activity mediated by interaction of the 14089 protein with a 14089 receptor. Based on the above-described sequence similarities, the 14089 molecules of the present invention are predicted to have similar biological activities as serine protease family members. For example, the 14089 proteins of the present invention can have one or more of the following activities: (1) modulate (stimulate or inhibit) cellular proliferation (2) modulate cell differentiation; (3) modulate tumorigenesis and tumor invasion; (4) alter extracellular matrix composition; (5) catalyze polypeptide growth factor activation and release; (6) regulate the blood clotting cascade; (7) catalyze proteolytic cleavage of a substrate, e.g., a protein substrate (e.g., cleavage at an arginine or lysine residue; (8) catalyze the proteolytic activation of signaling molecules, e.g., other proteases, growth factor activation or release; or (9) regulate of cell motility or attachment.

Based on the above-described sequence similarities, the 14089 molecules of the present invention are predicted to have similar biological activities as other trypsin family members, such as hepsin proteases. Hepsin proteases are overexpressed in ovarian tumors and hepatoma cells (Tanimoto, H. et al. (1997) *Cancer Res.* 57:2884-2887). Further in vitro studies have shown inhibition of hepatoma cell proliferation using hepsin inhibitors (Torres-Rosado, A. et al. (1993) *Proc. Natl. Acad. Sci. USA* 90: 7181-7185). The 14089 molecules can serve as novel diagnostic targets and therapeutic agents for controlling disorders of cell proliferation, cell differentiation, organogenesis, coagulation, and cell signaling.

Thus, the 14089 molecules can act as novel diagnostic targets and therapeutic agents for controlling one or more of cellular proliferative and/or differentiative disorders. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

23436

One post-translational mechanism of regulating protein levels is the ubiquitin pathway. Ubiquitin is a highly conserved polypeptide expressed in all eukaryotic cells. Ubiquitin is covalently attached as a single molecule or as a conjugated form to lysine residue(s) of target proteins by formation of an isopeptide bond to the C-terminal glycine residue of ubiquitin. Most ubiquitinated proteins are subsequently targeted to the 26S proteasome, a multicatalytic protease, which cleaves the marked protein into peptide fragments.

Of the various enzymes involved in the ubiquitin protein degradation pathway, one type of enzyme, termed ubiquitin carboxy-terminal hydrolase (also "UCH" or "ubiquitin protease"), hydrolyzes the bond between ubiquitin and ubiquitin-tagged proteins and the bond linking ubiquitin-ubiquitin conjugates. This activity can provide a proofreading function, e.g., a function that reduces protein degradation. These enzymes can include determinants for substrate-specific recognition in order to selectively regulate degradation of their preferred substrates. They can also associate 19S regulatory complex of the 26S proteasome.

The regulatory function of ubiquitin carboxy-terminal hydrolases has been demonstrated for a number of cellular processes. For example, in *Drosophila* the ubiquitin carboxy-terminal hydrolase, fat facets (faf) is a regulator important for eye development (Chen and Fischer (2000) *Genetics* 156:1829-36). In yeast, the ubiquitin carboxy-terminal hydrolase UBP3 is associated with mating-type silencing (Moazed and Johnson (1996) *Cell* 86:667-77). These findings suggest that ubiquitin carboxy-terminal hydrolases exert a regulatory function by controlling de-ubiquitination of substrates.

Ubiquitination and de-ubiquitination are important processes through which protein levels and function are regulated in cells. Ubiquitination has been implicated in regulating numerous cellular processes including proliferation, differentiation, apoptosis (programmed cell death), transcription, signal-transduction, cell-cycle progression, receptor-mediated endocytosis, and organelle biogenesis. The activity of an enzyme mediating substrate de-ubiquitination or ubiquitin flux is key to the outcome of such processes.

Levels of ubiquitination can be altered in the diseased state. For example, in neuropathological conditions such as Alzheimer's and Pick's disease abnormal amounts of ubiquitinated proteins accumulate. In proliferative disorders, oncogenes (e.g., v-jun and v-fos) can be more resistant to ubiquitination in comparison to their normal cell counterparts. The failure to degrade oncogene protein products may contribute to their cell transformation capability.

The human 23436 sequence (SEQ ID NO:40), which is approximately 2446 nucleotides long including untranslated regions, contains a predicted methionine-initiated coding sequence of about 1458 nucleotides, including the TAA termination codon (nucleotides indicated as coding of SEQ ID NO:40; SEQ ID NO:42). The coding sequence encodes a 485 amino acid protein (SEQ ID NO:41).

Human 23436 contains the following regions or other structural features:

a ubiquitin carboxy-terminal hydrolase (family 2) domain with a first segment (PFAM Accession Number PF00442) located at about amino acid residues 89 to 120 of SEQ ID NO:41 and a second segment (PFAM Accession Number PF00443) located at about amino acid residues 332 to 420 of SEQ ID NO:41;

four predicted protein kinase C phosphorylation sites (PS00005) at about amino acids 17 to 19, 158 to 160, 280 to 282, and 398 to 400 of SEQ ID NO:41;

four predicted casein kinase II phosphorylation sites (PS00006) located at about amino acids 123 to 126, 143 to 146, 191 to 194, and 445 to 448 of SEQ ID NO:41;

two predicted cAMP/cGMP-dependent protein kinase phosphorylation sites (PS00004) located at about amino acids 84 to 87 and 458 to 461 of SEQ ID NO:41;

one predicted tyrosine kinase phosphorylation site (PS00007) located at about amino acids 261 to 268;

two predicted N-glycosylation sites (PS00001) from about amino acids 278 to 281 and 427 to 430 of SEQ ID NO:41;

one predicted amidation site (PS00009) from about amino acids 378 to 381 of SEQ ID NO:41; and three predicted N-myristylation sites (PS00008) from about amino acids 50 to 55, 173 to 178, and 406 to 411 of SEQ ID NO:41.

The ubiquitin carboxy-terminal hydrolase (family 2) domain of 23436 protein also features a conserved catalytic cysteine at about amino acid 98 of SEQ ID NO:41, and two conserved histidines at about amino acids 344 and 353 of SEQ ID NO:41. The two conserved histidines are contained within a ubiquitin specific carboxyl terminal hydrolase family signature domain (Prosite motif PS00973) located at about amino acid residues 336 to 354 (PFAM Accession PS00973);

For general information regarding PFAM identifiers, PS prefix and PF prefix domain identification numbers, refer to Sonnhammer et al. (1997) *Protein* 28:405-420.

The 23436 protein contains a significant number of characteristics in common with members of the ubiquitin carboxy-terminal hydrolase family 2. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Proteins of the ubiquitin carboxy-terminal hydrolase family 2 are characterized by a common fold with characteristics cysteine protease activity. The fold includes a conserved cysteine, e.g., the cysteine at about amino acid 98 of SEQ ID NO:41, which can be the catalytic cysteine for the protease domain. The fold also includes a conserved structural motif, characterized by the Prosite signature Y-X-L-X-[SAG]-[LIVMFT]-X(2)-H-x-G-X(4,5)-G-H-Y (wherein X is any amino acid; and numbers in parentheses indicate a repetition of a feature for the indicated number of residues or a range of residues; SEQ ID NO:45) which is located at about amino acids 336 to 354 of SEQ ID NO:41 and includes two conserved histidines, e.g., histidines at about amino acids 344 and 353 of SEQ ID NO:41. At least one of these histidines can participate in catalysis.

A 23436 polypeptide or subsequence thereof can include a "ubiquitin carboxy-terminal hydrolase domain," or a "ubiquitin protease domain," or sequences homologous with a "ubiquitin carboxy-terminal hydrolase or protease domain." As used herein the phrases, "ubiquitin carboxy-terminal hydrolase," "ubiquitin specific hydrolase," "ubiquitin hydrolase," "ubiquitin protease," or "ubiquitin specific protease" are used interchangeably and mean a polypeptide with the ability to remove one or more ubiquitin molecules from a protein that has one or more covalently attached molecules of ubiquitin. For example, the definition includes cleavage of conjugated forms of ubiquitin, e.g., at the peptide bond following the carboxy-terminal glycine (e.g., whether or not the ubiquitin conjugate is attached to a protein). In a preferred embodiment, the ubiquitin carboxy-terminal hydrolase can cleave a ubiquitin moiety from the $\epsilon$-NH$_2$ group of a lysine side chain of a target protein.

As used herein, the term "ubiquitin carboxy-terminal hydrolase domain" includes an amino acid sequence of about 300 to 450 amino acid residues in length and having a bit score for the alignment of the sequence to the first ubiquitin carboxy-terminal hydrolase (family 2) consensus (PFAM PF00442) of at least 20 and to the second ubiquitin carboxy-terminal hydrolase (family 2) consensus (PFAM PF00443) of at least 50. Preferably, a ubiquitin carboxy-terminal hydrolase domain includes at least about 300 to 450 amino acids, more preferably about 320 to 440 amino acid residues, or about 330 to 420 amino acids and has a bit score for the alignment of the sequence to the second ubiquitin carboxy-terminal hydrolase (family 2) domain consensus sequence (HMM) of at least 50, 60, 70, 75 or greater. The ubiquitin carboxy-terminal hydrolase (family 2) domain (HMM) has been assigned two non-contiguous consensus sequences PFAM Accession Numbers PF00442 and PF00443. An alignment of the ubiquitin carboxy-terminal hydrolase domain (amino acids 89 to 120 of SEQ ID NO:41) of human 23436 with the first ubiquitin carboxy-terminal hydrolase (family 2) consensus amino acid sequence (SEQ ID NO:43) derived from a hidden Markov model is depicted in FIG. 22A and an alignment of the ubiquitin carboxy-terminal hydrolase domain (amino acids 332 to 420 of SEQ ID NO:41) of human 23436 with the second ubiquitin carboxy-terminal hydrolase (family 2) consensus amino acid sequence (SEQ ID NO:44) derived from a hidden Markov model is depicted in FIG. 22B.

In a preferred embodiment, 23436 polypeptide or protein has a "ubiquitin carboxy-terminal hydrolase (family 2) domain" first signature region (PF00442) which includes at least about 10 to 70 more preferably about 20 to 50 or 24 to 35 amino acid residues and has at least about 50%, 60%, 70% 80% 90% 95%, 99%, or 100% homology with a "ubiquitin carboxy-terminal hydrolase (family 2) domain UCH-1," e.g., the first signature region of the ubiquitin carboxy-terminal hydrolase domain of human 23436 (e.g., residues 89 to 120 of SEQ ID NO:41). In a much preferred embodiment, the 23436 polypeptide includes a conserved catalytic cysteine at about residue 98 of SEQ ID NO:41.

In another preferred embodiment, 23436 polypeptide or protein has a "ubiquitin carboxy-terminal hydrolase (family 2) domain" second signature region (PF00443) which includes at least about 50 to 140 more preferably about 70 to 120, or 80 to 100 amino acid residues and has at least about 50%, 60%, 70% 80% 90% 95%, 99%, or 100% homology with a "ubiquitin carboxy-terminal hydrolase (family 2) domain UCH-2," e.g., the second signature region of the ubiquitin carboxy-terminal hydrolase domain of human 23436 (e.g., residues 379 to 420 of SEQ ID NO:41). In a much preferred embodiment, the 23436 polypeptide includes the two conserved histidines at about amino acids 344 and 353 of SEQ ID NO:41.

To identify the presence of a "ubiquitin carboxy-terminal hydrolase" domain in a 23436 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference. A search was performed against the HMM database resulting in the identification of a "ubiquitin carboxy-terminal hydrolase" domain in the amino acid sequence of human 23436 at about residues 89 to 420 (e.g., particularly the segments 89 to 120 and 332 to 420) of SEQ ID NO:41; see FIGS. 22A and 22B)).

A 23436 family member can include at least one ubiquitin carboxy-terminal hydrolase domain. Furthermore, a 23436 family member can include at least one, two, three, preferably four protein kinase C phosphorylation sites (PS00005); at least one, two, three, preferably four predicted casein kinase II phosphorylation sites (PS00006); at least one tyrosine kinase phosphorylation site (PS00009); at least one, preferably two cAMP and cGMP protein kinase phosphorylation sites (PS00004); at least one, preferably two N-glycosylation sites (PS00001); and at least one, two, preferably three predicted N-myristylation sites (PS00008).

As the 23436 polypeptides of the invention may modulate 23436-mediated activities, they may be useful as of for developing novel diagnostic and therapeutic agents for 23436-mediated or related disorders, as described below.

As used herein, a "23436 activity", "biological activity of 23436" or "functional activity of 23436", refers to an activity exerted by a 23436 protein, polypeptide or nucleic acid molecule. For example, a 23436 activity can be an activity exerted by 23436 in a physiological milieu on, e.g., a 23436-responsive cell or on a 23436 substrate, e.g., a ubiquitinated protein substrate or a ubiquitin-ubiquitin conjugate. A 23436 activity can be determined in vivo or in vitro. In one embodiment, a 23436 activity is a direct activity, such as an association with a 23436 target molecule. A "target molecule" or "binding partner" is a molecule with which a 23436 protein binds or interacts in nature. In a preferred embodiment, the target molecule is a ubiquitinated compound which is a substrate for 23436-mediated de-ubiquitination. In an exemplary embodiment, 23436 is an enzyme that catalyzes the removal of ubiquitin from a substrate, e.g., by hydrolyzing a peptide bond.

A 23436 activity can also be an indirect activity, e.g., decreased degradation or increased stability of a protein due to 23436-mediated de-ubiquitination, or a cellular signaling activity (e.g., proliferation, differentiation, apoptosis, etc.) that results from or is mediated by the 23436 protein or a protein de-ubiquitinated by 23436. For example, altered expression or activity of a 23436 molecule can cause an inhibition or failure to target proteins for degradation or, alternatively, excessive or undesirable protein degradation, leading to accumulation of protein in cells which, in turn, leads to a disorder of a tissue in which 23436 is normally expressed (e.g., the brain).

Based on the discovery disclosed herein, e.g., the above-described sequence similarities, the 23436 molecules of the present invention are predicted to have similar biological activities as ubiquitin carboxy-terminal hydrolase family 2 members. Protein ubiquitination is important in growth-factor-mediated cellular proliferation. The deubiquitinating enzymes act as regulatory enzymes that couple extracellular signaling to cell growth. 23436, which shows sequence similarity to a deubiquitinating hydrolase is believed to negatively regulates cytokine signaling in hematopoietic, e.g., erythroid, progenitors resulting in the inhibition of hematopoietic progenitor growth. Antagonists of this 23436 are expected to promote hematopoietic, e.g., erythroid, cell proliferation and differentiation.

Accordingly, the 23436 proteins of the present invention can have one or more of the following activities: (1) de-ubiquitinating polypeptides that are ubiquitinated; (2) cleaving ubiquitin conjugates (e.g., ubiquitin-tagged substrates, ubiquitin-tagged peptide fragments, head to tail linked ubiquitin molecules); (3) reversing targeting of a polypeptide to a proteasome (e.g., by removing ubiquitin targeting signals); or (4) altering flux in the ubiquitin pathway (e.g., by recycling ubiquitin from proteasome digestions products). Hence, modulation of 23436 polypeptide activity or expression are likely to influence degradation events, and thereby regulate cellular activities related to cell proliferation, cell signaling, cell death (e.g., apoptosis), cell motility, receptor-mediated endocytosis, organelle biogenesis, hematopoietic, e.g., erythroid, cell proliferation and differentiation, and cytokine-mediated signaling events.

Figure 25:
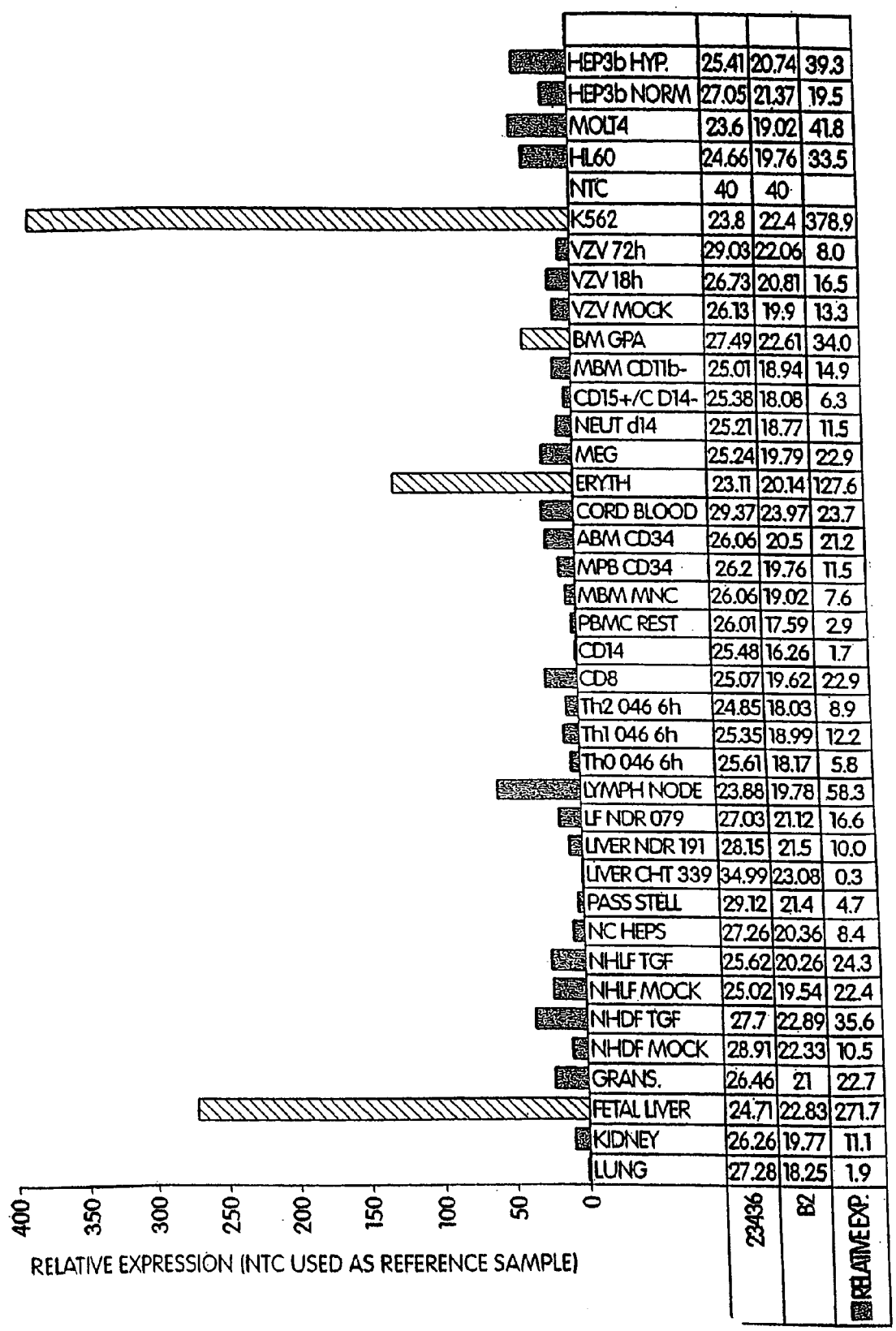
FIG. 25 is a bar graph depicting relative 23436 mRNA expression as determined by TaqMan assays on mRNA derived from the following cell types: (1) lung; (2) kidney; (3) fetal liver; (4) grans.; (5) NHDF mock; (6) NHDF TGF; (7) NHLF mock; (8) NHLF TGF; (9) NC Heps; (10) Pass Stell; (11) Liver CHT 339; (12) Liver NDR 191; (13) LF NDR 079; (14) Lymph Node; (15) Th0 046 6h; (16) Th1 046 6h; (17) Th2 046 6h; (18) CD8; (19) CD 14; (20) PBMC Rest; (21) MBM MNC; (22) MPB CD34; (23) ABM CD34; (24) Cord Blood; (25) Erythroid cells; (26) Megakaryocytes; (27) Neutrophil d14; (28) CD15+/CD14− cells; (29) MBM CD11b−; (30) BM GPA; (31) VZV mock; (32) VZV 18h; (33) VZV 72h; (34) K562; (35) NTC; (36) HL60; (37) Molt4; (38) Hep3b Normal; and (39) Hep3b Hyp. Erythroid K562 cells (34), erythroid cells (26), and fetal liver cells (3) have elevated 23436 mRNA expression levels.
Figure 26:
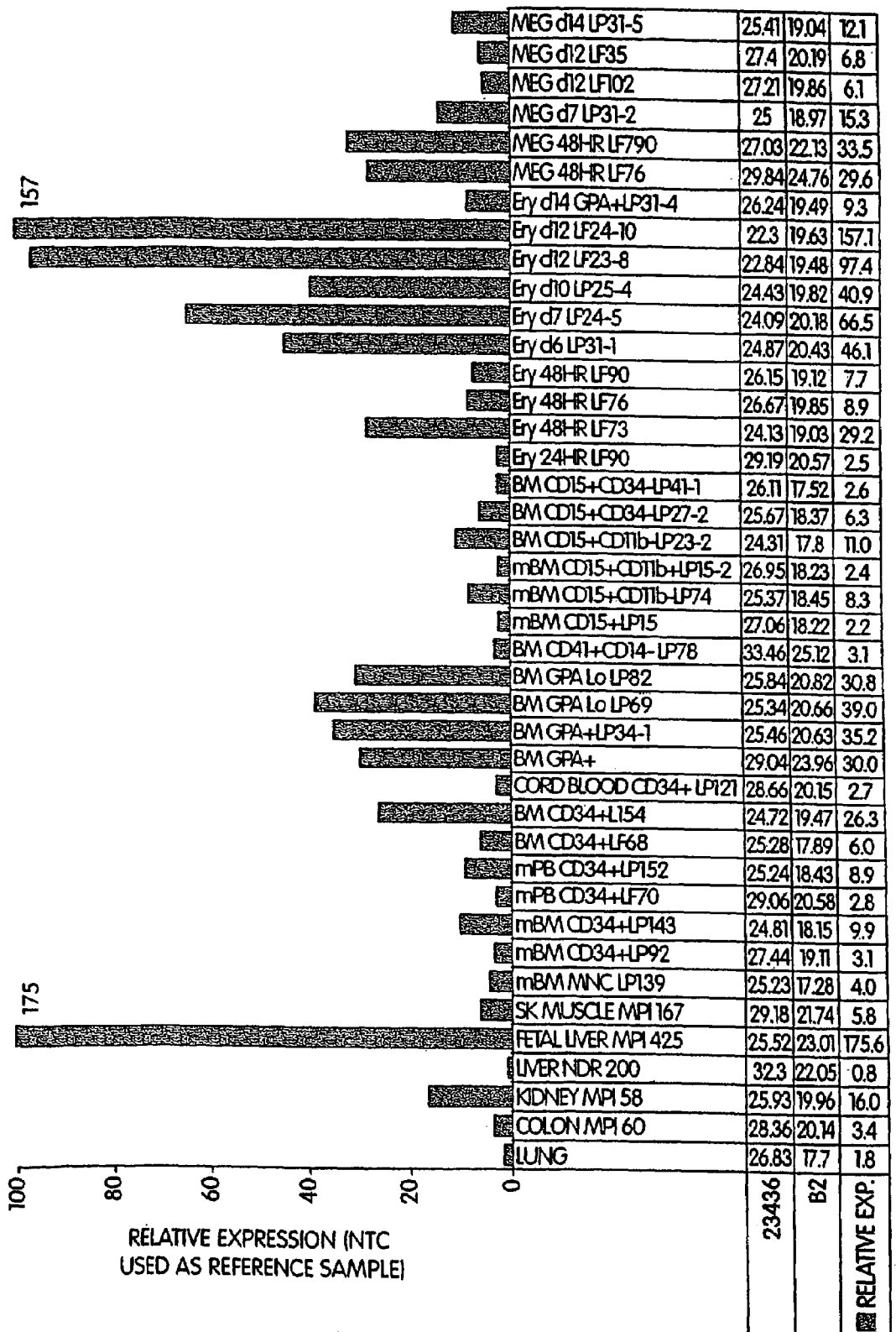
FIG. 26 is a bar graph depicting relative 23436 mRNA expression as determined by TaqMan assays on mRNA derived from the following cell types: (1) Lung; (2) Colon 60; (3) Kidney 58; (4) Liver NDR 200; (5) Fetal Liver 425; (6) Skeletal Muscle 167; (7) mBone Marrow MNC LP139; (8) mBone Marrow CD34+ LP92; (9) mBone Marrow CD34+LP143; (10) mPB CD34+ LF70; (11) mPB CD34+ LP152; (12) Bone Marrow CD34+LF68; (13) Bone Marrow CD34+ LF154; (14) Cord Blood CD34+ LP121; (15) Bone Marrow GPA+; (16) Bone Marrow GPA+ LP34-1; (17) Bone Marrow GPA Lo LP69; (18) Bone Marrow GPA Lo LP82; (19) Bone Marrow CD41+ CD14− LP78; (20) mBone Marrow CD15+ LP15; (21) mBone Marrow CD15+ CD11b− LP7-4; (22) mBone Marrow CD15+ CD11b+ LP15-2; (23) Bone Marrow CD15+ CD11b− LP23-2; (24) Bone Marrow CD15+ CD34− LP27-2; (25) Bone Marrow CD15+ CD34− LP41-1; (26) Erythroid 24 hr LF90; (27) Erythroid 48 hr LF73; (28) Erythroid 48 hr LF76; (29) Erythroid 48 hr LF90; (30) Erythroid d6 LP31-1; (31) Erythroid d7 LF24-5; (32) Erythroid d10 LP25-4; (33) Erythroid d12 LF23-8; (34) Erythroid d12 LF24-10; (35) Erythroid d14 GPA+LP31-4; (36) Meg 48 hr LF76; (37) Meg 48 hr LF790; (38) Meg d7 LP31-2; (39) Meg d12 LF102; (40) Meg d12 LF35; and (41) Meg d14 LP31-5. Fetal Liver (5) and day 12 erythroid cells (33) and (34) have elevated 23436 mRNA expression levels.

The molecules of the invention can be used to develop novel agents or compounds to treat and/or diagnose disorders involving aberrant activities of the cells in which 23436 nucleic acids and polypeptides are expressed. 23436 mRNA is found primarily in hematopoietic cells, and in particular, in cells of the erythroid lineage (FIGS. 25-26), as well as prostate, hypothalamus, and hepatoma cells. More specifically, high expression of 23436 was detected in fetal liver, bone marrow, erythroid progenitor and mature cells. Lower levels of expression were detected in the brain (e.g., the cortex), kidney, ovary, human vascular endothelial cells and hematopoietic progenitor cells. This pattern of expression suggests a role for 23436 in the function and development of the tissues in which it is expressed, and in particular in hematopoietic cells.

As the 23436 polypeptides of the invention may modulate 23436-mediated activities, they may be useful as of for developing novel diagnostic and therapeutic agents for 23436-mediated or related disorders, e.g., blood cell-associated or erythroid-associated disorders such as erythropoiesis, and other hematopoietic disorders.

As used herein, the term "erythroid associated disorders" include disorders involving aberrant (increased or deficient) erythroblast proliferation, e.g., an erythroleukemia; aberrant (increased or deficient) erythroblast differentiation, e.g., an anemia; anemias such as, for example, drug-(chemotherapy-) induced anemias, hemolytic anemias due to hereditary cell membrane abnormalities, such as hereditary spherocytosis, hereditary elliptocytosis, and hereditary pyropoikilocytosis; hemolytic anemias due to acquired cell membrane defects, such as paroxysmal nocturnal hemoglobinuria and spur cell anemia; hemolytic anemias caused by antibody reactions, for example to the RBC antigens, or antigens of the ABO system, Lewis system, Ii system, Rh system, Kidd system, Duffy system, and Kell system; methemoglobinemia; a failure of erythropoiesis, for example, as a result of aplastic anemia, pure red cell aplasia, myelodysplastic syndromes, sideroblastic anemias, and congenital dyserythropoietic anemia; secondary anemia in non-hematolic disorders, for example, as a result of chemotherapy, alcoholism, or liver disease; anemia of chronic disease, such as chronic renal failure; and endocrine deficiency diseases.

Agents that modulate 23436 polypeptide or nucleic acid activity or expression can be used to treat anemias, in particular, drug-induced anemias or anemias associated with cancer chemotherapy, chronic renal failure, malignancies, adult and juvenile rheumatoid arthritis, disorders of hemoglobin synthesis, prematurity, and zidovudine treatment of HIV infection. A subject receiving the treatment can be additionally treated with a second agent, e.g., erythropoietin, to further ameliorate the condition.

As used herein, the term "erythropoietin" or "EPO" refers to a glycoprotein produced in the kidney, which is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1,000-fold during hypoxia or anemia. Graber and Krantz (1978) *Ann. Rev. Med.* 29:51; Eschbach and Adamson (1985) *Kidney Intl.* 28:1. Recombinant human erythropoietin (rHuEpo or epoietin alpha) is commercially available as EPOGEN.RTM. (epoietin alpha, recombinant human erythropoietin) (Amgen Inc., Thousand Oaks, Calif.) and as PROCRIT.RTM. (epoietin alpha, recombinant human erythropoietin) (Ortho Biotech Inc., Raritan, N.J.).

Another example of an erythroid-associated disorder is erythrocytosis. Erythrocytosis, a disorder of red blood cell overproduction caused by excessive and/or ectopic erythropoietin production, can be caused by cancers, e.g., a renal cell cancer, a hepatocarcinoma, and a central nervous system cancer. Diseases associated with erythrocytosis include polycythemias, e.g., polycythemia vera, secondary polycythemia, and relative polycythemia.

Aberrant expression or activity of the 23436 molecules may be involved in neoplastic disorders. Accordingly, treatment, prevention and diagnosis of cancer or neoplastic disorders related to hematopoietic cells and, in particular, cells of the erythroid lineage are also included in the present invention. Such neoplastic disorders are exemplified by erythroid leukemias, or leukemias of erythroid precursor cells, e.g., poorly differentiated acute leukemias such as erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97). In particular, AML can include the uncontrolled proliferation of CD34+ cells such as AML subtypes M1 and M2, myeloblastic leukemias with and without maturation, and AML subtype M6, erythroleukemia (Di Guglielmo's disease). Additional neoplastic disorders include a myelodysplastic syndrome or preleukemic disorder, e.g., oligoblastic leukemia, smoldering leukemia. Additional cancers of the erythroid lineage include erythroblastosis, and other relevant diseases of the bone marrow.

The term "leukemia" or "leukemic cancer" is intended to have its clinical meaning, namely, a neoplastic disease in which white corpuscle maturation is arrested at a primitive stage of cell development. The disease is characterized by an increased number of leukemic blast cells in the bone marrow, and by varying degrees of failure to produce normal hematopoietic cells. The condition may be either acute or chronic. Leukemias are further typically categorized as being either lymphocytic i.e., being characterized by cells which have properties in common with normal lymphocytes, or myelocytic (or myelogenous), i.e., characterized by cells having some characteristics of normal granulocytic cells. Acute lymphocytic leukemia ("ALL") arises in lymphoid tissue, and ordinarily first manifests its presence in bone marrow. Acute myelocytic leukemia ("AML") arises from bone marrow hematopoietic stem cells or their progeny. The term acute myelocytic leukemia subsumes several subtypes of leukemia: myeloblastic leukemia, promyelocytic leukemia, and myelomonocytic leukemia. In addition, leukemias with erythroid or megakaryocytic properties are considered myelogenous leukemias as well.

The molecules of the invention may also modulate the activity of neoplastic, non-hematopoietic tissues in which they are expressed, e.g., liver and prostate. The 23436 molecules can act as novel diagnostic targets and therapeutic agents for controlling one or more of cellular proliferative and/or differentiative disorders. Examples of such cellular proliferative and/or differentiative disorders include cancer, e.g., carcinoma, sarcoma, or metastatic disorders. A metastatic tumor can arise from a multitude of primary tumor types, including but not limited to those of prostate and liver origin.

As used herein, the terms "cancer", "hyperproliferative", and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as those affecting lung, breast, thyroid, lymphoid, gastrointestinal, and the genitourinary tract. The terms "cancer" or "neoplasms" also includes adenocarcinomas that include malignancies such as prostate cancer and/or testicular tumors, and non-small cell carcinoma of the lung.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the prostate, and liver. The term also includes carcinosarcomas, e.g., malignant tumors composed of carcinomatous and sarcomatous tissues. The term "sarcoma" is art recognized and refers to malignant tumors of mesenchymal derivation.

An alteration in a 23436 nucleic acid or polypeptide can be associated with susceptibility for prostate cancer, e.g., early-onset prostate cancer, and/or brain cancer. As used herein, "a prostate disorder" refers to an abnormal condition occurring in the male pelvic region characterized by, e.g., male sexual dysfunction and/or urinary symptoms. This disorder may be manifested in the form of genitourinary inflammation (e.g., inflammation of smooth muscle cells) as in several common diseases of the prostate including prostatitis, benign prostatic hyperplasia and cancer, e.g., adenocarcinoma or carcinoma, of the prostate.

As used herein, the term "brain cancer" includes a hyperproliferative or neoplastic state of tissue in the brain, including tumors such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

The 53070, 15985, 26583, 21953, m32404, 14089, or 23436 protein, fragments thereof, and derivatives and other variants of the sequence in SEQ ID NO:2, 8, 15, 20, 25, 34, or 41 thereof are collectively referred to as "polypeptides or proteins of the invention" or "53070, 15985, 26583, 21953, m32404, 14089, or 23436 polypeptides or proteins." Nucleic acid molecules encoding such polypeptides or proteins are collectively referred to as "nucleic acids of the invention" or "53070, 15985, 26583, 21953, m32404, 14089, or 23436 nucleic acids." 53070, 15985, 26583, 21953, m32404, 14089, or 23436 molecules refer to 53070, 15985, 26583, 21953, m32404, 14089, or 23436 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:1, 3, 7, 9, 14, 16, 19, 21, 24, 26, 33, 35, 40, or 42, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a 53070, 15985, 26583, 21953, m32404, 14089, or 23436 protein. The gene can optionally further include non-coding sequences, e.g., regulatory sequences and introns. Preferably, a gene encodes a mammalian 53070, 15985, 26583, 21953, m32404, 14089, or 23436 protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 53070, 15985, 26583, 21953, m32404, 14089, or 23436 protein is at least 10% pure. In a preferred embodiment, the preparation of 53070, 15985, 26583, 21953, m32404, 14089, or 23436 protein has less than about 30%, 20%, 10% and more preferably 5% (by dry weight), of non-53070, 15985, 26583, 21953, m32404, 14089, or 23436 protein (also referred to herein as a "contaminating protein"), or of chemical precursors or non-53070, -15985, -26583, -21953, -m32404, -14089, or -23436 chemicals. When the 53070, 15985, 26583, 21953, m32404, 14089, or 23436 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 53070, 15985, 26583, 21953, m32404, 14089, or 23436 without abolishing or substantially altering a 53070, 15985, 26583, 21953, m32404, 14089, or 23436 activity. Preferably the alteration does not substantially alter the 53070, 15985, 26583, 21953, m32404, 14089, or 23436 activity, e.g., the activity is at least 20%, 40%, 60%, 70% or 80% of wild-type. An "essential" amino acid residue is a residue that, when altered from the wild-type sequence of 53070, 15985, 26583, 21953, m32404, 14089, or 23436, results in abolishing a 53070, 15985, 26583, 21953, m32404, 14089, or 23436 activity such that less than 20% of the wild-type activity is present. For example, conserved amino acid residues in 53070, 15985, 26583, 21953, m32404, 14089, or 23436 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a 53070, 15985, 26583, 21953, m32404, 14089, or 23436 protein is preferably replaced with another amino acid residue from the same side chain family. Alternatively, in another embodiment, mutations can be introduced randomly along all or part of a 53070, 15985, 26583, 21953, m32404, 14089, or 23436 coding sequence, such as by saturation mutagenesis, and the resultant mutants can be screened for 53070, 15985, 26583, 21953, m32404, 14089, or 23436 biological activity to identify mutants that retain activity. Following mutagenesis of SEQ ID NO: 1, 3, 7, 9, 14, 16, 19, 21, 24, 26, 33, 35, 40, or 42, the encoded protein can be expressed recombinantly and the activity of the protein can be determined.

As used herein, a "biologically active portion" of a 53070, 15985, 26583, 21953, m32404, 14089, or 23436 protein includes a fragment of a 53070, 15985, 26583, 21953, m32404, 14089, or 23436 protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 53070, 15985, 26583, 21953, m32404, 14089, or 23436 molecule and a non-53070, -15985, -26583, -21953, -m32404, -14089, or -23436 molecule or between a first 53070, 15985, 26583, 21953, m32404, 14089, or 23436 molecule and a second 53070, 15985, 26583, 21953, m32404, 14089, or 23436 molecule (e.g., a dimerization interaction). Biologically active portions of a 53070, 15985, 26583, 21953, m32404, 14089, or 23436 protein include peptides comprising amino acid sequences sufficiently homologous to or derived from the amino acid sequence of the 53070, 15985, 26583, 21953, m32404, 14089, or 23436 protein, e.g., the amino acid sequence shown in SEQ ID NO: 2, 8, 15, 20, 25, 34, or 41, which include less amino acids than the full length 53070, 15985, 26583, 21953, m32404, 14089, or 23436 proteins, and exhibit at least one activity of a 53070, 15985, 26583, 21953, m32404, 14089, or 23436 protein. Typically, biologically active portions comprise a domain or motif with at least one activity of the 53070, 15985, 26583, 21953, m32404, 14089, or 23436 protein, e.g., the ability to phosphorylate a substrate, to bind microtubules and/or phosphorylate proteins, to remove the phosphate from a serine or threonine residue of a phosphorylated protein, to bind and/or cleave polypeptide substrates, to bind peptide sequences and exhibit proteolytic activity, to bind proteolytic substrates, or to de-ubiquitinate substrates, respectively.

. A biologically active portion of a 53070, 15985, 26583, 21953, m32404, 14089, or 23436 protein can be a polypeptide which is, for example, 10, 25, 50, 100, 200 or more amino acids in length. Biologically active portions of a 53070, 15985, 26583, 21953, m32404, 14089, or 23436 protein can be used as targets for developing agents which modulate a 53070, 15985, 26583, 21953, m32404, 14089, or 23436 mediated activity, e.g., substrate phosphorylation; protein kinase activity or microtubule binding; prolyl oligopeptidase activity; protease activity; proteolytic cleavage of a substrate; or de-ubiquitinating activity or ubiquitin carboxy-terminal hydrolase activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 53070, 15985, 26583, 21953, m32404, 14089, or 23436 nucleic acid molecules of the invention. BLAST protein searches can be performed with the XBLAST program, score=50, wordlength=3 to obtain amino acid sequences homologous to 53070 protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

Particularly preferred 53070, 15985, 26583, 21953, m32404, 14089, or 23436 polypeptides of the present invention have an amino acid sequence substantially identical to the amino acid sequence of SEQ ID NO:2, 8, 15, 20, 25, 34, or 41, respectively. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about about 60%, or 65% identity, likely 75% identity, 80%, or 85% identity, likely 90% identity, more likely 91%, 92%, 93%, 94%, 95%, 96%, 97%, 98% or 99% identity to SEQ ID NO:2, 8, 15, 20, 25, 34, or 41 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65%, 70%, or 75% identity, likely 80% identity, more likely 85%, 90%. 91%, 92%, 93%, 94%, 95%, 96%, 97%, 98% or 99% identity to SEQ ID NO:1, 3, 7, 9, 14, 16, 19, 21, 24, 26, 33, 35, 40, or 42 are termed substantially identical.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules

In one aspect, the invention provides, isolated or purified, nucleic acid molecules that encode 53070, 15985, 26583, 21953, m32404, 14089, and 23436 polypeptides described herein, e.g., full-length 53070, 15985, 26583, 21953, m32404, 14089, or 23436 proteins or fragments thereof, e.g., a biologically active portion of 53070, 15985, 26583, 21953, m32404, 14089, or 23436 protein. Also included is a nucleic acid fragment suitable for use as a hybridization probe, which can be used, e.g., to identify a nucleic acid molecule encoding a polypeptide of the invention, 53070, 15985, 26583, 21953, m32404, 14089, or 23436 mRNA, and fragments suitable for use as primers, e.g., PCR primers for the amplification or mutation of nucleic acid molecules.

In one embodiment, an isolated nucleic acid molecule of the invention includes the nucleotide sequences shown in SEQ ID NO:1, 7, 14, 19, 24, 33, and 40, or a portion of any of these nucleotide sequences. In one embodiment, the nucleic acid molecule includes sequences encoding the human 53070, 15985, 26583, 21953, m32404, 14089, or 23436 protein (i.e., "the coding region" of SEQ ID NO:1, 7, 14, 19, 24, 33, or 40, as shown in SEQ ID NO: 3, 9, 16, 21, 26, 35, or 42), as well as 5' untranslated sequences. Alternatively, the nucleic acid molecule can include only the coding region of SEQ ID NO:1, 7, 14, 19, 24, 33, or 40 (e.g., SEQ ID NO3, 9, 16, 21, 26, 35, or 42) and, e.g., no flanking sequences which normally accompany the subject sequence. In another embodiment, the nucleic acid molecule encodes a sequence corresponding to a fragment of the 15985 protein from about amino acid 394 to 651 of SEQ ID NO:8; a fragment from about amino acid 67 to 158 of SEQ ID NO:8; or a fragment from about amino acid 192 to 280 of SEQ ID NO:8. In another embodiment, the nucleic acid molecule encodes a sequence corresponding to the mature 26583 protein from about amino acid 1 to amino acid 537 of SEQ ID NO:15. In another embodiment, the nucleic acid molecule encodes a sequence corresponding to a fragment of the 21953 protein that includes amino acid 672 to 744, 88 to 663, or 88 to 744 of SEQ ID NO:20. In another embodiment, the nucleic acid molecule encodes a sequence corresponding to a fragment of the m32404 protein from about amino acid 45 to 268 of SEQ ID NO:25. In another embodiment, the nucleic acid molecule encodes a sequence corresponding to a fragment of the m32404 protein from about amino acid 300 to 520 of SEQ ID NO:25. In another embodiment, the nucleic acid molecule encodes a sequence corresponding to a fragment of the 14089 protein from about amino acids 41 to 234 or 24 to 234 of SEQ ID NO:34 or the mature 14089 protein (about amino acids 19 to 241 of SEQ ID NO:34). In another embodiment, the nucleic acid molecule encodes a sequence corresponding to a fragment of the 23436 protein from about amino acid 89 to 420 of SEQ ID NO:41.

In another embodiment, an isolated nucleic acid molecule of the invention includes a nucleic acid molecule which is a complement of the nucleotide sequence shown in SEQ ID NO:1, 3, 7, 9, 14, 16, 19, 21, 24, 26, 33, 35, 40, or 42, or a portion of any of these nucleotide sequences. In other embodiments, the nucleic acid molecule of the invention is sufficiently complementary to the nucleotide sequence shown in SEQ ID NO:1, 3, 7, 9, 14, 16, 19, 21, 24, 26, 33, 35, 40, or 42, such that it can hybridize (e.g., under a stringency condition described herein) to the nucleotide sequence shown in SEQ ID NO: 1, 3, 7, 9, 14, 16, 19, 21, 24, 26, 33, 35, 40, or 42, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO: 1, 3, 7, 9, 14, 16, 19, 21, 24, 26, 33, 35, 40, or 42, or a portion, preferably of at least 260, 300, 350, 400, 450, 500, 520, 550, 590, 600, 650, 700, 750 800, 850, 900, 950, or 1000 nucleotides, of any of these nucleotide sequences.

Nucleic Acid Fragments

A nucleic acid molecule of the invention can include only a portion of the nucleic acid sequence of SEQ ID NO:1, 3, 7, 9, 14, 16, 19, 21, 24, 26, 33, 35, 40, or 42. For example, such a nucleic acid molecule can include a fragment which can be used as a probe or primer or a fragment encoding a portion of a 53070, 15985, 26583, 21953, m32404, 14089, or 23436 protein, e.g., an immunogenic or biologically active portion of a 53070, 15985, 26583, 21953, m32404, 14089, or 23436 protein. A fragment can comprise: those nucleotides of SEQ ID NO: 1 which encode a protein kinase domain of human 53070, e.g., about nucleotides 171 to 953 of SEQ ID NO:1; those nucleotides of SEQ ID NO:7, which encode a protein kinase domain or a doublecortin repeat of human 15985; those nucleotides encoding amino acids 172 to 461 or 99 to 523 of SEQ ID NO:15, which encode a phosphatase catalytic domain of human 26583; those nucleotides of SEQ ID NO:19 which encode a prolyl oligopeptidase domain of human 21953; those nucleotides of SEQ ID NO:24 which encode a trypsin domain of human m32404; those nucleotides of SEQ ID NO:33, which encode a trypsin domain of human 14809; or those nucleotides of SEQ ID NO:40, which encode a ubiquitin carboxy-terminal hydrolase domain of human 23436; The nucleotide sequence determined from the cloning of the 53070, 15985, 26583, 21953, m32404, 14089, or 23436 gene allows for the generation of probes and primers designed for use in identifying and/or cloning other 53070, 15985, 26583, 21953, m32404, 14089, or 23436 family members, or fragments thereof, as well as 53070, 15985, 26583, 21953, m32404, 14089, or 23436 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 50, 95, 100, 150, 200, 300, 360, 400, 600, 650, or 700 amino acids in length. Fragments also include nucleic acid sequences corresponding to specific amino acid sequences described above or fragments thereof. Nucleic acid fragments should not be construed as encompassing those fragments that may have been disclosed prior to the invention.

A nucleic acid fragment can include a sequence corresponding to a domain, region, or functional site described herein. A nucleic acid fragment can also include one or more domains, regions, or functional sites described herein. Thus, for example, a 53070 nucleic acid fragment can include a sequence corresponding to a protein kinase domain or a C-terminal non-kinase domain; a 15985 nucleic acid fragment can include a sequence corresponding to protein kinase domain or a doublecortin repeat; a 26583 nucleic acid fragment can include a serine/threonine phosphatase catalytic domain, a protein kinase C phosphorylation site, an N-glycosylation site, a casein kinase II phosphorylation site, an N-myristoylation sit, an amidation site, a protein phosphatase 2C signature domain, or any combination thereof; a 21953 nucleic acid fragment can include a sequence corresponding to a prolyl oligopeptidase domain; an m32404 nucleic acid fragment can include a sequence corresponding to a trypsin domain; a 14089 nucleic acid fragment can include a sequence corresponding to a trypsin domain; and a 23436 nucleic acid fragment can include a sequence corresponding to a ubiquitin carboxy-terminal hydrolase domain;

In one embodiment, a nucleic acid fragment can include nucleotides 1 to 250, 50 to 300, 100 to 350, 150 to 400, 200 to 450, 250 to 500, 300 to 650, 350 to 700, 400 to 700, 450 to 750, 500 to 800, 550 to 850, 600 to 900, 650 to 950, 700 to 1000, 800 to 1200, 900 to 1300, 1000 to 1400, 1100 to 1500, 1200 to 1600, 1300 to 1700, 1400 to 1800, 1500 to 1900, 1600 to 2000, 1700 to 2100, 1253 to 1307, 1253 to 1337, 1241 to 1379, 1382 to 1505, 1241 to 1505, 773 to 1514, 953 to 1118, 953 to 1226, 1121 to 1226, 1253 to 1367, 773 to 1514, 500 to 560, or 512 to 605 of SEQ ID NO:40, or any combination thereof.

In a preferred embodiment, the fragment is at least 300, 500, 520, 590, 600, 650, 700, 750, 800, 850, 900, 950, or 1000 nucleotides in length.

53070, 15985, 26583, 21953, m32404, 14089, or 23436 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, 3, 7, 9, 14, 16, 19, 21, 24, 26, 33, 35, 40, or 42, or of a naturally occurring allelic variant or mutant of SEQ ID NO:1, 3, 7, 9, 14, 16, 19, 21, 24, 26, 33, 35, 40, or 42.

In a preferred embodiment the nucleic acid is a probe which is at least 5, 10, 12, 15, 18, or 20 and less than 500, 300, or 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: a kinase domain of 53070, e.g., about nucleotides 171 to 953 of SEQ ID NO:1 or a portion thereof, or a C-terminal non-kinase domain of 53070, e.g., about nucleotides 954 to 1241 of SEQ ID NO:1 or a portion thereof; a protein kinase domain of 15985 from about amino acid 394 to 651 of SEQ ID NO:8; and/or doublecortin repeats from about amino acids 67 to 158 amino acids and from 192 to 280 of SEQ ID NO:8; a serine/threonine phosphatase catalytic domain of 26583: amino acids 172 to 461 or 99 to 523 of SEQ ID NO:15; a fragment of the 21953 protein that includes amino acid 672 to 744, 88 to 663, or 88 to 744 of SEQ ID NO:20; a trypsin domain of the 14089 polypeptide (about amino acid 24 to 234 or 41 to 234 of SEQ ID NO:34; or amino acids about 89 to 420, 89 to 120, 332 to 378, 379 to 420, 332 to 420, 236 to 291, 292 to 327, 336 to 374, 176 to 423 and 85 to 105 of SEQ ID NO:41.

In another embodiment a set of primers is provided, e.g., primers suitable for use in a PCR, which can be used to amplify a selected region of a 53070, 15985, 26583, 21953, m32404, 14089, or 23436 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: a molecule that encodes a protein kinase domain, from about nucleotides 171 to 593 of SEQ ID NO:1; a molecule that encodes a C-terminal non-kinase domain, from about nucleotides 954 to 1241 of SEQ ID NO:1 , a protein kinase domain from about amino acid 394 to 651 of SEQ ID NO:8; a doublecortin repeat from about amino acids 67 to 158 of SEQ ID NO:8, or a doublecortin repeat from 192 to 280 of SEQ ID NO:8; the serine/threonine phosphatase catalytic domain (amino acid residues 172 to 461 or 99 to 523 of SEQ ID NO:15); a prolyl oligopeptidase domain from about amino acid 672 to 744, 88 to 663, or 88 to 744 of SEQ ID NO:20; a trypsin domain from about amino acid 45 to 268 of SEQ ID NO:25; a trypsin domain from about amino acid 311 to 520 of SEQ ID NO:25; a histidine active site located at about amino acid 73 to 78 of SEQ ID NO:25; a histidine active site located at about amino acid 337 to 342 of SEQ ID NO:25; and a serine active site located at about amino acid 222 to 226 of SEQ ID NO:25; a trypsin domain from about amino acid 24 to 234 or 41 to 234 ofr SEQ ID NO:34; a conserved histidine residue present at about amino acid 56 of SEQ ID NO:34; a serine active site located at amino acid 195 of SEQ ID NO:34; and a ubiquitin carboxy-terminal hydrolase domain from about amino acid 89 to 420 of SEQ ID NO:41.

A nucleic acid fragment can encode an epitope bearing region of a polypeptide described herein.

A nucleic acid fragment encoding a "biologically active portion of a 53070, 15985, 26583, 21953, m32404, 14089, or 23436 polypeptide" can be prepared by isolating a portion of the nucleotide sequence of SEQ ID NO:1, 3, 7, 9, 14, 16, 19, 21, 24, 26, 33, 35, 40, or 42, which encodes a polypeptide having a 53070, 15985, 26583, 21953, m32404, 14089, or 23436 biological activity (e.g., the biological activities of the 53070, 15985, 26583, 21953, m32404, 14089, and 23436 proteins are described herein), expressing the encoded portion of the 53070, 15985, 26583, 21953, m32404, 14089, or 23436 protein (e.g., by recombinant expression in vitro) and assessing the activity of the encoded portion of the 53070, 15985, 26583, 21953, m32404, 14089, or 23436 protein. For example, a nucleic acid fragment encoding a biologically active portion of 53070 includes a protein kinase domain, e.g., about nucleotides 171 to 953 of SEQ ID NO:1. A nucleic acid fragment encoding a biologically active portion of 15985 includes a protein kinase domain, e.g., amino acid residues about 394 to 651 of SEQ ID NO:8, a doublecortin repeat from about amino acid 67 to 158 of SEQ ID NO:8, or a doublecortin repeat from about amino acid 192 to 280 of SEQ ID NO:8. A nucleic acid fragment encoding a biologically active portion of 26583 includes a serine/threonine phosphatase catalytic domain, e.g., amino acid residues 99 to 523 of SEQ ID NO:15. A nucleic acid fragment encoding a biologically active portion of 21953 includes a prolyl oligopeptidase domain e.g., amino acid residues about 672 to 744, 88 to 663, or 88 to 744 of SEQ ID NO:20. A nucleic acid fragment encoding a biologically active portion of m32404 includes a trypsin domain, e.g., amino acid residues about 45 to 268 or 311 to 520 of SEQ ID NO:25. A nucleic acid fragment encoding a biologically active portion of 14089 includes a trypsin domain, e.g., amino acid residues about 24 to 234 or 41 to 234 of SEQ ID NO:34. A nucleic acid fragment encoding a biologically active portion of 23436 includes a ubiquitin carboxy-terminal hydrolase domain, e.g. amino acid residues about 89 to 420 of SEQ ID NO:41. A nucleic acid fragment encoding a biologically active portion of a 53070, 15985, 26583, 21953, m32404, 14089, or 23436 polypeptide, may comprise a nucleotide sequence which is greater than 280, 300, 361, 400, 470, 800, 1000, 1600, or more nucleotides in length.

In preferred embodiments, the nucleic acid fragment includes a nucleotide sequence that is other than, e.g., differs by at least one, two, three of more nucleotides from, the sequence of AA498169 or AI480580. E.g., a nucleic acid fragment can: include one or more nucleotides from SEQ ID NO:24 or SEQ ID NO:26 outside the region of nucleotides 1699-2033 or 1711-2034 of SEQ ID NO:24; not include all of the nucleotides of AA498169 or AI480580, e.g., can be one or more nucleotides shorter (at one or both ends) than the sequence of AA498169 or AI480580; or can differ by one or more nucleotides in the region of overlap.

In preferred embodiments, the fragment comprises the coding region of 46508, e.g., the nucleotide sequence of SEQ ID NO:26. In other embodiments, the fragment comprises nucleotides 1-1698 or 2034-2219 of SEQ ID NO:24, or a fragment thereof (e.g., nucleotides 1-500, 500-1000, 1000-1698, 2034-2100, 2100-2200, or 2200-2219 of SEQ ID NO:24).

In preferred embodiments, a nucleic acid includes a nucleotide sequence which is about 300, 340, 400, 500, 590, 600, 650, 700, 750, 800, 850, 900, 1000, 1100, 1200, 1300, 1400, 1500, 1600, 1700, 1800, 1900, 2100, 2200, 2300, 2400, 2500, 2600, 2700, 2800, 2900, 3000, 3100, 3200, 3300, 3400, 3500, 3550, or more nucleotides in length and hybridizes under a stringency condition described herein to a nucleic acid molecule of SEQ ID NO:1, 3, 7, 9, 14, 16, 19, 21, 24, 26, 33, 35, 40, or 42. In a preferred embodiment, a nucleic acid includes at least one contiguous nucleotide from the region about nucleotides 1-200, 138-301, 171-401, 302-569, 402-692, 531-812, 660-932, 773-953, 873-1112, 954-1160, 1053-1241, 1161-1400, 1242-1550, 1350-1600, 1550-1704 of SEQ ID NO:1 or SEQ ID NO:3. In a preferred embodiment, the nucleic acid includes a contiguous sequence that includes approximately nucleotide 1640, or 1642 of SEQ ID NO:19, e.g., the region from nucleotide 1635 to 1645 of SEQ ID NO:19. In other embodiment the nucleic acid includes a contiguous sequence that includes about nucleotides 1 to 25, 1 to 66, 100 to 300, 300 to 700, 500 to 800, 800 to 1200, 1000 to 1400, or 1200 to 1600 of SEQ ID NO:19.

In a preferred embodiment, a nucleic acid fragment differs by at least 1, 2, 3, 10, 20, or more nucleotides from, the sequence of Genbank accession number U66059, e.g., from nucleotides 315-571 of SEQ ID NO:33; the sequence of SEQ ID NO:247 of WO 01/40466; the sequence of SEQ ID NO:5 or 6 of WO 01/72961; the sequence of SEQ ID NO:22 of WO 01/71004. Differences can include differing in length or sequence identity. For example, a nucleic acid fragment can: include one or more nucleotides from SEQ ID NO:33 or SEQ ID NO:35 located outside the region of nucleotides 315 to 571, 94 to 938, 136 to 861, 173 to 861, 1-570, 572 to 947 of SEQ ID NO:33, e.g., can be one or more nucleotides shorter (at one or both ends) than the sequence of Genbank accession number U66059, e.g., from nucleotides 315-571 of SEQ ID NO:33; the sequence of SEQ ID NO:247 of WO 01/40466; the sequence of SEQ ID NO:5 or 6 of WO 01/72961; the sequence of SEQ ID NO:22 of WO 01/71004; or can differ by one or more nucleotides in the region of overlap.

Nucleic Acid Variants

The invention further encompasses nucleic acid molecules that differ from the nucleotide sequence shown in SEQ ID NO: 1, 3, 7, 9, 14, 16, 19, 21, 24, 26, 33, 35, 40, or 42. Such differences can be due to degeneracy of the genetic code (and result in a nucleic acid which encodes the same 53070, 15985, 26583, 21953, m32404, 14089, or 23436 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO: 2, 8, 15, 20, 25, 34, or 41. If alignment is needed for this comparison the sequences should be aligned for maximum homology. "Looped" out sequences from deletions or insertions, or mismatches, are considered differences.

Nucleic acids of the invention can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO: 1, 3, 7, 9, 14, 16, 19, 21, 24, 26, 33, 35, 40, or 42, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the sequence shown in SEQ ID NO:2, 8, 15, 20, 25, 34, or 41 or a fragment of this sequence. Such nucleic acid molecules can readily be identified as being able to hybridize under a stringency condition described herein, to the nucleotide sequence shown in SEQ ID NO: 1, 7, 14, 19, 24, 33, or 40 or a fragment of the sequence. Nucleic acid molecules corresponding to orthologs, homologs, and allelic variants of the 53070, 15985, 26583, 21953, m32404, 14089, or 23436 cDNAs of the invention can further be isolated by mapping to the same chromosome or locus as the 53070, 15985, 26583, 21953, m32404, 14089, or 23436 gene.

Preferred 53070 variants include those that are correlated with protein kinase activity, particularly serine/threonine protein kinase activity. Preferred 15985 variants include those that are correlated with protein kinase and/or microtubule binding activity. Preferred 26583 variants include those that are correlated with phosphatase activity, e.g., serine/threonine phosphatase activity. Preferred 21953 variants include those that are correlated with dipeptidyl peptidase or prolyl endopeptidases activity. Preferred m32404 variants include those that are correlated with modulating (stimulating and/or enhancing or inhibiting) cellular proliferation, differentiation, or tumorigenesis; modulating an immune response (i.e. modulating the complementation system); modulating hormone production; modulating the blood clotting cascade; or modulating proteolysis of protein substrates. Preferred 14089 variants include those that are correlated with proteolytic cleave of substrates. Preferred 23436 variants include those that are correlated with de-ubiquitinating activity.

Allelic variants of 53070, 15985, 26583, 21953, m32404, 14089, or 23436, e.g., human 53070, 15985, 26583, 21953, m32404, 14089, or 23436, include both functional and non-functional proteins. Functional allelic variants are naturally occurring amino acid sequence variants of the 53070 protein within a population that maintain the ability to bind ATP and phosphorylate substrates. Functional allelic variants of the 15985 protein maintain the ability to bind microtubules and/or phosphorylate proteins. Functional allelic variants of the 26583 protein maintain the ability to remove the phosphate from a serine or threonine residue of a phosphorylated protein. Functional allelic variants of the 21953 protein maintain the ability to bind and/or cleave polypeptide substrates, e.g., a polypeptide having a proline residue. Functional allelic variants of the m32404 protein maintain the ability to bind peptide sequences and exhibit proteolytic activity. Functional allelic variants of the 14089 protein maintain the ability to bind proteolytic substrates. Functional allelic variants of the 23436 protein maintain the ability to de-ubiquitinate substrates. Functional allelic variants will typically contain only conservative substitution of one or more amino acids of SEQ ID NO:2, 8, 15, 20, 25, 34, or 41, or substitution, deletion or insertion of non-critical residues in non-critical regions of the protein. Non-functional allelic variants are naturally-occurring amino acid sequence variants of the 53070, e.g., human 53070, protein within a population that do not have the ability to bind ATP or phosphorylate some or all substrates. Non-functional allelic variants of the 15985 protein not have the ability to bind to cytoskeletal proteins, e.g., microtubules, or phosphorylate proteins. Non-functional allelic variants of the 26583 protein not have the ability to to remove the phosphate from a serine or threonine residue of a phosphorylated protein. Non-functional allelic variants of the 21953 protein not have the ability to bind and/or cleave polypeptide substrates, e.g., a polypeptide having a proline residue. Non-functional allelic variants of the m32404 protein not have the ability to peptide sequences and exhibit proteolytic activity. Non-functional allelic variants of the 14089 protein not have the ability to cleave a substrate. Non-functional allelic variants of the 23436 protein not have the ability to de-ubiquitinate substrates. Non-functional allelic variants will typically contain a non-conservative substitution, a deletion, or insertion, or premature truncation of the amino acid sequence of SEQ ID NO:2, 8, 15, 20, 25, 34, or 41, or a substitution, insertion, or deletion in critical residues or critical regions of the protein.

Moreover, nucleic acid molecules encoding other 53070, 15985, 26583, 21953, m32404, 14089, or 23436 family members and, thus, which have a nucleotide sequence which differs from the 53070, 15985, 26583, 21953, m32404, 14089, or 23436 sequences of SEQ ID NO:1, 3, 7, 9, 14, 16, 19, 21, 24, 26, 33, 35, 40, or 42 are intended to be within the scope of the invention.

Antisense Nucleic Acid Molecules, Ribozymes and Modified Nucleic Acid Molecules

In still another embodiment, a ribozyme. A ribozyme having specificity for a 53070-, 15985-, 26583-, 21953-, m32404-, 14089-, or 23436-encoding nucleic acid can include one or more sequences complementary to the nucleotide sequence of a 53070, 15985, 26583, 21953, m32404, 14089, or 23436 cDNA disclosed herein (i.e., 1, 3, 7, 9, 14, 16, 19, 21, 24, 26, 33, 35, 40, or 42), and a sequence having known catalytic sequence responsible for mRNA cleavage (see U.S. Pat. No. 5,093,246 or Haselhoff and Gerlach (1988) *Nature* 334:585-591). For example, a derivative of a *Tetrahymena* L-19 IVS RNA can be constructed in which the nucleotide sequence of the active site is complementary to the nucleotide sequence to be cleaved in a 53070-, 15985-, 26583-, 21953-, m32404-, 14089-, or 23436-encoding mRNA. See, e.g., Cech et al. U.S. Pat. No. 4,987,071; and Cech et al. U.S. Pat. No. 5,116,742. Alternatively, 53070, 15985, 26583, 21953, m32404, 14089, or 23436 mRNA can be used to select a catalytic RNA having a specific ribonuclease activity from a pool of RNA molecules. See, e.g., Bartel, D. and Szostak, J. W. (1993) Science 261:1411-1418.

53070, 15985, 26583, 21953, m32404, 14089, or 23436 gene expression can be inhibited by targeting nucleotide sequences complementary to the regulatory region of the 53070, 15985, 26583, 21953, m32404, 14089, or 23436 (e.g., the 53070, 15985, 26583, 21953, m32404, 14089, or 23436 promoter and/or enhancers) to form triple helical structures that prevent transcription of the 53070, 15985, 26583, 21953, m32404, 14089, or 23436 gene in target cells. See generally, Helene, C. (1991) *Anticancer Drug Des.* 6:569-84; Helene, C. i (1992) *Ann. N. Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 53070, 15985, 26583, 21953, m32404, 14089, or 23436 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulme (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of 53070, 15985, 26583, 21953, m32404, 14089, or 23436 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 53070, 15985, 26583, 21953, m32404, 14089, or 23436 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958-976) or intercalating agents. (see, e.g., Zon (1988) *Phann. Res.* 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 53070, 15985, 26583, 21953, m32404, 14089, or 23436 nucleic acid of the invention, two complementary regions one having a fluorophore and one a quencher such that the molecular beacon is useful for quantitating the presence of the 53070, 15985, 26583, 21953, m32404, 14089, or 23436 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated Polypeptides of the Invention

In another aspect, the invention features, an isolated 53070, 15985, 26583, 21953, m32404, 14089, or 23436 protein, or fragment, e.g., a biologically active portion, for use as immunogens or antigens to raise or test (or more generally to bind) anti-53070, -15985, -26583, -21953, -m32404, -14089, or -23436 antibodies. 53070, 15985, 26583, 21953, m32404, 14089, or 23436 protein can be isolated from cells or tissue sources using standard protein purification techniques. 53070, 15985, 26583, 21953, m32404, 14089, or 23436 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present when expressed in a native cell.

In a preferred embodiment, a 53070 polypeptide has one or more of the following characteristics:

it has the ability to bind a nucleoside tri-phosphate, e.g., ATP;

it has the ability to phosphorylate a substrate protein, e.g., another protein or itself;

it has a molecular weight, e.g., a deduced molecular weight, preferably ignoring any contribution of post translational modifications, amino acid composition or other physical characteristic of a 53070 polypeptide, e.g., a polypeptide of SEQ ID NO:2;

it has an overall sequence similarity of at least 60%, 70%, preferably at least 75%, more preferably at least 80%, 90%, or 95%, with a polypeptide of SEQ ID NO:2;

it has a protein kinase domain which is preferably about 80%, 90%, 95%, or more homologous with amino acid residues about 12 to 272 of SEQ ID NO:2;

it has a serine/threonine protein kinase active-site signature motif (PS00108);

it has at least one, preferably two, three, four, five, six, seven, eight, nine, ten, eleven, twelve, or more preferably thirteen of the invariant amino acid residues present in protein kinase family members, and described above;

it has at least one, two, three, four, preferably five predicted Protein kinase C phosphorylation sites (PS00005);

it has at least one, two, preferably three predicted Casein kinase II phosphorylation sites (PS00006); and it has at least one predicted N-myristoylation site (PS00008).

In a preferred embodiment, a 15985 polypeptide has one or more of the following characteristics:

it has the ability to phosphorylate a protein substrate, e.g., a serine and/or threonine side chains of a protein substrate;

it has the ability to bind to cytoskeletal proteins, e.g., microtubules;

it has the ability to modulate cell morphology and/or migration;

it has a molecular weight, e.g., a deduced molecular weight, preferably ignoring any contribution of post translational modifications, amino acid composition or other physical characteristic of a 15985 polypeptide, e.g., a polypeptide of SEQ ID NO:8;

it has an overall sequence similarity of at least 60%, more preferably at least 70, 80, 90, or 95%, with a polypeptide of SEQ ID NO:8;

it can be found in a tumor cell (e.g., an ovarian, lung, or breast tumor cell), neuronal cells;

it has a protein kinase domain which is preferably about 70%, 80%, 90% or 95% identical with amino acid residues about 394 to 651 of SEQ ID NO:8;

it can colocalize with microtubules; or it has at least one, and preferably two doublecortin repeats which are preferably about 70%, 80%, 90% or 95% identical with amino acid residues from about amino acids 67 to 158 and/or 192 to 280 of SEQ ID NO:8.

In a preferred embodiment, a 26583 polypeptide has one or more of the following characteristics:

it has the ability to promote removal of phosphate from phosphorylated serine or threonine residues of protein;

it has a molecular weight (e.g., a deduced molecular weight), amino acid composition or other physical characteristic of a 26583 protein, e.g., a 26583 protein of SEQ ID NO:15;

it has an overall sequence similarity of at least 60%, more preferably at least 70, 80, 90, 95%, most preferably at least 99%, with a polypeptide encoded by SEQ ID NO:16;

it has a phosphatase catalytic domain which is preferably about 70%, 80%, 90%, 95%, most preferably at least 99%, identical to amino acid residues 99-523 of SEQ ID NO:15;

it has a phosphatase catalytic domain which is preferably about 70%, 80%, 90%, 95%, most preferably at least 99%, identical to with amino acid residues 172 to 461 of SEQ ID NO:15; or it has at least 70%, preferably at least 80%, and most preferably at least 95% of the cysteines found in the amino acid sequence of the native protein.

In a preferred embodiment, a 21953 polypeptide has one or more of the following characteristics:

it has the ability to promote the degradation of proline-containing peptides by cleaving the peptide bond at the carboxyl side of proline residues;

it has a molecular weight, (e.g., about 97 KDa), amino acid composition, or other physical characteristic, of a 21953 polypeptide, e.g., a polypeptide of SEQ ID NO:20;

it has an overall sequence similarity of at least 60%, more preferably at least 70, 80, 90, or 95%, with a polypeptide of SEQ ID NO:20;

it has a prolyl oligopeptidase domain which has preferably about 70%, 80%, 90% or 95% sequence similarity with amino acid residues 672-744 of SEQ ID NO:20; or it has at least 70%, preferably 80%, and most preferably 90% of the cysteines found in the amino acid sequence of the native protein (SEQ ID NO:20).

In a preferred embodiment, an m32404 polypeptide has one or more of the following characteristics:

it exhibits proteolytic activity;

it has a molecular weight, or an amino acid composition of an m32404 polypeptide, e.g., a polypeptide of SEQ ID NO:25.

it has an overall sequence similarity of at least 60%, more preferably at least 70, 80, 90, or 95%, with a polypeptide of SEQ ID NO:25;

it can be found in human tissue;

it has a trypsin domain with a sequence which is preferably about 70%, 80%, 90% or 95% similar with amino acid residues about 45 to 268 or 311 to 520 of SEQ ID NO:25; or it has at least 10, preferably at least 12, and most preferably at least 16 of the 22 cysteines found in the amino acid sequence of the native protein.

In a preferred embodiment, a 14089 polypeptide has one or more of the following characteristics:

it has protease activity;

it has a molecular weight, e.g., a deduced molecular weight, preferably ignoring any contribution of post-translational modifications, amino acid composition or other physical characteristic of a 14089 polypeptide, e.g., a polypeptide of SEQ ID NO:34;

it has an overall sequence similarity of at least 60%, more preferably at least 70, 80, 90, or 95%, with a polypeptide of SEQ ID NO:34;

it has a trypsin domain which is preferably about 70%, 80%, 90% or 95% with amino acid residues about 24 to 234 or 41 to 234 of SEQ ID NO:34; or it has at least 5, preferably 7, and most preferably 8 of the 9 cysteines found in the amino acid sequence of the native protein.

In a preferred embodiment, a 23436 polypeptide has one or more of the following characteristics:

it has the ability to de-ubiquitinate substrates, e.g., by means of a ubiquitin carboxy-terminal hydrolase activity;

it has a molecular weight, e.g., a deduced molecular weight, preferably ignoring any contribution of post trans-lational modifications, amino acid composition or other physical characteristic of SEQ ID NO:41;

it has an overall sequence similarity of at least 60%, more preferably at least 70, 80, 90, 95%, 97%, 98% or 99%, with a polypeptide a of SEQ ID NO:41;

it can be found in erythroid cells, erythroid precursors, liver, prostate, and hypothalamus;

it has a ubiquitin carboxy-terminal hydrolase (family 2) domain which is preferably about 70%, 80%, 90%, 95%, 98%, or 99% homologous with amino acid residues about 89 to 420 of SEQ ID NO:41; and/or it has a conserved cysteine at about amino acid 98 of SEQ ID NO:41 and two conserved histidines at about amino acids 344 and 353 of SEQ ID NO:41.

In a preferred embodiment the 53070, 15985, 26583, 21953, m32404, 14089, or 23436 protein, or fragment thereof, differs from the corresponding sequence in SEQ ID: 2, 8, 15, 20, 25, 34, or 41. In one embodiment it differs by at least one but by less than 15, 10 or 5 amino acid residues. In another it differs from the corresponding sequence in SEQ ID NO: 2, 8, 15, 20, 25, 34, or 41 by at least one residue but less than 20%, 15%, 10% or 5% of the residues in it differ from the corresponding sequence in SEQ ID NO: 2, 8, 15, 20, 25, 34, or 41. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In a preferred embodiment the differences are not in the 53070 protein kinase domain, e.g., about amino acid residues 12 to 272 of SEQ ID NO:2. In another preferred embodiment one or more differences are in the 53070 protein kinase domain, e.g., about amino acid residues 12 to 272 of SEQ ID NO:2 . In a preferred embodiment the differences are not in the 15985 protein kinase domain nor in the 15985 doublecortin repeats.

In another preferred embodiment one or more differences are in the 15985 protein kinase domain and/or the 15985 doublecortin repeats. In a preferred embodiment, the differences are not in the 26583 serine/threonine phosphatase catalytic domain. In another preferred embodiment one or more differences are at 26583 non-active site residues, e.g., amino acids 1-98, or 524 to 537 of SEQ ID NO:15. In a preferred embodiment the differences are not in the 21953 prolyl oligopeptidase domain and/or the DPP IV N-terminal domain. In another preferred embodiment one or more differences are in the 21953 prolyl oligopeptidase domain and/or the DPP IV N-terminal domain. In a preferred embodiment the differences are not in the m32404 trypsin domain, i.e., from about amino acid 45 to 268 or 311 to 520 of SEQ ID NO:25. In another preferred embodiment one or more differences are in the m32404 trypsin domain, i.e., from about amino acid 45 to 268 or 311 to 520 of SEQ ID NO:25. In a preferred embodiment the differences are not in the 14089 trypsin domain. In another preferred embodiment one or more differences are in the 14089 trypsin domain. In a preferred embodiment the differences are not in the 23436 ubiquitin carboxy-terminal hydrolase domain, e.g., the region from about amino acid 89 to 120 and 332 to 420 of SEQ ID NO:41. In another preferred embodiment one or more differences are in the 23436 ubiquitin carboxy-terminal hydrolase domain, e.g., the region from about amino acid 89 to 120 and 332 to 420 of SEQ ID NO:41.

Other embodiments include a protein that contain one or more changes in amino acid sequence, e.g., a change in an amino acid residue which is not essential for activity. Such 53070, 15985, 26583, 21953, m32404, 14089, or 23436 proteins differ in amino acid sequence from SEQ ID NO: 2, 8, 15, 20, 25, 34, or 41, yet retain biological activity.

In one embodiment, the protein includes an amino acid sequence at least about 60%, 65%, 70%, 75%, 80%, 85%, 90%, 95%, 98%, 99% or more homologous to SEQ ID NO: 2, 8, 15, 20, 25, 34, or 41.

The present invention also pertains to fragments of the 53070, 15985, 26583, 21953, m32404, 14089, or 23436 polypeptides. For examples, fragments of the 53070 polypeptides which include amino acid residues about 103 to 119, about 226 to 247, or about 301 to 329 of SEQ ID NO:2, which correspond to hydrophilic regions of the 53070 protein. Similarly, fragments of 53070 which include residues about 63 to 73, about 86 to 102, or about 199 to 216 of SEQ ID NO:2 correspond to hydrophobic regions of the 53070 protein. Fragments of 53070 which include residues about 12 to 45, about 125 to 150, or about 150 to 175 of SEQ ID NO:2 correspond to protein kinase domain of the 53070 protein; and fragments of 53070 which include amino acid residues about 1 to 11 and 273 to 367 of SEQ ID NO:2 correspond to non-kinase domain region of the 53070 protein.

A 53070 protein or fragment is provided which varies from the sequence of SEQ ID NO:2 in regions defined by amino acids about 273 to 367 by at least one but by less than 15, 10 or 5 amino acid residues in the protein or fragment but which does not differ from SEQ ID NO:2 in regions defined by amino acids about 1 to 272. Additionally, a 53070 protein is provided which varies from the sequence of SEQ ID NO:2 in regions defined by amino acids about 1 to 90 or, alternatively, 91 to 272 by at least one but by less than 15, 10, or 5 amino acid residues in the protein or fragment, but which does not differ from SEQ ID NO:2 in regions defined by amino acids 91 to 367 or 1 to 90 and 273 to 367, respectively. (If these comparisons require alignment, the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

A 15985 protein or fragment is provided which varies from the sequence of SEQ ID NO:8 in regions defined by amino acids about 67 to 158, 192 to 280, and 394 to 651 by at least one but by less than 15, 10 or 5 amino acid residues in the protein or fragment but which does not differ from SEQ ID NO:8 in regions defined by amino acids about 67 to 158, 192 to 280, and 394 to 651. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 15985 protein includes a protein kinase domain and/or doublecortin repeats. Moreover, other biologically active portions, in which other regions of the protein are deleted, can be prepared by recombinant techniques and evaluated for one or more of the functional activities of a native 15985 protein.

In another embodiment, the protein includes an amino acid sequence at least 213 amino acids in length, and about 60%, 65%, 70%, 75%, 80%, 85%, 90%, 95%, 98%, homologous to SEQ ID NO:15.

In another embodiment, a 26583 protein or fragment has an amino acid sequence which differs from the sequence of AAA30697 by at least one, two, three, five or more amino acids. The variations may include the addition, replacement, and/or deletion of amino acid residues.

A 26583 protein or fragment is provided which varies from the sequence of SEQ ID NO:15 in non-active site residues by at least one but by less than 15, 10 or 5 amino acid residues in the protein or fragment, but which does not differ from SEQ ID NO:15 in regions having phosphatase catalytic activity. (If this comparison requires alignment the sequences should be aligned for maximum homology. "Looped" out sequences from deletions, insertions, or mismatches, are considered differences.) In some embodiments, the difference is at a non-essential residue or is a conservative substitution, while in others, the difference is at an essential residue or is a non conservative substitution.

A 21953 protein or fragment is provided which varies from the sequence of SEQ ID NO:20 in regions defined by amino acids about 672 to 744 by at least one but by less than 15, 10 or 5 amino acid residues in the protein or fragment but which does not differ from SEQ ID NO:20 in regions defined by amino acids about 672 to 744. In some embodiments, the 21953 protein includes at least one contiguous amino acid from the region of about amino acid 1 to 200, 100 to 300, 200 to 400, 300 to 500, 400 to 600, 500 to 700, or 600 to 800 of SEQ ID NO:20.

In another preferred embodiment, the 21953 protein has a $K_m$ for the substrate H-Gly-Pro-p-nitroanilide (NA)/HCl (Sigma Corp, MO, USA) (H-Gly-Pro-pNA) of less than about 10 mM, 5 mM, 1 mM, 0.5 mM, 0.2 mM, or 0.1 mM, and/or a $V_{max}$ for H-Gly-Pro-pNA of about at least 100, 500, 1000, 3000, 5000, or 10000 absorbance units·min$^{-1}$. Such parameters can be determined using a prolyl oligopeptidase assay described herein, e.g., as described in "Screening Assays," below.

An m32404 protein or fragment is provided which varies from the sequence of SEQ ID NO:25 in regions defined by amino acids about 1 to 46 and 269 to 520 by at least one but by less than 15, 10 or 5 amino acid residues in the protein or fragment but which does not differ from SEQ ID NO:25 in regions defined by amino acids about 45 to 268. An m32404 protein or fragment is also provided which varies from the sequence of SEQ ID NO:25 in regions defined by amino acids about 1 to 310, and 521 to 552, of SEQ ID NO:25 by at least one but by less than 15, 10 or 5 amino acid residues in the protein or fragment but which does not differ from SEQ ID NO:25 in regions defined by amino acids about 311 to 520 of SEQ ID NO:25.

A 14089 protein or fragment is provided which varies from the sequence of SEQ ID NO:34 in regions defined by amino acids about 41 to 234 by at least one but by less than 15, 10 or 5 amino acid residues in the protein or fragment but which does not differ from SEQ ID NO:34 in regions defined by amino acids about 41 to 234.

In a preferred embodiment, a 14089 fragment differs by at least 1, 2, 3, 10, 20, or more amino acid residues encoded by a sequence present in Genbank accession number U66059, e.g., from nucleotides 315-571 of SEQ ID NO:33; the sequence of SEQ ID NO:247 of WO 01/40466; the sequence of SEQ ID NO:5 or 6 of WO 01/72961; the sequence of SEQ ID NO:22 of WO 01/71004. Differences can include differing in length or sequence identity. For example, a fragment can: include one or more amino acid residues from SEQ ID NO:34 outside the region encoded by nucleotides 315 to 571, 94 to 938, 136 to 861, 173 to 861, 1-570, 572 to 947 of SEQ ID NO:33; not include all of the amino acid residues encoded by a nucleotide sequence in Genbank accession number U66059, e.g., from nucleotides 315-571 of SEQ ID NO:33; the sequence of SEQ ID NO:247 of WO 01/40466; the sequence of SEQ ID NO:5 or 6 of WO 01/72961; the sequence of SEQ ID NO:22 of WO 01/71004, e.g., can be one or more amino acid residues shorter (at one or both ends) than a sequence encoded by the nucleotide sequence in Genbank accession number U66059, e.g., from nucleotides 315-571 of SEQ ID NO:33; the sequence of SEQ ID NO:247 of WO 01/40466; the sequence of SEQ ID NO:5 or 6 of WO 01/72961; the sequence of SEQ ID NO:22 of WO 01/71004; or can differ by one or more amino acid residues in the region of overlap.

A 23436 protein or fragment is provided which varies from the sequence of SEQ ID NO:41 in regions defined by amino acids about 1 to 88, 121 to 331, and 421 to 485 by at least one but by less than 15, 10 or 5 amino acid residues in the protein or fragment but which does not differ from SEQ ID NO:41 in regions defined by amino acids about 89 to 120, and 332 to 420. Such polypeptide fragments of 23436 containing functional domains, signatures, and/or modification sites, and nucleic acids encoding same can be useful, e.g., as immunogens or as competitive inhibitors. For example, to inhibit 23436 mediated de-ubiquitination, a ubiquitinated protein can be contacted with a substrate binding subsequence of 23436 which lacks de-ubiquitination activity thereby inhibiting or blocking de-ubiquitination by 23436 having the activity. A variant of 23436 lacking de-ubiquitination activity can be generated by mutating the conserved cysteine at about amino acid 98 of SEQ ID NO:41, e.g., to alanine, or the conserved histidines at about amino acids 344 and 353 of SEQ ID NO:41, e.g., to alanine. To inhibit phosphorylation of a particular site of 23436 polypeptide in a cell, a 23436 polypeptide having a mutation at the site, e.g., to alanine, can be introduced or expressed in cells. To alter the activity of a 23436 polypeptide in a cell, a 23436 polypeptide having an activating mutation, e.g., a mutation to aspartic or glutamic acid, of a phosphorylation site, e.g., a predicted phosphorylation site described herein, can be introduced or expressed in cells.

In one embodiment, a biologically active portion of a 53070, 15985, 26583, 21953, m32404, 14089, or 23436 protein includes a protein kinase domain, a protein kinase domain and/or doublecortin repeats, a serine/threonine phosphatase catalytic domain, a prolyl oligopeptidase domain and/or a DPP IV N-terminal domain, a trypsin domain, a trypsin domain, or a ubiquitin carboxy-terminal hydrolase domain, respectively. Moreover, other biologically active portions, in which other regions of the protein are deleted, can be prepared by recombinant techniques and evaluated for one or more of the functional activities of a native 53070, 15985, 26583, 21953, m32404, 14089, or 23436 protein.

In a preferred embodiment, the 53070, 15985, 26583, 21953, m32404, 14089, or 23436 protein has an amino acid sequence shown in SEQ ID NO:2, 8, 15, 20, 25, 34, or 41, respectively. In other embodiments, the 53070, 15985, 26583, 21953, m32404, 14089, or 23436 protein is substantially identical to SEQ ID NO:2, 8, 15, 20, 25, 34, or 41, respectively. In yet another embodiment, the 53070, 15985, 26583, 21953, m32404, 14089, or 23436 protein is substantially identical to SEQ ID NO:2, 8, 15, 20, 25, 34, or 41 and retains the functional activity of the protein of SEQ ID NO:2, 8, 15, 20, 25, 34, or 41, as described in detail in the subsections above.

Chimeric or Fusion Proteins

In another aspect, the invention provides 53070, 15985, 26583, 21953, m32404, 14089, or 23436 chimeric or fusion proteins. As used herein, a 53070, 15985, 26583, 21953, m32404, 14089, or 23436 "chimeric protein" or "fusion protein" includes a 53070, 15985, 26583, 21953, m32404, 14089, or 23436 polypeptide linked to a non-53070, -15985, -26583, -21953, -m32404, -14089, or -23436 polypeptide. A "non-53070, -15985, -26583, -21953, -m32404, -14089, or -23436 polypeptide" refers to a polypeptide having an amino acid sequence corresponding to a protein which is not substantially homologous to the 53070, 15985, 26583, 21953, m32404, 14089, or 23436 protein, e.g., a protein which is different from the 53070, 15985, 26583, 21953, m32404, 14089, or 23436 protein and which is derived from the same or a different organism. The 53070, 15985, 26583, 21953, m32404, 14089, or 23436 polypeptide of the fusion protein can correspond to all or a portion e.g., a fragment described herein of a 53070, 15985, 26583, 21953, m32404, 14089, or 23436 amino acid sequence. In a preferred embodiment, a 53070, 15985, 26583, 21953, m32404, 14089, or 23436 fusion protein includes at least one (or two) biologically active portion of a 53070, 15985, 26583, 21953, m32404, 14089, or 23436 protein. The non-53070, -15985, -26583, -21953, -m32404, -14089, or -23436 polypeptide can be fused to the N-terminus or C-terminus of the 53070, 15985, 26583, 21953, m32404, 14089, or 23436 polypeptide.

The fusion protein can include a moiety which has a high affinity for a ligand. For example, the fusion protein can be a GST-53070, -15985, -26583, -21953, -m32404, -14089, or -23436 fusion protein in which the 53070, 15985, 26583, 21953, m32404, 14089, or 23436 sequences are fused to the C-terminus of the GST sequences. Such fusion proteins can facilitate the purification of recombinant 53070, 15985, 26583, 21953, m32404, 14089, or 23436. Alternatively, the fusion protein can be a 53070, 15985, 26583, 21953, m32404, 14089, or 23436 protein containing a heterologous signal sequence at its N-terminus. In certain host cells (e.g., mammalian host cells), expression and/or secretion of 53070, 15985, 26583, 21953, m32404, 14089, or 23436 can be increased through use of a heterologous signal sequence.

Fusion proteins can include all or a part of a serum protein, e.g., an IgG constant region, or human serum albumin.

The 53070, 15985, 26583, 21953, m32404, 14089, or 23436 fusion proteins of the invention can be incorporated into pharmaceutical compositions and administered to a subject in vivo. The 53070, 15985, 26583, 21953, m32404, 14089, or 23436 fusion proteins can be used to affect the bioavailability of a 53070, 15985, 26583, 21953, m32404, 14089, or 23436 substrate. 53070, 15985, 26583, 21953, m32404, 14089, or 23436 fusion proteins may be useful therapeutically for the treatment of disorders caused by, for example, (i) aberrant modification or mutation of a gene encoding a 53070, 15985, 26583, 21953, m32404, 14089, or 23436 protein; (ii) mis-regulation of the 53070, 15985, 26583, 21953, m32404, 14089, or 23436 gene; and (iii) aberrant post-translational modification of a 53070, 15985, 26583, 21953, m32404, 14089, or 23436 protein.

Moreover, the 53070-, 15985-, 26583-, 21953-, m32404-, 14089-, or 23436-fusion proteins of the invention can be used as immunogens to produce anti-53070, -15985, -26583, -21953, -m32404, -14089, or -23436 antibodies in a subject, to purify 53070, 15985, 26583, 21953, m32404, 14089, or 23436 ligands and in screening assays to identify molecules which inhibit the interaction of 53070, 15985, 26583, 21953, m32404, 14089, or 23436 with a 53070, 15985, 26583, 21953, m32404, 14089, or 23436 substrate.

Expression vectors are commercially available that already encode a fusion moiety (e.g., a GST polypeptide). A 53070-, 15985-, 26583-, 21953-, m32404-, 14089-, or 23436-encoding nucleic acid can be cloned into such an expression vector such that the fusion moiety is linked in-frame to the 53070, 15985, 26583, 21953, m32404, 14089, or 23436 protein.

Variants of 53070, 15985, 26583, 21953, m32404, 14089, or 23436 Proteins

In another aspect, the invention also features a variant of a 53070, 15985, 26583, 21953, m32404, 14089, or 23436 polypeptide, e.g., which functions as an agonist (mimetics) or as an antagonist. Variants of the 53070, 15985, 26583, 21953, m32404, 14089, or 23436 proteins can be generated by mutagenesis, e.g., discrete point mutation, the insertion or deletion of sequences or the truncation of a 53070, 15985, 26583, 21953, m32404, 14089, or 23436 protein. An agonist of the 53070, 15985, 26583, 21953, m32404, 14089, or 23436 proteins can retain substantially the same, or a subset, of the biological activities of the naturally occurring form of a 53070, 15985, 26583, 21953, m32404, 14089, or 23436 protein. An antagonist of a 53070, 15985, 26583, 21953, m32404, 14089, or 23436 protein can inhibit one or more of the activities of the naturally occurring form of the 53070, 15985, 26583, 21953, m32404, 14089, or 23436 protein by, for example, competitively modulating a 53070-, 15985-, 26583-, 21953-, m32404-, 14089-, or 23436-mediated activity of a 53070, 15985, 26583, 21953, m32404, 14089, or 23436 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 53070, 15985, 26583, 21953, m32404, 14089, or 23436 protein.

Variants of a 53070, 15985, 26583, 21953, m32404, 14089, or 23436 protein can be identified by screening combinatorial libraries of mutants, e.g., truncation mutants, of a 53070, 15985, 26583, 21953, m32404, 14089, or 23436 protein for agonist or antagonist activity.

Libraries of fragments e.g., N terminal, C terminal, or internal fragments, of a 53070, 15985, 26583, 21953, m32404, 14089, or 23436 protein coding sequence can be used to generate a variegated population of fragments for screening and subsequent selection of variants of a 53070, 15985, 26583, 21953, m32404, 14089, or 23436 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 53070, 15985, 26583, 21953, m32404, 14089, or 23436 proteins. Recursive ensemble mutagenesis (REM), a new technique which enhances the frequency of functional mutants in the libraries, can be used in combination with the screening assays to identify 53070, 15985, 26583, 21953, m32404, 14089, or 23436 variants (Arkin and Yourvan (1992) *Proc. Natl. Acad. Sci. USA* 89:7811-7815; Delgrave et al. (1993) *Protein Engineering* 6:327-331).

Cell-based assays can be exploited to analyze a variegated 53070, 15985, 26583, 21953, m32404, 14089, or 23436 library. For example, a library of expression vectors can be transfected into a cell line, e.g., a cell line, which ordinarily responds to 53070, 15985, 26583, 21953, m32404, 14089, or 23436 in a substrate-dependent manner. The transfected cells are then contacted with 53070, 15985, 26583, 21953, m32404, 14089, or 23436 and the effect of the expression of the mutant on signaling by the 53070, 15985, 26583, 21953, m32404, 14089, or 23436 substrate can be detected, e.g., by measuring the phosphorylation of a substrate, by measuring protein kinase activity and/or microtubule binding, by measuring phosphorylation of serine or threonine residues, by measuring prolyl oligopeptidase as described below, by measuring m32404 protease activity, by measuring 14089 protease activity, or by measuring de-ubiquitinating activity, respectively. Plasmid DNA can then be recovered from the cells which score for inhibition, or alternatively, potentiation of signaling by the 53070, 15985, 26583, 21953, m32404, 14089, or 23436 substrate, and the individual clones further characterized.

In another aspect, the invention features a method of making a 53070, 15985, 26583, 21953, m32404, 14089, or 23436 polypeptide, e.g., a peptide having a non-wild type activity, e.g., an antagonist, agonist, or super agonist of a naturally occurring 53070, 15985, 26583, 21953, m32404, 14089, or 23436 polypeptide, e.g., a naturally occurring 53070, 15985, 26583, 21953, m32404, 14089, or 23436 polypeptide. The method includes: altering the sequence of a 53070, 15985, 26583, 21953, m32404, 14089, or 23436 polypeptide, e.g., altering the sequence , e.g., by substitution or deletion of one or more residues of a non-conserved region, a domain or residue disclosed herein, and testing the altered polypeptide for the desired activity.

In another aspect, the invention features a method of making a fragment or analog of a 53070, 15985, 26583, 21953, m32404, 14089, or 23436 polypeptide a biological activity of a naturally occurring 53070, 15985, 26583, 21953, m32404, 14089, or 23436 polypeptide. The method includes: altering the sequence, e.g., by substitution or deletion of one or more residues, of a 53070, 15985, 26583, 21953, m32404, 14089, or 23436 polypeptide, e.g., altering the sequence of a non-conserved region, or a domain or residue described herein, and testing the altered polypeptide for the desired activity.

Anti-53070, -15985, -26583, -21953, -m32404, -14089, or -23436 Antibodies

In another aspect, the invention provides an anti-53070, -15985, -26583, -21953, -m32404, -14089, or -23436 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-53070, -15985, -26583, -21953, -m32404, -14089, or -23436 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH--terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 53070, 15985, 26583, 21953, m32404, 14089, or 23436 polypeptide or fragment thereof. Examples of antigen-binding fragments of the anti-53070, -15985, -26583, -21953, -m32404, -14089, or -23436 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-53070, -15985, -26583, -21953, -m32404, -14089, or -23436 antibody can be a polyclonal or a monoclonal antibody. In other embodiments, the antibody can be recombinantly produced, e.g., produced by phage display or by combinatorial methods.

Phage display and combinatorial methods for generating anti-53070, -15985, -26583, -21953, -m32404, -14089, or -23436 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, the contents of all of which are incorporated by reference herein).

In one embodiment, the anti-53070, -15985, -26583, -21953, -m32404, -14089, or -23436 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-53070, -15985, -26583, -21953, -m32404, -14089, or -23436 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 53070, 15985, 26583, 21953, m32404, 14089, or 23436 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *Bio Techniques* 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 53070, 15985, 26583, 21953, m32404, 14089, or 23436 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585, 089, the contents of which are hereby incorporated by reference. Other techniques for humanizing antibodies are described in Padlan et al. EP 519596 A1, published on Dec. 23, 1992.

In preferred embodiments an antibody can be made by immunizing with purified 53070, 15985, 26583, 21953, m32404, 14089, or 23436 antigen, or a fragment thereof, e.g., a fragment described herein, membrane associated antigen, tissue, e.g., crude tissue preparations, whole cells, preferably living cells, lysed cells, or cell fractions, e.g., cytosolic fractions.

A full-length 53070, 15985, 26583, 21953, m32404, 14089, or 23436 protein or, antigenic peptide fragment of 53070, 15985, 26583, 21953, m32404, 14089, or 23436 can be used as an immunogen or can be used to identify anti-53070, -15985, -26583, -21953, -m32404, -14089, or -23436 antibodies made with other immunogens, e.g., cells, membrane preparations, and the like. The antigenic peptide of 53070, 15985, 26583, 21953, m32404, 14089, or 23436 should include at least 8 amino acid residues of the amino acid sequence shown in SEQ ID NO: 2, 8, 15, 20, 25, 34, or 41 and encompass an epitope of 53070, 15985, 26583, 21953, m32404, 14089, or 23436. Preferably, the antigenic peptide includes at least 10 amino acid residues, more preferably at least 15 amino acid residues, even more preferably at least 20 amino acid residues, and most preferably at least 30 amino acid residues.

Fragments of 53070, 15985, 26583, 21953, m32404, 14089, or 23436 can be used as immunogens or to characterize the specificity of an antibody.

Fragments of 53070 which include amino acid residues about 103 to 119, about 226 to 247, or about 301 to 329 of SEQ ID NO:2, for example, can be used to make antibodies against hydrophilic regions of the 53070 protein. Similarly, fragments of 53070 which include residues about 63 to 73, about 86 to 102, or about 199 to 216 of SEQ ID NO:2 can be used to make an antibody against a hydrophobic region of the 53070 protein; fragments of 53070 which include residues about 12 to 45, about 125 to 150, or about 150 to 175 of SEQ ID NO:2 can be used to make an antibody against the protein kinase domain of the 53070 protein; and fragments of 53070 which include amino acid residues about 1 to 11 and 273 to 367 of SEQ ID NO:2 can be used to make antibodies against a non-kinase domain region of the 53070 protein.

Fragments of 15985 which include residues 8 to 20, from about 592 to 600, or from about 652 to 672 can be used to make, e.g., used as immunogens or used to characterize the specificity of an antibody, antibodies against hydrophilic regions of the 15985 protein. Similarly, fragments of 15985 which include residues 83 to 91, from about 465 to 472, or from about 568 to 585 of SEQ ID NO:8 can be used to make an antibody against a hydrophobic region of the 15985 protein; a fragment of 15985 which include residues 394 to 651 can be used to make an antibody against the protein kinase region of the 15985 protein; and a fragment of 15985 which includes residues 67 to 158 or residues 192 to 280 can be used to make an antibody against a doublecortin repeat of the 15985 protein.

Fragments of 26583 which include residues about 60-70 can be used to make, e.g., used as immunogens or used to characterize the specificity of an antibody, antibodies against hydrophilic regions of the 26583 protein. Similarly, fragments of 26583 which include residues 262-279 can be used to make an antibody against a hydrophobic region of the 26583 protein; a fragment of 26583 which includes residues about 172 to 461 or 99 to 523 can be used to make an antibody against the phosphatase region of the 26583 protein.

Hydrophilic fragments of 21953, e.g., those which include residues 20 to 40, 65 to 80, or 780 to 790, can be used to make, e.g., used as immunogens or used to characterize the specificity of an antibody, antibodies against hydrophilic regions of the 21953 protein. Similarly, a hydrophobic fragment of 21953, e.g. which include residues 250 to 270, 370 to 390, or 681 to 695, can be used to make an antibody against a hydrophobic region of the 21953 protein; a fragment of 21953 which include residues about 672 to 744, 672 to 690, 690 to 710, or 710 to 744 can be used to make an antibody against the prolyl oligopeptidase domain of the 21953 protein.

Fragments of m32404 which include residues about 30 to 60 of SEQ ID NO:25 can be used to make, e.g., can be used as immunogens or used to characterize the specificity of an antibody, antibodies against hydrophilic regions of the m32404 protein. Similarly, a fragment of m32404 which includes residues about 320 to 340, or about 450 to 470 of SEQ ID NO:25 can be used to make an antibody against a hydrophobic region of the m32404 protein; a fragment of m32404 which include residues about 45 to 268, or about 311 to 520 of SEQ ID NO:25 (or a fragment thereof, e.g., residues 45 to 100, 73 to 78, 100 to 150, 150 to 200, 200 to 250, 218 to 229, 250 to 268, 311 to 360, 337 to 342, 360 to 400, 400 to 450, 450 to 500, 500 to 520 of SEQ ID NO:25) can be used to make an antibody against the trypsin region of the m32404 protein.

Fragments of 14089 that include residues about 71 to 79, about 161 to 171, or about 185 to 192 of SEQ ID NO:34 can be used to make, e.g., used as immunogens or used to characterize the specificity of an antibody, antibodies against hydrophilic regions of the 14089 protein. Similarly, fragments of 14089 that include residues about 35 to 55, 58 to 70, or 175 to 184 of SEQ ID NO:34 can be used to make an antibody against a hydrophobic region of the 14089 protein; a fragment of 14089 that includes residues about 41-234 of SEQ ID NO:34, or small fragments, e.g., 24 to 44, 74 to 94, or 170 to 190 of SEQ ID NO:34 can be used to make an antibody against the trypsin region of the 14089 protein. In a preferred embodiment, the antibody can bind to the extracellular portion of the 14089 protein, e.g., it can bind to a whole cell which expresses the 14089 protein.

Fragments of 23436 which include residues about 76 to 87, from about 138 to 143, and from about 458 to 478 of SEQ ID NO:41 can be used to make, e.g., used as immunogens or used to characterize the specificity of an antibody, antibodies against hydrophilic regions of the 23436 protein. Similarly, fragments of 23436 which include residues about 103 to 114, from about 285 to 297, and from about 413 to 420 of SEQ ID NO:41 can be used to make an antibody against a hydrophobic region of the 23436 protein; fragments of 23436 which include residues about 89 to 120, 332 to 420, or 89 to 420 of SEQ ID NO:41 can be used to make an antibody against the ubiquitin carboxy-terminal hydrolase region of the 23436 protein.

Antibodies reactive with, or specific for, any of these regions, or other regions or domains described herein are provided.

Antibodies which bind only native 53070, 15985, 26583, 21953, m32404, 14089, or 23436 protein, only denatured or otherwise non-native 53070, 15985, 26583, 21953, m32404, 14089, or 23436 protein, or which bind both, are with in the invention. Antibodies with linear or conformational epitopes are within the invention. Conformational epitopes can sometimes be identified by identifying antibodies which bind to native but not denatured 53070, 15985, 26583, 21953, m32404, 14089, or 23436 protein.

Preferred epitopes encompassed by the antigenic peptide are regions of 53070, 15985, 26583, 21953, m32404, 14089, or 23436 are located on the surface of the protein, e.g., hydrophilic regions, as well as regions with high antigenicity. For example, an Emini surface probability analysis of the human 53070, 15985, 26583, 21953, m32404, 14089, or 23436 protein sequence can be used to indicate the regions that have a particularly high probability of being localized to the surface of the 53070, 15985, 26583, 21953, m32404, 14089, or 23436 protein and are thus likely to constitute surface residues useful for targeting antibody production.

In preferred embodiments antibodies can bind one or more of purified antigen, membrane associated antigen, tissue, e.g., tissue sections, whole cells, preferably living cells, lysed cells, cell fractions, e.g., cytosolic fractions.

The anti-53070, -15985, -26583, -21953, -m32404, -14089, or -23436 antibody can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target 53070, 15985, 26583, 21953, m32404, 14089, or 23436 protein.

In a preferred embodiment, the antibody has effector function, and/or can fix complement. In other embodiments, the antibody does not, recruit effector cells, or fix complement.

In a preferred embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

In a preferred embodiment, an anti-53070 antibody alters (e.g., increases or decreases) the kinase activity of a 53070 polypeptide. For example, the antibody can bind at or in proximity to the active site, e.g., to an epitope that includes a residue located from about 120 to 180 of SEQ ID NO:2.

In a preferred embodiment, an anti-15985 antibody alters (e.g., increases or decreases) an activity of a 15985 polypeptide, e.g. phosphorylation of a protein substrate.

In a preferred embodiment, an anti-21953 antibody alters (e.g., increases or decreases) the prolyl oligopeptidase activity of a 21953 polypeptide. For example, the antibody can specifically bind a residue of the active site of 21953 polypeptide, e.g., a residue located between about 730 to 750, 805 to 830, 835 to 860 of SEQ ID NO:20. The antibody can block the binding of substrate to the 21953 polypeptide. In another preferred embodiment, the antibody specifically binds a residue in the 21953 prolyl oligopeptidase domain, e.g., from about amino acid 672 to 744, or 610 to 883 of SEQ ID NO:20, or in the DPP IV N-terminal residue, e.g., a residue between about amino acids 88 to 663 of SEQ ID NO:20.

In a preferred embodiment, an anti-m32404 antibody alters (e.g., increases or decreases) the proteolytic activity of an m32404 polypeptide. For example, the antibody can bind at or in proximity to the active site, e.g., to an epitope that includes a residue located from about 73 to 78, 337 to 342, or 218 to 229 of SEQ ID NO:25.

In a preferred embodiment, the antibody alters (e.g., increases or decreases) the de-ubiquitinating activity of a 23436 polypeptide.

The antibody can be coupled to a toxin, e.g., a polypeptide toxin, e,g, ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-53070, -15985, -26583, -21953, -m32404, -14089, or -23436 antibody (e.g., monoclonal antibody) can be used to isolate 53070, 15985, 26583, 21953, m32404, 14089, or 23436 by standard techniques, such as affinity chromatography or immunoprecipitation. Moreover, an anti-53070, -15985, -26583, -21953, -m32404, -14089, or -23436 antibody can be used to detect 53070, 15985, 26583, 21953, m32404, 14089, or 23436 protein (e.g., in a cellular lysate or cell supernatant) in order to evaluate the abundance and pattern of expression of the protein. Anti-53070, -15985, -26583, -21953, -m32404, -14089, or -23436 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The invention also includes a nucleic acid which encodes an anti-53070, -15985, -26583, -21953, -m32404, -14089, or -23436 antibody, e.g., an anti-53070, -15985, -26583, -21953, -m32404, -14089, or -23436 antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-53070, -15985, -26583, -21953, -m32404, -14089, or -23436 antibody, e.g., and antibody described herein, and method of using said cells to make a 53070, 15985, 26583, 21953, m32404, 14089, or 23436 antibody.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 53070, 15985, 26583, 21953, m32404, 14089, or 23436 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 53070, 15985, 26583, 21953, m32404, 14089, or 23436 proteins, mutant forms of 53070, 15985, 26583, 21953, m32404, 14089, or 23436 proteins, fusion proteins, and the like).

The recombinant expression vectors of the invention can be designed for expression of 53070, 15985, 26583, 21953, m32404, 14089, or 23436 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 53070, 15985, 26583, 21953, m32404, 14089, or 23436 activity assays, (e.g., direct assays or competitive assays described in detail below), or to generate antibodies specific for 53070, 15985, 26583, 21953, m32404, 14089, or 23436 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The 53070, 15985, 26583, 21953, m32404, 14089, or 23436 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 53070, 15985, 26583, 21953, m32404, 14089, or 23436 nucleic acid molecule within a recombinant expression vector or a 53070, 15985, 26583, 21953, m32404, 14089, or 23436 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 53070, 15985, 26583, 21953, m32404, 14089, or 23436 protein can be expressed in bacterial cells (such as *E. coli*), insect cells, yeast or mammalian cells (such as Chinese hamster ovary cells (CHO) or COS cells (African green monkey kidney cells CV-1 origin SV40 cells; Gluzman (1981) *Cell* 23:175-182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 53070, 15985, 26583, 21953, m32404, 14089, or 23436 protein. Accordingly, the invention further provides methods for producing a 53070, 15985, 26583, 21953, m32404, 14089, or 23436 protein using the host cells of the invention. In one embodiment, the method includes culturing the host cell of the invention (into which a recombinant expression vector encoding a 53070, 15985, 26583, 21953, m32404, 14089, or 23436 protein has been introduced) in a suitable medium such that a 53070, 15985, 26583, 21953, m32404, 14089, or 23436 protein is produced. In another embodiment, the method further includes isolating a 53070, 15985, 26583, 21953, m32404, 14089, or 23436 protein from the medium or the host cell.

In another aspect, the invention features, a cell or purified preparation of cells which include a 53070, 15985, 26583, 21953, m32404, 14089, or 23436 transgene, or which otherwise misexpress 53070, 15985, 26583, 21953, m32404, 14089, or 23436. The cell preparation can consist of human or non-human cells, e.g., rodent cells, e.g., mouse or rat cells, rabbit cells, or pig cells. In preferred embodiments, the cell or cells include a 53070, 15985, 26583, 21953, m32404, 14089, or 23436 transgene, e.g., a heterologous form of a 53070, 15985, 26583, 21953, m32404, 14089, or 23436, e.g., a gene derived from humans (in the case of a non-human cell). The 53070, 15985, 26583, 21953, m32404, 14089, or 23436 transgene can be misexpressed, e.g., overexpressed or underexpressed. In other preferred embodiments, the cell or cells include a gene that mis-expresses an endogenous 53070, 15985, 26583, 21953, m32404, 14089, or 23436, e.g., a gene the expression of which is disrupted, e.g., a knockout. Such cells can serve as a model for studying disorders that are related to mutated or mis-expressed 53070, 15985, 26583, 21953, m32404, 14089, or 23436 alleles or for use in drug screening.

In another aspect, the invention features, a human cell, e.g., a hematopoietic stem cell, transformed with nucleic acid which encodes a subject 53070, 15985, 26583, 21953, m32404, 14089, or 23436 polypeptide.

Also provided are cells, preferably human cells, e.g., human hematopoietic or fibroblast cells, in which an endogenous 53070, 15985, 26583, 21953, m32404, 14089, or 23436 is under the control of a regulatory sequence that does not normally control the expression of the endogenous 53070, 15985, 26583, 21953, m32404, 14089, or 23436 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 53070, 15985, 26583, 21953, m32404, 14089, or 23436 gene. For example, an endogenous 53070, 15985, 26583, 21953, m32404, 14089, or 23436 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 53070, 15985, 26583, 21953, m32404, 14089, or 23436 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of 53070, 15985, 26583, 21953, m32404, 14089, or 23436 polypeptide can be regulated in the subject by administering an agent (e.g., a steroid hormone) to the subject. In another preferred embodiment, the implanted recombinant cells express and secrete an antibody specific for a 53070, 15985, 26583, 21953, m32404, 14089, or 23436 polypeptide. The antibody can be any antibody or any antibody derivative described herein.

53070, 15985, 26583, 21953, m32404, 14089, or 23436 Transgenic Animals

The invention provides non-human transgenic animals. Such animals are useful for studying the function and/or activity of a 53070, 15985, 26583, 21953, m32404, 14089, or 23436 protein and for identifying and/or evaluating modulators of 53070, 15985, 26583, 21953, m32404, 14089, or 23436 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 53070, 15985, 26583, 21953, m32404, 14089, or 23436 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 53070, 15985, 26583, 21953, m32404, 14089, or 23436 protein to particular cells. A transgenic founder animal can be identified based upon the presence of a 53070, 15985, 26583, 21953, m32404, 14089, or 23436 transgene in its genome and/or expression of 53070, 15985, 26583, 21953, m32404, 14089, or 23436 mRNA in tissues or cells of the animals. A transgenic founder animal can then be used to breed additional animals carrying the transgene. Moreover, transgenic animals carrying a transgene encoding a 53070, 15985, 26583, 21953, m32404, 14089, or 23436 protein can further be bred to other transgenic animals carrying other transgenes.

53070, 15985, 26583, 21953, m32404, 14089, or 23436 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 53070, 15985, 26583, 21953, m32404, 14089, and 23436

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 53070, 15985, 26583, 21953, m32404, 14089, or 23436 protein (e.g., via a recombinant expression vector in a host cell in gene therapy applications), to detect a 53070, 15985, 26583, 21953, m32404, 14089, or 23436 mRNA (e.g., in a biological sample) or a genetic alteration in a 53070, 15985, 26583, 21953, m32404, 14089, or 23436 gene, and to modulate 53070, 15985, 26583, 21953, m32404, 14089, or 23436 activity, as described further below. The 53070, 15985, 26583, 21953, m32404, 14089, or 23436 proteins can be used to treat disorders characterized by insufficient or excessive production of a 53070, 15985, 26583, 21953, m32404, 14089, or 23436 substrate or production of 53070, 15985, 26583, 21953, m32404, 14089, or 23436 inhibitors. In addition, the 53070, 15985, 26583, 21953, m32404, 14089, or 23436 proteins can be used to screen for naturally occurring 53070, 15985, 26583, 21953, m32404, 14089, or 23436 substrates, to screen for drugs or compounds which modulate 53070, 15985, 26583, 21953, m32404, 14089, or 23436 activity, as well as to treat disorders characterized by insufficient or excessive production of 53070, 15985, 26583, 21953, m32404, 14089, or 23436 protein or production of 53070, 15985, 26583, 21953, m32404, 14089, or 23436 protein forms which have decreased, aberrant or unwanted activity compared to 53070, 15985, 26583, 21953, m32404, 14089, or 23436 wild type protein (e.g., a cellular proliferative and/or differentiative disorder; imbalance of protein serine/threonine kinase and protein serine/threonine phosphorylase activities, leading to an increase or decrease in lipid biosynthesis, such as cholesterol or cell cycle progression and neoplastic transformation; a cancer, e.g., a cancer of the lung, prostate, breast, ovary, or colon; or an erythroid cell disorder or a proliferative disorder of erythroid, liver, prostate, or brain cells). Moreover, the anti-53070, -15985, -26583, -21953, -m32404, -14089, or -23436 antibodies of the invention can be used to detect and isolate 53070, 15985, 26583, 21953, m32404, 14089, or 23436 proteins, regulate the bioavailability of 53070, 15985, 26583, 21953, m32404, 14089, or 23436 proteins, and modulate 53070, 15985, 26583, 21953, m32404, 14089, or 23436 activity.

A method of evaluating a compound for the ability to interact with, e.g., bind, a subject 53070, 15985, 26583, 21953, m32404, 14089, or 23436 polypeptide is provided. The method includes: contacting the compound with the subject 53070, 15985, 26583, 21953, m32404, 14089, or 23436 polypeptide; and evaluating ability of the compound to interact with, e.g., to bind or form a complex with the subject 53070, 15985, 26583, 21953, m32404, 14089, or 23436 polypeptide. This method can be performed in vitro, e.g., in a cell free system, or in vivo, e.g., in a two-hybrid interaction trap assay. This method can be used to identify naturally occurring molecules that interact with subject 53070, 15985, 26583, 21953, m32404, 14089, or 23436 polypeptide. It can also be used to find natural or synthetic inhibitors of subject 53070, 15985, 26583, 21953, m32404, 14089, or 23436 polypeptide. Screening methods are discussed in more detail below.

The 21953 polypeptide is also an enzyme useful for processing polypeptide hormone precursors. For example, the 21953 polypeptide can be used in a method that includes a) providing a polypeptide hormone precursor; b) combining the polypeptide hormone polypeptide with a 21953 polypeptide or active fragment thereof (e.g., in an effective amount) to provide a reaction mixture; and c) maintaining the mixture under conditions such that the polypeptide hormone precursor is modified to yield the processed polypeptide hormone, e.g., an active form thereof. The method can further include d) separating the processed polypeptide hormone from the 21953 polypeptide. The polypeptide hormone precursor can be obtained from a synthetic process or from a producing cell. The method can be used in the preparation of a pharmaceutical composition that includes the processed hormone.

53070, 15985, 26583, 21953, m32404, 14089, and 23436 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 53070, 15985, 26583, 21953, m32404, 14089, or 23436 proteins, have a stimulatory or inhibitory effect on, for example, 53070, 15985, 26583, 21953, m32404, 14089, or 23436 expression or 53070, 15985, 26583, 21953, m32404, 14089, or 23436 activity, or have a stimulatory or inhibitory effect on, for example, the expression or activity of a 53070, 15985, 26583, 21953, m32404, 14089, or 23436 substrate. Compounds thus identified can be used to modulate the activity of target gene products (e.g., 53070, 15985, 26583, 21953, m32404, 14089, or 23436 genes) in a therapeutic protocol, to elaborate the biological function of the target gene product, or to identify compounds that disrupt normal target gene interactions.

In any screening assay, a 26583 polypeptide that may have, e.g., a serine/threonine phosphatase domain, can be used.

In one embodiment, the invention provides assays for screening candidate or test compounds which are substrates of a 53070, 15985, 26583, 21953, m32404, 14089, or 23436 protein or polypeptide or a biologically active portion thereof. In another embodiment, the invention provides assays for screening candidate or test compounds that bind to or modulate an activity of a 53070, 15985, 26583, 21953, m32404, 14089, or 23436 protein or polypeptide or a biologically active portion thereof.

In one embodiment, an activity of a 53070 protein can be assayed directly in vitro by: expressing an affinity tagged 53070 protein in either bacteria or an appropriate mammalian cell line; purifiying the 53070 protein, e.g., by immunoprecipitation or in an affinity column; mixing the 53070 protein with radioactively labeled ATP, e.g., K$^{32}$P-ATP; and determining the amount of radioactive phosphate that is transferred to proteins in the presence and absence of a suitable substrate. Alternatively, an activity of a 53070 protein can be assayed indirectly by overexpressing the protein in an appropriate mammalian cell line and then assaying for an increase in phosporylation of a 53070 substrate that is present in the cells, or by assaying for a cellular response, e.g., altered cell morphology, the adoption of a transformed phenotype, increased cell migration, or increased cell growth or cell death. Assays like these are well known in the art and could easily be adapted to allow for the analysis of 53070 proteins.

In one embodiment, the activity of a 15985 protein can be assayed in a manner acceptable for detecting kinase activity. For example, kinase activity can be assayed in kinase reaction buffer containing 20 mM MgAcetate, 20 mM ATP, 100 mM NaCl, 100 mM Tris-HCl pH 6.8, 1 mM ZnCl 2 and 2.5 mCi □g32P]ATP and 1 mg myelin basic protein. The kinase reaction can be allowed to proceed for 30 minutes before termination by addition of sample buffer with 10 mM EDTA. Following separation by SDS-PAGE, gels can be stained with Coomassie Blue and subjected to autoradiography. Burgess et al. (2001) *J. Biol. Chem.* published Jul. 25, 2001 as 10.1074/jbc.M105153200.

The prolyl oligopeptidase activity of a 21953 polypeptide can be assayed in vitro using an enzymatic assay such as described in Abbott et al. (199) *FEBS Lett.* 458:278-284 and Abbott et al. (2000) *Eur. J. Biochem* 267:6140-4150. A sample to be assayed is combined with substrate in phosphate buffer pH 7.4. Substrates include H-Gly-Pro-p-nitroanilide (NA)/HCl (Sigma Corp, MO, USA), and Gly-Pro-7-amino-4-trifluoromethylcoumarin (Calbiochem, San Diego, Calif., USA) and other peptidyl substrates. The reaction is incubated for 30 minutes at 37° C. For example, hydrolysis of H-Gly-Pro-pNA is monitored spectroscopically at 405 nm. The sample to be assayed can be a purified 21953 polypeptide, e.g., a 21953 polypeptide or a 21953 fusion protein purified by a method described herein. Routine Michaelis-Menten analysis of kinetic parameters can be used to quantify the enzymatic activity. Alternatively, the reaction can be quenched and total substrate hydrolyzed can be measured as indication of the activity.

De-ubiquitination assays useful for detecting a ubiquitin carboxy-terminal hydrolase activity are described, for example, in Zhu et al. (1997) *Journal of Biological Chemistry* 272:51-57, Mitch et al. (1999) *American Journal of Physiology* 276:C1132-C1138, Liu et al. (1999) *Molecular and Cell Biology* 19:3029-3038, and such as those cited in various reviews, for example, Ciechanover et al. (1994) *The FASEB Journal* 8:182-192, Chiechanover (1994) *Biol. Chem. Hoppe-Seyler* 375:565-581, Hershko et al. (1998) *Annual Review of Biochemistry* 67:425-479, Swartz (1999) *Annual Review of Medicine* 50:57-74, Ciechanover (1998) *EMBO Journal* 17:7151-7160, and D'Andrea et al. (1998) *Critical Reviews in Biochemistry and Molecular Biology* 33:337-352. These assays include, but are not limited to, the disappearance of substrate, including a decrease in the amount of polyubiquitin or ubiquitinated substrate protein or protein remnant, appearance of intermediate and end products, such as appearance of free ubiquitin monomers, general protein turnover, specific protein turnover, ubiquitin binding, binding to ubiquitinated substrate protein, subunit interaction, interaction with ATP, interaction with cellular components such as trans-acting regulatory factors, stabilization of specific proteins, and the like.

For example, in order to identify a polypeptide having ubiquitin carboxy-terminal hydrolase activity in vitro, a reporter protein (e.g., green fluorescent protein or β-galactosidase) is engineered as a translation fusion with an amino-terminal ubiquitin moiety. The substrate is incubated in solution with a polypeptide such as 23436 or a fragment thereof suspected of having ubiquitin specific protease activity. The production of free ubiquitin or the de-ubiquitinated reporter protein can be determined, e.g., by PAGE electrophoresis and comparion to a control incubation lacking the 23436 polypeptide (Zhu et al. (1997) *Journal of Biological Chemistry* 272:51-57). A similar assay can be performed using a reporter polypeptide having a lysine side chain to which a ubiquitin moiety is conjugated.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses a 53070, 15985, 26583, 21953, m32404, 14089, or 23436 protein or biologically active portion thereof is contacted with a test compound, and the ability of the test compound to modulate 53070, 15985, 26583, 21953, m32404, 14089, or 23436 activity is determined. Determining the ability of the test compound to modulate 53070 activity can be accomplished by monitoring, for example, substrate phosphorylation. Determining the ability of the test compound to modulate 15985 activity can be accomplished by monitoring, for example, protein kinase activity and/or microtubule binding. Determining the ability of the test compound to modulate 26583 activity can be accomplished by monitoring, for example, serine/threonine phosphatase activity. Determining the ability of the test compound to modulate 21953 activity can be accomplished by monitoring, for example, prolyl oligopeptidase activity. Determining the ability of the test compound to modulate m32404 activity can be accomplished by monitoring, for example, trypsin protease activity. Determining the ability of the test compound to modulate 14089 activity can be accomplished by monitoring, for example, protease activity. Determining the ability of the test compound to modulate 23436 activity can be accomplished by monitoring, for example, de-ubiquitinating activity.

The cell, for example, can be of mammalian origin, e.g., human.

The ability of the test compound to modulate 53070, 15985, 26583, 21953, m32404, 14089, or 23436 binding to a compound, e.g., a 53070, 15985, 26583, 21953, m32404, 14089, or 23436 substrate, or to bind to 53070, 15985, 26583, 21953, m32404, 14089, or 23436 can also be evaluated. This can be accomplished, for example, by coupling the compound, e.g., the substrate, with a radioisotope or enzymatic label such that binding of the compound, e.g., the substrate, to 53070, 15985, 26583, 21953, m32404, 14089, or 23436 can be determined by detecting the labeled compound, e.g., substrate, in a complex. Alternatively, 53070, 15985, 26583, 21953, m32404, 14089, or 23436 could be coupled with a radioisotope or enzymatic label to monitor the ability of a test compound to modulate 53070, 15985, 26583, 21953, m32404, 14089, or 23436 binding to a 53070, 15985, 26583, 21953, m32404, 14089, or 23436 substrate in a complex. For example, compounds (e.g., 53070, 15985, 26583, 21953, m32404, 14089, or 23436 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 53070, 15985, 26583, 21953, m32404, 14089, or 23436 substrate) to interact with 53070, 15985, 26583, 21953, m32404, 14089, or 23436 with or without the labeling of any of the interactants can be evaluated. For example, a microphysiometer can be used to detect the interaction of a compound with 53070, 15985, 26583, 21953, m32404, 14089, or 23436 without the labeling of either the compound or the 53070, 15985, 26583, 21953, m32404, 14089, or 23436. McConnell, H. M. et al. (1992) Science 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 53070, 15985, 26583, 21953, m32404, 14089, or 23436.

In yet another embodiment, a cell-free assay is provided in which a 53070, 15985, 26583, 21953, m32404, 14089, or 23436 protein or biologically active portion thereof is contacted with a test compound and the ability of the test compound to bind to the 53070, 15985, 26583, 21953, m32404, 14089, or 23436 protein or biologically active portion thereof is evaluated. Preferred biologically active portions of the 53070, 15985, 26583, 21953, m32404, 14089, or 23436 proteins to be used in assays of the present invention include fragments which participate in interactions with non-53070, 15985, 26583, 21953, m32404, 14089, or 23436 molecules, e.g., fragments with high surface probability scores.

Soluble and/or membrane-bound forms of isolated proteins (e.g., 53070, 15985, 26583, 21953, m32404, 14089, or 23436 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 53070, 15985, 26583, 21953, m32404, 14089, or 23436 protein to bind to a target molecule can be accomplished using real-time Biomolecular Interaction Analysis (BIA) (see, e.g., Sjolander, S. and Urbaniczky, C. (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 53070, 15985, 26583, 21953, m32404, 14089, or 23436, an anti-53070, -15985, -26583, -21953, -m32404, -14089, or -23436 antibody or its target molecule to facilitate separation of complexed from uncomplexed forms of one or both of the proteins, as well as to accommodate automation of the assay. Binding of a test compound to a 53070, 15985, 26583, 21953, m32404, 14089, or 23436 protein, or interaction of a 53070, 15985, 26583, 21953, m32404, 14089, or 23436 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/53070, 15985, 26583, 21953, m32404, 14089, or 23436 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 53070, 15985, 26583, 21953, m32404, 14089, or 23436 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 53070, 15985, 26583, 21953, m32404, 14089, or 23436 binding or activity determined using standard techniques.

Other techniques for immobilizing either a 53070, 15985, 26583, 21953, m32404, 14089, or 23436 protein or a target molecule on matrices include using conjugation of biotin and streptavidin. Biotinylated 53070, 15985, 26583, 21953, m32404, 14089, or 23436 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 53070, 15985, 26583, 21953, m32404, 14089, or 23436 protein or target molecules but which do not interfere with binding of the 53070, 15985, 26583, 21953, m32404, 14089, or 23436 protein to its target molecule. Such antibodies can be derivatized to the wells of the plate, and unbound target or 53070, 15985, 26583, 21953, m32404, 14089, or 23436 protein trapped in the wells by antibody conjugation. Methods for detecting such complexes, in addition to those described above for the GST-immobilized complexes, include immunodetection of complexes using antibodies reactive with the 53070, 15985, 26583, 21953, m32404, 14089, or 23436 protein or target molecule, as well as enzyme-linked assays which rely on detecting an enzymatic activity associated with the 53070, 15985, 26583, 21953, m32404, 14089, or 23436 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) Trends Biochem Sci 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) Current Protocols in Molecular Biology, J. Wiley: New York). Such resins and chromatographic techniques are known to one skilled in the art (see, e.g., Heegaard, N. H., (1998) J Mol Recognit 11:141-8; Hage, D. S., and Tweed, S. A. (1997) J Chromatogr B Biomed Sci Appl. 699:499-525). Further, fluorescence energy transfer may also be conveniently utilized, as described herein, to detect binding without further purification of the complex from solution.

In a preferred embodiment, the assay includes contacting the 53070, 15985, 26583, 21953, m32404, 14089, or 23436 protein or biologically active portion thereof with a known compound which binds 53070, 15985, 26583, 21953, m32404, 14089, or 23436 to form an assay mixture, contacting the assay mixture with a test compound, and determining the ability of the test compound to interact with a 53070, 15985, 26583, 21953, m32404, 14089, or 23436 protein, wherein determining the ability of the test compound to interact with a 53070, 15985, 26583, 21953, m32404, 14089, or 23436 protein includes determining the ability of the test compound to preferentially bind to 53070, 15985, 26583, 21953, m32404, 14089, or 23436 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 53070, 15985, 26583, 21953, m32404, 14089, or 23436 genes herein identified. In an alternative embodiment, the invention provides methods for determining the ability of the test compound to modulate the activity of a 53070, 15985, 26583, 21953, m32404, 14089, or 23436 protein through modulation of the activity of a downstream effector of a 53070, 15985, 26583, 21953, m32404, 14089, or 23436 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 53070, 15985, 26583, 21953, m32404, 14089, or 23436 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 53070, 15985, 26583, 21953, m32404, 14089, or 23436 ("53070-, 15985-, 26583-, 21953-, m32404-, 14089-, or 23436-binding proteins" or "53070-, 15985-, 26583-, 21953-, m32404-, 14089-, or 23436-bp") and are involved in 53070, 15985, 26583, 21953, m32404, 14089, or 23436 activity. Such 53070-, 15985-, 26583-, 21953-, m32404-, 14089-, or 23436-bps can be activators or inhibitors of signals by the 53070, 15985, 26583, 21953, m32404, 14089, or 23436 proteins or 53070, 15985, 26583, 21953, m32404, 14089, or 23436 targets as, for example, downstream elements of a 53070-, 15985-, 26583-, 21953-, m32404-, 14089-, or 23436-mediated signaling pathway.

The two-hybrid system is based on the modular nature of most transcription factors, which consist of separable DNA-binding and activation domains. Briefly, the assay utilizes two different DNA constructs. In one construct, the gene that codes for a 53070, 15985, 26583, 21953, m32404, 14089, or 23436 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 53070, 15985, 26583, 21953, m32404, 14089, or 23436 protein can be the fused to the activator domain.) If the "bait" and the "prey" proteins are able to interact, in vivo, forming a 53070-, 15985-, 26583-, 21953-, m32404-, 14089-, or 23436-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 53070, 15985, 26583, 21953, m32404, 14089, or 23436 protein.

In another embodiment, modulators of 53070, 15985, 26583, 21953, m32404, 14089, or 23436 expression are identified. For example, a cell or cell free mixture is contacted with a candidate compound and the expression of 53070, 15985, 26583, 21953, m32404, 14089, or 23436 mRNA or protein evaluated relative to the level of expression of 53070, 15985, 26583, 21953, m32404, 14089, or 23436 mRNA or protein in the absence of the candidate compound. When expression of 53070, 15985, 26583, 21953, m32404, 14089, or 23436 mRNA or protein is greater in the presence of the candidate compound than in its absence, the candidate compound is identified as a stimulator of 53070, 15985, 26583, 21953, m32404, 14089, or 23436 mRNA or protein expression. Alternatively, when expression of 53070, 15985, 26583, 21953, m32404, 14089, or 23436 mRNA or protein is less (statistically significantly less) in the presence of the candidate compound than in its absence, the candidate compound is identified as an inhibitor of 53070, 15985, 26583, 21953, m32404, 14089, or 23436 mRNA or protein expression. The level of 53070, 15985, 26583, 21953, m32404, 14089, or 23436 mRNA or protein expression can be determined by methods described herein for detecting 53070, 15985, 26583, 21953, m32404, 14089, or 23436 mRNA or protein.

In another aspect, the invention pertains to a combination of two or more of the assays described herein. For example, a modulating agent can be identified using a cell-based or a cell free assay, and the ability of the agent to modulate the activity of a 53070 protein can be confirmed in vivo, e.g., in an animal such as an animal model for cellular proliferative and/or differentiative disorder. For example, a modulating agent can be identified using a cell-based or a cell free assay, and the ability of the agent to modulate the activity of a 15985 protein can be confirmed in vivo, e.g., in an animal such as an animal model for neural migration defects, immune cell migration defects, or metastasis. For example, a modulating agent can be identified using a cell-based or a cell free assay, and the ability of the agent to modulate the activity of a 26583 protein can be confirmed in vivo, e.g., in an animal such as an animal model overexpressing a gene encoding a protein serine/threonine kinase. For example, a modulating agent can be identified using a cell-based or a cell free assay, and the ability of the agent to modulate the activity of a 21953 protein can be confirmed in vivo, e.g., in an animal such as an animal model for a cell proliferative or cell differentiative disorder, e.g., a cancer, e.g., a cancer of the lung, prostate, breast, or colon; an animal model for an immunological disorder; or an animal model for a neurological disorder. For example, a modulating agent can be identified using a cell-based or a cell free assay, and the ability of the agent to modulate the activity of an m32404 protein can be confirmed in vivo, e.g., in an animal such as an animal model for cancer. For example, a modulating agent can be identified using a cell-based or a cell free assay, and the ability of the agent to modulate the activity of a 14089 protein can be confirmed in vivo, e.g., in an animal such as an animal model for cancer. For example, a modulating agent can be identified using a cell-based or a cell free assay, and the ability of the agent to modulate the activity of a 23436 protein can be confirmed in vivo, e.g., in an animal such as an animal model for an erythroid cell disorder or a proliferative disorder of erythroid, liver, prostate, or brain cells.

This invention further pertains to novel agents identified by the above-described screening assays. Accordingly, it is within the scope of this invention to further use an agent identified as described herein (e.g., a 53070, 15985, 26583, 21953, m32404, 14089, or 23436 modulating agent, an antisense 53070, 15985, 26583, 21953, m32404, 14089, or 23436 nucleic acid molecule, a 53070-, 15985-, 26583-, 21953-, m32404-, 14089-, or 23436-specific antibody, or a 53070-, 15985-, 26583-, 21953-, m32404-, 14089-, or 23436-binding partner) in an appropriate animal model to determine the efficacy, toxicity, side effects, or mechanism of action, of treatment with such an agent. Furthermore, novel agents identified by the above-described screening assays can be used for treatments as described herein.

53070, 15985, 26583, 21953, m32404, 14089, and 23436 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 53070, 15985, 26583, 21953, m32404, 14089, or 23436 with a disease; (ii) identify an individual from a minute biological sample (tissue typing); and (iii) aid in forensic identification of a biological sample. These applications are described in the subsections below.

53070, 15985, 26583, 21953, m32404, 14089, and 23436 Chromosome Mapping

The 53070, 15985, 26583, 21953, m32404, 14089, and 23436 nucleotide sequences or portions thereof can be used to map the location of the 53070, 15985, 26583, 21953, m32404, 14089, and 23436 genes on a chromosome. This process is called chromosome mapping. Chromosome mapping is useful in correlating the 53070, 15985, 26583, 21953, m32404, 14089, or 23436 sequences with genes associated with disease.

The 23436 nucleotide sequences or portions thereof can be used to map the location of the 23436 genes on a chromosome, particularly chromosome 1, e.g., chromosomal cytogenetic region 1p36. This process is called chromosome mapping. Chromosome mapping is useful in correlating the 23436 sequences with genes associated with disease such prostate cancer and/or brain cancer (see, e.g., Gibbs et al. (1999) *Am. J. Hum. Genet.* 64:776).

Briefly, 53070, 15985, 26583, 21953, m32404, 14089, or 23436 genes can be mapped to chromosomes by preparing PCR primers (preferably 15-25 bp in length) from the 53070, 15985, 26583, 21953, m32404, 14089, or 23436 nucleotide sequences. These primers can then be used for PCR screening of somatic cell hybrids containing individual human chromosomes. Only those hybrids containing the human gene corresponding to the 53070, 15985, 26583, 21953, m32404, 14089, or 23436 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919-924).

Other mapping strategies e.g., in situ hybridization (described in Fan, Y. et al. (1990) *Proc. Natl. Acad. Sci. USA*, 87:6223-27), pre-screening with labeled flow-sorted chromosomes, and pre-selection by hybridization to chromosome specific cDNA libraries can be used to map 53070, 15985, 26583, 21953, m32404, 14089, or 23436 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783-787.

Moreover, differences in the DNA sequences between individuals affected and unaffected with a disease associated with the 53070, 15985, 26583, 21953, m32404, 14089, or 23436 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

53070, 15985, 26583, 21953, m32404, 14089, and 23436 Tissue Typing 53070, 15985, 26583, 21953, m32404, 14089, or 23436 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 53070, 15985, 26583, 21953, m32404, 14089, or 23436 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, 7, 14, 19, 24, 33, or 40 can provide positive individual identification with a panel of perhaps 10 to 1,000 primers which each yield a noncoding amplified sequence of 100 bases. If predicted coding sequences, such as those in SEQ ID NO:3, 9, 16, 21, 26, 35, or 42 are used, a more appropriate number of primers for positive individual identification would be 500-2,000.

If a panel of reagents from 53070, 15985, 26583, 21953, m32404, 14089, or 23436 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 53070, 15985, 26583, 21953, m32404, 14089, or 23436 Sequences in Forensic Biology DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, 7, 14, 19, 24, 33, or 40 (e.g., fragments derived from the noncoding regions of SEQ ID NO:1, 7, 14, 19, 24, 33, or 40 having a length of at least 20 bases, preferably at least 30 bases) are particularly appropriate for this use.

The 53070, 15985, 26583, 21953, m32404, 14089, or 23436 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 53070, 15985, 26583, 21953, m32404, 14089, or 23436 probes can be used to identify tissue by species and/or by organ type.

The 26583 nucleotide sequences described herein can further be used to provide polynucleotide reagents, e.g., labeled or labelable probes which can be used in, for example, an in situ hybridization technique, to identify a specific tissue, e.g., a tissue containing 26583 serine/threonine phosphatase activity.

In a similar fashion, these reagents, e.g., 53070, 15985, 26583, 21953, m32404, 14089, or 23436 primers or probes can be used to screen tissue culture for contamination (i.e. screen for the presence of a mixture of different types of cells in a culture).

Predictive Medicine of 53070, 15985, 26583, 21953, m32404, 14089, or 23436

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 53070, 15985, 26583, 21953, m32404, 14089, or 23436.

Such disorders include, e.g., a disorder associated with the misexpression of 53070 gene, such as a cellular proliferative and/or differentiative disorder; a disorder associated with the misexpression of 15985 gene, e.g., a cancer, a neurological or a cardiovascular (e.g., blood vessel) disorder; a disorder associated with the misexpression of 21953 gene, a disorder of cell proliferation (such as lung, breast, colon, prostate, or ovarian cancer) or of the nervous system; a disorder associated with the misexpression of the m32404 gene, a disorder of cell differentiation or proliferaiton, or of the immune system or blood clotting system; a disorder associated with the misexpression of 14089 gene, a disorder of the complement system; and a disorder associated with the misexpression of 23436 gene, a disorder of the hematopoietic system, e.g., of erythroid cells or erythroid cell precursors.

The method includes one or more of the following:

detecting, in a tissue of the subject, the presence or absence of a mutation which affects the expression of the 53070, 15985, 26583, 21953, m32404, 14089, or 23436 gene, or detecting the presence or absence of a mutation in a region which controls the expression of the gene, e.g., a mutation in the 5' control region;

detecting, in a tissue of the subject, the presence or absence of a mutation which alters the structure of the 53070, 15985, 26583, 21953, m32404, 14089, or 23436 gene;

detecting, in a tissue of the subject, the misexpression of the 53070, 15985, 26583, 21953, m32404, 14089, or 23436 gene, at the mRNA level, e.g., detecting a non-wild type level of a mRNA;

detecting, in a tissue of the subject, the misexpression of the gene, at the protein level, e.g., detecting a non-wild type level of a 53070, 15985, 26583, 21953, m32404, 14089, or 23436 polypeptide.

In preferred embodiments the method includes: ascertaining the existence of at least one of: a deletion of one or more nucleotides from the 53070, 15985, 26583, 21953, m32404, 14089, or 23436 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, 7, 14, 19, 24, 33, or 40, or naturally occurring mutants thereof or 5' or 3' flanking sequences naturally associated with the 53070, 15985, 26583, 21953, m32404, 14089, or 23436 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 53070, 15985, 26583, 21953, m32404, 14089, or 23436 gene; the presence of a non-wild type splicing pattern of a messenger RNA transcript of the gene; or a non-wild type level of 53070, 15985, 26583, 21953, m32404, 14089, or 23436.

Methods of the invention can be used prenatally or to determine if a subject's offspring will be at risk for a disorder.

In preferred embodiments the method includes determining the structure of a 53070, 15985, 26583, 21953, m32404, 14089, or 23436 gene, an abnormal structure being indicative of risk for the disorder.

In preferred embodiments the method includes contacting a sample from the subject with an antibody to the 53070, 15985, 26583, 21953, m32404, 14089, or 23436 protein or a nucleic acid, which hybridizes specifically with the gene. These and other embodiments are discussed below.

Diagnostic and Prognostic Assays of 53070, 15985, 26583, 21953, m32404, 14089, or 23436

Diagnostic and prognostic assays of the invention include method for assessing the expression level of 53070, 15985, 26583, 21953, m32404, 14089, or 23436 molecules and for identifying variations and mutations in the sequence of 53070, 15985, 26583, 21953, m32404, 14089, or 23436 molecules.

Expression Monitoring and Profiling:

The presence, level, or absence of 53070, 15985, 26583, 21953, m32404, 14089, or 23436 protein or nucleic acid in a biological sample can be evaluated by obtaining a biological sample from a test subject and contacting the biological sample with a compound or an agent capable of detecting 53070, 15985, 26583, 21953, m32404, 14089, or 23436 protein or nucleic acid (e.g., mRNA, genomic DNA) that encodes 53070, 15985, 26583, 21953, m32404, 14089, or 23436 protein such that the presence of 53070, 15985, 26583, 21953, m32404, 14089, or 23436 protein or nucleic acid is detected in the biological sample. The term "biological sample" includes tissues, cells and biological fluids isolated from a subject, as well as tissues, cells and fluids present within a subject. A preferred biological sample is serum. The level of expression of the 53070, 15985, 26583, 21953, m32404, 14089, or 23436 gene can be measured in a number of ways, including, but not limited to: measuring the mRNA encoded by the 53070, 15985, 26583, 21953, m32404, 14089, or 23436 genes; measuring the amount of protein encoded by the 53070, 15985, 26583, 21953, m32404, 14089, or 23436 genes; or measuring the activity of the protein encoded by the 53070, 15985, 26583, 21953, m32404, 14089, or 23436 genes.

The level of mRNA corresponding to the 53070, 15985, 26583, 21953, m32404, 14089, or 23436 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 53070, 15985, 26583, 21953, m32404, 14089, or 23436 nucleic acid, such as the nucleic acid of SEQ ID NO:1, 7, 14, 19, 24, 33, or 40, respectively, or a portion thereof, such as an oligonucleotide of at least 7, 15, 30, 50, 100, 250 or 500 nucleotides in length and sufficient to specifically hybridize under stringent conditions to 53070, 15985, 26583, 21953, m32404, 14089, or 23436 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 53070, 15985, 26583, 21953, m32404, 14089, or 23436 genes.

The level of mRNA in a sample that is encoded by one of 53070, 15985, 26583, 21953, m32404, 14089, or 23436 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 53070, 15985, 26583, 21953, m32404, 14089, or 23436 gene being analyzed.

In another embodiment, the methods further contacting a control sample with a compound or agent capable of detecting 53070, 15985, 26583, 21953, m32404, 14089, or 23436 mRNA, or genomic DNA, and comparing the presence of 53070, 15985, 26583, 21953, m32404, 14089, or 23436 mRNA or genomic DNA in the control sample with the presence of 53070, 15985, 26583, 21953, m32404, 14089, or 23436 mRNA or genomic DNA in the test sample. In still another embodiment, serial analysis of gene expression, as described in U.S. Pat. No. 5,695,937, is used to detect 53070, 15985, 26583, 21953, m32404, 14089, or 23436 transcript levels.

A variety of methods can be used to determine the level of protein encoded by 53070, 15985, 26583, 21953, m32404, 14089, or 23436. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 53070, 15985, 26583, 21953, m32404, 14089, or 23436 protein in a biological sample in vitro as well as in vivo. In vitro techniques for detection of 53070, 15985, 26583, 21953, m32404, 14089, or 23436 protein include enzyme linked immunosorbent assays (ELISAs), immunoprecipitations, immunofluorescence, enzyme immunoassay (EIA), radio-immunoassay (RIA), and Western blot analysis. In vivo techniques for detection of 53070, 15985, 26583, 21953, m32404, 14089, or 23436 protein include introducing into a subject a labeled anti-53070, -15985, -26583, -21953, -m32404, -14089, or -23436 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-53070, -15985, -26583, -21953, -m32404, -14089, or -23436 antibody positioned on an antibody array (as described below). The sample can be detected, e.g., with avidin coupled to a fluorescent label.

In another embodiment, the methods further include contacting the control sample with a compound or agent capable of detecting 53070, 15985, 26583, 21953, m32404, 14089, or 23436 protein, and comparing the presence of 53070, 15985, 26583, 21953, m32404, 14089, or 23436 protein in the control sample with the presence of 53070, 15985, 26583, 21953, m32404, 14089, or 23436 protein in the test sample.

The invention also includes kits for detecting the presence of 53070, 15985, 26583, 21953, m32404, 14089, or 23436 in a biological sample. For example, the kit can include a compound or agent capable of detecting 53070, 15985, 26583, 21953, m32404, 14089, or 23436 protein or mRNA in a biological sample; and a standard. The compound or agent can be packaged in a suitable container. The kit can further comprise instructions for using the kit to detect 53070, 15985, 26583, 21953, m32404, 14089, or 23436 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 53070, 15985, 26583, 21953, m32404, 14089, or 23436 expression or activity. As used herein, the term "unwanted" includes an unwanted phenomenon involved in a biological response such as deregulated cell proliferation;

pain; a cell proliferative or cell differentiative disorder, e.g., a cancer, e.g., a cancer of the lung, prostate, breast, or colon or deregulated cell proliferation; or cell proliferation, cell differentiation, coagulation, or cell signaling.

In one embodiment, a disease or disorder associated with aberrant or unwanted 53070, 15985, 26583, 21953, m32404, 14089, or 23436 expression or activity is identified. A test sample is obtained from a subject and 53070, 15985, 26583, 21953, m32404, 14089, or 23436 protein or nucleic acid (e.g., mRNA or genomic DNA) is evaluated, wherein the level, e.g., the presence or absence, of 53070, 15985, 26583, 21953, m32404, 14089, or 23436 protein or nucleic acid is diagnostic for a subject having or at risk of developing a disease or disorder associated with aberrant or unwanted 53070, 15985, 26583, 21953, m32404, 14089, or 23436 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 53070, 15985, 26583, 21953, m32404, 14089, or 23436 expression or activity. For example, such methods can be used to determine whether a subject can be effectively treated with an agent for a cellular proliferative and/or differentiative disorder; a cell motility disorder; a metabolic disorder, e.g., a mitochondrial related disorder or a cholesterol biosynthesis related disorder, or a cell proliferation or differentiation disorder, e.g., a tumor; a cell proliferative or cell differentiative disorder, e.g., a cancer, e.g., a cancer of the lung, prostate, breast, or colon disorder; cell proliferation, cell differentiation, coagulation, or cell signaling; or an erythroid cell disorder or a proliferative disorder of erythroid, liver, prostate, or brain cells.

In another aspect, the invention features a computer medium having a plurality of digitally encoded data records. Each data record includes a value representing the level of expression of 53070, 15985, 26583, 21953, m32404, 14089, or 23436 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 53070, 15985, 26583, 21953, m32404, 14089, or 23436 (e.g., other genes associated with a 53070-, 15985-, 26583-, 21953-, m32404-, 14089-, or 23436-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 53070, 15985, 26583, 21953, m32404, 14089, or 23436 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a disorder, e.g., a cellular proliferative and/or differentiative disorder; a metabolic disorder, e.g., a mitochondrial related disorder or a cholesterol biosynthesis related disorder, or a cell proliferation or differentiation disorder, e.g., a tumor; a cell proliferative or cell differentiative disorder, e.g., a cancer, e.g., a cancer of the lung; or an erythroid cell disorder or a proliferative disorder of erythroid, liver, prostate, or brain cells, in a subject wherein either an increase or a decrease in 53070, 15985, 26583, 21953, m32404, 14089, or 23436 expression may be an indication that the subject has or is disposed to having a the disorder. The method can be used to monitor a treatment for a disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 53070, 15985, 26583, 21953, m32404, 14089, or 23436 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 53070, 15985, 26583, 21953, m32404, 14089, or 23436 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 53070, 15985, 26583, 21953, m32404, 14089, or 23436 expression.

53070, 15985, 26583, 21953, m32404, 14089, or 23436 Arrays and Uses Thereof

In another aspect, the invention features an array that includes a substrate having a plurality of addresses. At least one address of the plurality includes a capture probe that binds specifically to a 53070, 15985, 26583, 21953, m32404, 14089, or 23436 molecule (e.g., a 53070, 15985, 26583, 21953, m32404, 14089, or 23436 nucleic acid or a 53070, 15985, 26583, 21953, m32404, 14089, or 23436 polypeptide). The array can have a density of at least than 10, 50, 100, 200, 500, 1,000, 2,000, or 10,000 or more addresses/cm, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 53070, 15985, 26583, 21953, m32404, 14089, or 23436 nucleic acid, e.g., the sense or anti-sense strand. In one preferred embodiment, a subset of addresses of the plurality of addresses has a nucleic acid capture probe for 53070, 15985, 26583, 21953, m32404, 14089, or 23436. Each address of the subset can include a capture probe that hybridizes to a different region of a 53070, 15985, 26583, 21953, m32404, 14089, or 23436 nucleic acid. In another preferred embodiment, addresses of the subset include a capture probe for a 53070, 15985, 26583, 21953, m32404, 14089, or 23436 nucleic acid. Each address of the subset is unique, overlapping, and complementary to a different variant of 53070, 15985, 26583, 21953, m32404, 14089, or 23436 (e.g., an allelic variant, or all possible hypothetical variants). The array can be used to sequence 53070, 15985, 26583, 21953, m32404, 14089, or 23436 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 53070, 15985, 26583, 21953, m32404, 14089, or 23436 polypeptide or fragment thereof. The polypeptide can be a naturally-occurring interaction partner of 53070, 15985, 26583, 21953, m32404, 14089, or 23436 polypeptide. Preferably, the polypeptide is an antibody, e.g., an antibody described herein (see "Anti-53070, -15985, -26583, -21953, -m32404, -14089, or -23436 Antibodies," above), such as a monoclonal antibody or a single-chain antibody.

In another aspect, the invention features a method of analyzing the expression of 53070, 15985, 26583, 21953, m32404, 14089, or 23436. The method includes providing an array as described above; contacting the array with a sample and detecting binding of a 53070, 15985, 26583, 21953, m32404, 14089, or 23436 molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 53070, 15985, 26583, 21953, m32404, 14089, or 23436. If a sufficient number of diverse samples is analyzed, clustering (e.g., hierarchical clustering, k-means clustering, Bayesian clustering and the like) can be used to identify other genes which are co-regulated with 53070, 15985, 26583, 21953, m32404, 14089, or 23436. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 53070, 15985, 26583, 21953, m32404, 14089, or 23436 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 53070-, 15985-, 26583-, 21953-, m32404-, 14089-, or 23436-associated disease or disorder; and processes, such as a cellular transformation associated with a 53070-, 15985-, 26583-, 21953-, m32404-, 14089-, or 23436-associated disease or disorder. The method can also evaluate the treatment and/or progression of a 53070-, 15985-, 26583-, 21953-, m32404-, 14089-, or 23436-associated disease or disorder.

The array is also useful for ascertaining differential expression patterns of one or more genes in normal and abnormal cells. This provides a battery of genes (e.g., including 53070, 15985, 26583, 21953, m32404, 14089, or 23436) that could serve as a molecular target for diagnosis or therapeutic intervention.

In another aspect, the invention features an array having a plurality of addresses. Each address of the plurality includes a unique polypeptide. At least one address of the plurality has disposed thereon a 53070, 15985, 26583, 21953, m32404, 14089, or 23436 polypeptide or fragment thereof. Methods of producing polypeptide arrays are described in the art, e.g., in De Wildt et al. (2000). *Nature*

*Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80,85, 90, 95 or 99% identical to a 53070, 15985, 26583, 21953, m32404, 14089, or 23436 polypeptide or fragment thereof. For example, multiple variants of a 53070, 15985, 26583, 21953, m32404, 14089, or 23436 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 53070, 15985, 26583, 21953, m32404, 14089, or 23436 binding compound, e.g., an antibody in a sample from a subject with specificity for a 53070, 15985, 26583, 21953, m32404, 14089, or 23436 polypeptide or the presence of a 53070-, 15985-, 26583-, 21953-, m32404-, 14089-, or 23436-binding protein or ligand.

The array is also useful for ascertaining the effect of the expression of a gene on the expression of other genes in the same cell or in different cells (e.g., ascertaining the effect of 53070, 15985, 26583, 21953, m32404, 14089, or 23436 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 53070, 15985, 26583, 21953, m32404, 14089, or 23436 or from a cell or subject in which a 53070, 15985, 26583, 21953, m32404, 14089, or 23436 mediated response has been elicited, e.g., by contact of the cell with 53070, 15985, 26583, 21953, m32404, 14089, or 23436 nucleic acid or protein, or administration to the cell or subject 53070, 15985, 26583, 21953, m32404, 14089, or 23436 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 53070, 15985, 26583, 21953, m32404, 14089, or 23436 (or does not express as highly as in the case of the 53070, 15985, 26583, 21953, m32404, 14089, or 23436 positive plurality of capture probes) or from a cell or subject which in which a 53070, 15985, 26583, 21953, m32404, 14089, or 23436 mediated response has not been elicited (or has been elicited to a lesser extent than in the first sample); contacting the array with one or more inquiry probes (which is preferably other than a 53070, 15985, 26583, 21953, m32404, 14089, or 23436 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 53070, 15985, 26583, 21953, m32404, 14089, or 23436 or from a cell or subject in which a 53070-, 15985-, 26583-, 21953-, m32404-, 14089-, or 23436-mediated response has been elicited, e.g., by contact of the cell with 53070, 15985, 26583, 21953, m32404, 14089, or 23436 nucleic acid or protein, or administration to the cell or subject 53070, 15985, 26583, 21953, m32404, 14089, or 23436 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 53070, 15985, 26583, 21953, m32404, 14089, or 23436 (or does not express as highly as in the case of the 53070, 15985, 26583, 21953, m32404, 14089, or 23436 positive plurality of capture probes) or from a cell or subject which in which a 53070, 15985, 26583, 21953, m32404, 14089, or 23436 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 53070, 15985, 26583, 21953, m32404, 14089, or 23436, e.g., analyzing structure, function, or relatedness to other nucleic acid or amino acid sequences. The method includes: providing a 53070, 15985, 26583, 21953, m32404, 14089, or 23436 nucleic acid or amino acid sequence; comparing the 53070, 15985, 26583, 21953, m32404, 14089, or 23436 sequence with one or more preferably a plurality of sequences from a collection of sequences, e.g., a nucleic acid or protein sequence database; to thereby analyze 53070, 15985, 26583, 21953, m32404, 14089, or 23436.

Detection of 53070, 15985, 26583, 21953, m32404, 14089, or 23436 Variations or Mutations The methods of the invention can also be used to detect genetic alterations in a 53070, 15985, 26583, 21953, m32404, 14089, or 23436 gene, thereby determining if a subject with the altered gene is at risk for a disorder characterized by misregulation in 53070, 15985, 26583, 21953, m32404, 14089, or 23436 protein activity or nucleic acid expression, such as a cellular proliferative and/or differentiative disorder; a cancer or a neurological disorder; a metabolic disorder, e.g., a mitochondrial related disorder or a cholesterol biosynthesis related disorder, or a cell proliferation or differentiation disorder, e.g., a tumor; coagulation, or cell signaling disorders; or an erythroid cell disorder or a proliferative disorder of erythroid, liver, prostate, or brain cells disorder. In preferred embodiments, the methods include detecting, in a sample from the subject, the presence or absence of a genetic alteration characterized by at least one of an alteration affecting the integrity of a gene encoding a 53070, 15985, 26583, 21953, m32404, 14089, or 23436-protein, or the mis-expression of the 53070, 15985, 26583, 21953, m32404, 14089, or 23436 gene. For example, such genetic alterations can be detected by ascertaining the existence of at least one of 1) a deletion of one or more nucleotides from a 53070, 15985, 26583, 21953, m32404, 14089, or 23436 gene; 2) an addition of one or more nucleotides to a 53070, 15985, 26583, 21953, m32404, 14089, or 23436 gene; 3) a substitution of one or more nucleotides of a 53070, 15985, 26583, 21953, m32404, 14089, or 23436 gene, 4) a chromosomal rearrangement of a 53070, 15985, 26583, 21953, m32404, 14089, or 23436 gene; 5) an alteration in the level of a messenger RNA transcript of a 53070, 15985, 26583, 21953, m32404, 14089, or 23436 gene, 6) aberrant modification of a 53070, 15985, 26583, 21953, m32404, 14089, or 23436 gene, such as of the methylation pattern of the genomic DNA, 7) the presence of a non-wild type splicing pattern of a messenger RNA transcript of a 53070, 15985, 26583, 21953, m32404, 14089, or 23436 gene, 8) a non-wild type level of a 53070, 15985, 26583, 21953, m32404, 14089, or 23436-protein, 9) allelic loss of a 53070, 15985, 26583, 21953, m32404, 14089, or 23436 gene, and 10) inappropriate post-translational modification of a 53070, 15985, 26583, 21953, m32404, 14089, or 23436-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 53070, 15985, 26583, 21953, m32404, 14089, or 23436-gene. This method can include the steps of collecting a sample of cells from a subject, isolating nucleic acid (e.g., genomic, mRNA or both) from the sample, contacting the nucleic acid sample with one or more primers which specifically hybridize to a 53070, 15985, 26583, 21953, m32404, 14089, or 23436 gene under conditions such that hybridization and amplification of the 53070, 15985, 26583, 21953, m32404, 14089, or 23436-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 53070, 15985, 26583, 21953, m32404, 14089, or 23436 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 53070, 15985, 26583, 21953, m32404, 14089, or 23436 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 53070, 15985, 26583, 21953, m32404, 14089, or 23436 nucleic acid or a putative variant (e.g., allelic variant) thereof. A probe can have one or more mismatches to a region of a 53070, 15985, 26583, 21953, m32404, 14089, or 23436 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in 53070, 15985, 26583, 21953, m32404, 14089, or 23436 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 53070, 15985, 26583, 21953, m32404, 14089, or 23436 gene and detect mutations by comparing the sequence of the sample 53070, 15985, 26583, 21953, m32404, 14089, or 23436 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 53070, 15985, 26583, 21953, m32404, 14089, or 23436 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 53070, 15985, 26583, 21953, m32404, 14089, or 23436 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 53070, 15985, 26583, 21953, m32404, 14089, or 23436 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 53070, 15985, 26583, 21953, m32404, 14089, or 23436 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 53070, 15985, 26583, 21953, m32404, 14089, or 23436 nucleic acid.

In a preferred embodiment the set includes a first and a second oligonucleotide. The first and second oligonucleotide can hybridize to the same or to different locations of SEQ ID NO:1, 7, 14, 19, 24, 33, or 40 or the complement of SEQ ID NO: 1, 7, 14, 19, 24, 33, or 40. Different locations can be different but overlapping, or non-overlapping on the same strand. The first and second oligonucleotide can hybridize to sites on the same or on different strands.

The set can be useful, e.g., for identifying SNP's, or identifying specific alleles of 53070, 15985, 26583, 21953, m32404, 14089, or 23436. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 53070, 15985, 26583, 21953, m32404, 14089, or 23436 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 53070, 15985, 26583, 21953, m32404, 14089, or 23436 gene.

Use of 53070, 15985, 26583, 21953, m32404, 14089, or 23436 Molecules as Surrogate Markers The 53070, 15985, 26583, 21953, m32404, 14089, or 23436 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 53070, 15985, 26583, 21953, m32404, 14089, or 23436 molecules of the invention may be detected, and may be correlated with one or more biological states in vivo. For example, the 53070, 15985, 26583, 21953, m32404, 14089, or 23436 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 53070, 15985, 26583, 21953, m32404, 14089, or 23436 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 53070, 15985, 26583, 21953, m32404, 14089, or 23436 marker) transcription or expression, the amplified marker may be in a quantity which is more readily detectable than the drug itself. Also, the marker may be more easily detected due to the nature of the marker itself; for example, using the methods described herein, anti-53070, -15985, -26583, -21953, -m32404, -14089, or -23436 antibodies may be employed in an immune-based detection system for a 53070, 15985, 26583, 21953, m32404, 14089, or 23436 protein marker, or 53070-, 15985-, 26583-, 21953-, m32404-, 14089-, or 23436-specific radiolabeled probes may be used to detect a 53070, 15985, 26583, 21953, m32404, 14089, or 23436 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S 16-S20.

The 53070, 15985, 26583, 21953, m32404, 14089, or 23436 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 53070, 15985, 26583, 21953, m32404, 14089, or 23436 protein or RNA) for specific tumor markers in a subject, a drug or course of treatment may be selected that is optimized for the treatment of the specific tumor likely to be present in the subject. Similarly, the presence or absence of a specific sequence mutation in 53070, 15985, 26583, 21953, m32404, 14089, or 23436 DNA may correlate 53070, 15985, 26583, 21953, m32404, 14089, or 23436 drug response. The use of pharmacogenomic markers therefore permits the application of the most appropriate treatment for each subject without having to administer the therapy.

Pharmaceutical Compositions of 53070, 15985, 26583, 21953, m32404, 14089, or 23436

The nucleic acid and polypeptides, fragments thereof, as well as anti-53070, -15985, -26583, -21953, -m32404, -14089, or -23436 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 53070, 15985, 26583, 21953, m32404, 14089, or 23436

The present invention provides for both prophylactic and therapeutic methods of treating a subject at risk of (or susceptible to) a disorder or having a disorder associated with aberrant or unwanted 53070, 15985, 26583, 21953, m32404, 14089, or 23436 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 53070, 15985, 26583, 21953, m32404, 14089, or 23436 molecules of the present invention or 53070, 15985, 26583, 21953, m32404, 14089, or 23436 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 53070, 15985, 26583, 21953, m32404, 14089, or 23436 expression or activity, by administering to the subject a 53070, 15985, 26583, 21953, m32404, 14089, or 23436 or an agent which modulates 53070, 15985, 26583, 21953, m32404, 14089, or 23436 expression or at least one 53070, 15985, 26583, 21953, m32404, 14089, or 23436 activity. Subjects at risk for a disease which is caused or contributed to by aberrant or unwanted 53070, 15985, 26583, 21953, m32404, 14089, or 23436 expression or activity can be identified by, for example, any or a combination of diagnostic or prognostic assays as described herein. Administration of a prophylactic agent can occur prior to the manifestation of symptoms characteristic of the 53070, 15985, 26583, 21953, m32404, 14089, or 23436 aberrance, such that a disease or disorder is prevented or, alternatively, delayed in its progression. Depending on the type of 53070, 15985, 26583, 21953, m32404, 14089, or 23436 aberrance, for example, a 53070, 15985, 26583, 21953, m32404, 14089, or 23436, 53070, 15985, 26583, 21953, m32404, 14089, or 23436 agonist or 53070, 15985, 26583, 21953, m32404, 14089, or 23436 antagonist agent can be used for treating the subject. The appropriate agent can be determined based on screening assays described herein.

It is possible that some 53070, 15985, 26583, 21953, m32404, 14089, or 23436 disorders can be caused, at least in part, by an abnormal level of gene product, or by the presence of a gene product exhibiting abnormal activity. As such, the reduction in the level and/or activity of such gene products would bring about the amelioration of disorder symptoms.

The 53070 molecules can act as novel diagnostic targets and therapeutic agents for controlling one or more of cellular proliferative and/or differentiative disorders, disorders associated with bone metabolism, immune disorders, cardiovascular disorders, liver disorders, viral diseases, pain or metabolic disorders.

The 15985 molecules can act as novel diagnostic targets and therapeutic agents for controlling one or more of cellular proliferative and/or differentiative disorders, immune disorders, cardiovascular disorders, as described above, as well as liver disorders, lung disorders, ovarian disorders, viral diseases, pain or metabolic disorders.

The 21953 molecules can act as novel diagnostic targets and therapeutic agents for controlling one or more of cellular proliferative and/or differentiative disorders, disorders associated with bone metabolism, immune disorders, cardiovascular disorders, liver disorders, viral diseases, pain or metabolic disorders.

The m32404 molecules can act as novel diagnostic targets and therapeutic agents for controlling one or more of cellular proliferative and/or differentiative disorders, disorders associated with bone metabolism, immune disorders, hematopoietic disorders, cardiovascular disorders, liver disorders, viral diseases, pain or metabolic disorders The 14089 molecules can act as novel diagnostic targets and therapeutic agents for controlling one or more of cellular proliferative and/or differentiative disorders as described above, disorders associated with bone metabolism, immune disorders, hematopoietic disorders, cardiovascular disorders, liver disorders, viral diseases, pain or metabolic disorders.

The 23436 molecules can act as novel diagnostic targets and therapeutic agents for controlling one or more of cellular proliferative and/or differentiative disorders (e.g., lymphomas, leukemias, prostate, liver, and brain cancers), and disorders associated with erythroid cell differentiation and erythroid cell function, e.g., a disorder described herein.

Examples of such disorders are discussed above and below.

Aberrant expression and/or activity of 53070, 21953, m32404, or 14089 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 53070, 21953, m32404, or 14089 molecules effects in bone cells, e.g. osteoclasts and osteoblasts, that may in turn result in bone formation and degeneration. For example, 53070, 21953, m32404, or 14089 molecules may support different activities of bone resorbing osteoclasts such as the stimulation of differentiation of monocytes and mononuclear phagocytes into osteoclasts. Accordingly, 53070, 21953, m32404, or 14089 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Disorders associated with the liver include, but are not limited to, those arising from an accumulation in the liver of fibrous tissue, such as that resulting from an imbalance between production and degradation of the extracellular matrix accompanied by the collapse and condensation of preexisting fibers; hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic); and portal hypertension or hepatic fibrosis, e.g., fibrosis resulting from a storage disorder such as Gaucher's disease (lipid abnormalities) or a glycogen storage disease, Al-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, liver disorders can include injury associated with the administration of various chemicals or drugs, such as for example, methotrexate, isonizaid, oxyphenisatin, methyldopa, chlorpromazine, tolbutamide or alcohol, or a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Examples of disorders of the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Examples of cellular proliferative and/or differentiative disorders include cancers and proliferative disorders mentioned above. Further examples of cancers or neoplastic conditions, in addition to the ones described above include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sézary syndrome, and Hodgkin disease.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure. coronary artery disease, valvular disease, arrhythmias, and cardiomyopathies. Other disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, artherosclerosis, and hypertensive vascular disease; inflammatory disease—the vasculitides, such as giant cell (temporal) arteritis, Takayasu arterisis, polyarterisis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders of the blood coagulation systems include, but are not limited to, hemorrhagic diatheses, nonthrombocytopenic purpuras, thrombocytopenia, idiopathic thrombocytopenic purpura (ITP), HIV-associated thrombocytopenia, thrombotic microangiopathies, hemorrhagic diatheses, and disseminated intravascular coagulation (DIC).

m32404 may also be involved in disorders involving the thymus, including the developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lymphomas, Hodgkin disease, and carcinoids. Thymomas can include benign or encapsulated thymoma, and malignant thymoma Type I (invasive thymoma) or Type II, designated thymic carcinoma.

Examples of hematopoieitic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Additionally, 53070, 15985, 21953, m32404, or 14089 molecules may play an important role in the etiology of certain viral diseases, including but not limited to Hepatitis B, Hepatitis C and Herpes Simplex Virus (HSV). Modulators of 53070, 15985, 21953, m32404, or 14089 activity could be used to control viral diseases. The modulators can be used in the treatment and/or diagnosis of viral infected tissue or virus-associated tissue fibrosis, especially liver and liver fibrosis. Also, 53070, 15985, 21953, m32404, or 14089 modulators can be used in the treatment and/or diagnosis of virus-associated carcinoma, especially hepatocellular cancer.

Additionally, 53070, 15985, 21953, m32404, or 14089 may play an important role in the regulation of metabolism or pain disorders, e.g. by 21953 processing neuropeptides and metabolic peptide hormones. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with musculoskeletal disorders, e.g., joint pain; tooth pain; headaches; pain associated with surgery; pain related to irritable bowel syndrome; or chest pain.

Modulators of 15985 activity could be used to control viral diseases. The modulators can be used in the treatment and/or diagnosis of viral infected tissue or virus-associated tissue fibrosis, especially liver and liver fibrosis. Also, 15985 modulators can be used in the treatment and/or diagnosis of virus-associated carcinoma, especially hepatocellular cancer.

As discussed, successful treatment of 53070, 15985, 26583, 21953, m32404, 14089, or 23436 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 53070, 15985, 26583, 21953, m32404, 14089, or 23436 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, $F(ab')_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 53070, 15985, 26583, 21953, m32404, 14089, or 23436 expression is through the use of aptamer molecules specific for 53070, 15985, 26583, 21953, m32404, 14089, or 23436 protein. Aptamers are nucleic acid molecules having a tertiary structure which permits them to specifically bind to protein ligands (see, e.g., Osborne, et al. (1997) *Curr. Opin. Chem Biol.* 1:5-9; and Patel, D. J. (1997) *Curr Opin Chem Biol* 1:32-46). Since nucleic acid molecules may in many cases be more conveniently introduced into target cells than therapeutic protein molecules may be, aptamers offer a method by which 53070, 15985, 26583, 21953, m32404, 14089, or 23436 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 53070, 15985, 26583, 21953, m32404, 14089, or 23436 disorders. For a description of antibodies, see the Antibody section above.

In circumstances wherein injection of an animal or a human subject with a 53070, 15985, 26583, 21953, m32404, 14089, or 23436 protein or epitope for stimulating antibody production is harmful to the subject, it is possible to generate an immune response against 53070, 15985, 26583, 21953, m32404, 14089, or 23436 through the use of anti-idiotypic antibodies (see, for example, Herlyn, D. (1999) *Ann Med* 31:66-78; and Bhattacharya-Chatterjee, M., and Foon, K. A. (1998) *Cancer Treat Res.* 94:51-68). If an anti-idiotypic antibody is introduced into a mammal or human subject, it should stimulate the production of anti-anti-idiotypic antibodies, which should be specific to the 53070, 15985, 26583, 21953, m32404, 14089, or 23436 protein. Vaccines directed to a disease characterized by 53070, 15985, 26583, 21953, m32404, 14089, or 23436 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 53070, 15985, 26583, 21953, m32404, 14089, or 23436 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 53070, 15985, 26583, 21953, m32404, 14089, or 23436 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89-94 and in Shea, K. J. (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound which modulates the expression or activity of 53070, 15985, 26583, 21953, m32404, 14089, or 23436 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al (1995) *Analytical Chemistry* 67:2142-2144.

Another aspect of the invention pertains to methods of modulating 53070, 15985, 26583, 21953, m32404, 14089, or 23436 expression or activity for therapeutic purposes. Accordingly, in an exemplary embodiment, the modulatory method of the invention involves contacting a cell with a 53070, 15985, 26583, 21953, m32404, 14089, or 23436 or agent that modulates one or more of the activities of 53070, 15985, 26583, 21953, m32404, 14089, or 23436 protein activity associated with the cell. An agent that modulates 53070, 15985, 26583, 21953, m32404, 14089, or 23436 protein activity can be an agent as described herein, such as a nucleic acid or a protein, a naturally-occurring target molecule of a 53070, 15985, 26583, 21953, m32404, 14089, or 23436 protein (e.g., a 53070, 15985, 26583, 21953, m32404, 14089, or 23436 substrate or receptor), a 53070, 15985, 26583, 21953, m32404, 14089, or 23436 antibody, a 53070, 15985, 26583, 21953, m32404, 14089, or 23436 agonist or antagonist, a peptidomimetic of a 53070, 15985, 26583, 21953, m32404, 14089, or 23436 agonist or antagonist, or other small molecule.

In one embodiment, the agent stimulates one or more 53070, 15985, 26583, 21953, m32404, 14089, or 23436 activities. Examples of such stimulatory agents include activated 53070, 15985, 26583, 21953, m32404, 14089, or 23436 protein and a nucleic acid molecule encoding 53070, 15985, 26583, 21953, m32404, 14089, or 23436. In another embodiment, the agent inhibits one or more 53070, 15985, 26583, 21953, m32404, 14089, or 23436 activities. Examples of such inhibitory agents include antisense 53070, 15985, 26583, 21953, m32404, 14089, or 23436 nucleic acid molecules, anti-53070, -15985, -26583, -21953, -m32404, -14089, or -23436 antibodies, and 53070, 15985, 26583, 21953, m32404, 14089, or 23436 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 53070, 15985, 26583, 21953, m32404, 14089, or 23436 protein or nucleic acid molecule. In one embodiment, the method involves administering an agent (e.g., an agent identified by a screening assay described herein), or combination of agents that modulates (e.g., up regulates or down regulates) 53070, 15985, 26583, 21953, m32404, 14089, or 23436 expression or activity. In another embodiment, the method involves administering a 53070, 15985, 26583, 21953, m32404, 14089, or 23436 protein or nucleic acid molecule as therapy to compensate for reduced, aberrant, or unwanted 53070, 15985, 26583, 21953, m32404, 14089, or 23436 expression or activity.

Stimulation of 53070, 15985, 26583, 21953, m32404, 14089, or 23436 activity is desirable in situations in which 53070, 15985, 26583, 21953, m32404, 14089, or 23436 is abnormally downregulated and/or in which increased 53070, 15985, 26583, 21953, m32404, 14089, or 23436 activity is likely to have a beneficial effect. For example, stimulation of 53070, 15985, 26583, 21953, m32404, 14089, or 23436 activity is desirable in situations in which a 53070, 15985, 26583, 21953, m32404, 14089, or 23436 is downregulated and/or in which increased 53070, 15985, 26583, 21953, m32404, 14089, or 23436 activity is likely to have a beneficial effect. Likewise, inhibition of 53070, 15985, 26583, 21953, m32404, 14089, or 23436 activity is desirable in situations in which 53070, 15985, 26583, 21953, m32404, 14089, or 23436 is abnormally upregulated and/or in which decreased 53070, 15985, 26583, 21953, m32404, 14089, or 23436 activity is likely to have a beneficial effect.

53070, 15985, 26583, 21953, m32404, 14089, or 23436 Pharmacogenomics

The 53070, 15985, 26583, 21953, m32404, 14089, or 23436 molecules of the present invention, as well as agents, or modulators which have a stimulatory or inhibitory effect on 53070, 15985, 26583, 21953, m32404, 14089, or 23436 activity (e.g., 53070, 15985, 26583, 21953, m32404, 14089, or 23436 gene expression) as identified by a screening assay described herein can be administered to individuals to treat (prophylactically or therapeutically) 53070, 15985, 26583, 21953, m32404, 14089, or 23436 associated disorders (e.g., cellular proliferative and/or differentiative disorders; neuronal migration; hyperproliferative disorders; a cancer, e.g., a cancer of the lung, prostate, breast, or colon in the case of 21953; coagulative disorders, organogenetic disorders, complement activation disorders, hormone production disorders; or an erythroid cell disorder or a proliferative disorder of erythroid, liver, prostate, or brain cells) associated with aberrant or unwanted 53070, 15985, 26583, 21953, m32404, 14089, or 23436 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 53070, 15985, 26583, 21953, m32404, 14089, or 23436 molecule or 53070, 15985, 26583, 21953, m32404, 14089, or 23436 modulator as well as tailoring the dosage and/or therapeutic regimen of treatment with a 53070, 15985, 26583, 21953, m32404, 14089, or 23436 molecule or 53070, 15985, 26583, 21953, m32404, 14089, or 23436 modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23:983-985 and Linder, M. W. et al. (1997) Clin. Chem. 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 53070, 15985, 26583, 21953, m32404, 14089, or 23436 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 53070, 15985, 26583, 21953, m32404, 14089, or 23436 molecule or 53070, 15985, 26583, 21953, m32404, 14089, or 23436 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 53070, 15985, 26583, 21953, m32404, 14089, or 23436 molecule or 53070, 15985, 26583, 21953, m32404, 14089, or 23436 modulator, such as a modulator identified by one of the exemplary screening assays described herein.

The present invention further provides methods for identifying new agents, or combinations, that are based on identifying agents that modulate the activity of one or more of the gene products encoded by one or more of the 53070, 15985, 26583, 21953, m32404, 14089, or 23436 genes of the present invention, wherein these products may be associated with resistance of the cells to a therapeutic agent. Specifically, the activity of the proteins encoded by the 53070, 15985, 26583, 21953, m32404, 14089, or 23436 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 53070, 15985, 26583, 21953, m32404, 14089, or 23436 protein can be applied in clinical trials. For example, the effectiveness of an agent determined by a screening assay as described herein to increase 53070, 15985, 26583, 21953, m32404, 14089, or 23436 gene expression, protein levels, or upregulate 53070, 15985, 26583, 21953, m32404, 14089, or 23436 activity, can be monitored in clinical trials of subjects exhibiting decreased 53070, 15985, 26583, 21953, m32404, 14089, or 23436 gene expression, protein levels, or downregulated 53070, 15985, 26583, 21953, m32404, 14089, or 23436 activity. Alternatively, the effectiveness of an agent determined by a screening assay to decrease 53070, 15985, 26583, 21953, m32404, 14089, or 23436 gene expression, protein levels, or downregulate 53070, 15985, 26583, 21953, m32404, 14089, or 23436 activity, can be monitored in clinical trials of subjects exhibiting increased 53070, 15985, 26583, 21953, m32404, 14089, or 23436 gene expression, protein levels, or upregulated 53070, 15985, 26583, 21953, m32404, 14089, or 23436 activity. In such clinical trials, the expression or activity of a 53070, 15985, 26583, 21953, m32404, 14089, or 23436 gene, and preferably, other genes that have been implicated in, for example, a 53070, 15985, 26583, 21953, m32404, 14089, or 23436-associated disorder can be used as a "read out" or markers of the phenotype of a particular cell.

This invention is further illustrated by the following examples that should not be construed as limiting. The contents of all references, patents and published patent applications cited throughout this application are incorporated herein by reference.

EXAMPLES

Examples for 53070

Example 1

Identification and Characterization of Human 53070 cDNA

The human 53070 sequence (FIG. 1; SEQ ID NO:1), which is approximately 1704 nucleotides long. The nucleic acid sequence includes an initiation codon (ATG) and a termination codon (TGA). The region between and inclusive of the initiation codon and the termination codon is a methionine-initiated coding sequence of about 1104 nucleotides, including the termination codon (nucleotides indicated as "coding" of SEQ ID NO:1; SEQ ID NO:3). The coding sequence encodes a 367 amino acid protein (SEQ ID NO:2).

Example 2

Tissue Distribution of 53070 mRNA by TaqMan Analysis

Endogenous human 53070 gene expression can be determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of 53070 in various human tissues a primer/probe set can be designed. Total RNA can be prepared from a series of human tissues using an RNeasy kit from Qiagen. First strand cDNA can be prepared from 1 μg total RNA using an oligo-dT primer and Superscript II reverse transcriptase (Gibco/BRL). cDNA obtained from approximately 50 ng total RNA is used per TaqMan reaction. Tissues tested can include human tissues, e.g., colon, liver, lung, breast, heart, brain, blood, or testes, as well as cell lines of human origin, e.g., cell lines obtains from tumors.

Example 3

Tissue Distribution of 53070 mRNA by Northern Analysis

Northern blot hybridizations with various RNA samples can be performed under standard conditions and washed under stringent conditions, i.e., 0.2×SSC at 65° C. A DNA probe corresponding to all or a portion of the 53070 cDNA (SEQ ID NO:1) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 4

Recombinant Expression of 53070 in Bacterial Cells

In this example, 53070 is expressed as a recombinant glutathione-S-transferase (GST) fusion polypeptide in *E. coli* and the fusion polypeptide is isolated and characterized. Specifically, 53070 is fused to GST and this fusion polypeptide is expressed in *E. coli*, e.g., strain PEB 199. Expression of the GST-53070 fusion protein in PEB 199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 5

Expression of Recombinant 53070 Protein in COS Cells

To express the 53070 gene in COS cells (e.g., COS-7 cells, CV-1 origin SV40 cells; Gluzman (1981) *Cell* 23: 175-182), the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 53070 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 53070 DNA sequence is amplified by PCR using two primers. The 5' primer contains the restriction site of interest followed by approximately twenty nucleotides of the 53070 coding sequence starting from the initiation codon; the 3' end sequence contains complementary sequences to the other restriction site of interest, a translation stop codon, the HA tag or FLAG tag and the last 20 nucleotides of the 53070 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 53070 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 53070-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual.* 2nd, ed., Cold Spring Harbor Laboratory, Cold Spring Harbor Laboratory Press, Cold Spring Harbor, N.Y. The expression of the 53070 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 53070 coding sequence is cloned directly into the polylinker of the pCDNA/Amp vector using the appropriate restriction sites. The resulting plasmid is transfected into COS cells in the manner described above, and the expression of the 53070 polypeptide is detected by radiolabelling and immunoprecipitation using a 53070 specific monoclonal antibody.

Examples for 15985

Example 6

Identification and Characterization of Human 15985 cDNA

Figure 4:
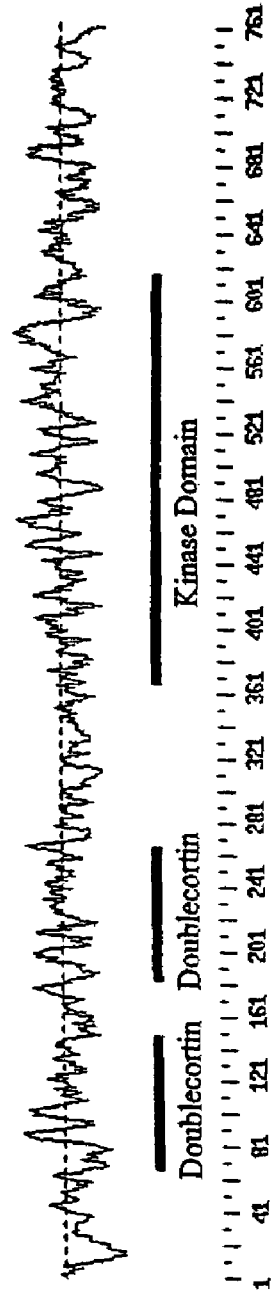
FIG. 4 depicts a hydropathy plot of human 15985. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 15985 are indicated. Polypeptides of the invention include fragments which include: all or part of a hydrophobic sequence, i.e., a sequence above the dashed line, e.g., the sequence from about amino acid 83 to 91, from about 465 to 472, and from about 568 to 585 of SEQ ID NO:8; all or part of a hydrophilic sequence, i.e., a sequence below the dashed line, e.g., the sequence of from about amino acid 8 to 20, from about 592 to 600, and from about 652 to 672 of SEQ ID NO:8; a sequence which includes a Cys, or a glycosylation site.
Figure 9:
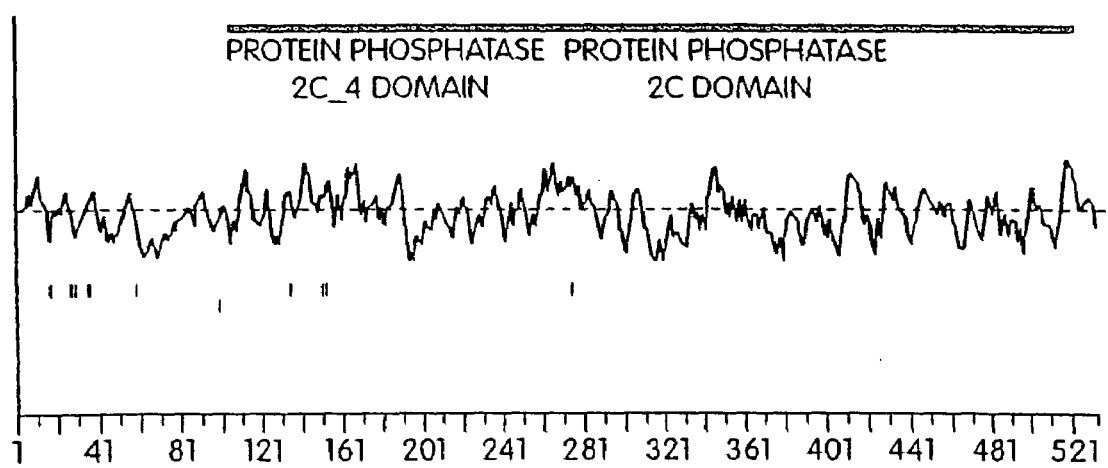
FIG. 9 depicts a hydropathy plot of human 26583. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 26583 are indicated. Polypeptides of the invention include fragments which include: all or part of a hydrophobic sequence, i.e., a sequence above the dashed line, e.g., the sequence of 262-279; all or part of a hydrophilic sequence, i.e., a sequence below the dashed line, e.g., the sequence of 60-70; a sequence which includes a Cys, or a glycosylation site.

The human 15985 sequence (FIG. 4; SEQ ID NO:7), which is approximately 3552 nucleotides long. The nucleic acid sequence includes an initiation codon (ATG) and a termination codon (TGA). The region between and inclusive of the initiation codon and the termination codon is a methionine-initiated coding sequence of about 2301 nucleotides, including the termination codon (nucleotides indicated as "coding" of SEQ ID NO:7; SEQ ID NO:9). The coding sequence encodes a 766 amino acid protein (SEQ ID NO:8).

Example 7

Tissue Distribution of 15985 mRNA by TaqMan Analysis

Endogenous human 15985 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of 15985 in various human tissues a primer/probe set was designed. Total RNA was prepared from a series of human tissues using an RNeasy kit from Qiagen. First strand cDNA was prepared from 1 µg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in Tables 1, 2, and 3.

Table 1 below depicts the expression of 15985 mRNA in a panel of normal and tumor human tissues using TaqMan analysis. Elevated expression of 15985 mRNA was found in the following tissues: normal vein, hemangionoma, heart (Congestive Heart Failure), normal adiopose, normal brain cortex, ovary and ovary tumor, normal prostate, normal colon, and normal lung.

| Tissue Type     | Expression |
|-----------------|------------|
| Artery normal   | 0.0132     |
| Aorta diseased  | 0.0252     |
| Vein normal     | 2.5329     |
| Coronary SMC    | 0.0116     |
| HUVEC           | 0.0922     |
| Hemangioma      | 0.3513     |
| Heart normal    | 0.0321     |

-continued

| Tissue Type | Expression |
|---|---|
| Heart CHF | 0.2163 |
| Kidney | 0.017 |
| Skeletal Muscle | 0.0386 |
| Adipose normal | 0.2672 |
| Pancreas | 0.0301 |
| primary osteoblasts | 0.0087 |
| Osteoclasts (diff) | 0.0015 |
| Skin normal | 0.0687 |
| Spinal cord normal | 0.0519 |
| Brain Cortex normal | 0.3335 |
| Brain Hypothalamus normal | 0.9017 |
| Nerve | 0.0074 |
| DRG (Dorsal Root Ganglion) | 0.2644 |
| Breast normal | 0.0258 |
| Breast tumor | 0.026 |
| Ovary normal | 0.1373 |
| Ovary Tumor | 0.5143 |
| Prostate Normal | 0.2493 |
| Prostate Tumor | 0.0182 |
| Salivary glands | 0.0049 |
| Colon normal | 0.2718 |
| Colon Tumor | 0.0223 |
| Lung normal | 0.2785 |
| Lung tumor | 0.0585 |
| Lung COPD | 0.1005 |
| Liver normal | 0.017 |
| Liver fibrosis | 0.0494 |
| Spleen normal | 0.0491 |
| Tonsil normal | 0.0432 |
| Lymph node normal | 0.0211 |
| Small intestine normal | 0.0922 |
| Skin-Decubitus | 0.0321 |
| Synovium | 0.0275 |
| BM-MNC | 0.0041 |
| Activated PBMC | 0.0043 |
| Neutrophils | 0.0003 |
| Megakaryocytes | 0.0108 |
| Erythroid | 0.0009 |
| Lung COPD | 0.0998 |

Table 2 below depicts the expression of 15985 mRNA in a panel of normal and tumor breast tissues using TaqMan analysis. Increased expression of 15985 mRNA can be observed in SkBr3 and Hs578Bst cells.

| Tissue Type | Expression |
|---|---|
| MCF10MS | 0.00 |
| MCF10A | 0.00 |
| MCF10AT.cl1 | 0.05 |
| MCF10AT.cl3 | 0.09 |
| MCF10AT1 | 0.00 |
| MCF10AT3B | 0.08 |
| MCF10CA1a.cl1 | 0.00 |
| MCF10CA1a.cl1 Agar | 0.00 |
| MCF10A.m25 Plastic | 0.00 |
| MCF10CA Agar | 0.00 |
| MCF10CA Plastic | 0.00 |
| MCF3B Agar | 0.00 |
| MCF3B Plastic | 0.00 |
| MCF10A EGF 0 hr | 0.02 |
| MCF10A EGF 0.5 hr | 0.01 |
| MCF10A EGF 1 hr | 0.02 |
| MCF10A EGF 2 hr | 0.00 |
| MCF10A EGF 4 hr | 0.00 |
| MCF10A EGF 8 hr | 0.00 |
| MCF10A IGF1A 0 hr | 0.00 |
| MCF10A IGF1A 0.5 hr | 0.00 |
| MCF10A IGF1A 1 hr | 0.00 |
| MCF10A IGF1A 3 hr | 0.00 |
| MCF10A IGF1A 24 hr | 0.00 |
| MCF10AT3B.cl5 Plastic | 0.33 |
| MCF10AT3B.cl6 Plastic | 0.00 |
| MCF10AT3B.cl3 Plastic | 0.00 |
| MCF10AT3B.cl1 Plastic | 0.35 |
| MCF10AT3B.cl4 Plastic | 0.19 |
| MCF10AT3B.cl2 Plastic | 0.23 |
| MCF10AT3B.cl5 Agar | 0.00 |
| MCF10AT3B.cl6 Agar | 0.00 |
| MCF-7 | 0.00 |
| ZR-75 | 0.00 |
| T47D | 0.00 |
| MDA-231 | 0.12 |
| MDA-435 | 0.00 |
| SkBr3 | 1.93 |
| Hs578Bst | 1.46 |
| Hs578T | 0.12 |
| MCF10AT3B Agar | 0.31 |

Table 3 below also depicts the expression of 15985 mRNA in a panel of normal and tumor human tissue. Increased expression can be observed in ovary tumor and lung tumor samples.

| Tissue Type | Expression |
|---|---|
| PIT 400 Breast N | 0.36 |
| PIT 372 Breast N | 0.35 |
| CHT 1228 Breast Normal | 0.09 |
| MDA 304 Breast T: MD-IDC | 0.05 |
| CHT 2002 Breast T: IDC | 0.25 |
| MDA 236-Breast T: PD-IDC(ILC?) | 0.00 |
| CHT 562 Breast T: IDC | 0.04 |
| NDR 138 Breast T ILC (LG) | 0.10 |
| CHT 1841 Lymph node (Breast met) | 0.00 |
| PIT 58 Lung (Breast met) | 0.00 |
| CHT 620 Ovary N | 1.32 |
| PIT 208 Ovary N | 2.15 |
| CLN 012 Ovary T | 26.46 |
| CLN 07 Ovary T | 2.87 |
| CLN 17 Ovary T | 4.52 |
| MDA 25 Ovary T | 0.00 |
| CLN 08 Ovary T | 0.87 |
| PIT 298 Lung N | 0.03 |
| MDA 185 Lung N | 0.07 |
| CLN 930 Lung N | 0.29 |
| MPI 215 Lung T-SmC | 2.95 |
| MDA 259 Lung T-PDNSCCL | 12.78 |
| CHT 832 Lung T-PDNSCCL | 0.07 |
| MDA 262 Lung T-SCC | 2.27 |
| CHT 793 Lung T-ACA | 0.03 |
| CHT 331 Lung T-ACA | 0.91 |
| CHT 405 Colon N | 0.03 |
| CHT 523 Colon N | 0.25 |
| CHT 371 Colon N | 0.01 |
| CHT 382 Colon T: MD | 0.00 |
| CHT 528 Colon T: MD | 0.03 |
| CLN 609 Colon T | 1.74 |
| NDR 210 Colon T: MD-PD | 0.46 |
| CHT 340 Colon-Liver Met | 0.00 |
| CHT 1637 Colon-Liver Met | 0.00 |
| PIT 260 Liver N (female) | 0.00 |
| CHT 1653 Cervix Squamous CC | 0.23 |
| CHT 569 Cervix Squamous CC | 0.00 |
| A24 HMVEC-Arr | 0.08 |
| C48 HMVEC-Prol | 0.04 |
| Pooled Hemangiomas | 0.12 |
| HCT116N22 Normoxic | 2.08 |
| HCT116H22 Hypoxic | 0.00 |

Example 8

Tissue Distribution of 15985 mRNA by Northern Analysis

Northern blot hybridizations with various RNA samples can be performed under standard conditions and washed under stringent conditions, i.e., 0.2×SSC at 65° C. A DNA probe corresponding to all or a portion of the 15985 cDNA (SEQ ID NO:7) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 9

Recombinant Expression of 15985 in Bacterial Cells

In this example, 15985 is expressed as a recombinant glutathione-S-transferase (GST) fusion polypeptide in *E. coli* and the fusion polypeptide is isolated and characterized. Specifically, 15985 is fused to GST and this fusion polypeptide is expressed in *E. coli*, e.g., strain PEB199. Expression of the GST-15985 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 10

Expression of Recombinant 15985 Protein in COS Cells

To express the 15985 gene in COS cells (e.g., COS-7 cells, CV-1 origin SV40 cells; Gluzman (1981) *Cell*123: 175-182), the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 15985 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 15985 DNA sequence is amplified by PCR using two primers. The 5' primer contains the restriction site of interest followed by approximately twenty nucleotides of the 15985 coding sequence starting from the initiation codon; the 3' end sequence contains complementary sequences to the other restriction site of interest, a translation stop codon, the HA tag or FLAG tag and the last 20 nucleotides of the 15985 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 15985 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 15985-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual*. 2nd, ed., Cold Spring Harbor Laboratory, Cold Spring Harbor Laboratory Press, Cold Spring Harbor, N.Y. The expression of the 15985 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 15985 coding sequence is cloned directly into the polylinker of the pCDNA/Amp vector using the appropriate restriction sites. The resulting plasmid is transfected into COS cells in the manner described above, and the expression of the 15985 polypeptide is detected by radiolabelling and immunoprecipitation using a 15985 specific monoclonal antibody.

Examples for 26583

Example 11

Identification and Characterization of Human 26583 cDNA

The human 26583 sequence (SEQ ID NO:14), which is approximately 2838 nucleotides long including untranslated regions, contains a predicted methionine-initiated coding sequence of about 1613 nucleotides (nucleotides 462 to 2075 of SEQ ID NO:14; SEQ ID NO:16). The coding sequence encodes a 537 amino acid protein (SEQ ID NO:15).

Example 12

Tissue Distribution of 26583 mRNA

Endogenous human 26583 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Samples can be internally controlled by the addition of a second set of primers/probe specific for a housekeeping gene such as GAPDH which has been labeled with a different fluorophore on the 5' end (typically VIC).

To determine the level of 26583 in various human tissues a primer/probe set was designed using Primer Express (Perkin-Elmer) software and primary cDNA sequence information. Total RNA was prepared from a series of human tissues using an RNeasy kit from Qiagen. First strand cDNA was prepared from 1 µg total RNA using an oligo-dT primer and Superscript II reverse transcriptase (Gibco/BRL). cDNA obtained from approximately 50 ng total RNA was used per TaqMan reaction.

26583 mRNA was analyzed in a variety of normal and tumor clinical tissue samples. 26853 expression was found in human breast, lung, colon, liver, and brain. FIG. 11 shows relative 26583 mRNA expression on mRNA derived from the following tissue samples: columns 1-3, normal breast; columns 4-10, breast tumor; columns 11-13, normal lung; columns 14-20, lung tumor; columns 21-23, normal colon; columns 24-31, colon tumor; columns 32-35, colon metastases; columns 36-37, normal liver; columns 38-39, normal brain; columns 40-42, brain tumor. On average, 26583 expression was increased in lung tumor tissue as compared to normal lung tissue. 26583 expression levels were substantially lower in brain tumor tissue compared to normal brain.

Northern blot hybridizations with various RNA samples can be performed under standard conditions and washed under stringent conditions, i.e., 0.2×SSC at 65° C. A DNA probe corresponding to all or a portion of the 26583 cDNA (SEQ ID NO:14) can be used. The DNA can be radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 13

Recombinant Expression of 26583 in Bacterial Cells

In this example, 26583 is expressed as a recombinant glutathione-S-transferase (GST) fusion polypeptide in *E. coli* and the fusion polypeptide is isolated and characterized. Specifically, 26583 is fused to GST and this fusion polypeptide is expressed in *E. coli*, e.g., strain PEB 199. Expression of the GST-26583 fusion protein in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 14

Expression of Recombinant 26583 Protein in COS Cells

To express the 26583 gene in COS cells, the pCDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 26583 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 26583 DNA sequence is amplified by PCR using two primers. The 5' primer contains the restriction site of interest followed by approximately twenty nucleotides of the 26583 coding sequence starting from the initiation codon; the 3' end sequence contains complementary sequences to the other restriction site of interest, a translation stop codon, the HA tag or FLAG tag and the last 20 nucleotides of the 26583 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 26583 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 26583-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989. The expression of the 26583 polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 26583 coding sequence is cloned directly into the polylinker of the pCDNA/Amp vector using the appropriate restriction sites. The resulting plasmid is transfected into COS cells in the manner described above, and the expression of the 26583 polypeptide is detected by radiolabelling and immunoprecipitation using a 26583 specific monoclonal antibody.

Examples for 21953

Example 15

Identification and Characterization of Human 21953 cDNA

The human 21953 nucleic acid sequence (SEQ ID NO:19) is approximately 3143 nucleotides long. The nucleic acid sequence includes an initiation codon (ATG) and a termination codon (TAA). The region between and inclusive of the initiation codon and the termination codon is a methionine-initiated coding sequence of about 2646 nucleotides (nucleotides 229-2874 of SEQ ID NO:19, designated as SEQ ID NO:21). The coding sequence encodes an 882 amino acid protein.

Example 16

21953 mRNA Expression

Endogenous human 21953 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples were internally controlled by the addition of a second set of primers/probe specific for a reference gene such as β2-macroglobulin, GAPDH which has been labeled with a different fluorophore on the 5' end (typically VIC).

To determine the level of 21953 in various human tissues a primer/probe set was designed. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in the left column of the tables below.

21953 mRNA expression was elevated in 85% of clinical lung tumor samples tested, and is similarly elevated in a number of breast tumor and colon tumor samples (see, e.g., Table 4 below).

TABLE 4

| Sample | Relative Expression |
|---|---|
| Breast Normal | 0.02 |
| Breast Normal | 0.07 |
| Breast Tumor | 0.08 |
| Breast Tumor | 0.07 |
| Breast Tumor | 0.19 |
| Breast Tumor | 0.21 |
| Breast Tumor | 0.07 |
| Breast Tumor | 0.30 |
| Ovary Normal | 0.37 |
| Ovary Normal | 0.26 |
| Ovary Normal | 0.33 |
| Ovary Tumor | 0.16 |
| Ovary Tumor | 0.13 |
| Ovary Tumor | 0.17 |
| Ovary Tumor | 0.10 |
| Ovary Tumor | 0.12 |
| Ovary Tumor | 0.08 |
| Ovary Tumor | 0.52 |
| Ovary Tumor | 0.06 |
| Lung Normal | 0.02 |
| Lung Normal | 0.01 |
| Lung Normal | 0.10 |
| Lung Normal | 0.01 |
| Lung Tumor | 0.59 |
| Lung Tumor | 0.18 |
| Lung Tumor | 0.24 |
| Lung Tumor | 0.04 |
| Lung Tumor | 0.78 |

TABLE 4-continued

| Sample | Relative Expression |
|---|---|
| Lung Tumor | 0.37 |
| Lung Tumor | 0.16 |

Many tested lung tumor samples in Table 4 (6 of 7) expressed 21953 mRNA at higher levels than did normal lung tumor samples. Similarly, a number of breast tumor samples expressed 21953 mRNA to a greater extent that did normal breast tumor samples.

TABLE 5

| Sample | Relative Expression |
|---|---|
| Colon Normal | 0.00 |
| Colon Normal | 0.02 |
| Colon Normal | 0.05 |
| Colon Normal | 0.01 |
| Colon Tumor | 0.03 |
| Colon Tumor | 0.24 |
| Colon Tumor | 0.07 |
| Colon Tumor | 0.03 |
| Colon Tumor | 0.03 |
| Colon Tumor | 0.04 |
| Liver Metastatic | 0.07 |
| Liver Metastatic | 0.16 |
| Liver Metastatic | 0.23 |
| Liver Normal | 0.05 |
| Liver Normal | 0.19 |
| Brain Normal | 1.50 |
| Brain Normal | 0.98 |
| Astrocyte | 0.37 |
| Brain Tumor | 0.04 |
| Brain Tumor | 0.10 |
| Brain Tumor | 0.04 |
| Brain Tumor | 0.13 |
| HMVEC-Arr | 0.22 |
| HMVEC-Prol | 0.26 |
| Placenta | 0.11 |
| Fetal Adrenal | 0.15 |
| Fetal Adrenal | 0.18 |
| Fetal Liver | 0.71 |
| Fetal Liver | 0.18 |

The mRNA expression data for 21953 mRNA tabulated in Table 5 indicated that (1) 21953 mRNA can be overexpressed in some colon tumor samples relative to normal colon tissue samples; (2) 21953 mRNA is well expressed in metastatic liver samples; (3) 21953 mRNA is highly expressed in normal brain tissue (e.g., increased expression relative to brain tumors), astrocytes, and fetal liver; and (4) 21953 mRNA is also expressed in HMVEC (human microvascular endothelial cells), and fetal adrenal cells.

TABLE 6

| Sample | Relative Expression |
|---|---|
| Aorta/normal | 0.00 |
| Fetal heart/normal | 2.42 |
| Heart normal | 0.66 |
| Heart/CHF | 0.72 |
| Vein/Normal | 0.13 |
| SMC (Aortic) | 0.89 |
| Spinal cord/Normal | 0.66 |
| Brain cortex/Normal | 5.94 |
| Brain hypothalamus/Normal | 4.13 |
| Glial cells (Astrocytes) | 1.35 |
| Brain/Glioblastoma | 1.12 |
| Breast/Normal | 0.18 |
| Breast tumor/IDC | 0.38 |
| Ovary/Normal | 0.39 |

TABLE 6-continued

| Sample | Relative Expression |
| --- | --- |
| Ovary/Tumor | 0.16 |
| Pancreas | 0.25 |
| Prostate/Normal | 0.18 |
| Prostate/Tumor | 0.15 |
| Colon/normal | 0.07 |
| Colon/tumor | 0.56 |
| Colon/IBD | 0.10 |
| Kidney/normal | 0.71 |
| Liver/normal | 0.10 |
| Liver fibrosis | 0.22 |
| Fetal Liver/normal | 2.21 |
| Lung/normal | 0.16 |
| Lung/tumor | 0.39 |
| Lung/COPD | 0.22 |
| Spleen/normal | 0.14 |
| Tonsil/normal | 0.11 |
| Lymph node/normal | 0.27 |
| Thymus/normal | 1.16 |
| Epithelial Cells (prostate) | 2.04 |
| Endothelial Cells (aortic) | 0.27 |
| Skeletal Muscle/Normal | 1.22 |
| Fibroblasts (Dermal) | 0.18 |
| Skin/normal | 0.35 |
| Adipose/Normal | 0.06 |
| Osteoblasts (primary) | 0.44 |
| Osteoblasts (Undiff) | 0.32 |
| Osteoblasts(Diff) | 0.29 |
| Osteoclasts | 0.08 |
| Aortic SMC Early | 1.27 |
| Aortic SMC Late | 2.61 |
| shear HUVEC | 3.39 |
| static HUVEC | 2.14 |

The mRNA expression data for 21953 mRNA tabulated in Table 6 indicated that 21953 mRNA is highly expressed, for example, in fetal heart, brain cortex, brain hypothalamus, fetal liver, epithelial cells from prostate, aortic smooth muscle cells, and human umbilical vein endothelial cells under both shear and static conditions.

TABLE 7

| Sample | Relative Expression |
| --- | --- |
| MCF-7 Breast Tumor | 15.15 |
| ZR75 Breast Tumor | 6.11 |
| T47D Breast Tumor | 1.50 |
| MDA 231 Breast Tumor | 0.01 |
| MDA 435 Breast Tumor | 0.00 |
| DLD 1 ColonT (stageC) | 22.33 |
| SW480 ColonT (stageB) | 0.06 |
| SW620 ColonT (stageC) | 5.23 |
| HCT116 | 0.63 |
| HT29 | 0.01 |
| Colo 205 | 0.00 |
| NCIH125 | 0.75 |
| NCIH69 | 23.28 |
| NCIH322 | 20.91 |
| NCIH460 | 1.25 |
| A549 | 7.11 |
| NHBE | 0.83 |
| SKOV-3 ovary | 0.22 |
| OVCAR-3 ovary | 17.28 |
| 293 ovary | 44.97 |
| 293T ovary | 59.75 |
| A549 t6 | 0.83 |
| A549 t9 | 1.27 |
| A549 t18 | 14.63 |
| A549 t24 | 1.99 |

Tumor cell lines were xenografted into nude mice. Expression of human 21953 mRNA in tumors harvested from the mice was analyzed using TaqMan. Results are tabulated in Table 7 (excepting the final four rows, see below). The results indicated that, for example, 21953 mRNA is highly expressed in some xenografted colon tumor samples (colonT), some xenografted breast tumor samples, and xenografted ovarian cell lines.

The final four rows of Table 7 tabulate relative 21953 mRNA expression in samples of A549 human lung cancer cells at various hourly time points (time in hours being indicated with the prefix t) after release from aphidocolin treatment. 21953 mRNA expression peaked at the G1 to S phase transition.

TABLE 8

| Sample | Relative Expression |
| --- | --- |
| PIT 337 Colon Normal | 0.28 |
| CHT 410 Colon Normal | 0.03 |
| CHT 425 Colon Normal | 0.13 |
| CHT 371 Colon Normal | 0.03 |
| CHT 414 Colonic ACA-B | 0.16 |
| CHT 841 Colonic ACA-B | 0.07 |
| CHT 807 Colonic ACA-B | 0.21 |
| CHT 382 Colonic ACA-B | 0.32 |
| CHT 596 Colonic ACA-C | 0.00 |
| CHT 907 Colonic ACA-C | 0.13 |
| CHT 372 Colonic ACA-C | 0.49 |
| NDR 210 Colonic ACA-C | 0.13 |
| CHT 1365 Colonic ACA-C | 0.03 |
| CLN 741 Liver Normal | 0.00 |
| NDR 165 Liver Normal | 0.00 |
| NDR 150 Liver Normal | 0.06 |
| PIT 236 Liver Normal | 0.00 |
| CHT 077 Col Liver Metastatis | 0.06 |
| CHT 119 Col Liver Metastatis | 4.79 |
| CHT 131 Col Liver Metastatis | 0.76 |
| CHT 218 Col Liver Metastatis | 1.12 |
| CHT 739 Col Liver Metastatis | 0.18 |
| CHT 215 Col Abdominal Metastatis | 0.01 |

21953 mRNA is cell cycle regulated in the lung carcinoma cell line A549. A549 cells were synchronized with aphidocholin, and then released. mRNA was prepared from the cells at regular intervals after release. 21953 expression peaked during the G1 to S phase transition.

In situ hybridization experiments which provided additional confirmatory results are tabulated in Table 9. 21953 mRNA was observed by in situ hybridization in lung small cell carcinoma and differentiated tumors, but not in normal lung tissue. Similarly, by this analysis, 21953 mRNA expression was elevated in colon tumor samples (2 of 2), metastatic colon tumor samples (2 of 2), and in a differentiated papillary ovarian tumor sample. 21953 mRNA was also detected in normal breast tissue (1 of 1), normal ovarian tissue (1 of 1), and ovarian tumors (2 of 2).

TABLE 9

| Tissue | Diagnosis | Results |
| --- | --- | --- |
| Breast | Normal | + |
| Breast | Intraductal Carcinoma | − |
| Colon | Normal | − |
| Colon | Normal | − |
| Colon | Tumor | + |
| Colon | Tumor | + |
| Colon | Metastasis | + |
| Colon | Metastasis | ++ |
| Liver | Normal | − |
| Lung | Normal | − |
| Lung | Small Cell Carcinoma | ++ |
| Lung | Differentiated | ++ |
| Lung | Differentiated | +/− |

TABLE 9-continued

| Tissue | Diagnosis | Results |
|---|---|---|
| Lung | Differentiated | ++ |
| Ovary | Normal | + |
| Ovary | Tumor (well differentiated carcinoma) | + |
| Ovary | Tumor (moderately differentiated papillary) | ++ |

Example 17

Recombinant Expression of 21953 in Bacterial Cells

In this example, 21953 is expressed as a recombinant glutathione-S-transferase (GST) fusion polypeptide in E. coli and the fusion polypeptide is isolated and characterized. Specifically, 21953 is fused to GST and this fusion polypeptide is expressed in E. coli, e.g., strain PEB199. Expression of the GST-21953 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 18

Expression of Recombinant 21953 Protein in COS Cells

To express the 21953 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire 21953 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 21953 DNA sequence is amplified by PCR using two primers. The 5' primer contains the restriction site of interest followed by approximately twenty nucleotides of the 21953 coding sequence starting from the initiation codon; the 3' end sequence contains complementary sequences to the other restriction site of interest, a translation stop codon, the HA tag or FLAG tag and the last 20 nucleotides of the 21953 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 21953 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 21953-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) Molecular Cloning: A Laboratory Manual. 2nd, ed., Cold Spring Harbor Laboratory, Cold Spring Harbor Laboratory Press, Cold Spring Harbor, N.Y. The expression of the 21953 polypeptide is detected by radiolabelling ($^{35}$S-methionine or $^{35}$S-cysteine available from NEN, Boston, Mass., can be used) and immunoprecipitation (Harlow, E. and Lane, D. (1988) Antibodies: A Laboratory Manual, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 21953 coding sequence is cloned directly into the polylinker of the pCDNA/Amp vector using the appropriate restriction sites. The resulting plasmid is transfected into COS cells in the manner described above, and the expression of the 21953 polypeptide is detected by radiolabelling and immunoprecipitation using a 21953 specific monoclonal antibody.

Examples for m32404

Example 19

Identification and Characterization of Human m32404 cDNA

The human m32404 sequence (SEQ ID NO:24), which is approximately 2219 nucleotides long. The nucleic acid sequence includes an initiation codon (ATG) and a termination codon (TGA). The region between and inclusive of the initiation codon and the termination codon is a methionine-initiated coding sequence of about 1659 nucleotides, including the termination codon (nucleotides indicated as "coding" of SEQ ID NO:24; SEQ ID NO:26). The coding sequence encodes a 552 amino acid protein (SEQ ID NO:25).

Example 20

Tissue Distribution of m32404 mRNA by TaqMan Analysis

Endogenous human m32404 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of m32404 in various human tissues a primer/probe set was designed. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA obtained from approximately 50 ng total RNA was used per TaqMan reaction.

Example 21

Tissue Distribution of m32404 mRNA by Northern Analysis

Northern blot hybridizations with various RNA samples can be performed under standard conditions and washed under stringent conditions, i.e., 0.2×SSC at 65° C. A DNA probe corresponding to all or a portion of the m32404 cDNA (SEQ ID NO:24) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 22

Recombinant Expression of m32404 in Bacterial Cells

In this example, m32404 is expressed as a recombinant glutathione-S-transferase (GST) fusion polypeptide in *E. coli* and the fusion polypeptide is isolated and characterized. Specifically, m32404 is fused to GST and this fusion polypeptide is expressed in *E. coli*, e.g., strain PEB199. Expression of the GST-m32404 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 23

Expression of Recombinant m32404 Protein in COS Cells

To express the m32404 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire m32404 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the m32404 DNA sequence is amplified by PCR using two primers. The 5' primer contains the restriction site of interest followed by approximately twenty nucleotides of the m32404 coding sequence starting from the initiation codon; the 3' end sequence contains complementary sequences to the other restriction site of interest, a translation stop codon, the HA tag or FLAG tag and the last 20 nucleotides of the m32404 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the m32404 gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the m32404-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the m32404 polypeptide is detected by radiolabelling (35S-methionine or 35S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with 35S-methionine (or 35S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the m32404 coding sequence is cloned directly into the polylinker of the pCDNA/Amp vector using the appropriate restriction sites. The resulting plasmid is transfected into COS cells in the manner described above, and the expression of the m32404 polypeptide is detected by radiolabelling and immunoprecipitation using an m32404 specific monoclonal antibody.

Examples for 14089

Example 24

Identification and Characterization of Human 14089 cDNA

The human 14089 sequence (SEQ ID NO:33) is approximately 957 nucleotides long. The nucleic acid sequence includes an initiation codon (ATG) and a termination codon (TGA). The region between and inclusive of the initiation codon and the termination codon is a methionine-initiated coding sequence of about 726 nucleotides, including the termination codon (nucleotides indicated as "coding" of SEQ ID NO:33; SEQ ID NO:35). The coding sequence encodes a 241 amino acid protein (SEQ ID NO:34).

Example 25

Tissue Distribution of 14089 mRNA

Northern blot hybridizations with various RNA samples can be performed under standard conditions and washed under stringent conditions, i.e., 0.2×SSC at 65° C. A DNA probe corresponding to all or a portion of the 14089 cDNA (SEQ ID NO:33) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 26

Recombinant Expression of 14089 in Bacterial Cells

In this example, 14089 is expressed as a recombinant glutathione-S-transferase (GST) fusion polypeptide in *E. coli* and the fusion polypeptide is isolated and characterized. Specifically, 14089 is fused to GST and this fusion polypeptide is expressed in *E. coli*, e.g., strain PEB199. Expression of the GST-14089 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 27

Expression of Recombinant 14089 Protein in COS Cells

To express the 14089 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 14089 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 14089 DNA sequence is amplified by PCR using two primers. The 5' primer contains the restriction site of interest followed by approximately twenty nucleotides of the 14089 coding sequence starting from the initiation codon; the 3' end sequence contains complementary sequences to the other restriction site of interest, a translation stop codon, the HA tag or FLAG tag and the last 20 nucleotides of the 14089 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 14089 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 14089-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual. 2nd, ed.*, Cold Spring Harbor Laboratory, Cold Spring Harbor Laboratory Press, Cold Spring Harbor, N.Y. The expression of the 14089 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 14089 coding sequence is cloned directly into the polylinker of the pCDNA/Amp vector using the appropriate restriction sites. The resulting plasmid is transfected into COS cells in the manner described above, and the expression of the 14089 polypeptide is detected by radiolabelling and immunoprecipitation using a 14089 specific monoclonal antibody.

Examples for 23436

Example 28

Identification and Characterization of Human 23436 cDNA

The human 23436 sequence (SEQ ID NO:40), which is approximately 2446 nucleotides long, including untranslated regions, contains a predicted methionine-initiated coding sequence of about 1458 nucleotides, including the termination codon (nucleotides indicated as "coding" of SEQ ID NO:40; SEQ ID NO:42). The coding sequence encodes a 485 amino acid protein (SEQ ID NO:41).

Example 29

Tissue Distribution of 23436 mRNA

Endogenous human 23436 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

Figure 27:
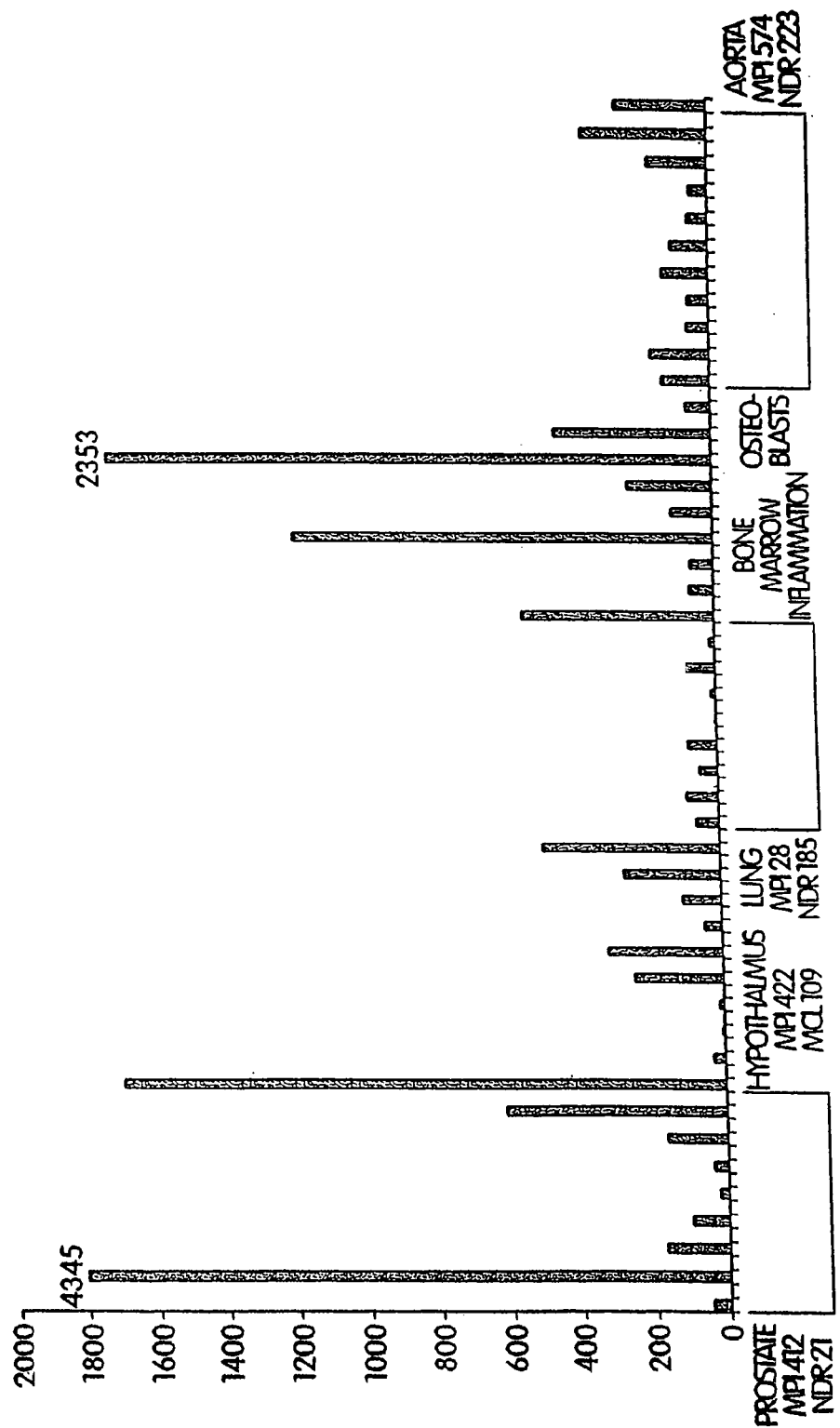
FIG. 27 is a bar graph depicting 23436 expression in human prostate, hypothalamus, lung, bone marrow, differentiated osteoblasts, and aorta cells as assessed by TaqMan analysis. Elevated expression is observed in some prostate, hypothalamus, and bone marrow cells. Relative expression levels were determined by normalizing against a trachea control.
Figure 28:
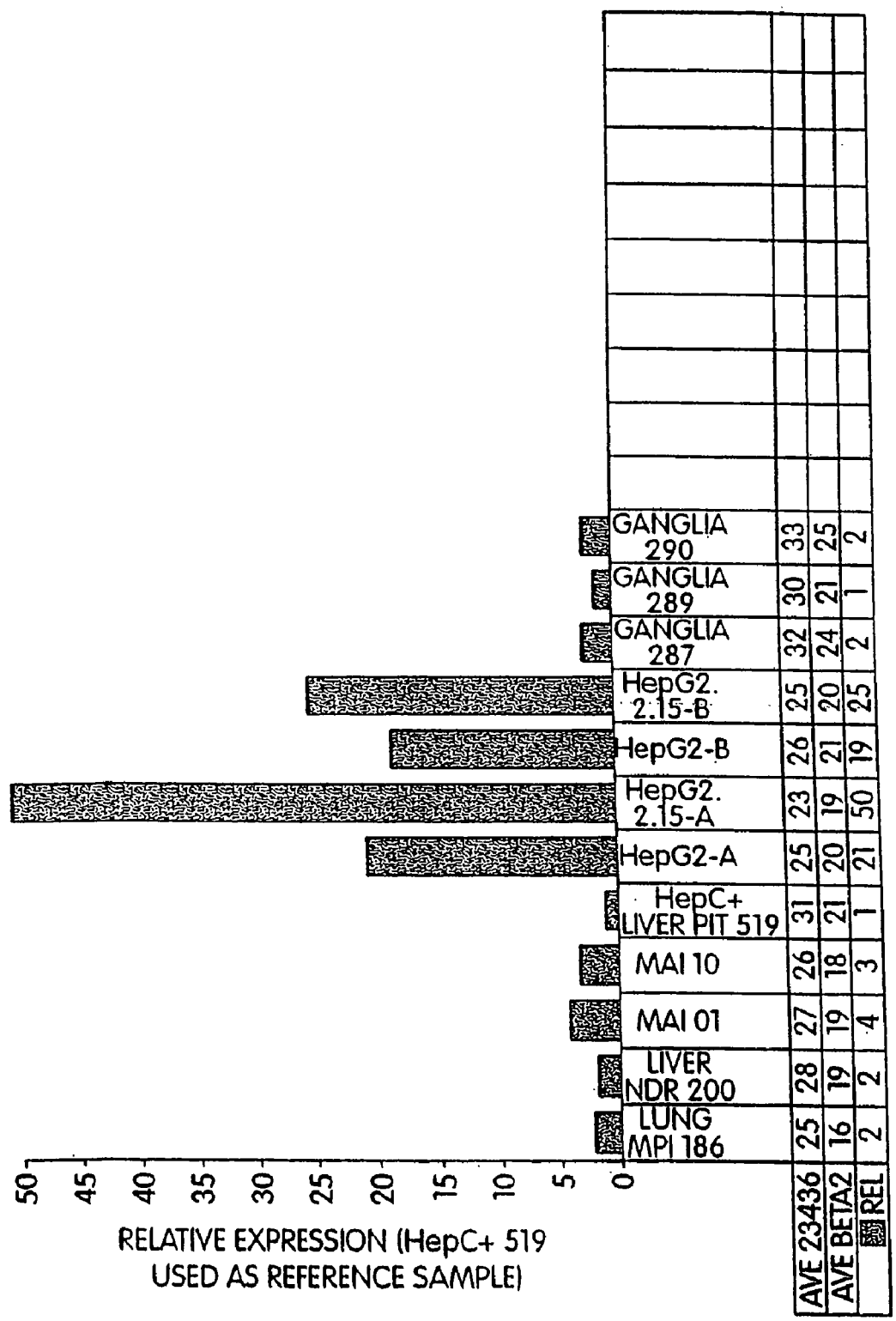
FIG. 28 is a bar graph depicting 23436 expression in human liver, several hepatoma cell lines (HepG2) and ganglia, as assessed by TaqMan analysis. Elevated expression is observed in hepatoma cells (HepG2 cell line). Relative expression levels were determined by normalizing against a trachea control.
Figure 29:
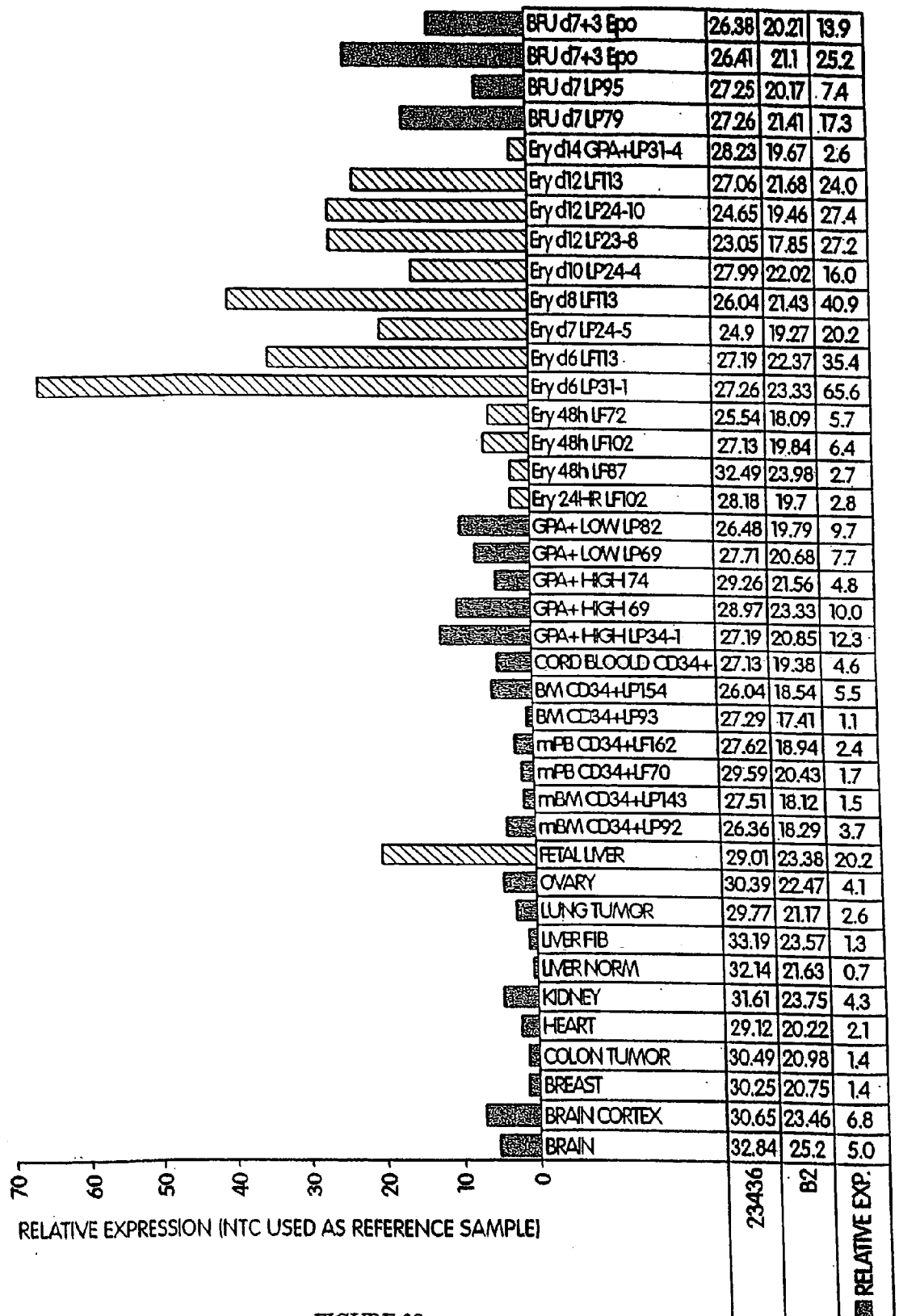
FIG. 29 is a bar graph depicting 23436 expression as determined by TaqMan assays on mRNA derived from the following cell types: (1) brain; (2) brain cortex; (3) breast; (4) colon tumor; (5) heart; (6) kidney; (7) liver norm; (8) liver fib; (9) lung tumor; (10) ovary; (11) fetal liver; (12) mBM CD34+ LP92; (13) mBM CD34+ LP143; (14) mPB CD34+ LF70; (15) mPB CD34+ LF162; (16) BM CD34+ LF93; (17) BM CD34+ LP154; (18) Cord Blood CD34+ LF101; (19) GPA+ High LP34-1; (20) GPA+ High 69; (21) GPA+ High 74; (22) GPA+ Low LP69; (23) GPA+ Low LP82; (24) Ery 24 hr LF102; (25) Ery 48 h LF87; (26) Ery 48 h LF102; (27) Ery 48 h LF72; (28) Ery d6 LP31-1; (29) Ery d6 LF113; (30) Ery d7 LF24-5; (31) Ery d8 LF113; (32) Ery d10 LP24-4; (33) Ery d12 LF23-8; (34) Ery d12 LF24-10; (35) Ery d12 LF113; (36) Ery d14 GPA+ LP31-4; (37) BFU d7 LP79; (38) BFU d7 LP95; (39) BFU d7+3 Epo LP81; and (40) BFU d7+3 Epo LP104.

To determine the level of 23436 in various human tissues a primer/probe set was designed. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in FIGS. 23 to 28. 23436 mRNA was detected in erythroid cells (FIGS. 23-26). 23436 expression was also found in prostate, hypothalamus and bone marrow (FIG. 27). The 23436 mRNA is also expressed in HepG2 cells, a liver derived cell line (FIG. 28).

Northern blot hybridizations with various RNA samples can be performed under standard conditions and washed under stringent conditions, i.e., 0.2×SSC at 65° C. A DNA probe corresponding to all or a portion of the 23436 cDNA (SEQ ID NO:40) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 30

Recombinant Expression of 23436 in Bacterial Cells

In this example, 23436 is expressed as a recombinant glutathione-S-transferase (GST) fusion polypeptide in *E. coli* and the fusion polypeptide is isolated and characterized. Specifically, 23436 is fused to GST and this fusion polypeptide is expressed in *E. coli*, e.g., strain PEB 199. Expression of the GST-23436 fusion protein in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 31

Expression of Recombinant 23436 Protein in COS Cells

To express the 23436 gene in COS cells, the pCDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 23436 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 23436 DNA sequence is amplified by PCR using two primers. The 5' primer contains the restriction site of interest followed by approximately twenty nucleotides of the 23436 coding sequence starting from the initiation codon; the 3' end sequence contains complementary sequences to the other restriction site of interest, a translation stop codon, the HA tag or FLAG tag and the last 20 nucleotides of the 23436 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 23436 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 23436-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual. 2nd, ed.*, Cold Spring Harbor Laboratory, Cold Spring Harbor Laboratory Press, Cold Spring Harbor, N.Y. The expression of the 23436 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual, Cold Spring Harbor Laboratory Press, Cold Spring Harbor, N.Y.)* using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 23436 coding sequence is cloned directly into the polylinker of the pCDNA/Amp vector using the appropriate restriction sites. The resulting plasmid is transfected into COS cells in the manner described above, and the expression of the 23436 polypeptide is detected by radiolabelling and immunoprecipitation using a 23436 specific monoclonal antibody.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:
   a) a nucleic acid molecule comprising the nucleotide sequence of SEQ ID NO:7 or SEQ ID NO:9;
   b) a nucleic acid molecule which encodes a polypeptide comprising the amino acid sequence of SEQ ID NO:8;
   c) a nucleic acid molecule comprising a nucleotide sequence which is at least 95% identical to the nucleotide sequence of SEQ ID NO:7 or SEQ ID NO:9, wherein the nucleotide sequence encodes a polypeptide which has kinase activity; and
   d) a nucleic acid molecule which encodes a polypeptide comprising an amino acid sequence which is at least 95% identical to the amino acid sequence of SEQ ID NO:8, wherein the polypeptide has kinase activity.

2. The nucleic acid molecule of claim 1, further comprising vector nucleic acid sequences.

3. The nucleic acid molecule of claim 1, further comprising nucleic acid sequences encoding a heterologous polypeptide.

4. A host cell which contains the nucleic acid molecule of claim 1.

5. A method for producing a polypeptide selected from the group consisting of:
   a) a polypeptide comprising the amino acid sequence of SEQ ID NO:8;
   b) a polypeptide encoded by a nucleic acid molecule comprising the nucleotide sequence of SEQ ID NO:7 or SEQ ID NO:9;
   c) a polypeptide comprising an amino acid sequence which is at least 95% identical to the amino acid sequence of SEQ ID NO:8, wherein the polypeptide has kinase activity; and
   d) a polypeptide encoded by a nucleic acid molecule comprising a nucleotide sequence which is at least 95% identical to the nucleotide sequence of SEQ ID NO:7 or SEQ ID NO:9, wherein the polypeptide has kinase activity;
   the method comprising culturing the host cell of claim 4 under conditions in which the nucleic acid molecule is expressed.

6. The isolated nucleic acid molecule of claim 1, comprising a nucleotide sequence which is at least 96% identical to the nucleotide sequence of SEQ ID NO:7 or SEQ ID NO:9, wherein the nucleotide sequence encodes a polypeptide which has kinase activity.

7. The isolated nucleic acid molecule of claim 1, comprising a nucleotide sequence which is at least 97% identical to the nucleotide sequence of SEQ ID NO:7 or SEQ ID NO:9, wherein the nucleotide sequence encodes a polypeptide which has kinase activity.

8. The isolated nucleic acid molecule of claim 1, comprising a nucleotide sequence which is at least 98% identical to the nucleotide sequence of SEQ ID NO:7 or SEQ ID NO:9. wherein the nucleotide sequence encodes a polypeptide which has kinase activity.

9. The isolated nucleic acid molecule of claim 1, comprising a nucleotide sequence which is at least 99% identical to the nucleotide sequence of SEQ ID NO:7 or SEQ ID NO:9, wherein the nucleotide sequence encodes a polypeptide which has kinase activity.

10. The isolated nucleic acid molecule of claim 1, comprising the nucleotide sequence of SEQ IDNO:7 or SEQ ID NO:9.

11. The isolated nucleic acid molecule of claim 1, consisting of the nucleotide sequence of SEQ ID NO:7 or SEQ ID NO:9.

12. The method of claim 5, wherein the polypeptide comprises an amino acid scquence which is at least 98% identical to the amino acid sequence of SEQ ID NO:8, and has kinase activity.

13. The method of claim 5, wherein the polypeptide comprises an amino acid sequence which is at least 99% identical to the amino acid sequence of SEQ ID NO:8, and has kinase activity.

14. The method of claim 5, wherein the polypeptide comprises the amino acid sequence of SEQ ID NO:8.

15. The method of claim 5, wherein the polypeptide consists of the amino acid sequence of SEQ ID NO:8.

* * * * *

UNITED STATES PATENT AND TRADEMARK OFFICE
CERTIFICATE OF CORRECTION

PATENT NO. : 7,282,360 B2 Page 1 of 1
APPLICATION NO. : 11/636948
DATED : October 16, 2007
INVENTOR(S) : Rosanna Kapeller-Libermann It is certified that error appears in the above-identified patent and that said Letters Patent is hereby corrected as shown below:

Title Page; item (12); (75);

INVENTORS: Please make the following corrections to the inventors as per the Amendment and Processing Fee Deleting Correctly Named Person(s) Who are Not Inventor(s) of Invention Now Being Claimed, which was filed on April 19, 2007, a copy of which is attached:

~~Rachel E. Meyers, Newton, MA (US); Peter J. Olandt, Newton, MA (US);~~ Rosanna Kapeller-Libermann, Chestnut Hill, MA (US); ~~Rory A.J. Curtis, Framingham, MA (US); Mark J. Williamson, Saugus, MA (US); Nadine Weich, Brookline, MA (US)~~

TITLE:

Please make the following corrections to the title:

On Page 1, Paragraph (54) please correct the title as follows:
"Novel Human Protein Kinase, Phosphatase, and Protease Family Members and Uses Thereof."

Signed and Sealed this

Nineteenth Day of May, 2009

JOHN DOLL
*Acting Director of the United States Patent and Trademark Office*

SEQUENCE LISTING

<160> NUMBER OF SEQ ID NOS: 45

<210> SEQ ID NO 1
<211> LENGTH: 1704
<212> TYPE: DNA
<213> ORGANISM: Homo sapiens
<220> FEATURE:
<221> NAME/KEY: CDS
<222> LOCATION: (138)...(1238)

<400> SEQUENCE: 1

-continued

```
ggcctctagg aggcaggaac agcaggcctg gcctgcccaa aggactctct atccaggatg      60
taaatgagca cactgctggc ccatgcgcct cggggctgta gagggcagcc tcagaggcac     120
tgggcattcc tggcacc atg gat gac gct gct gtc ctc aag cga cga ggc       170
                Met Asp Asp Ala Ala Val Leu Lys Arg Arg Gly
                 1               5                  10 tac ctc ctg ggg ata aat tta gga gag ggc tcc tat gca aaa gta aaa      218
Tyr Leu Leu Gly Ile Asn Leu Gly Glu Gly Ser Tyr Ala Lys Val Lys
         15                  20                  25 tct gct tac tct gag cgc ctg aag ttc aat gtg gcg atc aag atc atc      266
Ser Ala Tyr Ser Glu Arg Leu Lys Phe Asn Val Ala Ile Lys Ile Ile
             30                  35                  40 gac cgc aag aag gcc ccc gca gac ttc ttg gag aaa ttc ctt ccc cgg      314
Asp Arg Lys Lys Ala Pro Ala Asp Phe Leu Glu Lys Phe Leu Pro Arg
     45                  50                  55 gaa att gag att ctg gcc atg tta aac cac tgc tcc atc att aag acc      362
Glu Ile Glu Ile Leu Ala Met Leu Asn His Cys Ser Ile Ile Lys Thr
 60                  65                  70                  75 tac gag atc ttt gag aca tca cat ggc aag gtc tac atc gtc atg gag      410
Tyr Glu Ile Phe Glu Thr Ser His Gly Lys Val Tyr Ile Val Met Glu
                 80                  85                  90 ctc gcg gtc cag ggc gac ctc ctc gag tta atc aaa acc cgg gga gcc      458
Leu Ala Val Gln Gly Asp Leu Leu Glu Leu Ile Lys Thr Arg Gly Ala
             95                 100                 105 ctg cat gag gac gaa gct cgc aag aag ttc cac cag ctt tcc ttg gcc      506
Leu His Glu Asp Glu Ala Arg Lys Lys Phe His Gln Leu Ser Leu Ala
         110                 115                 120 atc aag tac tgc cac gac ctg gac gtc gtc cac cgg gac ctc aag tgt      554
Ile Lys Tyr Cys His Asp Leu Asp Val Val His Arg Asp Leu Lys Cys
     125                 130                 135 gac aac ctt ctc ctt gac aag gac ttc aac atc aag ctg tcc gac ttc      602
Asp Asn Leu Leu Leu Asp Lys Asp Phe Asn Ile Lys Leu Ser Asp Phe
140                 145                 150                 155 agc ttc tcc aag cgc tgc ctg cgg gat gac agt ggt cga atg gca tta      650
Ser Phe Ser Lys Arg Cys Leu Arg Asp Asp Ser Gly Arg Met Ala Leu
                 160                 165                 170 agc aag acc ttc tgt ggg tca cca gcg tat gcg gcc cca gag gtg ctg      698
Ser Lys Thr Phe Cys Gly Ser Pro Ala Tyr Ala Ala Pro Glu Val Leu
             175                 180                 185 cag ggc att ccc tac cag ccc aag gtg tac gac atc tgg agc cta ggc      746
Gln Gly Ile Pro Tyr Gln Pro Lys Val Tyr Asp Ile Trp Ser Leu Gly
         190                 195                 200 gtg atc ctc tac atc atg gtc tgc ggc tcc atg ccc tac gac gac tcc      794
Val Ile Leu Tyr Ile Met Val Cys Gly Ser Met Pro Tyr Asp Asp Ser
     205                 210                 215 aac atc aag aag atg ctg cgt atc cag aag gag cac cgc gtc aac ttc      842
Asn Ile Lys Lys Met Leu Arg Ile Gln Lys Glu His Arg Val Asn Phe
220                 225                 230                 235 cca cgc tcc aag cac ctg aca ggc gag tgc aag gac ctc atc tac cac      890
Pro Arg Ser Lys His Leu Thr Gly Glu Cys Lys Asp Leu Ile Tyr His
                 240                 245                 250 atg ctg cag ccc gac gtc aac cgg cgg ctc cac atc gac gag atc ctc      938
Met Leu Gln Pro Asp Val Asn Arg Arg Leu His Ile Asp Glu Ile Leu
             255                 260                 265 agc cac tgc tgg atg cag ccc aag gca cgg gga tct ccc tct gtg gcc      986
Ser His Cys Trp Met Gln Pro Lys Ala Arg Gly Ser Pro Ser Val Ala
         270                 275                 280 atc aac aag gag ggg gag agt tcc cgg gga act gaa ccc ttg tgg acc     1034
Ile Asn Lys Glu Gly Glu Ser Ser Arg Gly Thr Glu Pro Leu Trp Thr
```

|  |  |  |
|---|---|---|
| 285 | 290 | 295 |

```
ccc gaa cct ggc tct gac aag aag tct gcc acc aag ctg gag cct gag      1082
Pro Glu Pro Gly Ser Asp Lys Lys Ser Ala Thr Lys Leu Glu Pro Glu
300             305                 310                 315 gga gag gca cag ccc cag gca cag cct gag aca aaa ccc gag ggg aca      1130
Gly Glu Ala Gln Pro Gln Ala Gln Pro Glu Thr Lys Pro Glu Gly Thr
            320                 325                 330 gca atg caa atg tcc agg cag tcg gag atc ctg ggt ttc ccc agc aag      1178
Ala Met Gln Met Ser Arg Gln Ser Glu Ile Leu Gly Phe Pro Ser Lys
        335                 340                 345 ccg tcg act atg gag aca gag gaa ggg ccc ccc caa cag cct cca gag      1226
Pro Ser Thr Met Glu Thr Glu Glu Gly Pro Pro Gln Gln Pro Pro Glu
    350                 355                 360 acg cgg gcc cag tgagcttctt gcggcccagg gaatgagatg gagctcacgg          1278
Thr Arg Ala Gln
    365 cttaaagccc aagctctgaa gaagtcaagg gtggagccag agaaggaagg cagtcccaga    1338 tgagcctcta ttttcatcag cttcttctct ctccccttga acttggtaac ccacatggtt    1398 ctcccgtggc ccctaggtgg atgaggccaa agtcaaatcc aaggctgaga cagtcgtgcg    1458 actcctactc ccccagagcg tgacccggag caggtgctgg acacagagcc tgtctcagca    1518 gagggtcccc actggccgca acggctcagt gacagcaaga gcaggaagag cagcaggaag    1578 gcaccgctgt ccaccttggg caccatttat cctcctttca tcgtccccgg ggcagttgcg    1638 tgaccctgct gggaggccag accgggccag actgagggtc aggggaccca ggctgggttg    1698 gggggt                                                              1704
```

```
<210> SEQ ID NO 2
<211> LENGTH: 367
<212> TYPE: PRT
<213> ORGANISM: Homo sapiens

<400> SEQUENCE: 2

Met Asp Asp Ala Ala Val Leu Lys Arg Arg Gly Tyr Leu Leu Gly Ile
1               5                   10                  15

Asn Leu Gly Glu Gly Ser Tyr Ala Lys Val Lys Ser Ala Tyr Ser Glu
            20                  25                  30

Arg Leu Lys Phe Asn Val Ala Ile Lys Ile Ile Asp Arg Lys Lys Ala
        35                  40                  45

Pro Ala Asp Phe Leu Glu Lys Phe Leu Pro Arg Glu Ile Glu Ile Leu
    50                  55                  60

Ala Met Leu Asn His Cys Ser Ile Ile Lys Thr Tyr Glu Ile Phe Glu
65                  70                  75                  80

Thr Ser His Gly Lys Val Tyr Ile Val Met Glu Leu Ala Val Gln Gly
                85                  90                  95

Asp Leu Leu Glu Leu Ile Lys Thr Arg Gly Ala Leu His Glu Asp Glu
            100                 105                 110

Ala Arg Lys Lys Phe His Gln Leu Ser Leu Ala Ile Lys Tyr Cys His
        115                 120                 125

Asp Leu Asp Val Val His Arg Asp Leu Lys Cys Asp Asn Leu Leu Leu
    130                 135                 140

Asp Lys Asp Phe Asn Ile Lys Leu Ser Asp Phe Ser Phe Ser Lys Arg
145                 150                 155                 160

Cys Leu Arg Asp Asp Ser Gly Arg Met Ala Leu Ser Lys Thr Phe Cys
                165                 170                 175
```

```
Gly Ser Pro Ala Tyr Ala Ala Pro Glu Val Leu Gln Gly Ile Pro Tyr
            180                 185                 190
Gln Pro Lys Val Tyr Asp Ile Trp Ser Leu Gly Val Ile Leu Tyr Ile
        195                 200                 205
Met Val Cys Gly Ser Met Pro Tyr Asp Asp Ser Asn Ile Lys Lys Met
    210                 215                 220
Leu Arg Ile Gln Lys Glu His Arg Val Asn Phe Pro Arg Ser Lys His
225                 230                 235                 240
Leu Thr Gly Glu Cys Lys Asp Leu Ile Tyr His Met Leu Gln Pro Asp
                245                 250                 255
Val Asn Arg Arg Leu His Ile Asp Glu Ile Leu Ser His Cys Trp Met
            260                 265                 270
Gln Pro Lys Ala Arg Gly Ser Pro Ser Val Ala Ile Asn Lys Glu Gly
        275                 280                 285
Glu Ser Ser Arg Gly Thr Glu Pro Leu Trp Thr Pro Glu Pro Gly Ser
    290                 295                 300
Asp Lys Lys Ser Ala Thr Lys Leu Glu Pro Glu Gly Glu Ala Gln Pro
305                 310                 315                 320
Gln Ala Gln Pro Glu Thr Lys Pro Glu Gly Thr Ala Met Gln Met Ser
                325                 330                 335
Arg Gln Ser Glu Ile Leu Gly Phe Pro Ser Lys Pro Ser Thr Met Glu
            340                 345                 350
Thr Glu Glu Gly Pro Pro Gln Gln Pro Pro Glu Thr Arg Ala Gln
        355                 360                 365

<210> SEQ ID NO 3
<211> LENGTH: 1104
<212> TYPE: DNA
<213> ORGANISM: Homo sapiens

<400> SEQUENCE: 3
atggatgacg ctgctgtcct caagcgacga ggctaccctcc tggggataaa tttaggagag      60
ggctcctatg caaaagtaaa atctgcttac tctgagcgcc tgaagttcaa tgtggcgatc     120
aagatcatcg accgcaagaa gggccccgca gacttcttgg agaaattcct tccccgggaa     180
attgagattc tggccatgtt aaaccactgc tccatcatta gacctacga gatctttgag     240
acatcacatg gcaaggtcta catcgtcatg gagctcgcgg tccagggcga cctcctcgag     300
ttaatcaaaa cccggggagc cctgcatgag gacgaagctc gcaagaagtt ccaccagctt     360
tccttggcca tcaagtactg ccacgacctg acgtcgtcc accgggacct caagtgtgac     420
aaccttctcc ttgacaagga cttcaacatc aagctgtccg acttcagctt ctccaagcgc     480
tgcctgcggg atgacagtgg tcgaatggca ttaagcaaga ccttctgtgg gtcaccagcg     540
tatgcggccc cagaggtgct gcagggcatt ccctaccagc caaggtgta cgacatctgg     600
agcctaggcg tgatcctcta catcatggtc tgcggctcca tgccctacga cgactccaac     660
atcaagaaga tgctgcgtat ccagaaggag caccgcgtca acttcccacg ctccaagcac     720
ctgacaggcg agtgcaagga cctcatctac cacatgctgc agcccgacgt caaccggcgg     780
ctccacatcg acgagatcct cagccactgc tggatgcagc caaggcacg gggatctccc     840
tctgtggcca tcaacaagga gggggagagt tcccggggaa ctgaacccct gtggaccccc     900
gaacctggct ctgacaagaa gtctgccacc aagctggagc ctgagggaga ggcacagccc     960
caggcacagc ctgagacaaa acccgagggg acagcaatgc aaatgtccag gcagtcggag    1020
atcctgggtt tccccagcaa gccgtcgact atggagacag aggaagggcc ccccaacag    1080
```
cctccagaga cgcgggccca gtga                      1104

<210> SEQ ID NO 4
<211> LENGTH: 277
<212> TYPE: PRT
<213> ORGANISM: Artificial Sequence
<220> FEATURE:
<223> OTHER INFORMATION: consensus sequence

<400> SEQUENCE: 4

Tyr Glu Leu Leu Glu Lys Leu Gly Glu Gly Ser Phe Gly Lys Val Tyr
1               5                   10                  15

Lys Ala Lys His Lys Thr Gly Lys Ile Val Ala Val Lys Ile Leu Lys
            20                  25                  30

Lys Glu Ser Leu Ser Arg Glu Ile Gln Ile Leu Lys Arg Leu Ser His
        35                  40                  45

Pro Asn Ile Val Arg Leu Leu Gly Val Phe Glu Asp Thr Asp Asp His
    50                  55                  60

Leu Tyr Leu Val Met Glu Tyr Met Glu Gly Gly Asp Leu Phe Asp Tyr
65                  70                  75                  80

Leu Arg Arg Asn Gly Pro Leu Ser Glu Lys Glu Ala Lys Lys Ile Ala
                85                  90                  95

Leu Gln Ile Leu Arg Gly Leu Glu Tyr Leu His Ser Asn Gly Ile Val
            100                 105                 110

His Arg Asp Leu Lys Pro Glu Asn Ile Leu Leu Asp Glu Asn Gly Thr
        115                 120                 125

Val Lys Ile Ala Asp Phe Gly Leu Ala Arg Leu Leu Glu Lys Leu Thr
    130                 135                 140

Thr Phe Val Gly Thr Pro Trp Tyr Met Met Ala Pro Glu Val Ile Leu
145                 150                 155                 160

Glu Gly Arg Gly Tyr Ser Ser Lys Val Asp Val Trp Ser Leu Gly Val
                165                 170                 175

Ile Leu Tyr Glu Leu Leu Thr Gly Gly Pro Leu Phe Pro Gly Ala Asp
            180                 185                 190

Leu Pro Ala Phe Thr Gly Gly Asp Glu Val Asp Gln Leu Ile Ile Phe
        195                 200                 205

Val Leu Lys Leu Pro Phe Ser Asp Glu Leu Pro Lys Thr Arg Ile Asp
    210                 215                 220

Pro Leu Glu Glu Leu Phe Arg Ile Lys Lys Arg Leu Pro Leu Pro
225                 230                 235                 240

Ser Asn Cys Ser Glu Glu Leu Lys Asp Leu Leu Lys Lys Cys Leu Asn
                245                 250                 255

Lys Asp Pro Ser Lys Arg Pro Gly Ser Ala Thr Ala Lys Glu Ile Leu
            260                 265                 270

Asn His Pro Trp Phe
        275

<210> SEQ ID NO 5
<211> LENGTH: 231
<212> TYPE: PRT
<213> ORGANISM: Artificial Sequence
<220> FEATURE:
<223> OTHER INFORMATION: consensus sequence

<400> SEQUENCE: 5

Tyr Glu Leu Leu Lys Lys Leu Gly Lys Gly Ala Phe Gly Lys Val Tyr
1               5                   10                  15

```
Leu Ala Arg Asp Lys Lys Thr Gly Arg Leu Val Ala Ile Lys Val Ile
            20                  25                  30

Lys Glu Arg Ile Leu Arg Glu Ile Lys Ile Leu Lys Lys Asp His Pro
        35                  40                  45

Asn Ile Val Lys Leu Tyr Asp Val Phe Glu Asp Lys Leu Tyr Leu
    50                  55                  60

Val Met Glu Tyr Cys Glu Gly Asp Leu Gly Asp Leu Phe Asp Leu Leu
65                  70                  75                  80

Lys Lys Arg Gly Arg Arg Gly Leu Arg Lys Val Leu Ser Glu Ala
                85                  90                  95

Arg Phe Tyr Phe Arg Gln Ile Leu Ser Ala Leu Glu Tyr Leu His Ser
                100                 105                 110

Gln Gly Ile Ile His Arg Asp Leu Lys Pro Glu Asn Ile Leu Leu Asp
                115                 120                 125

Ser His Val Lys Leu Ala Asp Phe Gly Leu Ala Arg Gln Leu Thr Thr
    130                 135                 140

Phe Val Gly Thr Pro Glu Tyr Met Ala Pro Glu Val Leu Gly Tyr Gly
145                 150                 155                 160

Lys Pro Ala Val Asp Ile Trp Ser Leu Gly Cys Ile Leu Tyr Glu Leu
                165                 170                 175

Leu Thr Gly Lys Pro Pro Phe Pro Gln Leu Asp Leu Ile Phe Lys Lys
                180                 185                 190

Ile Gly Ser Pro Glu Ala Lys Asp Leu Ile Lys Lys Leu Leu Val Lys
                195                 200                 205

Asp Pro Glu Lys Arg Leu Thr Ala Glu Ala Leu Glu Asp Glu Leu Asp
    210                 215                 220

Ile Lys Ala His Pro Phe Phe
225                 230

<210> SEQ ID NO 6
<211> LENGTH: 13
<212> TYPE: PRT
<213> ORGANISM: Artificial Sequence
<220> FEATURE:
<223> OTHER INFORMATION: site signature motif
<220> FEATURE:
<221> NAME/KEY: VARIANT
<222> LOCATION: 1
<223> OTHER INFORMATION: Xaa = Leu, Ile, Val,  Met, Phe, Tyr, or Cys
<220> FEATURE:
<221> NAME/KEY: VARIANT
<222> LOCATION: 2,4,8,9
<223> OTHER INFORMATION: Xaa = Any Amino Acid
<220> FEATURE:
<221> NAME/KEY: VARIANT
<222> LOCATION: 3
<223> OTHER INFORMATION: Xaa = His, or Tyr
<220> FEATURE:
<221> NAME/KEY: VARIANT
<222> LOCATION: 6
<223> OTHER INFORMATION: Xaa = Leu, Ile, Val, Met, Phe, or Tyr
<220> FEATURE:
<221> NAME/KEY: VARIANT
<222> LOCATION: (11)...(13)
<223> OTHER INFORMATION: Xaa = Leu, Ile, Val, Met, Phe, Tyr, Cys, or Thr

<400> SEQUENCE: 6

Xaa Xaa Xaa Xaa Asp Xaa Lys Xaa Xaa Asn Xaa Xaa Xaa
 1               5                  10

<210> SEQ ID NO 7
<211> LENGTH: 3552
```

```
<212> TYPE: DNA
<213> ORGANISM: Homo sapiens
<220> FEATURE:
<221> NAME/KEY: CDS
<222> LOCATION: (208)...(2505)

<400> SEQUENCE: 7
ctcggcgctg cggacacttt tagctgaggg cgcgggcggg tcggctcctc cgcggctcct      60
cggccccacc tgcgcggaga gggcgggatg ccagagccag gtgtcccggc gcgttaaggg     120
ccctcgcagt cagacgtccc tgcaccggcg ctcgcaccct tagtcggccc ggaacgtctt     180
tttgcggacg ccctcggagc agccgcg atg gcc agc acc agg agt atc gag ctg     234
                                Met Ala Ser Thr Arg Ser Ile Glu Leu
                                 1               5
```

| | | | | | | | | | | | | | | | | |
|---|---|---|---|---|---|---|---|---|---|---|---|---|---|---|---|---|
| gag | cac | ttt | gag | gaa | cgg | gac | aaa | agg | ccg | cgg | ccg | ggg | tcg | cgg | aga | 282 |
| Glu | His | Phe | Glu | Glu | Arg | Asp | Lys | Arg | Pro | Arg | Pro | Gly | Ser | Arg | Arg | |
| 10 | | | | | 15 | | | | | 20 | | | | | 25 | |

```
ggg gcc ccc agc tcc tcc ggg ggc agc agc agc tcg ggc ccc aag ggg      330
Gly Ala Pro Ser Ser Ser Gly Gly Ser Ser Ser Ser Gly Pro Lys Gly
             30                  35                  40 aac ggg ctc atc ccc agt ccg gcg cac agt gcc cac tgc agc ttc tac      378
Asn Gly Leu Ile Pro Ser Pro Ala His Ser Ala His Cys Ser Phe Tyr
                 45                  50                  55 cgc acg cgg acc ctg cag gcc ctc agc tcg gag aag aag gcc aag aag      426
Arg Thr Arg Thr Leu Gln Ala Leu Ser Ser Glu Lys Lys Ala Lys Lys
         60                  65                  70 gcg cgc ttc tac cgg aac ggg gac cgc tac ttc aag ggc ctg gtg ttt      474
Ala Arg Phe Tyr Arg Asn Gly Asp Arg Tyr Phe Lys Gly Leu Val Phe
     75                  80                  85 gcc atc tcc agc gac cgc ttc cgg tcc ttc gat gcg ctc ctc ata gag      522
Ala Ile Ser Ser Asp Arg Phe Arg Ser Phe Asp Ala Leu Leu Ile Glu
 90                  95                 100                 105 ctc acc cgc tcc ctg tcg gac aac gtg aac ctg ccc cag ggt gtc cgc      570
Leu Thr Arg Ser Leu Ser Asp Asn Val Asn Leu Pro Gln Gly Val Arg
                110                 115                 120 act atc tac acc atc gac ggc agc cgg aag gtc acc agc ctg gac gag      618
Thr Ile Tyr Thr Ile Asp Gly Ser Arg Lys Val Thr Ser Leu Asp Glu
            125                 130                 135 ctg ctg gaa ggt gag agt tac gtg tgt gca tcc aat gaa cca ttt cgt      666
Leu Leu Glu Gly Glu Ser Tyr Val Cys Ala Ser Asn Glu Pro Phe Arg
        140                 145                 150 aaa gtc gat tac acc aaa aat att aat cca aac tgg tct gtg aac atc      714
Lys Val Asp Tyr Thr Lys Asn Ile Asn Pro Asn Trp Ser Val Asn Ile
    155                 160                 165 aag ggt ggg aca tcc cga gcg ctg gct gct gcc tcc tct gtg aaa agt      762
Lys Gly Gly Thr Ser Arg Ala Leu Ala Ala Ala Ser Ser Val Lys Ser
170                 175                 180                 185 gaa gta aaa gaa agt aaa gat ttc atc aaa ccc aag tta gtg act gtg      810
Glu Val Lys Glu Ser Lys Asp Phe Ile Lys Pro Lys Leu Val Thr Val
                190                 195                 200 att cga agt gga gtg aag cct aga aaa gcc gtg cgg atc ctt ctg aat      858
Ile Arg Ser Gly Val Lys Pro Arg Lys Ala Val Arg Ile Leu Leu Asn
            205                 210                 215 aaa aag act gct cat tcc ttt gaa caa gtc tta aca gat atc acc gaa      906
Lys Lys Thr Ala His Ser Phe Glu Gln Val Leu Thr Asp Ile Thr Glu
        220                 225                 230 gcc att aaa cta gac tca gga gtc gtc aag agg ctc tgc acc ctg gat      954
Ala Ile Lys Leu Asp Ser Gly Val Val Lys Arg Leu Cys Thr Leu Asp
    235                 240                 245 gga aag cag gtt act tgt ctg caa gac ttt ttt ggt gat gac gat gtt     1002
```

-continued

```
Gly Lys Gln Val Thr Cys Leu Gln Asp Phe Phe Gly Asp Asp Val
250             255                 260                 265 ttt att gca tgt gga cca gaa aaa ttt cgt tat gcc caa gat gac ttt    1050
Phe Ile Ala Cys Gly Pro Glu Lys Phe Arg Tyr Ala Gln Asp Asp Phe
                270                 275                 280 gtc ctg gat cat agt gaa tgt cgt gtc ctg aag tca tct tat tct cga    1098
Val Leu Asp His Ser Glu Cys Arg Val Leu Lys Ser Ser Tyr Ser Arg
            285                 290                 295 tcc tca gct gtt aag tat tct gga tcc aaa agc cct ggg ccc tct cga    1146
Ser Ser Ala Val Lys Tyr Ser Gly Ser Lys Ser Pro Gly Pro Ser Arg
        300                 305                 310 cgc agc aaa tca cca gct tca gtt aat gga act ccc agc agc caa ctt    1194
Arg Ser Lys Ser Pro Ala Ser Val Asn Gly Thr Pro Ser Ser Gln Leu
    315                 320                 325 tct act cct aaa tct acg aaa tcc tcc agt tcc tct cca act agt cca    1242
Ser Thr Pro Lys Ser Thr Lys Ser Ser Ser Ser Ser Pro Thr Ser Pro
330                 335                 340                 345 gga agt ttc aga gga tta aag cag att tct gct cat ggc aga tct tct    1290
Gly Ser Phe Arg Gly Leu Lys Gln Ile Ser Ala His Gly Arg Ser Ser
                350                 355                 360 tcc aat gta acc ggt gga cct gag ctt gac cgt tgc ata agt cct gaa    1338
Ser Asn Val Thr Gly Gly Pro Glu Leu Asp Arg Cys Ile Ser Pro Glu
            365                 370                 375 ggt gtg aat gga aac aga tgc tct gaa tca tca act ctt ctt gag aaa    1386
Gly Val Asn Gly Asn Arg Cys Ser Glu Ser Ser Thr Leu Leu Glu Lys
        380                 385                 390 tac aaa att gga aag gtc att ggt gat ggc aat ttt gca gta gtc aaa    1434
Tyr Lys Ile Gly Lys Val Ile Gly Asp Gly Asn Phe Ala Val Val Lys
    395                 400                 405 gag tgt ata gac agg tcc act gga aag gag ttt gcc cta aag att ata    1482
Glu Cys Ile Asp Arg Ser Thr Gly Lys Glu Phe Ala Leu Lys Ile Ile
410                 415                 420                 425 gac aaa gcc aaa tgt tgt gga aag gaa cac ctg att gag aat gaa gtg    1530
Asp Lys Ala Lys Cys Cys Gly Lys Glu His Leu Ile Glu Asn Glu Val
                430                 435                 440 tca ata ctg cgc cga gtg aaa cat ccc aat atc att atg ctg gtc gag    1578
Ser Ile Leu Arg Arg Val Lys His Pro Asn Ile Ile Met Leu Val Glu
            445                 450                 455 gag atg gaa aca gca act gag ctc ttt ctg gtg atg gaa ttg gtc aaa    1626
Glu Met Glu Thr Ala Thr Glu Leu Phe Leu Val Met Glu Leu Val Lys
        460                 465                 470 ggt gga gat ctc ttt gat gca att act tcg tcg acc aag tac act gag    1674
Gly Gly Asp Leu Phe Asp Ala Ile Thr Ser Ser Thr Lys Tyr Thr Glu
    475                 480                 485 aga gat ggc agt gcc atg gtg tac aac tta gcc aat gcc ctc agg tat    1722
Arg Asp Gly Ser Ala Met Val Tyr Asn Leu Ala Asn Ala Leu Arg Tyr
490                 495                 500                 505 ctc cat ggc ctc agc atc gtg cac aga gac atc aaa cca gag aat ctc    1770
Leu His Gly Leu Ser Ile Val His Arg Asp Ile Lys Pro Glu Asn Leu
                510                 515                 520 ttg gtg tgt gaa tat cct gat gga acc aag tct ttg aaa ctg gga gac    1818
Leu Val Cys Glu Tyr Pro Asp Gly Thr Lys Ser Leu Lys Leu Gly Asp
            525                 530                 535 ttt ggg ctt gcg act gtg gta gaa ggc cct tta tac aca gtc tgt ggc    1866
Phe Gly Leu Ala Thr Val Val Glu Gly Pro Leu Tyr Thr Val Cys Gly
        540                 545                 550 aca ccc act tat gtg gct cca gaa atc att gct gaa act gga tat ggc    1914
Thr Pro Thr Tyr Val Ala Pro Glu Ile Ile Ala Glu Thr Gly Tyr Gly
    555                 560                 565
```

-continued

```
ctg aag gtg gac att tgg gca gct ggt gtg atc aca tac ata ctt ctc      1962
Leu Lys Val Asp Ile Trp Ala Ala Gly Val Ile Thr Tyr Ile Leu Leu
570                 575                 580                 585 tgt gga ttc cca cca ttc cga agt gag aac aat ctc cag gaa gat ctc      2010
Cys Gly Phe Pro Pro Phe Arg Ser Glu Asn Asn Leu Gln Glu Asp Leu
                590                 595                 600 ttc gac cag atc ttg gct ggg aag ctg gag ttt ccg gcc ccc tac tgg      2058
Phe Asp Gln Ile Leu Ala Gly Lys Leu Glu Phe Pro Ala Pro Tyr Trp
            605                 610                 615 gat aac atc acg gac tct gcc aag gaa tta atc agt caa atg ctt cag      2106
Asp Asn Ile Thr Asp Ser Ala Lys Glu Leu Ile Ser Gln Met Leu Gln
        620                 625                 630 gta aat gtt gaa gct cgg tgt acc gcg gga caa atc ctg agt cac ccc      2154
Val Asn Val Glu Ala Arg Cys Thr Ala Gly Gln Ile Leu Ser His Pro
    635                 640                 645 tgg gtg tca gat gat gcc tcc cag gag aat aac atg caa gct gag gtg      2202
Trp Val Ser Asp Asp Ala Ser Gln Glu Asn Asn Met Gln Ala Glu Val
650                 655                 660                 665 aca ggt aaa cta aaa cag cac ttt aat aat gcg ctc ccc aaa cag aac      2250
Thr Gly Lys Leu Lys Gln His Phe Asn Asn Ala Leu Pro Lys Gln Asn
                670                 675                 680 agc act acc acc ggg gtc tcc gtc atc atg aac acg gct cta gat aag      2298
Ser Thr Thr Thr Gly Val Ser Val Ile Met Asn Thr Ala Leu Asp Lys
            685                 690                 695 gag ggg cag att ttc tgc agc aag cac tgt caa gac agc ggc agg cct      2346
Glu Gly Gln Ile Phe Cys Ser Lys His Cys Gln Asp Ser Gly Arg Pro
        700                 705                 710 ggg atg gag ccc atc tct cca gtt cct ccc tca gtg gag gag atc cct      2394
Gly Met Glu Pro Ile Ser Pro Val Pro Pro Ser Val Glu Glu Ile Pro
715                 720                 725 gtg cct ggg gaa gca gtc ccg gcc ccc acc cct ccg gaa tct ccc acc      2442
Val Pro Gly Glu Ala Val Pro Ala Pro Thr Pro Pro Glu Ser Pro Thr
                735                 740                 745
730 ccc cac tgt cct ccc gct gcc ccg ggt ggt gag cgg gca gga acc tgg      2490
Pro His Cys Pro Pro Ala Ala Pro Gly Gly Glu Arg Ala Gly Thr Trp
            750                 755                 760 cgc cgc cac cga gac tgagcctcct gcagacgggc gaagccgcct gctgccgccc      2545
Arg Arg His Arg Asp
        765 aggaagccag ccctctgctc ggcctcgccg gcctccctgc tgcaggcctc cctctcttca    2605 ccgcctgcgc ctgagttcgc gggtcctccg caggccgcct gggaaccgga gcctggcgtg    2665 ccggagcctg gcctggtgct ctgggctctg ccttctggtt cctggaggca tcaaaggctg    2725 catccgttct gccaacagct gttcggagag actcgttcca gatcatcccg tcattttcag    2785 tttgttggac attttacagc ttcaccagga gaatgtgcaa ctttattcca gcattcgatg    2845 catttttata gaaacacttt ggaaacactt tggatgaacc aaggcctttt ccttatttaa    2905 gtagactcag aacactccct ttcttttctt ttctctctct ctcttttttt tttacgaaag    2965 acttagaatt gcatttgtcc ttttgtgggt gtcctgtgag aggtgatatg ggggctaaga    3025 ggactggctt tctaatagaa gaagtgagcg cctgagagga caatttggtc attggacacg    3085 gattgcaggc tttgagaagc gctcagaggc ccagggcggc gggctcagcc attcggcttg    3145 gggcaccagg ctccccagag acaatgctca gtattcattc atacagac gatggaagaa      3205 gccacttctt ccctgggcgg tgtgggtttc cccagctct tcccacacgt gtgttaggaa     3265 atgcccgtga acttgccctc tgggcttttt aatgagaggc ttggcgcatg cggcacccag    3325 cggctgcttc cctgcaagcc agcgacttgc cgagcagaat gagctctgct cctgagcccc    3385
```

-continued

```
ggtagctgct tcctcatctg ctcttttta a taattgtaca taatccgtgt atttgtttta    3445
cctgctcatc ttctaaactg gcgagccct a tagttcgttc tcattgttag attttgcctt    3505
ttacaagtgt ccccaacctg caataaactt ttccctcttg aaaaaaa                   3552
```

<210> SEQ ID NO 8
<211> LENGTH: 766
<212> TYPE: PRT
<213> ORGANISM: Homo sapiens

<400> SEQUENCE: 8

```
Met Ala Ser Thr Arg Ser Ile Glu Leu Glu His Phe Glu Glu Arg Asp
1               5                   10                  15

Lys Arg Pro Arg Pro Gly Ser Arg Arg Gly Ala Pro Ser Ser Ser Gly
            20                  25                  30

Gly Ser Ser Ser Gly Pro Lys Gly Asn Gly Leu Ile Pro Ser Pro
        35                  40                  45

Ala His Ser Ala His Cys Ser Phe Tyr Arg Thr Arg Thr Leu Gln Ala
    50                  55                  60

Leu Ser Ser Glu Lys Lys Ala Lys Ala Arg Phe Tyr Arg Asn Gly
65                  70                  75                  80

Asp Arg Tyr Phe Lys Gly Leu Val Phe Ala Ile Ser Ser Asp Arg Phe
                85                  90                  95

Arg Ser Phe Asp Ala Leu Leu Ile Glu Leu Thr Arg Ser Leu Ser Asp
            100                 105                 110

Asn Val Asn Leu Pro Gln Gly Val Arg Thr Ile Tyr Thr Ile Asp Gly
        115                 120                 125

Ser Arg Lys Val Thr Ser Leu Asp Glu Leu Leu Glu Gly Glu Ser Tyr
    130                 135                 140

Val Cys Ala Ser Asn Glu Pro Phe Arg Lys Val Asp Tyr Thr Lys Asn
145                 150                 155                 160

Ile Asn Pro Asn Trp Ser Val Asn Ile Lys Gly Gly Thr Ser Arg Ala
                165                 170                 175

Leu Ala Ala Ser Ser Val Lys Ser Glu Val Lys Glu Ser Lys Asp
            180                 185                 190

Phe Ile Lys Pro Lys Leu Val Thr Val Ile Arg Ser Gly Val Lys Pro
        195                 200                 205

Arg Lys Ala Val Arg Ile Leu Leu Asn Lys Lys Thr Ala His Ser Phe
    210                 215                 220

Glu Gln Val Leu Thr Asp Ile Thr Glu Ala Ile Lys Leu Asp Ser Gly
225                 230                 235                 240

Val Val Lys Arg Leu Cys Thr Leu Asp Gly Lys Gln Val Thr Cys Leu
                245                 250                 255

Gln Asp Phe Phe Gly Asp Asp Val Phe Ile Ala Cys Gly Pro Glu
            260                 265                 270

Lys Phe Arg Tyr Ala Gln Asp Asp Phe Val Leu Asp His Ser Glu Cys
        275                 280                 285

Arg Val Leu Lys Ser Ser Tyr Ser Arg Ser Ser Ala Val Lys Tyr Ser
    290                 295                 300

Gly Ser Lys Ser Pro Gly Pro Ser Arg Arg Ser Lys Ser Pro Ala Ser
305                 310                 315                 320

Val Asn Gly Thr Pro Ser Ser Gln Leu Ser Thr Pro Lys Ser Thr Lys
                325                 330                 335

Ser Ser Ser Ser Ser Pro Thr Ser Pro Gly Ser Phe Arg Gly Leu Lys
```

-continued

```
            340                 345                 350
Gln Ile Ser Ala His Gly Arg Ser Ser Asn Val Thr Gly Gly Pro
            355                 360                 365
Glu Leu Asp Arg Cys Ile Ser Pro Glu Gly Val Asn Gly Asn Arg Cys
370                 375                 380
Ser Glu Ser Ser Thr Leu Leu Glu Lys Tyr Lys Ile Gly Lys Val Ile
385                 390                 395                 400
Gly Asp Gly Asn Phe Ala Val Val Lys Glu Cys Ile Asp Arg Ser Thr
                405                 410                 415
Gly Lys Glu Phe Ala Leu Lys Ile Ile Asp Lys Ala Lys Cys Cys Gly
            420                 425                 430
Lys Glu His Leu Ile Glu Asn Glu Val Ser Ile Leu Arg Arg Val Lys
            435                 440                 445
His Pro Asn Ile Ile Met Leu Val Glu Glu Met Glu Thr Ala Thr Glu
            450                 455                 460
Leu Phe Leu Val Met Glu Leu Val Lys Gly Gly Asp Leu Phe Asp Ala
465                 470                 475                 480
Ile Thr Ser Ser Thr Lys Tyr Thr Glu Arg Asp Gly Ser Ala Met Val
                485                 490                 495
Tyr Asn Leu Ala Asn Ala Leu Arg Tyr Leu His Gly Leu Ser Ile Val
            500                 505                 510
His Arg Asp Ile Lys Pro Glu Asn Leu Leu Val Cys Glu Tyr Pro Asp
            515                 520                 525
Gly Thr Lys Ser Leu Lys Leu Gly Asp Phe Gly Leu Ala Thr Val Val
            530                 535                 540
Glu Gly Pro Leu Tyr Thr Val Cys Gly Thr Pro Thr Tyr Val Ala Pro
545                 550                 555                 560
Glu Ile Ile Ala Glu Thr Gly Tyr Gly Leu Lys Val Asp Ile Trp Ala
                565                 570                 575
Ala Gly Val Ile Thr Tyr Ile Leu Leu Cys Gly Phe Pro Pro Phe Arg
            580                 585                 590
Ser Glu Asn Asn Leu Gln Glu Asp Leu Phe Asp Gln Ile Leu Ala Gly
            595                 600                 605
Lys Leu Glu Phe Pro Ala Pro Tyr Trp Asp Asn Ile Thr Asp Ser Ala
            610                 615                 620
Lys Glu Leu Ile Ser Gln Met Leu Gln Val Asn Val Glu Ala Arg Cys
625                 630                 635                 640
Thr Ala Gly Gln Ile Leu Ser His Pro Trp Val Ser Asp Asp Ala Ser
                645                 650                 655
Gln Glu Asn Asn Met Gln Ala Glu Val Thr Gly Lys Leu Lys Gln His
                660                 665                 670
Phe Asn Asn Ala Leu Pro Lys Gln Asn Ser Thr Thr Gly Val Ser
            675                 680                 685
Val Ile Met Asn Thr Ala Leu Asp Lys Glu Gly Gln Ile Phe Cys Ser
            690                 695                 700
Lys His Cys Gln Asp Ser Gly Arg Pro Gly Met Glu Pro Ile Ser Pro
705                 710                 715                 720
Val Pro Pro Ser Val Glu Glu Ile Pro Val Pro Gly Glu Ala Val Pro
                725                 730                 735
Ala Pro Thr Pro Pro Glu Ser Pro Thr Pro His Cys Pro Pro Ala Ala
            740                 745                 750
Pro Gly Gly Glu Arg Ala Gly Thr Trp Arg Arg His Arg Asp
            755                 760                 765
```

```
<210> SEQ ID NO 9
<211> LENGTH: 2301
<212> TYPE: DNA
<213> ORGANISM: Homo sapiens

<400> SEQUENCE: 9
atggccagca ccaggagtat cgagctggag cactttgagg aacgggacaa aaggccgcgg      60
ccggggtcgc ggagaggggc ccccagctcc tccgggggca gcagcagctc gggccccaag     120
gggaacgggc tcatccccag tccggcgcac agtgcccact gcagcttcta ccgcacgcgg     180
accctgcagg ccctcagctc ggagaagaag gccaagaagg cgcgcttcta ccggaacggg     240
gaccgctact tcaagggcct ggtgtttgcc atctccagcg accgcttccg gtccttcgat     300
gcgctcctca tagagctcac ccgctccctg tcggacaacg tgaacctgcc ccagggtgtc     360
cgcactatct acaccatcga cggcagccgg aaggtcacca gcctggacga gctgctggaa     420
ggtgagagtt acgtgtgtgc atccaatgaa ccatttcgta aagtcgatta caccaaaaat     480
attaatccaa actggtctgt gaacatcaag ggtgggacat cccgagcgct ggctgctgcc     540
tcctctgtga aaagtgaagt aaaagaaagt aaagatttca tcaaacccaa gttagtgact     600
gtgattcgaa gtggagtgaa gcctagaaaa gccgtgcgga tccttctgaa taaaaagact     660
gctcattcct ttgaacaagt cttaacagat atcaccgaag ccattaaact agactcagga     720
gtcgtcaaga ggctctgcac cctgatgga aagcaggtta cttgtctgca agactttttt     780
ggtgatgacg atgtttttat tgcatgtgga ccagaaaaat ttcgttatgc ccaagatgac     840
tttgtcctgg atcatagtga atgtcgtgtc ctgaagtcat cttattctcg atcctcagct     900
gttaagtatt ctggatccaa aagccctggg ccctctcgac gcagcaaatc accagcttca     960
gttaatggaa ctcccagcag ccaactttct actcctaaat ctacgaaatc ctccagttcc    1020
tctccaacta gtccaggaag tttcaggagga ttaaagcaga tttctgctca tggcagatct    1080
tcttccaatg taaccggtgg acctgagctt gaccgttgca taagtcctga aggtgtgaat    1140
ggaaacagat gctctgaatc atcaactctt cttgagaaat acaaaattgg aaaggtcatt    1200
ggtgatggca ttttgcagt agtcaaagag tgtatagaca ggtccactgg aaaggagttt    1260
gccctaaaga ttatagacaa agccaaatgt tgtggaaagg aacacctgat tgagaatgaa    1320
gtgtcaatac tgcgccgagt gaaacatccc aatatcatta tgctggtcga ggagatggaa    1380
acagcaactg agctcttttct ggtgatggaa ttggtcaaag tggagatct ctttgatgca    1440 attacttcgt cgaccaagta cactgagaga gatggcagtg ccatggtgta caacttagcc    1500
aatgccctca ggtatctcca tggcctcagc atcgtgcaca gagacatcaa accagagaat    1560
ctcttggtgt gtgaatatcc tgatggaacc aagtctttga aactgggaga ctttgggctt    1620
gcgactgtgg tagaaggccc tttatacaca gtctgtggca cacccactta tgtggctcca    1680
gaaatcattg ctgaaactgg ctatggcctg aaggtggaca tttgggcagc tggtgtgatc    1740
acatacatac ttctctgtgg attcccacca ttccgaagtg agaacaatct ccaggaagat    1800
ctcttcgacc agatcttggc tgggaagctg gagtttccgg ccccctactg ggataacatc    1860
acggactctg ccaaggaatt aatcagtcaa atgcttcagg taaatgttga agctcggtgt    1920
accgcgggac aaatcctgag tcacccctgg gtgtcagatg atgcctccca ggagaataac    1980
atgcaagctg aggtgacagg taaactaaaa cagcacttta ataatgcgct ccccaaacag    2040
aacagcacta ccaccggggt ctccgtcatc atgaacacgg ctctagataa ggaggggcag    2100
```

```
attttctgca gcaagcactg tcaagacagc ggcaggcctg ggatggagcc catctctcca    2160
gttcctccct cagtggagga gatccctgtg cctggggaag cagtcccggc ccccacccct    2220
ccggaatctc ccaccccca ctgtcctccc gctgccccgg gtggtgagcg ggcaggaacc     2280
tggcgccgcc accgagactg a                                              2301
```

<210> SEQ ID NO 10
<211> LENGTH: 278
<212> TYPE: PRT
<213> ORGANISM: Artificial Sequence
<220> FEATURE:
<223> OTHER INFORMATION: consensus sequence

<400> SEQUENCE: 10

```
Tyr Glu Leu Leu Glu Lys Leu Gly Glu Gly Ser Phe Gly Lys Val Tyr
 1               5                  10                  15

Lys Ala Lys His Lys Thr Gly Lys Ile Val Ala Val Lys Ile Leu Lys
            20                  25                  30

Lys Glu Ser Leu Ser Leu Arg Glu Ile Gln Ile Leu Lys Arg Leu Ser
        35                  40                  45

His Pro Asn Ile Val Arg Leu Leu Gly Val Phe Glu Asp Thr Asp Asp
    50                  55                  60

His Leu Tyr Leu Val Met Glu Tyr Met Glu Gly Gly Asp Leu Phe Asp
65                  70                  75                  80

Tyr Leu Arg Arg Asn Gly Pro Leu Ser Glu Lys Glu Ala Lys Lys Ile
                85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg Leu Leu Glu Lys Leu
    130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
        195                 200                 205

Phe Val Leu Lys Leu Pro Phe Ser Asp Glu Leu Pro Lys Thr Arg Ile
    210                 215                 220

Asp Pro Leu Glu Glu Leu Phe Arg Ile Lys Lys Arg Leu Pro Leu
225                 230                 235                 240

Pro Ser Asn Cys Ser Glu Glu Leu Lys Asp Leu Leu Lys Cys Leu
                245                 250                 255

Asn Lys Asp Pro Ser Lys Arg Pro Gly Ser Ala Thr Ala Lys Glu Ile
            260                 265                 270

Leu Asn His Pro Trp Phe
        275
```

<210> SEQ ID NO 11
<211> LENGTH: 96
<212> TYPE: PRT
<213> ORGANISM: Artificial Sequence
<220> FEATURE:
<223> OTHER INFORMATION: consensus sequence

```
<400> SEQUENCE: 11

Ser Leu Val Lys Pro Lys Arg Ile Arg Val Tyr Arg Asn Gly Asp Arg
1               5                   10                  15

Phe Phe Lys Gly Val Arg Leu Val Val Asn Arg Lys Arg Gln Phe Lys
            20                  25                  30

Ser Phe Glu Ala Leu Leu Gln Asp Leu Thr Glu Leu Lys Leu Val Val
        35                  40                  45

Lys Leu Asp Leu Pro Phe Ala Val Arg Lys Leu Tyr Thr Leu Asp Gly
    50                  55                  60

Gly Lys Lys Val Thr Ser Leu Asp Glu Leu Glu Asp Gly Asp Gly Val
65                  70                  75                  80

Tyr Val Ala Ser Gly Thr Glu Glu Lys Phe Lys Val Asp Tyr Gly
                85                  90                  95

<210> SEQ ID NO 12
<211> LENGTH: 231
<212> TYPE: PRT
<213> ORGANISM: Artificial Sequence
<220> FEATURE:
<223> OTHER INFORMATION: consensus sequence

<400> SEQUENCE: 12

Tyr Glu Leu Leu Lys Lys Leu Gly Lys Gly Ala Phe Gly Lys Val Tyr
1               5                   10                  15

Leu Ala Arg Asp Lys Lys Thr Gly Arg Leu Val Ala Ile Lys Val Ile
            20                  25                  30

Lys Glu Arg Ile Leu Arg Glu Ile Lys Ile Leu Lys Lys Asp His Pro
        35                  40                  45

Asn Ile Val Lys Leu Tyr Asp Val Phe Glu Asp Lys Leu Tyr Leu
    50                  55                  60

Val Met Glu Tyr Cys Glu Gly Asp Leu Gly Asp Leu Phe Asp Leu Leu
65                  70                  75                  80

Lys Lys Arg Gly Arg Arg Gly Leu Arg Lys Val Leu Ser Glu Ala
            85                  90                  95

Arg Phe Tyr Phe Arg Gln Ile Leu Ser Ala Leu Glu Tyr Leu His Ser
        100                 105                 110

Gln Gly Ile Ile His Arg Asp Leu Lys Pro Glu Asn Ile Leu Leu Asp
        115                 120                 125

Ser His Val Lys Leu Ala Asp Phe Gly Leu Ala Arg Gln Leu Thr Thr
    130                 135                 140

Phe Val Gly Thr Pro Glu Tyr Met Ala Pro Glu Val Leu Gly Tyr Gly
145                 150                 155                 160

Lys Pro Ala Val Asp Ile Trp Ser Leu Gly Cys Ile Leu Tyr Glu Leu
            165                 170                 175

Leu Thr Gly Lys Pro Pro Phe Pro Gln Leu Asp Leu Ile Phe Lys Lys
        180                 185                 190

Ile Gly Ser Pro Glu Ala Lys Asp Leu Ile Lys Leu Leu Val Lys
    195                 200                 205

Asp Pro Glu Lys Arg Leu Thr Ala Glu Ala Leu Glu Asp Glu Leu Asp
    210                 215                 220

Ile Lys Ala His Pro Phe Phe
225                 230

<210> SEQ ID NO 13
<211> LENGTH: 253
```

```
<212> TYPE: PRT
<213> ORGANISM: Artificial Sequence
<220> FEATURE:
<223> OTHER INFORMATION: consensus sequence

<400> SEQUENCE: 13

Asn Gly Leu Pro Ser Pro Thr His Ser Ala His Cys Ser Phe Tyr Arg
1               5                   10                  15

Thr Arg Thr Leu Gln Thr Leu Ser Asn Glu Lys Lys Ala Lys Lys Val
            20                  25                  30

Arg Phe Tyr Arg Asn Gly Asp Arg Tyr Phe Lys Gly Ile Val Tyr Ala
        35                  40                  45

Val Ser Pro Asp Arg Phe Arg Ser Phe Asp Ala Leu Leu Ala Asp Leu
    50                  55                  60

Thr Arg Thr Leu Ser Asp Asn Ile Asn Leu Pro Gln Gly Val Arg Tyr
65                  70                  75                  80

Ile Tyr Thr Ile Asp Gly Ser Arg Lys Ile Gly Ser Met Asp Glu Leu
                85                  90                  95

Glu Glu Gly Glu Ser Tyr Val Cys Gly Ser Asp Asn Pro Phe Lys Lys
            100                 105                 110

Val Glu Tyr Thr Lys Asn Val Asn Pro Asn Trp Ser Val Asn Val Lys
        115                 120                 125

Thr Thr Ala Asn Met Lys Ala Pro Gln Ser Leu Ala Thr Ser Asn Gly
    130                 135                 140

Ala Pro Ser Gln Ala Arg Glu Asn Lys Asp Phe Val Arg Pro Lys Leu
145                 150                 155                 160

Val Thr Ile Ile Arg Ser Gly Val Lys Pro Arg Lys Ala Val Arg Val
                165                 170                 175

Leu Leu Asn Lys Lys Thr Ala His Ser Phe Glu Gln Val Leu Thr Asp
            180                 185                 190

Ile Thr Asp Ala Ile Lys Leu Asp Thr Gly Val Val Lys Lys Leu Tyr
        195                 200                 205

Thr Leu Asp Gly Lys Gln Val Thr Cys Leu His Asp Phe Phe Gly Asp
    210                 215                 220

Asp Asp Val Phe Ile Ala Cys Gly Pro Glu Lys Phe Arg Tyr Ala Gln
225                 230                 235                 240

Asp Asp Phe Ser Leu Asp Glu Asn Glu Cys Arg Val Met
                245                 250

<210> SEQ ID NO 14
<211> LENGTH: 2838
<212> TYPE: DNA
<213> ORGANISM: Homo sapiens
<220> FEATURE:
<221> NAME/KEY: CDS
<222> LOCATION: (462)...(2072)
<220> FEATURE:
<221> NAME/KEY: misc_feature
<222> LOCATION: (1)...(2838)
<223> OTHER INFORMATION: n = A,T,C or G

<400> SEQUENCE: 14
ggttttccac gttttgcntg accctgtttg ctcaactrwc ktytktktyk ykttytstkt      60
trygcssykw yamrakmymm rmkttkaaaa amcmrraaag ttaaytggta agtttagtct     120
ttttgtcttt tatttcaagg tcccggatcc ggtggtggtg caaatcaaag aactgctcct     180
cagtggatgt tgcctttact tctaggcctg tacggaagtg ttacttctgc tctaaaagct     240
gcggaattct aatacgactc actatagggag tcgacccac gcgtccggtg ggcaggccgg     300
```

```
gggtgagggc tcgcgctccg ggagctgcac ggggctgcgt ggaaagagcg ccgagcggtg      360
gcgtcgttgt cgcccctcc tcgtcgggaa gaatcgtttg gtctcctgcc gtgcccggaa      420
tcccagtcag aagttccagc ctgccactgt tctctgatgc c atg cca gca cca act     476
                                             Met Pro Ala Pro Thr
                                               1               5 caa ctg ttt ttt cct ctc atc cgt aac tgt gaa ctg agc agg atc tat      524
Gln Leu Phe Phe Pro Leu Ile Arg Asn Cys Glu Leu Ser Arg Ile Tyr
             10                  15                  20 ggc act gca tgt tac tgc cac cac aaa cat ctc tgt tgt tcc tca tcg      572
Gly Thr Ala Cys Tyr Cys His His Lys His Leu Cys Cys Ser Ser Ser
         25                  30                  35 tac att cct cag agt cga ctg aga tac aca cct cat cca gca tat gct      620
Tyr Ile Pro Gln Ser Arg Leu Arg Tyr Thr Pro His Pro Ala Tyr Ala
         40                  45                  50 acc ttt tgc agg cca aag gag aac tgg tgg cag tac acc caa gga agg      668
Thr Phe Cys Arg Pro Lys Glu Asn Trp Trp Gln Tyr Thr Gln Gly Arg
     55                  60                  65 aga tat gct tcc aca cca cag aaa ttt tac ctc aca cct cca caa gtc      716
Arg Tyr Ala Ser Thr Pro Gln Lys Phe Tyr Leu Thr Pro Pro Gln Val
 70                  75                  80                  85 aat agc atc ctt aaa gct aat gaa tac agt ttc aaa gtg cca gaa ttt      764
Asn Ser Ile Leu Lys Ala Asn Glu Tyr Ser Phe Lys Val Pro Glu Phe
                 90                  95                 100 gac ggc aaa aat gtc agt tct atc ctt gga ttt gac agc aat cag ctg      812
Asp Gly Lys Asn Val Ser Ser Ile Leu Gly Phe Asp Ser Asn Gln Leu
                105                 110                 115 cct gca aat gca ccc att gag gac cgg aga agt gca gca acc tgc ttg      860
Pro Ala Asn Ala Pro Ile Glu Asp Arg Arg Ser Ala Ala Thr Cys Leu
            120                 125                 130 cag acc aga ggg atg ctt ttg ggg gtt ttt gat ggc cat gca ggt tgt      908
Gln Thr Arg Gly Met Leu Leu Gly Val Phe Asp Gly His Ala Gly Cys
        135                 140                 145 gct tgt tcc cag gca gtc agt gaa aga ctc ttt tat tat att gct gtc      956
Ala Cys Ser Gln Ala Val Ser Glu Arg Leu Phe Tyr Tyr Ile Ala Val
150                 155                 160                 165 tct ttg tta ccc cat gag act ttg cta gag att gaa aat gca gtg gag     1004
Ser Leu Leu Pro His Glu Thr Leu Leu Glu Ile Glu Asn Ala Val Glu
                170                 175                 180 agc ggc cgg gca ctg cta ccc att ctc cag tgg cac aag cac ccc aat     1052
Ser Gly Arg Ala Leu Leu Pro Ile Leu Gln Trp His Lys His Pro Asn
            185                 190                 195 gat tac ttt agt aag gag gca tcc aaa ttg tac ttt aac agc ttg agg     1100
Asp Tyr Phe Ser Lys Glu Ala Ser Lys Leu Tyr Phe Asn Ser Leu Arg
        200                 205                 210 act tac tgg caa gag ctt ata gac ctc aac act ggt gag tcg act gat     1148
Thr Tyr Trp Gln Glu Leu Ile Asp Leu Asn Thr Gly Glu Ser Thr Asp
    215                 220                 225 att gat gtt aag gag gct cta att aat gcc ttc aag agg ctt gat aat     1196
Ile Asp Val Lys Glu Ala Leu Ile Asn Ala Phe Lys Arg Leu Asp Asn
230                 235                 240                 245 gac atc tcc ttg gag gcg caa gtt ggt gat cct aat tct ttt ctc aac     1244
Asp Ile Ser Leu Glu Ala Gln Val Gly Asp Pro Asn Ser Phe Leu Asn
                250                 255                 260 tac ctg gtg ctt cga gtg gca ttt tct gga gcc act gct tgt gtg gcc     1292
Tyr Leu Val Leu Arg Val Ala Phe Ser Gly Ala Thr Ala Cys Val Ala
            265                 270                 275 cat gtg gat ggt gtt gac ctt cat gtg gcc aat act ggc gat agc aga     1340
His Val Asp Gly Val Asp Leu His Val Ala Asn Thr Gly Asp Ser Arg
```

```
                280                 285                 290
gcc atg ctg ggt gtg cag gaa gag gac ggc tca tgg tca gca gtc acg    1388
Ala Met Leu Gly Val Gln Glu Glu Asp Gly Ser Trp Ser Ala Val Thr
    295                 300                 305 ctg tct aat gac cac aat gct caa aat gaa aga gaa cta gaa cgg ctg    1436
Leu Ser Asn Asp His Asn Ala Gln Asn Glu Arg Glu Leu Glu Arg Leu
310                 315                 320                 325 aaa ttg gaa cat cca aag agt gag gcc aag agt gtc gtg aaa cag gat    1484
Lys Leu Glu His Pro Lys Ser Glu Ala Lys Ser Val Val Lys Gln Asp
                330                 335                 340 cgg ctg ctt ggc ttg ctg atg cca ttt agg gca ttt gga gat gta aag    1532
Arg Leu Leu Gly Leu Leu Met Pro Phe Arg Ala Phe Gly Asp Val Lys
            345                 350                 355 ttc aaa tgg agc att gac ctt caa aag aga gtg ata gaa tct ggc cca    1580
Phe Lys Trp Ser Ile Asp Leu Gln Lys Arg Val Ile Glu Ser Gly Pro
        360                 365                 370 gac cag ttg aat gac aat gaa tat acc aag ttt att cct cct aat tat    1628
Asp Gln Leu Asn Asp Asn Glu Tyr Thr Lys Phe Ile Pro Pro Asn Tyr
    375                 380                 385 cac aca cct cct tat ctc act gct gag cca gag gta act tac cac cga    1676
His Thr Pro Pro Tyr Leu Thr Ala Glu Pro Glu Val Thr Tyr His Arg
390                 395                 400                 405 tta agg cca cag gat aag ttt ctg gtg ttg gct act gat ggg ttg tgg    1724
Leu Arg Pro Gln Asp Lys Phe Leu Val Leu Ala Thr Asp Gly Leu Trp
                410                 415                 420 gag act atg cat agg cag gat gtg gtt agg att gtg ggt gag tac cta    1772
Glu Thr Met His Arg Gln Asp Val Val Arg Ile Val Gly Glu Tyr Leu
            425                 430                 435 act ggc atg cat cac caa cag cca ata gct gtt ggt ggc tac aag gtg    1820
Thr Gly Met His His Gln Gln Pro Ile Ala Val Gly Gly Tyr Lys Val
        440                 445                 450 act ctg gga cag atg cat ggc ctt tta aca gaa agg aga acc aaa atg    1868
Thr Leu Gly Gln Met His Gly Leu Leu Thr Glu Arg Arg Thr Lys Met
    455                 460                 465 tcc tcg gta ttt gag gat cag aac gca gca acc cat ctc att cgc cac    1916
Ser Ser Val Phe Glu Asp Gln Asn Ala Ala Thr His Leu Ile Arg His
470                 475                 480                 485 gct gtg ggc aac aac gag ttt ggg act gtt gat cat gag cgc ctc tct    1964
Ala Val Gly Asn Asn Glu Phe Gly Thr Val Asp His Glu Arg Leu Ser
                490                 495                 500 aaa atg ctt agt ctt cct gaa gag ctt gct cga atg tac aga gat gac    2012
Lys Met Leu Ser Leu Pro Glu Glu Leu Ala Arg Met Tyr Arg Asp Asp
            505                 510                 515 att aca atc att gta gtt cag ttc aat tct cat gtt gta ggg gcg tat    2060
Ile Thr Ile Ile Val Val Gln Phe Asn Ser His Val Val Gly Ala Tyr
        520                 525                 530 caa aac caa gaa tagtgagtgg ctctttcact ggcaattctc aaatgatata        2112
Gln Asn Gln Glu
    535 catttaaagg gcagattttt taaaagata ctactataat aaacatttcc agttggtcat   2172 tctaagcatt tacccttttg atactctagc tagtcaggta ctccaaattg actttgcagc   2232 agggtggcag ggtcaggaga gtctggtcct gcctagctca gatttcatgg cacctgcact   2292 tgaagcaagt cacttcttta tcacaggtgt cttgaaacat tagcttcttt taccaacctg   2352 agaaaattag gatgacctgg caaataagat cttgaatagg ccaaaagcaa gtatcttgct   2412 gtgtgtagtc tcttggttaa agtgaagaaa cagtactgtt cacacctttc ttcactgaga   2472 ttccagtgta catgagaaca tatatttatt ksmwkrwttt yywrrtacac agtctatgca   2532
```

-continued

```
ttwttcataw wmawttattt twgcctaaat aargtkkttw wcamatcyag tthwtcmatc    2592
matraacras mamcaascaa tctrtatktr tttttktkwk trwttrwytg rmakgmwtsy    2652
twaktrrrak ramtawmcwc mstyatccay ccgmyykmyt wmykwaaktr attgaaatat    2712
tttttwtttt gccccccct tggagtcaag aagggttttt agttttatct tctyttctat    2772
tgaagttaaa aaaaaaaaa aaaaaaaaa aaaaaaaaa aaaaaaaaa aaaaaaaag        2832 ggcgaa                                                               2838
```

<210> SEQ ID NO 15
<211> LENGTH: 537
<212> TYPE: PRT
<213> ORGANISM: Homo sapiens

<400> SEQUENCE: 15

| | | | | | | | | | | | | | | |
|---|---|---|---|---|---|---|---|---|---|---|---|---|---|---|
| Met | Pro | Ala | Pro | Thr | Gln | Leu | Phe | Phe | Pro | Leu | Ile | Arg | Asn | Cys | Glu |
| 1 | | | | 5 | | | | | 10 | | | | | 15 | |

Leu Ser Arg Ile Tyr Gly Thr Ala Cys Tyr Cys His His Lys His Leu
                20                  25                  30

Cys Cys Ser Ser Tyr Ile Pro Gln Ser Arg Leu Arg Tyr Thr Pro
        35                  40                  45

His Pro Ala Tyr Ala Thr Phe Cys Arg Pro Lys Glu Asn Trp Trp Gln
 50                  55                  60

Tyr Thr Gln Gly Arg Arg Tyr Ala Ser Thr Pro Gln Lys Phe Tyr Leu
 65                  70                  75                  80

Thr Pro Pro Gln Val Asn Ser Ile Leu Lys Ala Asn Glu Tyr Ser Phe
                 85                  90                  95

Lys Val Pro Glu Phe Asp Gly Lys Asn Val Ser Ser Ile Leu Gly Phe
            100                 105                 110

Asp Ser Asn Gln Leu Pro Ala Asn Ala Pro Ile Glu Asp Arg Arg Ser
        115                 120                 125

Ala Ala Thr Cys Leu Gln Thr Arg Gly Met Leu Leu Gly Val Phe Asp
130                 135                 140

Gly His Ala Gly Cys Ala Cys Ser Gln Ala Val Ser Glu Arg Leu Phe
145                 150                 155                 160

Tyr Tyr Ile Ala Val Ser Leu Leu Pro His Glu Thr Leu Glu Ile
                165                 170                 175

Glu Asn Ala Val Glu Ser Gly Arg Ala Leu Leu Pro Ile Leu Gln Trp
            180                 185                 190

His Lys His Pro Asn Asp Tyr Phe Ser Lys Glu Ala Ser Lys Leu Tyr
        195                 200                 205

Phe Asn Ser Leu Arg Thr Tyr Trp Gln Glu Leu Ile Asp Leu Asn Thr
    210                 215                 220

Gly Glu Ser Thr Asp Ile Asp Val Lys Glu Ala Leu Ile Asn Ala Phe
225                 230                 235                 240

Lys Arg Leu Asp Asn Asp Ile Ser Leu Glu Ala Gln Val Gly Asp Pro
                245                 250                 255

Asn Ser Phe Leu Asn Tyr Leu Val Leu Arg Val Ala Phe Ser Gly Ala
            260                 265                 270

Thr Ala Cys Val Ala His Val Asp Gly Val Asp Leu His Val Ala Asn
        275                 280                 285

Thr Gly Asp Ser Arg Ala Met Leu Gly Val Gln Glu Glu Asp Gly Ser
    290                 295                 300

Trp Ser Ala Val Thr Leu Ser Asn Asp His Asn Ala Gln Asn Glu Arg

```
                305                 310                 315                 320
Glu Leu Glu Arg Leu Lys Leu Glu His Pro Lys Ser Glu Ala Lys Ser
                    325                 330                 335
Val Val Lys Gln Asp Arg Leu Leu Gly Leu Leu Met Pro Phe Arg Ala
                340                 345                 350
Phe Gly Asp Val Lys Phe Lys Trp Ser Ile Asp Leu Gln Lys Arg Val
            355                 360                 365
Ile Glu Ser Gly Pro Asp Gln Leu Asn Asp Asn Glu Tyr Thr Lys Phe
        370                 375                 380
Ile Pro Pro Asn Tyr His Thr Pro Tyr Leu Thr Ala Glu Pro Glu
385                 390                 395                 400
Val Thr Tyr His Arg Leu Arg Pro Gln Asp Lys Phe Leu Val Leu Ala
                405                 410                 415
Thr Asp Gly Leu Trp Glu Thr Met His Arg Gln Asp Val Val Arg Ile
            420                 425                 430
Val Gly Glu Tyr Leu Thr Gly Met His His Gln Pro Ile Ala Val
        435                 440                 445
Gly Gly Tyr Lys Val Thr Leu Gly Gln Met His Gly Leu Leu Thr Glu
    450                 455                 460
Arg Arg Thr Lys Met Ser Ser Val Phe Glu Asp Gln Asn Ala Ala Thr
465                 470                 475                 480
His Leu Ile Arg His Ala Val Gly Asn Asn Glu Phe Gly Thr Val Asp
                485                 490                 495
His Glu Arg Leu Ser Lys Met Leu Ser Leu Pro Glu Gly Leu Ala Arg
                500                 505                 510
Met Tyr Arg Asp Asp Ile Thr Ile Ile Val Val Gln Phe Asn Ser His
                515                 520                 525
Val Val Gly Ala Tyr Gln Asn Gln Glu
    530                 535

<210> SEQ ID NO 16
<211> LENGTH: 1611
<212> TYPE: DNA
<213> ORGANISM: Homo sapiens

<400> SEQUENCE: 16
atgccagcac caactcaact gttttttcct ctcatccgta actgtgaact gagcaggatc      60
tatggcactg catgttactg ccaccacaaa catctctgtt gttcctcatc gtacattcct     120
cagagtcgac tgagatacac acctcatcca gcatatgcta ccttttgcag gccaaaggag     180
aactggtggc agtacaccca aggaaggaga tatgcttcca caccacagaa attttacctc     240
acacctccac aagtcaatag catccttaaa gctaatgaat acagtttcaa agtgccagaa     300
tttgacggca aaaatgtcag ttctatcctt ggatttgaca gcaatcagct gcctgcaaat     360
gcacccattg aggaccggag aagtgcagca acctgcttgc agaccagagg gatgcttttg     420 ggggttttg atggccatgc aggttgtgct tgttcccagg cagtcagtga agactcttt      480 tattatattg ctgtctcttt gttacccat gagactttgc tagagattga aaatgcagtg     540
gagagcggcc gggcactgct acccattctc cagtggcaca gcaccccaa tgattacttt     600 agtaaggagg catccaaatt gtactttaac agcttgagga cttactggca agagcttata     660
gacctcaaca ctggtgagtc gactgatatt gatgttaagg aggctctaat taatgccttc     720
aagaggcttg ataatgacat ctccttggag gcgcaagttg gtgatcctaa ttcttttctc     780
aactacctgg tgcttcgagt ggcatttct ggagccactg cttgtgtggc ccatgtggat     840
```

-continued

```
ggtgttgacc ttcatgtggc caatactggc gatagcagag ccatgctggg tgtgcaggaa    900
gaggacggct catggtcagc agtcacgctg tctaatgacc acaatgctca aaatgaaaga    960
gaactagaac ggctgaaatt ggaacatcca agagtgagg ccaagagtgt cgtgaaacag   1020
gatcggctgc ttggcttgct gatgccattt agggcatttg agatgtaaa gttcaaatgg   1080
agcattgacc ttcaaaagag agtgatagaa tctggcccag accagttgaa tgacaatgaa   1140
tataccaagt ttattcctcc taattatcac acacctcctt atctcactgc tgagccagag   1200
gtaacttacc accgattaag gccacaggat aagtttctgg tgttggctac tgatgggttg   1260
tgggagacta tgcataggca ggatgtggtt aggattgtgg gtgagtacct aactggcatg   1320
catcaccaac agccaatagc tgttggtggc tacaaggtga ctctgggaca gatgcatggc   1380
cttttaacag aaaggagaac caaaatgtcc tcggtatttg aggatcagaa cgcagcaacc   1440
catctcattc gccacgctgt gggcaacaac gagtttggga ctgttgatca tgagcgcctc   1500
tctaaaatgc ttagtcttcc tgaagagctt gctcgaatgt acagagatga cattacaatc   1560
attgtagttc agttcaattc tcatgttgta ggggcgtatc aaaaccaaga a           1611
```

<210> SEQ ID NO 17
<211> LENGTH: 300
<212> TYPE: PRT
<213> ORGANISM: Artificial Sequence
<220> FEATURE:
<223> OTHER INFORMATION: consensus sequence

<400> SEQUENCE: 17

```
Leu Asp Val Gly Val Ser Arg Met Gln Gly Trp Arg Lys Ser Met Glu
 1               5                   10                  15

Asp Ala His Ile Ala Leu Lys Asn Leu Asn Ser Ser Ser Gly Lys
            20                  25                  30

Asp Ser Trp Ser Phe Phe Ala Val Phe Asp Gly His Gly Ser Gln Ala
        35                  40                  45

Ala Lys Tyr Ala Gly Lys His Leu His Lys Thr Ile Leu Ala Glu Arg
    50                  55                  60

Lys Ser Phe Pro Glu Gly Asp Pro Trp Glu Met Lys Leu Ser Asp Leu
65                  70                  75                  80

Glu Asp Ala Leu Lys Glu Ser Phe Leu Glu Ala Asp Thr Asp Glu Glu
                85                  90                  95

Leu Arg Ser Ala Glu Ala Ser Ala Ala Asn Lys Val Leu Thr Lys Glu
            100                 105                 110

Asp Leu Ser Ser Gly Ser Thr Ala Val Val Ala Leu Ile Arg Gly Asn
        115                 120                 125

Lys Leu Tyr Val Ala Asn Val Gly Asp Ser Arg Ala Val Leu Cys Arg
    130                 135                 140

Asn Gly Asn Ala Ile Lys Trp Ala Val Thr Leu Thr Glu Asp His Lys
145                 150                 155                 160

Pro Ser Asn Glu Asp Glu Arg Glu Arg Ile Glu Ala Ala Gly Gly Phe
                165                 170                 175

Val Ser Arg Val Ser Asn Gly Arg Val Asn Gly Val Leu Ala Val Ser
            180                 185                 190

Arg Ala Phe Gly Asp Phe Glu Leu Lys Pro Gly Ser Lys Leu Gly Pro
        195                 200                 205

Glu Glu Ser Leu Glu Ala Asn Tyr Glu Tyr Ile Lys Ser Pro Glu Gln
    210                 215                 220
```

```
Leu Val Thr Ala Glu Pro Asp Val Thr Ser Ser Thr Asp Leu Thr Pro
225                 230                 235                 240

Asp Lys Asp Glu Phe Leu Ile Leu Ala Cys Asp Gly Leu Trp Asp Val
                245                 250                 255

Val Ser Asp Gln Glu Val Val Asp Ile Val Arg Ser Glu Leu Ser Asp
                260                 265                 270

Gly Asn Lys Ser Ala Glu Asp Pro Met Glu Ala Ala Glu Lys Leu Val
            275                 280                 285

Asp Glu Ala Ile Ala Arg Gly Ser Glu Asp Asn Ile
290                 295                 300

<210> SEQ ID NO 18
<211> LENGTH: 338
<212> TYPE: PRT
<213> ORGANISM: Artificial Sequence
<220> FEATURE:
<223> OTHER INFORMATION: consensus sequence

<400> SEQUENCE: 18

Glu Ser Ser Gly Lys Asn Leu Gly Leu Arg Tyr Gly Leu Gly Glu Ser
1               5                   10                  15

Ser Met Gln Gly Trp Arg Lys Pro Met Glu Asp Ala His Val Ile Arg
                20                  25                  30

Pro Phe Phe Gly Val Phe Asp Gly His Gly Gly Ser Glu Ala Ala Lys
            35                  40                  45

Phe Leu Ser Lys Asn Leu His Glu Ile Leu Ala Glu Leu Ser Phe
    50                  55                  60

Asp Lys Asp Glu Ser Leu Lys Glu Asn Glu Glu Leu Lys Asp Glu Pro
65                  70                  75                  80

Glu Ser Ser Glu Arg Leu Asn Gly Asp Lys Ser Leu Glu Asp Val Glu
                85                  90                  95

Glu Ala Leu Arg Lys Ala Phe Leu Arg Thr Asp Glu Glu Ile Ser Thr
            100                 105                 110

Ala Val Val Ala Leu Ile Arg Gly Asn Lys Leu Tyr Val Ala Asn Val
        115                 120                 125

Gly Asp Ser Arg Ala Val Leu Cys Arg Asn Gly Lys Asp Ser Trp Glu
    130                 135                 140

Gly Val Arg Thr Tyr Ser Ala Val Gln Leu Thr Glu Asp His Lys Pro
145                 150                 155                 160

Ser Asn Glu Asp Glu Arg Glu Arg Ile Glu Ala Ala Gly Gly Glu Val
                165                 170                 175

Glu Pro Ile Asp Arg Glu Phe Val Ser Asn Gly Gly Val Val Trp
            180                 185                 190

Arg Val Asn Gly Val Val Ile Ser Leu Ala Val Ser Arg Ala Leu Gly
        195                 200                 205

Asp Phe Glu Leu Lys Lys Lys Glu Asp Glu Leu Ile Glu Glu Asn Arg
    210                 215                 220

Leu Tyr Glu Lys Phe Asp Pro Arg Leu Pro Gly Lys Glu Pro Tyr Val
225                 230                 235                 240

Ser Ala Glu Pro Glu Val Thr Val Val Glu Leu Ser Gln Thr Leu Val
                245                 250                 255

Pro Thr Glu Asp Asp Phe Leu Ile Leu Ala Ser Asp Gly Leu Trp
            260                 265                 270

Asp Val Leu Ser Asn Gln Glu Ala Val Asp Ile Val Arg Lys His Leu
    275                 280                 285
```

-continued

```
Arg Lys Gly Asp Asp Lys Glu Val Lys Ser Ala Ala Gln Glu Leu Ala
    290                 295                 300

Arg Ala Asp Ser Leu Arg Ser Lys Lys His Asn Asp Pro Lys Glu Ala
305                 310                 315                 320

Ala Lys Leu Leu Val Asp Leu Ala Leu Lys Asp Asn Ile Thr Val Val
                325                 330                 335

Val Val

<210> SEQ ID NO 19
<211> LENGTH: 3143
<212> TYPE: DNA
<213> ORGANISM: Homo sapiens
<220> FEATURE:
<221> NAME/KEY: CDS
<222> LOCATION: (229)...(2874)

<400> SEQUENCE: 19 ctataggggag tcgcccacgc gtccggcctc cgaggccaag gccgctgcta ctgccgccgc      60
tgcttcttag tgccgcgttc gccgcctggg ttgtcaccgg cgccgccgcc gaggaagcca     120
ctacaaccag gaccggagtg gaggcggcgc agcatgaagc ggcgcaggcc cgctccatag     180
cgcacgtcgg gacggtccgg gcggggccgg ggggaaggaa aatgcaac atg gca gca      237
                                                    Met Ala Ala
                                                      1 gca atg gaa aca gaa cag ctg ggt gtt gag ata ttt gaa act gcg gac       285
Ala Met Glu Thr Glu Gln Leu Gly Val Glu Ile Phe Glu Thr Ala Asp
  5                  10                  15 tgt gag gag aat att gaa tca cag gat cgg cct aaa ttg gag cct ttt       333
Cys Glu Glu Asn Ile Glu Ser Gln Asp Arg Pro Lys Leu Glu Pro Phe
 20                  25                  30                  35 tat gtt gag cgg tat tcc tgg agt cag ctt aaa aag ctg ctt gcc gat       381
Tyr Val Glu Arg Tyr Ser Trp Ser Gln Leu Lys Lys Leu Leu Ala Asp
                 40                  45                  50 acc aga aaa tat cat ggc tac atg atg gct aag gca cca cat gat ttc       429
Thr Arg Lys Tyr His Gly Tyr Met Met Ala Lys Ala Pro His Asp Phe
             55                  60                  65 atg ttt gtg aag agg aat gat cca gat gga cct cat tca gac aga atc       477
Met Phe Val Lys Arg Asn Asp Pro Asp Gly Pro His Ser Asp Arg Ile
         70                  75                  80 tat tac ctt gcc atg tct ggt gag aac aga gaa aat aca ctg ttt tat       525
Tyr Tyr Leu Ala Met Ser Gly Glu Asn Arg Glu Asn Thr Leu Phe Tyr
     85                  90                  95 tct gaa att ccc aaa act atc aat aga gca gca gtc tta atg ctc tct       573
Ser Glu Ile Pro Lys Thr Ile Asn Arg Ala Ala Val Leu Met Leu Ser
100                 105                 110                 115 tgg aag cct ctt ttg gat ctt ttt cag gca aca ctg gac tat gga atg       621
Trp Lys Pro Leu Leu Asp Leu Phe Gln Ala Thr Leu Asp Tyr Gly Met
                120                 125                 130 tat tct cga gaa gaa gaa cta tta aga gaa aga aaa cgc att gga aca       669
Tyr Ser Arg Glu Glu Glu Leu Leu Arg Glu Arg Lys Arg Ile Gly Thr
            135                 140                 145 gtc gga att gct tct tac gat tat cac caa gga agt gga aca ttt ctg       717
Val Gly Ile Ala Ser Tyr Asp Tyr His Gln Gly Ser Gly Thr Phe Leu
        150                 155                 160 ttt caa gcc ggt agt gga att tat cac gta aaa gat gga ggg cca caa       765
Phe Gln Ala Gly Ser Gly Ile Tyr His Val Lys Asp Gly Gly Pro Gln
    165                 170                 175 gga ttt acg caa caa cct tta agg ccc aat cta gtg gaa act agt tgt       813
Gly Phe Thr Gln Gln Pro Leu Arg Pro Asn Leu Val Glu Thr Ser Cys
180                 185                 190                 195
```

```
                                                                    -continued ccc aac ata cgg atg gat cca aaa tta tgc cct gct gat cca gac tgg       861
Pro Asn Ile Arg Met Asp Pro Lys Leu Cys Pro Ala Asp Pro Asp Trp
            200                 205                 210 att gct ttt ata cat agc aac gat att tgg ata tct aac atc gta acc       909
Ile Ala Phe Ile His Ser Asn Asp Ile Trp Ile Ser Asn Ile Val Thr
        215                 220                 225 aga gaa gaa agg aga ctc act tat gtg cac aat gag cta gcc aac atg       957
Arg Glu Glu Arg Arg Leu Thr Tyr Val His Asn Glu Leu Ala Asn Met
    230                 235                 240 gaa gaa gat gcc aga tca gct gga gtc gct acc ttt gtt ctc caa gaa      1005
Glu Glu Asp Ala Arg Ser Ala Gly Val Ala Thr Phe Val Leu Gln Glu
245                 250                 255 gaa ttt gat aga tat tct ggc tat tgg tgg tgt cca aaa gct gaa aca      1053
Glu Phe Asp Arg Tyr Ser Gly Tyr Trp Trp Cys Pro Lys Ala Glu Thr
260                 265                 270                 275 act ccc agt ggt ggt aaa att ctt aga att cta tat gaa gaa aat gat      1101
Thr Pro Ser Gly Gly Lys Ile Leu Arg Ile Leu Tyr Glu Glu Asn Asp
            280                 285                 290 gaa tct gag gtg gaa att att cat gtt aca tcc cct atg ttg gaa aca      1149
Glu Ser Glu Val Glu Ile Ile His Val Thr Ser Pro Met Leu Glu Thr
        295                 300                 305 agg agg gca gat tca ttc cgt tat cct aaa aca ggt aca gca aat cct      1197
Arg Arg Ala Asp Ser Phe Arg Tyr Pro Lys Thr Gly Thr Ala Asn Pro
    310                 315                 320 aaa gtc act ttt aag atg tca gaa ata atg att gat gct gaa gga agg      1245
Lys Val Thr Phe Lys Met Ser Glu Ile Met Ile Asp Ala Glu Gly Arg
325                 330                 335 atc ata gat gtc ata gat aag gaa cta att caa cct ttt gag att cta      1293
Ile Ile Asp Val Ile Asp Lys Glu Leu Ile Gln Pro Phe Glu Ile Leu
340                 345                 350                 355 ttt gaa gga gtt gaa tat att gcc aga gct gga tgg act cct gag gga      1341
Phe Glu Gly Val Glu Tyr Ile Ala Arg Ala Gly Trp Thr Pro Glu Gly
            360                 365                 370 aaa tat gct tgg tcc atc cta cta gat cgc tcc cag act cgc ctg cag      1389
Lys Tyr Ala Trp Ser Ile Leu Leu Asp Arg Ser Gln Thr Arg Leu Gln
        375                 380                 385 ata gtg ttg atc tca cct gaa tta ttt atc cca gta gaa gat gat gtt      1437
Ile Val Leu Ile Ser Pro Glu Leu Phe Ile Pro Val Glu Asp Asp Val
    390                 395                 400 atg gaa agg cag aga ctc att gag tca gtg cct gat tct gtg acg cca      1485
Met Glu Arg Gln Arg Leu Ile Glu Ser Val Pro Asp Ser Val Thr Pro
405                 410                 415 cta att atc tat gaa gaa aca aca gac atc tgg ata aat atc cat gac      1533
Leu Ile Ile Tyr Glu Glu Thr Thr Asp Ile Trp Ile Asn Ile His Asp
420                 425                 430                 435 atc ttt cat gtt ttt ccc caa agt cac gaa gag gaa att gag ttt att      1581
Ile Phe His Val Phe Pro Gln Ser His Glu Glu Glu Ile Glu Phe Ile
            440                 445                 450 ttt gcc tct gaa tgc aaa aca ggt ttc cgt cat tta tac aaa att aca      1629
Phe Ala Ser Glu Cys Lys Thr Gly Phe Arg His Leu Tyr Lys Ile Thr
        455                 460                 465 tct att tta aag gaa agc aaa tat aaa cga tcc agt ggt ggg ctg cct      1677
Ser Ile Leu Lys Glu Ser Lys Tyr Lys Arg Ser Ser Gly Gly Leu Pro
    470                 475                 480 gct cca agt gat ttc aag tgt cct atc aaa gag gag ata gca att acc      1725
Ala Pro Ser Asp Phe Lys Cys Pro Ile Lys Glu Glu Ile Ala Ile Thr
485                 490                 495 agt ggt gaa tgg gaa gtt ctt ggc cgg cat gga tct aat atc caa gtt      1773
Ser Gly Glu Trp Glu Val Leu Gly Arg His Gly Ser Asn Ile Gln Val
```

-continued

| | | | | | | | | | | | | | | | | |
|---|---|---|---|---|---|---|---|---|---|---|---|---|---|---|---|---|
| 500 | | | | | 505 | | | | | 510 | | | | | 515 | |
| gat | gaa | gtc | aga | agg | ctg | gta | tat | ttt | gaa | ggc | acc | aaa | gac | tcc | cct | 1821 |
| Asp | Glu | Val | Arg | Arg | Leu | Val | Tyr | Phe | Glu | Gly | Thr | Lys | Asp | Ser | Pro | |
| | | | 520 | | | | | 525 | | | | | 530 | | | |
| tta | gag | cat | cac | ctg | tac | gta | gtc | agt | tac | gta | aat | cct | gga | gag | gtg | 1869 |
| Leu | Glu | His | His | Leu | Tyr | Val | Val | Ser | Tyr | Val | Asn | Pro | Gly | Glu | Val | |
| | | | 535 | | | | | 540 | | | | | 545 | | | |
| aca | agg | ctg | act | gac | cgt | ggc | tac | tca | cat | tct | tgc | tgc | atc | agt | cag | 1917 |
| Thr | Arg | Leu | Thr | Asp | Arg | Gly | Tyr | Ser | His | Ser | Cys | Cys | Ile | Ser | Gln | |
| | | | 550 | | | | | 555 | | | | | 560 | | | |
| cac | tgt | gac | ttc | ttt | ata | agt | aag | tat | agt | aac | cag | aag | aat | cca | cac | 1965 |
| His | Cys | Asp | Phe | Phe | Ile | Ser | Lys | Tyr | Ser | Asn | Gln | Lys | Asn | Pro | His | |
| | | 565 | | | | | 570 | | | | | 575 | | | | |
| tgt | gtg | tcc | ctt | tac | aag | cta | tca | agt | cct | gaa | gat | gac | cca | act | tgc | 2013 |
| Cys | Val | Ser | Leu | Tyr | Lys | Leu | Ser | Ser | Pro | Glu | Asp | Asp | Pro | Thr | Cys | |
| 580 | | | | | 585 | | | | | 590 | | | | | 595 | |
| aaa | aca | aag | gaa | ttt | tgg | gcc | acc | att | ttg | gat | tca | gca | ggt | cct | ctt | 2061 |
| Lys | Thr | Lys | Glu | Phe | Trp | Ala | Thr | Ile | Leu | Asp | Ser | Ala | Gly | Pro | Leu | |
| | | | | 600 | | | | | 605 | | | | | 610 | | |
| cct | gac | tat | act | cct | cca | gaa | att | ttc | tct | ttt | gaa | agt | act | act | gga | 2109 |
| Pro | Asp | Tyr | Thr | Pro | Pro | Glu | Ile | Phe | Ser | Phe | Glu | Ser | Thr | Thr | Gly | |
| | | | 615 | | | | | 620 | | | | | 625 | | | |
| ttt | aca | ttg | tat | ggg | atg | ctc | tac | aag | cct | cat | gat | cta | cag | cct | gga | 2157 |
| Phe | Thr | Leu | Tyr | Gly | Met | Leu | Tyr | Lys | Pro | His | Asp | Leu | Gln | Pro | Gly | |
| | | | 630 | | | | | 635 | | | | | 640 | | | |
| aag | aaa | tat | cct | act | gtg | ctg | ttc | ata | tat | ggt | ggt | cct | cag | gtg | cag | 2205 |
| Lys | Lys | Tyr | Pro | Thr | Val | Leu | Phe | Ile | Tyr | Gly | Gly | Pro | Gln | Val | Gln | |
| | | 645 | | | | | 650 | | | | | 655 | | | | |
| ttg | gtg | aat | aat | cgg | ttt | aaa | gga | gtc | aag | tat | ttc | cgc | ttg | aat | acc | 2253 |
| Leu | Val | Asn | Asn | Arg | Phe | Lys | Gly | Val | Lys | Tyr | Phe | Arg | Leu | Asn | Thr | |
| 660 | | | | | 665 | | | | | 670 | | | | | 675 | |
| cta | gcc | tct | cta | ggt | tat | gtg | gtt | gta | gtg | ata | gac | aac | agg | gga | tcc | 2301 |
| Leu | Ala | Ser | Leu | Gly | Tyr | Val | Val | Val | Val | Ile | Asp | Asn | Arg | Gly | Ser | |
| | | | | 680 | | | | | 685 | | | | | 690 | | |
| tgt | cac | cga | ggg | ctt | aaa | ttt | gaa | ggc | gcc | ttt | aaa | tat | aaa | atg | ggt | 2349 |
| Cys | His | Arg | Gly | Leu | Lys | Phe | Glu | Gly | Ala | Phe | Lys | Tyr | Lys | Met | Gly | |
| | | | 695 | | | | | 700 | | | | | 705 | | | |
| caa | ata | gaa | att | gac | gat | cag | gtg | gaa | gga | ctc | caa | tat | cta | gct | tct | 2397 |
| Gln | Ile | Glu | Ile | Asp | Asp | Gln | Val | Glu | Gly | Leu | Gln | Tyr | Leu | Ala | Ser | |
| | | 710 | | | | | 715 | | | | | 720 | | | | |
| cga | tat | gat | ttc | att | gac | tta | gat | cgt | gtg | ggc | atc | cac | ggc | tgg | tcc | 2445 |
| Arg | Tyr | Asp | Phe | Ile | Asp | Leu | Asp | Arg | Val | Gly | Ile | His | Gly | Trp | Ser | |
| 725 | | | | | 730 | | | | | 735 | | | | | | |
| tat | gga | gga | tac | ctc | tcc | ctg | atg | gca | tta | atg | cag | agg | tca | gat | atc | 2493 |
| Tyr | Gly | Gly | Tyr | Leu | Ser | Leu | Met | Ala | Leu | Met | Gln | Arg | Ser | Asp | Ile | |
| 740 | | | | | 745 | | | | | 750 | | | | | 755 | |
| ttc | agg | gtt | gct | att | gct | ggg | gcc | cca | gtc | act | ctg | tgg | atc | ttc | tat | 2541 |
| Phe | Arg | Val | Ala | Ile | Ala | Gly | Ala | Pro | Val | Thr | Leu | Trp | Ile | Phe | Tyr | |
| | | | | 760 | | | | | 765 | | | | | 770 | | |
| gat | aca | gga | tac | acg | gaa | cgt | tat | atg | ggt | cac | cct | gac | cag | aat | gaa | 2589 |
| Asp | Thr | Gly | Tyr | Thr | Glu | Arg | Tyr | Met | Gly | His | Pro | Asp | Gln | Asn | Glu | |
| | | | 775 | | | | | 780 | | | | | 785 | | | |
| cag | ggc | tat | tac | tta | gga | tct | gtg | gcc | atg | caa | gca | gaa | aag | ttc | ccc | 2637 |
| Gln | Gly | Tyr | Tyr | Leu | Gly | Ser | Val | Ala | Met | Gln | Ala | Glu | Lys | Phe | Pro | |
| | | | 790 | | | | | 795 | | | | | 800 | | | |
| tct | gaa | cca | aat | cgt | tta | ctg | ctc | tta | cat | ggt | ttc | ctg | gat | gag | aat | 2685 |
| Ser | Glu | Pro | Asn | Arg | Leu | Leu | Leu | Leu | His | Gly | Phe | Leu | Asp | Glu | Asn | |
| 805 | | | | | 810 | | | | | 815 | | | | | | |
| gtc | cat | ttt | gca | cat | acc | agt | ata | tta | ctg | agt | ttt | tta | gtg | agg | gct | 2733 |

```
Val His Phe Ala His Thr Ser Ile Leu Leu Ser Phe Leu Val Arg Ala
820                 825                 830                 835 gga aag cca tat gat tta cag atc tat cct cag gag aga cac agc ata    2781
Gly Lys Pro Tyr Asp Leu Gln Ile Tyr Pro Gln Glu Arg His Ser Ile
            840                 845                 850 aga gtt cct gaa tcg gga gaa cat tat gaa ctg cat ctt ttg cac tac    2829
Arg Val Pro Glu Ser Gly Glu His Tyr Glu Leu His Leu Leu His Tyr
                855                 860                 865 ctt caa gaa aac ctt gga tca cgt att gct gct cta aaa gtg ata        2874
Leu Gln Glu Asn Leu Gly Ser Arg Ile Ala Ala Leu Lys Val Ile
            870                 875                 880 taattttgac ctgtgtagaa ctctctggta tacactggct atttaaccaa atgaggaggt   2934
ttaatcaaca gaaacacag aattgatcat cacattttga tacctgccat gtaacatcta   2994
ctcctgaaaa taaatgtggt gccatgcagg ggtctacggt ttgtggtagt aatctaatac   3054 cttaaccca catgctcaaa atcaaatgat acatattcct gagagaccca gcaataccat   3114
aagaattact aaaaaaaaaa aaaaaaaaa                                    3143
```

<210> SEQ ID NO 20
<211> LENGTH: 882
<212> TYPE: PRT
<213> ORGANISM: Homo sapiens

<400> SEQUENCE: 20

```
Met Ala Ala Met Glu Thr Glu Gln Leu Gly Val Glu Ile Phe Glu
1               5                   10                  15

Thr Ala Asp Cys Glu Glu Asn Ile Glu Ser Gln Asp Arg Pro Lys Leu
                20                  25                  30

Glu Pro Phe Tyr Val Glu Arg Tyr Ser Trp Ser Gln Leu Lys Lys Leu
            35                  40                  45

Leu Ala Asp Thr Arg Lys Tyr His Gly Tyr Met Met Ala Lys Ala Pro
50                  55                  60

His Asp Phe Met Phe Val Lys Arg Asn Asp Pro Asp Gly Pro His Ser
65                  70                  75                  80

Asp Arg Ile Tyr Tyr Leu Ala Met Ser Gly Asn Arg Glu Asn Thr
                85                  90                  95

Leu Phe Tyr Ser Glu Ile Pro Lys Thr Ile Asn Arg Ala Ala Val Leu
            100                 105                 110

Met Leu Ser Trp Lys Pro Leu Leu Asp Leu Phe Gln Ala Thr Leu Asp
        115                 120                 125

Tyr Gly Met Tyr Ser Arg Glu Glu Leu Leu Arg Glu Arg Lys Arg
130                 135                 140

Ile Gly Thr Val Gly Ile Ala Ser Tyr Asp Tyr His Gln Gly Ser Gly
145                 150                 155                 160

Thr Phe Leu Phe Gln Ala Gly Ser Gly Ile Tyr His Val Lys Asp Gly
                165                 170                 175

Gly Pro Gln Gly Phe Thr Gln Pro Leu Arg Pro Asn Leu Val Glu
            180                 185                 190

Thr Ser Cys Pro Asn Ile Arg Met Asp Pro Lys Leu Cys Pro Ala Asp
        195                 200                 205

Pro Asp Trp Ile Ala Phe Ile His Ser Asn Asp Ile Trp Ile Ser Asn
    210                 215                 220

Ile Val Thr Arg Glu Glu Arg Leu Thr Tyr Val His Asn Glu Leu
225                 230                 235                 240

Ala Asn Met Glu Glu Asp Ala Arg Ser Ala Gly Val Ala Thr Phe Val
```

```
                    245                 250                 255
Leu Gln Glu Glu Phe Asp Arg Tyr Ser Gly Tyr Trp Trp Cys Pro Lys
                260                 265                 270
Ala Glu Thr Thr Pro Ser Gly Gly Lys Ile Leu Arg Ile Leu Tyr Glu
            275                 280                 285
Glu Asn Asp Glu Ser Glu Val Glu Ile Ile His Val Thr Ser Pro Met
        290                 295                 300
Leu Glu Thr Arg Arg Ala Asp Ser Phe Arg Tyr Pro Lys Thr Gly Thr
305                 310                 315                 320
Ala Asn Pro Lys Val Thr Phe Lys Met Ser Glu Ile Met Ile Asp Ala
                325                 330                 335
Glu Gly Arg Ile Ile Asp Val Ile Asp Lys Glu Leu Ile Gln Pro Phe
                340                 345                 350
Glu Ile Leu Phe Glu Gly Val Glu Tyr Ile Ala Arg Ala Gly Trp Thr
            355                 360                 365
Pro Glu Gly Lys Tyr Ala Trp Ser Ile Leu Leu Asp Arg Ser Gln Thr
        370                 375                 380
Arg Leu Gln Ile Val Leu Ile Ser Pro Glu Leu Phe Ile Pro Val Glu
385                 390                 395                 400
Asp Asp Val Met Glu Arg Gln Arg Leu Ile Glu Ser Val Pro Asp Ser
                405                 410                 415
Val Thr Pro Leu Ile Ile Tyr Glu Glu Thr Thr Asp Ile Trp Ile Asn
                420                 425                 430
Ile His Asp Ile Phe His Val Phe Pro Gln Ser His Glu Glu Glu Ile
            435                 440                 445
Glu Phe Ile Phe Ala Ser Glu Cys Lys Thr Gly Phe Arg His Leu Tyr
        450                 455                 460
Lys Ile Thr Ser Ile Leu Lys Glu Ser Lys Tyr Lys Arg Ser Ser Gly
465                 470                 475                 480
Gly Leu Pro Ala Pro Ser Asp Phe Lys Cys Pro Ile Lys Glu Glu Ile
                485                 490                 495
Ala Ile Thr Ser Gly Glu Trp Glu Val Leu Gly Arg His Gly Ser Asn
                500                 505                 510
Ile Gln Val Asp Glu Val Arg Arg Leu Val Tyr Phe Glu Gly Thr Lys
            515                 520                 525
Asp Ser Pro Leu Glu His His Leu Tyr Val Val Ser Tyr Val Asn Pro
        530                 535                 540
Gly Glu Val Thr Arg Leu Thr Asp Arg Gly Tyr Ser His Ser Cys Cys
545                 550                 555                 560
Ile Ser Gln His Cys Asp Phe Phe Ile Ser Lys Tyr Ser Asn Gln Lys
                565                 570                 575
Asn Pro His Cys Val Ser Leu Tyr Lys Leu Ser Ser Pro Glu Asp Asp
                580                 585                 590
Pro Thr Cys Lys Thr Lys Glu Phe Trp Ala Thr Ile Leu Asp Ser Ala
            595                 600                 605
Gly Pro Leu Pro Asp Tyr Thr Pro Pro Glu Ile Phe Ser Phe Glu Ser
        610                 615                 620
Thr Thr Gly Phe Thr Leu Tyr Gly Met Leu Tyr Lys Pro His Asp Leu
625                 630                 635                 640
Gln Pro Gly Lys Lys Tyr Pro Thr Val Leu Phe Ile Tyr Gly Gly Pro
                645                 650                 655
Gln Val Gln Leu Val Asn Asn Arg Phe Lys Gly Val Lys Tyr Phe Arg
                660                 665                 670
```

| | | | | | | | | | | | | |
|---|---|---|---|---|---|---|---|---|---|---|---|---|
|Leu|Asn|Thr|Leu|Ala|Ser|Leu|Gly|Tyr|Val|Val|Val|Ile|Asp|Asn|
| | |675| | | |680| | | |685| | |

Arg Gly Ser Cys His Arg Gly Leu Lys Phe Glu Gly Ala Phe Lys Tyr
        690                 695                 700

Lys Met Gly Gln Ile Glu Ile Asp Asp Gln Val Glu Gly Leu Gln Tyr
705                 710                 715                 720

Leu Ala Ser Arg Tyr Asp Phe Ile Asp Leu Asp Arg Val Gly Ile His
                725                 730                 735

Gly Trp Ser Tyr Gly Gly Tyr Leu Ser Leu Met Ala Leu Met Gln Arg
            740                 745                 750

Ser Asp Ile Phe Arg Val Ala Ile Ala Gly Ala Pro Val Thr Leu Trp
        755                 760                 765

Ile Phe Tyr Asp Thr Gly Tyr Thr Glu Arg Tyr Met Gly His Pro Asp
    770                 775                 780

Gln Asn Glu Gln Gly Tyr Tyr Leu Gly Ser Val Ala Met Gln Ala Glu
785                 790                 795                 800

Lys Phe Pro Ser Glu Pro Asn Arg Leu Leu Leu Leu His Gly Phe Leu
                805                 810                 815

Asp Glu Asn Val His Phe Ala His Thr Ser Ile Leu Leu Ser Phe Leu
            820                 825                 830

Val Arg Ala Gly Lys Pro Tyr Asp Leu Gln Ile Tyr Pro Gln Glu Arg
        835                 840                 845

His Ser Ile Arg Val Pro Glu Ser Gly Glu His Tyr Glu Leu His Leu
    850                 855                 860

Leu His Tyr Leu Gln Glu Asn Leu Gly Ser Arg Ile Ala Ala Leu Lys
865                 870                 875                 880

Val Ile

<210> SEQ ID NO 21
<211> LENGTH: 2649
<212> TYPE: DNA
<213> ORGANISM: Homo sapiens

<400> SEQUENCE: 21

```
atggcagcag caatggaaac agaacagctg ggtgttgaga tatttgaaac tgcggactgt     60
gaggagaata ttgaatcaca ggatcggcct aaattggagc ctttttatgt tgagcggtat    120
tcctggagtc agcttaaaaa gctgcttgcc gataccagaa aatatcatgg ctacatgatg    180
gctaaggcac acatgatttt catgtttgtg aagaggaatg atccagatgg acctcattca    240
gacagaatct attaccttgc catgtctggt gagaacagag aaaatacact gttttattct    300
gaaattccca aaactatcaa tagagcagca gtcttaatgc tctcttggaa gcctcttttg    360
gatcttttc aggcaacact ggactatgga atgtattctc gagaagaaga actattaaga    420
gaaagaaaac gcattggaac agtcggaatt gcttcttacg attatcacca aggaagtgga    480
acatttctgt ttcaagccgg tagtggaatt tatcacgtaa agatggaggg ccacaagga    540
tttacgcaac aacctttaag gcccaatcta gtggaaacta gttgtcccaa catacggatg    600
gatccaaaat tatgccctgc tgatccagac tggattgctt ttatacatag caacgatatt    660
tggatatcta acatcgtaac cagagaagaa aggagactca cttatgtgca caatgagcta    720
gccaacatgg aagaagatgc cagatcagct ggagtcgcta cctttgttct ccaagaagaa    780
tttgatagat attctggcta ttggtggtgt ccaaaagctg aaacaactcc cagtggtggt    840
aaaattctta gaattctata tgaagaaaat gatgaatctg aggtggaaat tattcatgtt    900
```

-continued

```
acatcccta tgttggaaac aaggagggca gattcattcc gttatcctaa aacaggtaca      960
gcaaatccta aagtcacttt taagatgtca gaaataatga ttgatgctga aggaaggatc     1020
atagatgtca tagataagga actaattcaa ccttttgaga ttctatttga aggagttgaa     1080
tatattgcca gagctggatg gactcctgag ggaaaatatg cttggtccat cctactagat     1140
cgctcccaga ctcgcctgca gatagtgttg atctcacctg aattatttat cccagtagaa     1200
gatgatgtta tggaaaggca gagactcatt gagtcagtgc ctgattctgt gacgccacta     1260
attatctatg aagaaacaac agacatctgg ataaatatcc atgacatctt tcatgttttt     1320
ccccaaagtc acgaagagga aattgagttt attttttgcct ctgaatgcaa aacaggtttc    1380
cgtcatttat acaaaattac atctatttta aaggaaagca aatataaacg atccagtggt     1440
gggctgcctg ctccaagtga tttcaagtgt cctatcaaag aggagatagc aattaccagt     1500
ggtgaatggg aagttcttgg ccggcatgga tctaatatcc aagttgatga agtcagaagg     1560
ctggtatatt ttgaaggcac caaagactcc cctttagagc atcacctgta cgtagtcagt     1620
tacgtaaatc ctggagaggt gacaaggctg actgaccgtg ctactcaca ttcttgctgc      1680 atcagtcagc actgtgactt ctttataagt aagtatagta accagaagaa tccacactgt     1740
gtgtcccttt acaagctatc aagtcctgaa gatgacccaa cttgcaaaac aaaggaattt     1800
tgggccacca ttttggattc agcaggtcct cttcctgact atactcctcc agaaattttc     1860
tcttttgaaa gtactactgg atttacattg tatgggatgc tctacaagcc tcatgatcta     1920
cagcctggaa agaaatatcc tactgtgctg ttcatatatg gtggtcctca ggtgcagttg     1980
gtgaataatc ggtttaaagg agtcaagtat ttccgcttga ataccctagc ctctctaggt     2040
tatgtggttg tagtgataga caacagggga tcctgtcacc gagggcttaa atttgaaggc     2100
gcctttaaat ataaaatggg tcaaatagaa attgacgatc aggtggaagg actccaatat     2160
ctagcttctc gatatgattt cattgactta gatcgtgtgg gcatccacgg ctggtcctat     2220
ggaggatacc tctccctgat ggcattaatg cagaggtcag atatcttcag ggttgctatt     2280 gctgggccc cagtcactct gtggatcttc tatgatacag gatacacgga acgttatatg      2340
ggtcaccctg accagaatga acagggctat tacttaggat ctgtggccat gcaagcagaa     2400 aagttccct ctgaaccaaa tcgtttactg ctcttacatg gtttcctgga tgagaatgtc      2460 catttttgcac ataccagtat attactgagt tttttagtga gggctggaaa gccatatgat    2520
ttacagatct atcctcagga gagacacagc ataagagttc ctgaatcggg agaacattat     2580
gaactgcatc ttttgcacta ccttcaagaa aaccttggat cacgtattgc tgctctaaaa     2640
gtgatataa                                                             2649
```

<210> SEQ ID NO 22
<211> LENGTH: 72
<212> TYPE: PRT
<213> ORGANISM: Artificial Sequence
<220> FEATURE:
<223> OTHER INFORMATION: consensus sequence

<400> SEQUENCE: 22

```
Val Ala Ser Leu Leu Asn His Arg Gly Gly Ile Tyr Ala Val Val Asp
 1               5                  10                  15

Ile Arg Gly Gly Gly Glu Tyr Gly Gln Lys Trp His Glu Ala Gly Thr
                20                  25                  30

Arg Arg Leu Lys Lys Asn Glu Phe Asn Asp Phe Ile Ala Ala Ala Glu
            35                  40                  45
```

```
Tyr Leu Ser Lys Leu Gly Tyr Thr Ser Pro Lys Arg Ile Ala Ile Phe
    50                  55                  60

Gly Gly Ser Asn Gly Gly Leu Leu
 65              70
```

```
<210> SEQ ID NO 23
<211> LENGTH: 710
<212> TYPE: PRT
<213> ORGANISM: Artificial Sequence
<220> FEATURE:
<223> OTHER INFORMATION: consensus sequence

<400> SEQUENCE: 23

Met Leu Ser Phe Gln Tyr Pro Asp Val Tyr Arg Asp Glu Thr Ala Val
  1               5                  10                  15

Gln Asp Tyr His Gly His Lys Ile Cys Asp Pro Tyr Ala Trp Leu Glu
             20                  25                  30

Asp Pro Asp Ser Glu Gln Thr Lys Ala Phe Val Glu Ala Gln Asn Lys
         35                  40                  45

Ile Thr Val Pro Phe Leu Glu Gln Cys Pro Ile Arg Gly Leu Tyr Lys
 50                  55                  60

Glu Arg Met Thr Glu Leu Tyr Asp Tyr Pro Lys Tyr Ser Cys His Phe
 65                  70                  75                  80

Lys Lys Gly Lys Arg Tyr Phe Tyr Phe Tyr Asn Thr Gly Leu Gln Asn
                 85                  90                  95

Gln Arg Val Leu Tyr Val Gln Asp Ser Leu Glu Gly Glu Ala Arg Val
            100                 105                 110

Phe Leu Asp Pro Asn Ile Leu Ser Asp Asp Gly Thr Val Ala Leu Arg
        115                 120                 125

Gly Tyr Ala Phe Ser Glu Asp Gly Glu Tyr Phe Ala Tyr Gly Leu Ser
130                 135                 140

Ala Ser Gly Ser Asp Trp Val Thr Ile Lys Phe Met Lys Val Asp Gly
145                 150                 155                 160

Ala Lys Glu Leu Pro Asp Val Leu Glu Arg Val Lys Phe Ser Cys Met
                165                 170                 175

Ala Trp Thr His Asp Gly Lys Gly Met Phe Tyr Asn Ser Tyr Pro Gln
            180                 185                 190

Gln Asp Gly Lys Ser Asp Gly Thr Glu Thr Ser Thr Asn Leu His Gln
        195                 200                 205

Lys Leu Tyr Tyr His Val Leu Gly Thr Asp Gln Ser Glu Asp Ile Leu
    210                 215                 220

Cys Ala Glu Phe Pro Asp Glu Pro Lys Trp Met Gly Ala Glu Leu
225                 230                 235                 240

Ser Asp Asp Gly Arg Tyr Val Leu Leu Ser Ile Arg Glu Gly Cys Asp
                245                 250                 255

Pro Val Asn Arg Leu Trp Tyr Cys Asp Leu Gln Gln Glu Ser Ser Gly
            260                 265                 270

Ile Ala Gly Ile Leu Lys Trp Val Lys Leu Ile Asp Asn Phe Glu Gly
        275                 280                 285

Glu Tyr Asp Tyr Val Thr Asn Glu Gly Thr Val Phe Thr Phe Lys Thr
    290                 295                 300

Asn Arg Gln Ser Pro Asn Tyr Arg Val Ile Asn Ile Asp Phe Trp Asp
305                 310                 315                 320

Pro Glu Glu Ser Lys Trp Lys Val Leu Val Pro Glu His Glu Lys Asp
                325                 330                 335
```

-continued

Val Leu Glu Trp Ile Ala Cys Val Arg Ser Asn Phe Leu Val Leu Cys
            340                 345                 350

Tyr Leu His Asp Val Lys Asn Ile Leu Gln Leu His Asp Leu Thr Thr
        355                 360                 365

Gly Ala Leu Leu Lys Thr Phe Pro Leu Asp Val Gly Ser Ile Val Gly
    370                 375                 380

Tyr Ser Gly Gln Lys Lys Asp Thr Glu Ile Phe Tyr Gln Phe Thr Ser
385                 390                 395                 400

Phe Leu Ser Pro Gly Ile Ile Tyr His Cys Asp Leu Thr Lys Glu Glu
                405                 410                 415

Leu Glu Pro Arg Val Phe Arg Glu Val Thr Val Lys Gly Ile Asp Ala
            420                 425                 430

Ser Asp Tyr Gln Thr Val Gln Ile Phe Tyr Pro Ser Lys Asp Gly Thr
        435                 440                 445

Lys Ile Pro Met Phe Ile Val His Lys Gly Ile Lys Leu Asp Gly
    450                 455                 460

Ser His Pro Ala Phe Leu Tyr Gly Tyr Gly Gly Phe Asn Ile Ser Ile
465                 470                 475                 480

Thr Pro Asn Tyr Ser Val Ser Arg Leu Ile Phe Val Arg His Met Gly
                485                 490                 495

Gly Ile Leu Ala Val Ala Asn Ile Arg Gly Gly Gly Glu Tyr Gly Glu
            500                 505                 510

Thr Trp His Lys Gly Ile Leu Ala Asn Lys Gln Asn Cys Phe Asp
        515                 520                 525

Asp Phe Gln Cys Ala Ala Glu Tyr Leu Ile Lys Glu Gly Tyr Thr Ser
    530                 535                 540

Pro Lys Arg Leu Thr Ile Asn Gly Gly Ser Asn Gly Gly Leu Leu Val
545                 550                 555                 560

Ala Ala Cys Ala Asn Gln Arg Pro Asp Leu Phe Gly Cys Val Ile Ala
                565                 570                 575

Gln Val Gly Val Met Asp Met Leu Lys Phe His Lys Tyr Thr Ile Gly
            580                 585                 590

His Ala Trp Thr Thr Asp Tyr Gly Cys Ser Asp Ser Lys Gln His Phe
        595                 600                 605

Glu Trp Leu Val Lys Tyr Ser Pro Leu His Asn Val Lys Leu Pro Glu
    610                 615                 620

Ala Asp Asp Ile Gln Tyr Pro Ser Met Leu Leu Thr Ala Asp His
625                 630                 635                 640

Asp Asp Arg Val Val Pro Leu His Ser Leu Lys Phe Ile Ala Thr Leu
                645                 650                 655

Gln Tyr Ile Val Gly Arg Ser Arg Lys Gln Ser Asn Pro Leu Leu Ile
            660                 665                 670

His Val Asp Thr Lys Ala Gly His Gly Ala Gly Lys Pro Thr Ala Lys
        675                 680                 685

Val Ile Glu Glu Val Ser Asp Met Phe Ala Phe Ile Ala Arg Cys Leu
    690                 695                 700

Asn Val Asp Trp Ile Pro
705                 710

<210> SEQ ID NO 24
<211> LENGTH: 2219
<212> TYPE: DNA
<213> ORGANISM: Homo sapiens
<220> FEATURE:

-continued

```
<221> NAME/KEY: CDS
<222> LOCATION: (103)...(1758)
<220> FEATURE:
<221> NAME/KEY: misc_feature
<222> LOCATION: (1)...(2219)
<223> OTHER INFORMATION: n = A,T,C or G

<400> SEQUENCE: 24
gaagtgttac ttntgctcta aaagctgcgg aattctaata cgactcacta tagggagtcg      60
acccacgcgt ccgagccgga gcactgagtg gcctggagca gc atg agg cag agc       114
                                                 Met Arg Gln Ser
                                                  1 tgg aga cca gag ctg ctt att gtg gga gct gtg gtc gtg ata gag ggt      162
Trp Arg Pro Glu Leu Leu Ile Val Gly Ala Val Val Val Ile Glu Gly
  5              10                  15                  20 ctt caa gca gct cag cgt gca tgc ggg cag cgt ggc cct ggc cct cca      210
Leu Gln Ala Ala Gln Arg Ala Cys Gly Gln Arg Gly Pro Gly Pro Pro
             25                  30                  35 gag ccc cag gaa ggc aac aca tta cct ggt gaa tgg ccc tgg cag gcc      258
Glu Pro Gln Glu Gly Asn Thr Leu Pro Gly Glu Trp Pro Trp Gln Ala
         40                  45                  50 agt gtg agg cga cag ggt gta cac atc tgc agt ggc tcc ttg gtg gca      306
Ser Val Arg Arg Gln Gly Val His Ile Cys Ser Gly Ser Leu Val Ala
     55                  60                  65 gac act tgg gtc ctc aca gct gct cac tgc ttt gaa aag atg gcc aca      354
Asp Thr Trp Val Leu Thr Ala Ala His Cys Phe Glu Lys Met Ala Thr
 70                  75                  80 gca gaa ctg agc tcc tgg tcc gtg gtc ctg ggt tct ctc aag cag gag      402
Ala Glu Leu Ser Ser Trp Ser Val Val Leu Gly Ser Leu Lys Gln Glu
 85                  90                  95                 100 ggg cag agc ccg ggg gct gag gag gtg gga gtt gct gcc ctg cag ttg      450
Gly Gln Ser Pro Gly Ala Glu Glu Val Gly Val Ala Ala Leu Gln Leu
                105                 110                 115 ccc aag gcc tat aac cac tat agc cag gga tca gat ctg gcc ctg ctc      498
Pro Lys Ala Tyr Asn His Tyr Ser Gln Gly Ser Asp Leu Ala Leu Leu
            120                 125                 130 cag ctc acc cac ccc acc gtt cag aca acc ctc tgc ttg ccc caa ccc      546
Gln Leu Thr His Pro Thr Val Gln Thr Thr Leu Cys Leu Pro Gln Pro
        135                 140                 145 acc tac cac ttc ccc ttt gga gct tct tgc tgg gcc act ggc tgg gac      594
Thr Tyr His Phe Pro Phe Gly Ala Ser Cys Trp Ala Thr Gly Trp Asp
    150                 155                 160 cag aac acc agt gat gtt tcc aga acc cta cgg aat ctg cgc ctc cgt      642
Gln Asn Thr Ser Asp Val Ser Arg Thr Leu Arg Asn Leu Arg Leu Arg
165                 170                 175                 180 ctc atc agc cgc ccc act tgt aac tgt ctc tac aat cgg ttg cac cag      690
Leu Ile Ser Arg Pro Thr Cys Asn Cys Leu Tyr Asn Arg Leu His Gln
                185                 190                 195 agg ttg ctg tcc aac cca gca aga cct ggg atg ctc tgt ggg ggt gca      738
Arg Leu Leu Ser Asn Pro Ala Arg Pro Gly Met Leu Cys Gly Gly Ala
            200                 205                 210 cag cct ggg gaa cag ggg ccc tgc cag gga gat tct ggg gga cct gtg      786
Gln Pro Gly Glu Gln Gly Pro Cys Gln Gly Asp Ser Gly Gly Pro Val
        215                 220                 225 atg tgc cgt gag cct gat gga cac tgg gtc cag gtt gga atc att agt      834
Met Cys Arg Glu Pro Asp Gly His Trp Val Gln Val Gly Ile Ile Ser
    230                 235                 240 ttc aca tca aaa tgt gcc caa gag gac acc cct gtg ctg ttg act gac      882
Phe Thr Ser Lys Cys Ala Gln Glu Asp Thr Pro Val Leu Leu Thr Asp
245                 250                 255                 260
```

```
atg gca gta cac agt tca tgg ctg cag gcc cat gtt cac gag gca gct    930
Met Ala Val His Ser Ser Trp Leu Gln Ala His Val His Glu Ala Ala
            265                 270                 275 ttc ttg gtg cag gcc cca gga gtt gtg aag atg agc gac gag aac agc    978
Phe Leu Val Gln Ala Pro Gly Val Val Lys Met Ser Asp Glu Asn Ser
        280                 285                 290 tgt gta gca tgt ggc tcc ttg agg agt gca gga ccc cag gca gga gcg    1026
Cys Val Ala Cys Gly Ser Leu Arg Ser Ala Gly Pro Gln Ala Gly Ala
            295                 300                 305 ctc tct cag tgg ccc tgg gat gcc agg ctg aag cac cac ggg aag ctg    1074
Leu Ser Gln Trp Pro Trp Asp Ala Arg Leu Lys His His Gly Lys Leu
        310                 315                 320 gct tgt ggt gga gct ctg gta tcg gag gtg gtg gtg ctg acg gct gct    1122
Ala Cys Gly Gly Ala Leu Val Ser Glu Val Val Val Leu Thr Ala Ala
325                 330                 335                 340 cac tgc ttt atc ggg cgc caa acc cta gag gaa tgg agc gta gga ctg    1170
His Cys Phe Ile Gly Arg Gln Thr Leu Glu Glu Trp Ser Val Gly Leu
                345                 350                 355 ggg gct gga cca gag gaa tgg ggc ctg aag caa ctc att ctg cac ggg    1218
Gly Ala Gly Pro Glu Glu Trp Gly Leu Lys Gln Leu Ile Leu His Gly
            360                 365                 370 gcc tac acc cac cca gaa ggc ggc tat gat gtg gcc ttc ctg ctg ctg    1266
Ala Tyr Thr His Pro Glu Gly Gly Tyr Asp Val Ala Phe Leu Leu Leu
        375                 380                 385 gct cag cct gtg aca ttg ggc cct ggc cta agg ccc ctc tgc ttg ccc    1314
Ala Gln Pro Val Thr Leu Gly Pro Gly Leu Arg Pro Leu Cys Leu Pro
        390                 395                 400 tat gct gac cac cac ctg cct gat ggt gaa cat ggc tgg gtt ctt ggg    1362
Tyr Ala Asp His His Leu Pro Asp Gly Glu His Gly Trp Val Leu Gly
405                 410                 415                 420 ctg acc caa aaa gca ggc atc aac tac ccc cag aca gta cct gtg aca    1410
Leu Thr Gln Lys Ala Gly Ile Asn Tyr Pro Gln Thr Val Pro Val Thr
                425                 430                 435 gtc ctg ggg ccg atg gcc tgt agc aga cag cat gca gct cct ggg ggc    1458
Val Leu Gly Pro Met Ala Cys Ser Arg Gln His Ala Ala Pro Gly Gly
            440                 445                 450 aca ggc atc ccc atc ctg cca ggg atg gta tgc acc act gtc gtg ggt    1506
Thr Gly Ile Pro Ile Leu Pro Gly Met Val Cys Thr Thr Val Val Gly
        455                 460                 465 gag ccc cct cac tgt gag ggc ctc tct ggg gcg cca ctt gta cat gag    1554
Glu Pro Pro His Cys Glu Gly Leu Ser Gly Ala Pro Leu Val His Glu
        470                 475                 480 atc agg ggc aca tgg ttc ctg gtt gga ctg cac agc ttt gga gac acc    1602
Ile Arg Gly Thr Trp Phe Leu Val Gly Leu His Ser Phe Gly Asp Thr
485                 490                 495                 500 tgt caa agc tct gca aag cct gca gtt ttt gca gca ctc tct gcc tac    1650
Cys Gln Ser Ser Ala Lys Pro Ala Val Phe Ala Ala Leu Ser Ala Tyr
                505                 510                 515 gag gac tgg atc agc aat cta gac tgg cag gtc tac ttc gct gag gag    1698
Glu Asp Trp Ile Ser Asn Leu Asp Trp Gln Val Tyr Phe Ala Glu Glu
            520                 525                 530 cca gag cct gag gct gag act gga agc tgc ttg gtc aac tcg agc caa    1746
Pro Glu Pro Glu Ala Glu Thr Gly Ser Cys Leu Val Asn Ser Ser Gln
        535                 540                 545 cca gcc agt tgt tgactggtga ctctagttta ctcacaggac gccagaaacg        1798
Pro Ala Ser Cys
        550 ccagacaact cccacgtcaa cacccagtty tacactcctg cccctcccct cccggtcttg    1858 tggttcccag ccctgaggca ggtccaacag ctggctggct ggctgagaat gagcctgccc    1918
```

-continued

```
agagatgctt tcatgtgtg ccatggcccc gcccccaagt tytgctttcc aacagagatg    1978
tctccagtat tccctagcca atccttcaga tataaccaca ccagtagctg ttgtgaaaaa    2038
aaaagttgtt ttttttttc cttggggtg gggggtttgg ggagcaattt ccttttttaa     2098
aacttaaatt gktacaaaat agattttaga aataagttc caaactatag taaaaggctc    2158
ccctgtccca ggcaaaaaaa aaaaaaaaaa aaaaaaaaa aaaaaaaaaa aaaaaaaag     2218 g                                                                   2219
```

<210> SEQ ID NO 25
<211> LENGTH: 552
<212> TYPE: PRT
<213> ORGANISM: Homo sapiens

<400> SEQUENCE: 25

```
Met Arg Gln Ser Trp Arg Pro Glu Leu Leu Ile Val Gly Ala Val Val
1               5                   10                  15

Val Ile Glu Gly Leu Gln Ala Ala Gln Arg Ala Cys Gly Gln Arg Gly
                20                  25                  30

Pro Gly Pro Pro Glu Pro Gln Gly Asn Thr Leu Pro Gly Glu Trp
            35                  40                  45

Pro Trp Gln Ala Ser Val Arg Arg Gln Gly Val His Ile Cys Ser Gly
        50                  55                  60

Ser Leu Val Ala Asp Thr Trp Val Leu Thr Ala Ala His Cys Phe Glu
65                  70                  75                  80

Lys Met Ala Thr Ala Glu Leu Ser Ser Trp Ser Val Val Leu Gly Ser
                85                  90                  95

Leu Lys Gln Glu Gly Gln Ser Pro Gly Ala Glu Glu Val Gly Val Ala
            100                 105                 110

Ala Leu Gln Leu Pro Lys Ala Tyr Asn His Tyr Ser Gln Gly Ser Asp
        115                 120                 125

Leu Ala Leu Leu Gln Leu Thr His Pro Thr Val Gln Thr Thr Leu Cys
130                 135                 140

Leu Pro Gln Pro Thr Tyr His Phe Pro Phe Gly Ala Ser Cys Trp Ala
145                 150                 155                 160

Thr Gly Trp Asp Gln Asn Thr Ser Asp Val Ser Arg Thr Leu Arg Asn
                165                 170                 175

Leu Arg Leu Arg Leu Ile Ser Arg Pro Thr Cys Asn Cys Leu Tyr Asn
            180                 185                 190

Arg Leu His Gln Arg Leu Leu Ser Asn Pro Ala Arg Pro Gly Met Leu
        195                 200                 205

Cys Gly Gly Ala Gln Pro Gly Glu Gln Gly Pro Cys Gln Gly Asp Ser
    210                 215                 220

Gly Gly Pro Val Met Cys Arg Glu Pro Asp Gly His Trp Val Gln Val
225                 230                 235                 240

Gly Ile Ile Ser Phe Thr Ser Lys Cys Ala Gln Glu Asp Thr Pro Val
                245                 250                 255

Leu Leu Thr Asp Met Ala Val His Ser Ser Trp Leu Gln Ala His Val
            260                 265                 270

His Glu Ala Ala Phe Leu Val Gln Ala Pro Gly Val Val Lys Met Ser
        275                 280                 285

Asp Glu Asn Ser Cys Val Ala Cys Gly Ser Leu Arg Ser Ala Gly Pro
    290                 295                 300

Gln Ala Gly Ala Leu Ser Gln Trp Pro Trp Asp Ala Arg Leu Lys His
```

```
                305                 310                 315                 320
        His Gly Lys Leu Ala Cys Gly Gly Ala Leu Val Ser Glu Val Val Val
                        325                 330                 335

Leu Thr Ala Ala His Cys Phe Ile Gly Arg Gln Thr Leu Glu Glu Trp
                        340                 345                 350

Ser Val Gly Leu Gly Ala Gly Pro Glu Glu Trp Gly Leu Lys Gln Leu
                        355                 360                 365

Ile Leu His Gly Ala Tyr Thr His Pro Glu Gly Gly Tyr Asp Val Ala
                    370                 375                 380

Phe Leu Leu Ala Gln Pro Val Thr Leu Gly Pro Gly Leu Arg Pro
        385                 390                 395                 400

Leu Cys Leu Pro Tyr Ala Asp His His Leu Pro Asp Gly Glu His Gly
                        405                 410                 415

Trp Val Leu Gly Leu Thr Gln Lys Ala Gly Ile Asn Tyr Pro Gln Thr
                        420                 425                 430

Val Pro Val Thr Val Leu Gly Pro Met Ala Cys Ser Arg Gln His Ala
                        435                 440                 445

Ala Pro Gly Gly Thr Gly Ile Pro Ile Leu Pro Gly Met Val Cys Thr
                    450                 455                 460

Thr Val Val Gly Glu Pro His Cys Glu Gly Leu Ser Gly Ala Pro
        465                 470                 475                 480

Leu Val His Glu Ile Arg Gly Thr Trp Phe Leu Val Gly Leu His Ser
                        485                 490                 495

Phe Gly Asp Thr Cys Gln Ser Ser Ala Lys Pro Ala Val Phe Ala Ala
                        500                 505                 510

Leu Ser Ala Tyr Glu Asp Trp Ile Ser Asn Leu Asp Trp Gln Val Tyr
                        515                 520                 525

Phe Ala Glu Glu Pro Glu Pro Glu Ala Glu Thr Gly Ser Cys Leu Val
                    530                 535                 540

Asn Ser Ser Gln Pro Ala Ser Cys
        545                 550

<210> SEQ ID NO 26
<211> LENGTH: 1659
<212> TYPE: DNA
<213> ORGANISM: Homo sapiens

<400> SEQUENCE: 26
atgaggcaga gctggagacc agagctgctt attgtgggag ctgtggtcgt gatagaggt      60 cttcaagcag ctcagcgtgc atgcgggcag cgtggccctg ccctccaga gccccaggaa     120 ggcaacacat tacctggtga atggccctgg caggccagtg tgaggcgaca gggtgtacac    180
atctgcagtg gctccttggt ggcagacact tgggtcctca cagctgctca ctgctttgaa    240
aagatggcca gcagaaact gagctcctgg tccgtggtcc tgggttctct caagcaggag    300
gggcagagcc cggggctga ggaggtggga gttgctgccc tgcagttgcc caaggcctat    360
aaccactata gccagggatc agatctggcc ctgctccagc tcacccaccc caccgttcag    420
acaaccctct gcttgcccca acccacctac cacttcccct ttggagcttc ttgctgggcc    480
actggctggg accagaacac cagtgatgtt ccagaaccc tacggaatct gcgcctccgt    540
ctcatcagcc gccccacttg taactgtctc tacaatcggt tgcaccagag gttgctgtcc    600
aacccagcaa gacctgggat gctctgtggg ggtgcacagc ctggggaaca ggggccctgc    660
cagggagatt ctgggggacc tgtgatgtgc cgtgagcctg atggacactg ggtccaggtt    720
```

```
ggaatcatta gtttcacatc aaaatgtgcc aagaggaca cccctgtgct gttgactgac    780
atggcagtac acagttcatg gctgcaggcc catgttcacg aggcagcttt cttggtgcag    840
gccccaggag ttgtgaagat gagcgacgag aacagctgtg tagcatgtgg ctccttgagg    900
agtgcaggac cccaggcagg agcgctctct cagtggccct gggatgccag gctgaagcac    960
cacgggaagc tggcttgtgg tggagctctg gtatcggagg tggtggtgct gacggctgct   1020
cactgcttta tcgggcgcca aaccctagag gaatggagcg taggactggg ggctggacca   1080
gaggaatggg gcctgaagca actcattctg cacggggcct acacccaccc agaaggcggc   1140
tatgatgtgg ccttcctgct gctggctcag cctgtgacat tgggccctgg cctaaggccc   1200
ctctgcttgc cctatgctga ccaccacctg cctgatggtg aacatggctg ggttcttggg   1260
ctgacccaaa aagcaggcat caactacccc cagacagtac ctgtgacagt cctggggccg   1320
atggcctgta gcagacagca tgcagctcct gggggcacag gcatccccat cctgccaggg   1380
atggtatgca ccactgtcgt gggtgagccc cctcactgtg agggcctctc tggggcgcca   1440
cttgtacatg agatcagggg cacatggttc ctggttggac tgcacagctt tggagacacc   1500
tgtcaaagct ctgcaaagcc tgcagttttt gcagcactct ctgcctacga ggactggatc   1560
agcaatctag actggcaggt ctacttcgct gaggagccag agcctgaggc tgagactgga   1620
agctgcttgg tcaactcgag ccaaccagcc agttgttga                          1659
```

<210> SEQ ID NO 27
<211> LENGTH: 251
<212> TYPE: PRT
<213> ORGANISM: Artificial Sequence
<220> FEATURE:
<223> OTHER INFORMATION: consensus sequence

<400> SEQUENCE: 27

Pro Gly Ser Phe Gly Ser Pro Trp Gln Val Ser Leu Gln Val Arg Ser
1               5                   10                  15
Gly Gly Gly Ser Arg Lys His Phe Cys Gly Gly Ser Leu Ile Ser Glu
            20                  25                  30
Asn Trp Val Leu Thr Ala Ala His Cys Val Ser Gly Ala Ala Ser Ala
        35                  40                  45
Pro Ala Ser Ser Val Arg Val Ser Leu Ser Val Arg Leu Gly Glu His
    50                  55                  60
Asn Leu Ser Leu Thr Glu Gly Thr Glu Gln Lys Phe Asp Val Lys Lys
65                  70                  75                  80
Thr Ile Ile Val His Pro Asn Tyr Asn Pro Asp Thr Leu Asp Asn Gly
                85                  90                  95
Ala Tyr Asp Asn Asp Ile Ala Leu Leu Lys Leu Lys Ser Pro Gly Val
            100                 105                 110
Thr Leu Gly Asp Thr Val Arg Pro Ile Cys Leu Pro Ser Ala Ser Ser
        115                 120                 125
Asp Leu Pro Val Gly Thr Thr Cys Thr Val Ser Gly Trp Gly Arg Arg
    130                 135                 140
Pro Thr Lys Asn Leu Gly Leu Ser Asp Thr Leu Gln Glu Val Val Val
145                 150                 155                 160
Pro Val Val Ser Arg Glu Thr Cys Arg Ser Ala Tyr Glu Tyr Gly Gly
                165                 170                 175
Thr Asp Asp Lys Val Glu Phe Val Thr Asp Asn Met Ile Cys Ala Gly
            180                 185                 190
Ala Leu Gly Gly Lys Asp Ala Cys Gln Gly Asp Ser Gly Gly Pro Leu

-continued

```
                195                 200                 205
Val Cys Ser Asp Gly Asn Arg Asp Gly Arg Trp Glu Leu Val Gly Ile
    210                 215                 220

Val Ser Trp Gly Ser Tyr Gly Cys Ala Arg Gly Asn Lys Pro Gly Val
225                 230                 235                 240

Tyr Thr Arg Val Ser Ser Tyr Leu Asp Trp Ile
                245                 250

<210> SEQ ID NO 28
<211> LENGTH: 249
<212> TYPE: PRT
<213> ORGANISM: Artificial Sequence
<220> FEATURE:
<223> OTHER INFORMATION: consensus sequence

<400> SEQUENCE: 28

Ser Phe Gly Ser Pro Trp Gln Val Ser Leu Gln Val Arg Ser Gly Gly
1               5                   10                  15

Gly Ser Arg Lys His Phe Cys Gly Gly Ser Leu Ile Ser Glu Asn Trp
                20                  25                  30

Val Leu Thr Ala Ala His Cys Val Ser Gly Ala Ala Ser Ala Pro Ala
            35                  40                  45

Ser Ser Val Arg Val Ser Leu Ser Val Arg Leu Gly Glu His Asn Leu
        50                  55                  60

Ser Leu Thr Glu Gly Thr Glu Gln Lys Phe Asp Val Lys Lys Thr Ile
65                  70                  75                  80

Ile Val His Pro Asn Tyr Asn Pro Asp Thr Leu Asp Asn Gly Ala Tyr
                85                  90                  95

Asp Asn Asp Ile Ala Leu Leu Lys Leu Lys Ser Pro Gly Val Thr Leu
            100                 105                 110

Gly Asp Thr Val Arg Pro Ile Cys Leu Pro Ser Ala Ser Ser Asp Leu
        115                 120                 125

Pro Val Gly Thr Thr Cys Thr Val Ser Gly Trp Gly Arg Arg Pro Thr
130                 135                 140

Lys Asn Leu Gly Leu Ser Asp Thr Leu Gln Glu Val Val Val Pro Val
145                 150                 155                 160

Val Ser Arg Glu Thr Cys Arg Ser Ala Tyr Glu Tyr Gly Gly Thr Asp
                165                 170                 175

Asp Lys Val Glu Phe Val Thr Asp Asn Met Ile Cys Ala Gly Ala Leu
            180                 185                 190

Gly Gly Lys Asp Ala Cys Gln Gly Asp Ser Gly Gly Pro Leu Val Cys
        195                 200                 205

Ser Asp Gly Asn Arg Asp Gly Arg Trp Glu Leu Val Gly Ile Val Ser
    210                 215                 220

Trp Gly Ser Tyr Gly Cys Ala Arg Gly Asn Lys Pro Gly Val Tyr Thr
225                 230                 235                 240

Arg Val Ser Ser Tyr Leu Asp Trp Ile
                245

<210> SEQ ID NO 29
<211> LENGTH: 226
<212> TYPE: PRT
<213> ORGANISM: Artificial Sequence
<220> FEATURE:
<223> OTHER INFORMATION: consensus sequence

<400> SEQUENCE: 29
```

-continued

```
Arg Ile Val Gly Gly Ser Glu Ala Lys Ile Gly Ser Phe Pro Trp Gln
 1               5                  10                  15

Val Ser Leu Gln Cys Gly Gly Ser Leu Ile Ser Pro Arg Trp Val Leu
                20                  25                  30

Thr Ala Ala His Cys Arg Val Arg Leu Gly Ser His Asp Leu Ser Ser
            35                  40                  45

Gly Glu Glu Thr Glu Gly Pro Arg Leu Asp Ser Pro Gly Gly Gln
50                  55                  60

Val Ile Lys Val Ser Lys Ile Ile Glu Val His Pro Asn Tyr Asn Asn
65                  70                  75                  80

Asp Ile Ala Leu Leu Lys Leu Lys Glu Pro Val Thr Leu Ser Asp Ser
                85                  90                  95

Asn Thr Val Arg Pro Ile Cys Leu Pro Ser Ser Asn Glu Ile Lys Thr
                100                 105                 110

Ser Glu Gly Asn Thr Val Pro Ala Gly Thr Thr Cys Thr Val Ser Gly
                115                 120                 125

Trp Gly Arg Thr Ser Glu Gly Pro Glu Glu Ser Gly Gly Ser Leu
                130                 135             140

Pro Asp Val Leu Gln Glu Val Asn Val Pro Ile Val Ser Asn Glu Thr
145                 150                 155                 160

Cys Arg Met Leu Cys Ala Gly Tyr Leu Glu Gly Gly Asn Thr Pro Gly
                165                 170                 175

Gly Lys Asp Ala Cys Gln Gly Asp Ser Gly Gly Pro Leu Val Cys Val
            180                 185                 190

Leu Val Gly Ile Val Ser Trp Gly Ser Ser Leu Tyr Gly Cys Ala
                195                 200                 205

Arg Pro Asn Lys Pro Gly Val Tyr Thr Arg Val Ser Ser Tyr Leu Asp
            210                 215                 220

Trp Ile
225
```

```
<210> SEQ ID NO 30
<211> LENGTH: 5
<212> TYPE: PRT
<213> ORGANISM: Artificial Sequence
<220> FEATURE:
<223> OTHER INFORMATION: activation and cleavage site

<400> SEQUENCE: 30

Arg Ile Val Gly Gly
 1               5

<210> SEQ ID NO 31
<211> LENGTH: 6
<212> TYPE: PRT
<213> ORGANISM: Homo sapiens

<400> SEQUENCE: 31

Leu Thr Ala Ala His Cys
 1               5

<210> SEQ ID NO 32
<211> LENGTH: 5
<212> TYPE: PRT
<213> ORGANISM: Homo sapiens

<400> SEQUENCE: 32

Gly Asp Ser Gly Gly
 1               5
```

-continued

```
<210> SEQ ID NO 33
<211> LENGTH: 957
<212> TYPE: DNA
<213> ORGANISM: Homo sapiens
<220> FEATURE:
<221> NAME/KEY: CDS
<222> LOCATION: (136)...(858)

<400> SEQUENCE: 33
atttggccct cgaggccaag aattcggcac gaggcaaaaa ggagaccaga caggaggcgt        60
ctgtagagat atcatgaact tcaacttagc tttgttttcc agagactgga gctaaactgg       120
gctttcaaca tcatc atg aag ttt atc ctc ctc tgg gcc ctc ttg aat ctg        171
                Met Lys Phe Ile Leu Leu Trp Ala Leu Leu Asn Leu
                 1               5                  10 act gtt gct ttg gcc ttt aat cca gat tac aca gtc agc tcc act ccc         219
Thr Val Ala Leu Ala Phe Asn Pro Asp Tyr Thr Val Ser Ser Thr Pro
         15                  20                  25 cct tac ttg gtc tat ttg aaa tct gac tac ttg ccc tgc gct gga gtc         267
Pro Tyr Leu Val Tyr Leu Lys Ser Asp Tyr Leu Pro Cys Ala Gly Val
     30                  35                  40 ctg atc cac ccg ctt tgg gtg atc aca gct gca cac tgc aat tta cca         315
Leu Ile His Pro Leu Trp Val Ile Thr Ala Ala His Cys Asn Leu Pro
 45                  50                  55                  60 aag ctt cgg gtg ata ttg ggg gtt aca atc cca gca gac tct aat gaa         363
Lys Leu Arg Val Ile Leu Gly Val Thr Ile Pro Ala Asp Ser Asn Glu
                 65                  70                  75 aag cat ctg caa gtg att ggc tat gag aag atg att cat cat cca cac         411
Lys His Leu Gln Val Ile Gly Tyr Glu Lys Met Ile His His Pro His
             80                  85                  90 ttc tca gtc act tct att gat cat gac atc atg cta atc aag ctg aaa         459
Phe Ser Val Thr Ser Ile Asp His Asp Ile Met Leu Ile Lys Leu Lys
         95                 100                 105 aca gag gct gaa ctc aat gac tat gtg aaa tta gcc aac ctg ccc tac         507
Thr Glu Ala Glu Leu Asn Asp Tyr Val Lys Leu Ala Asn Leu Pro Tyr
    110                 115                 120 caa act atc tct gaa aat acc atg tgc tct gtc tct acc tgg agc tac         555
Gln Thr Ile Ser Glu Asn Thr Met Cys Ser Val Ser Thr Trp Ser Tyr
125                 130                 135                 140 aat gtg tgt gat atc tac aaa gag ccc gat tca ctg caa act gtg aac         603
Asn Val Cys Asp Ile Tyr Lys Glu Pro Asp Ser Leu Gln Thr Val Asn
                145                 150                 155 atc tct gta atc tcc aag cct cag tgt cgc gat gcc tat aaa acc tac         651
Ile Ser Val Ile Ser Lys Pro Gln Cys Arg Asp Ala Tyr Lys Thr Tyr
            160                 165                 170 aac atc acg gaa aat atg ctg tgt gtg ggc att gtg cca gga agg agg         699
Asn Ile Thr Glu Asn Met Leu Cys Val Gly Ile Val Pro Gly Arg Arg
        175                 180                 185 cag ccc tgc aag gaa gtt tct gct gcc ccg gca atc tgc aat ggg atg         747
Gln Pro Cys Lys Glu Val Ser Ala Ala Pro Ala Ile Cys Asn Gly Met
    190                 195                 200 ctt caa gga atc ctg tct ttt gcg gat gga tgt gtt ttg aga gcc gat         795
Leu Gln Gly Ile Leu Ser Phe Ala Asp Gly Cys Val Leu Arg Ala Asp
205                 210                 215                 220 gtt ggc atc tat gcc aaa att ttt tac tat ata ccc tgg att gaa aat         843
Val Gly Ile Tyr Ala Lys Ile Phe Tyr Tyr Ile Pro Trp Ile Glu Asn
                225                 230                 235 gta atc caa aat aac tgagctgtgg cagttgtgga ccatatgaca cagcttgtcc         898
Val Ile Gln Asn Asn
            240
```

-continued ccatcgttca cctttagaat taaatataaa ttaactcctc aaaaaaaaaa aaaaaaaaa    957

<210> SEQ ID NO 34
<211> LENGTH: 241
<212> TYPE: PRT
<213> ORGANISM: Homo sapiens

<400> SEQUENCE: 34

Met Lys Phe Ile Leu Leu Trp Ala Leu Leu Asn Leu Thr Val Ala Leu
1               5                   10                  15

Ala Phe Asn Pro Asp Tyr Thr Val Ser Ser Thr Pro Pro Tyr Leu Val
            20                  25                  30

Tyr Leu Lys Ser Asp Tyr Leu Pro Cys Ala Gly Val Leu Ile His Pro
        35                  40                  45

Leu Trp Val Ile Thr Ala Ala His Cys Asn Leu Pro Lys Leu Arg Val
50                  55                  60

Ile Leu Gly Val Thr Ile Pro Ala Asp Ser Asn Glu Lys His Leu Gln
65                  70                  75                  80

Val Ile Gly Tyr Glu Lys Met Ile His His Pro His Phe Ser Val Thr
                85                  90                  95

Ser Ile Asp His Asp Ile Met Leu Ile Lys Leu Lys Thr Glu Ala Glu
            100                 105                 110

Leu Asn Asp Tyr Val Lys Leu Ala Asn Leu Pro Tyr Gln Thr Ile Ser
        115                 120                 125

Glu Asn Thr Met Cys Ser Val Ser Thr Trp Ser Tyr Asn Val Cys Asp
130                 135                 140

Ile Tyr Lys Glu Pro Asp Ser Leu Gln Thr Val Asn Ile Ser Val Ile
145                 150                 155                 160

Ser Lys Pro Gln Cys Arg Asp Ala Tyr Lys Thr Tyr Asn Ile Thr Glu
                165                 170                 175

Asn Met Leu Cys Val Gly Ile Val Pro Gly Arg Arg Gln Pro Cys Lys
            180                 185                 190

Glu Val Ser Ala Ala Pro Ala Ile Cys Asn Gly Met Leu Gln Gly Ile
        195                 200                 205

Leu Ser Phe Ala Asp Gly Cys Val Leu Arg Ala Asp Val Gly Ile Tyr
210                 215                 220

Ala Lys Ile Phe Tyr Tyr Ile Pro Trp Ile Glu Asn Val Ile Gln Asn
225                 230                 235                 240

Asn

<210> SEQ ID NO 35
<211> LENGTH: 726
<212> TYPE: DNA
<213> ORGANISM: Homo sapiens

<400> SEQUENCE: 35
atgaagttta tcctcctctg ggccctcttg aatctgactg ttgctttggc ctttaatcca    60
gattacacag tcagctccac tccccttac ttggtctatt tgaaatctga ctacttgccc    120
tgcgctggag tcctgatcca cccgctttgg gtgatcacag ctgcacactg caatttacca    180
aagcttcggg tgatattggg ggttacaatc ccagcagact ctaatgaaaa gcatctgcaa    240
gtgattggct atgagaagat gattcatcat ccacacttct cagtcacttc tattgatcat    300
gacatcatgc taatcaagct gaaaacagag gctgaactca atgactatgt gaaattagcc    360
aacctgccct accaaactat ctctgaaaat accatgtgct ctgtctctac ctggagctac    420

```
aatgtgtgtg atatctacaa agagcccgat tcactgcaaa ctgtgaacat ctctgtaatc    480
tccaagcctc agtgtcgcga tgcctataaa acctacaaca tcacggaaaa tatgctgtgt    540
gtgggcattg tgccaggaag gaggcagccc tgcaaggaag tttctgctgc cccggcaatc    600
tgcaatggga tgcttcaagg aatcctgtct tttgcggatg gatgtgtttt gagagccgat    660
gttggcatct atgccaaaat tttttactat ataccctgga ttgaaaatgt aatccaaaat    720
aactga                                                              726
```

```
<210> SEQ ID NO 36
<211> LENGTH: 227
<212> TYPE: PRT
<213> ORGANISM: Artificial Sequence
<220> FEATURE:
<223> OTHER INFORMATION: consensus sequence

<400> SEQUENCE: 36
```

Cys Gly Gly Ser Leu Ile Ser Glu Asn Trp Val Leu Thr Ala Ala His
 1               5                  10                  15

Cys Val Ser Gly Ala Ala Ser Ala Pro Ala Ser Ser Val Arg Val Ser
            20                  25                  30

Leu Ser Val Arg Leu Gly Glu His Asn Leu Ser Leu Thr Glu Gly Thr
        35                  40                  45

Glu Gln Lys Phe Asp Val Lys Lys Thr Ile Ile Val His Pro Asn Tyr
    50                  55                  60

Asn Pro Asp Thr Leu Asp Asn Gly Ala Tyr Asp Asn Asp Ile Ala Leu
65                  70                  75                  80

Leu Lys Leu Lys Ser Pro Gly Val Thr Leu Gly Asp Thr Val Arg Pro
                85                  90                  95

Ile Cys Leu Pro Ser Ala Ser Ser Asp Leu Pro Val Gly Thr Thr Cys
            100                 105                 110

Thr Val Ser Gly Trp Gly Arg Arg Pro Thr Lys Asn Leu Gly Leu Ser
        115                 120                 125

Asp Thr Leu Gln Glu Val Val Pro Val Val Ser Arg Glu Thr Cys
    130                 135                 140

Arg Ser Ala Tyr Glu Tyr Gly Thr Asp Asp Lys Val Glu Phe Val
145                 150                 155                 160

Thr Asp Asn Met Ile Cys Ala Gly Ala Leu Gly Gly Lys Asp Ala Cys
                165                 170                 175

Gln Gly Asp Ser Gly Gly Pro Leu Val Cys Ser Asp Gly Asn Arg Asp
            180                 185                 190

Gly Arg Trp Glu Leu Val Gly Ile Val Ser Trp Gly Ser Tyr Gly Cys
        195                 200                 205

Ala Arg Gly Asn Lys Pro Gly Val Tyr Thr Arg Val Ser Ser Tyr Leu
    210                 215                 220

Asp Trp Ile
225

```
<210> SEQ ID NO 37
<211> LENGTH: 226
<212> TYPE: PRT
<213> ORGANISM: Artificial Sequence
<220> FEATURE:
<223> OTHER INFORMATION: consensus sequence

<400> SEQUENCE: 37
```

Arg Ile Val Gly Gly Ser Glu Ala Lys Ile Gly Ser Phe Pro Trp Gln

-continued

```
            1               5                  10                 15
          Val Ser Leu Gln Cys Gly Gly Ser Leu Ile Ser Pro Arg Trp Val Leu
                          20                  25                  30

Thr Ala Ala His Cys Arg Val Arg Leu Gly Ser His Asp Leu Ser Ser
                          35                  40                  45

Gly Glu Glu Thr Glu Gly Gly Pro Arg Leu Asp Ser Pro Gly Gly Gln
                          50                  55                  60

Val Ile Lys Val Ser Lys Ile Ile Glu Val His Pro Asn Tyr Asn Asn
          65                  70                  75                  80

Asp Ile Ala Leu Leu Lys Leu Lys Glu Pro Val Thr Leu Ser Asp Ser
                          85                  90                  95

Asn Thr Val Arg Pro Ile Cys Leu Pro Ser Ser Asn Glu Ile Lys Thr
                          100                 105                 110

Ser Glu Gly Asn Thr Val Pro Ala Gly Thr Thr Cys Thr Val Ser Gly
                          115                 120                 125

Trp Gly Arg Thr Ser Glu Gly Pro Glu Ser Gly Gly Ser Leu
                          130                 135                 140

Pro Asp Val Leu Gln Glu Val Asn Val Pro Ile Val Ser Asn Glu Thr
          145                 150                 155                 160

Cys Arg Met Leu Cys Ala Gly Tyr Leu Glu Gly Gly Asn Thr Pro Gly
                          165                 170                 175

Gly Lys Asp Ala Cys Gln Gly Asp Ser Gly Gly Pro Leu Val Cys Val
                          180                 185                 190

Leu Val Gly Ile Val Ser Trp Gly Ser Ser Leu Tyr Gly Cys Ala
                          195                 200                 205

Arg Pro Asn Lys Pro Gly Val Tyr Thr Arg Val Ser Ser Tyr Leu Asp
                          210                 215                 220

Trp Ile
          225

<210> SEQ ID NO 38
<211> LENGTH: 191
<212> TYPE: PRT
<213> ORGANISM: Artificial Sequence
<220> FEATURE:
<223> OTHER INFORMATION: consensus sequence

<400> SEQUENCE: 38

Ser Asn Asn Glu Glu Gly Ser Glu Gln Val Ile Ser Val Ser Lys Val
          1               5                   10                  15

Ile Val His Pro Asn Tyr Tyr Asn Ser Ser Thr Tyr Asp Asn Asp
                          20                  25                  30

Ile Ala Leu Leu Lys Leu Ser Ser Pro Val Ser Phe Thr Ser Ser Ala
                          35                  40                  45

Phe Ser Asp Asn Val Gln Pro Ile Cys Leu Pro Ser Ser Asn Glu Thr
                          50                  55                  60

Phe Pro Lys Pro Pro Gly Thr Cys Thr Val Ser Gly Trp Gly Arg
          65                  70                  75                  80

Thr Ser Ser Ser Gly Ser Ser Ser Tyr Pro Asp Thr Leu Gln Gln
                          85                  90                  95

Val Asn Ile Pro Ile Ile Ser Asn Glu Cys Lys Ser Ser Tyr Tyr
                          100                 105                 110

Ser Asn Gly Asn Lys Ser Thr Ile Thr Asp Asn Met Ile Cys Ala Gly
                          115                 120                 125

Tyr Tyr Ser Glu Gly Gly Lys Asp Ser Cys Gln Gly Asp Ser Gly Gly
```

-continued

```
            130                 135                 140
Pro Leu Val Cys Lys Asp Gln Lys Asn Gly Asn Trp Val Leu Val Gly
145                 150                 155                 160

Ile Val Ser Trp Gly Ser Ser Gly Cys Gly Cys Pro Ala Gln Pro Asn
                165                 170                 175

Lys Pro Gly Val Tyr Thr Arg Val Ser Ser Tyr Leu Asp Trp Ile
                180                 185                 190

<210> SEQ ID NO 39
<211> LENGTH: 81
<212> TYPE: PRT
<213> ORGANISM: Artificial Sequence
<220> FEATURE:
<223> OTHER INFORMATION: consensus sequence

<400> SEQUENCE: 39

Cys Gly Gly Ser Leu Ile Asn Glu Gln Trp Val Leu Thr Ala Ala His
1               5                   10                  15

Cys Phe Gln Asn Asn Gly Ser Ser Thr Ser Ser Tyr Gln Val Thr
                20                  25                  30

Leu Gly Glu His Asn Thr Ser Glu Asn Ser Asn Glu Glu Gly Ser
            35                  40                  45

Glu Gln Val Ile Ser Val Ser Lys Val Ile Val His Pro Asn Tyr Tyr
50                  55                  60

Asn Ser Ser Ser Thr Tyr Asp Asn Asp Ile Ala Leu Leu Lys Leu Ser
65                  70                  75                  80

Ser

<210> SEQ ID NO 40
<211> LENGTH: 2446
<212> TYPE: DNA
<213> ORGANISM: Homo sapiens
<220> FEATURE:
<221> NAME/KEY: CDS
<222> LOCATION: (243)...(1697)

<400> SEQUENCE: 40
ccacgcgtcc ggcgggcgcg gggtgtgtcg ggtgtcgacg gcggcgcttt gcggccggtc      60
gtgcgggtcg ggcgcgggcg ggcgcggcgg cagtggcgcg cacaggtgat tgactggcca     120
gctgcctgaa ggagcgccag gtcctccttg ctggcaggtg gcgaagccca ttggggcggc     180
ggtgcagacc gcggcggcgg ctgcggcggt ctggctcggg aggcgttcct ggggccaagg     240 cc atg gcc ccg cgg ctg cag ctg gag aag gcg gcc tgg cgc tgg gcg         287
   Met Ala Pro Arg Leu Gln Leu Glu Lys Ala Ala Trp Arg Trp Ala
   1               5                   10                  15 gag acg gtg cgg ccc gag gag gtg tcg cag gag cac atc gag acc gct         335
Glu Thr Val Arg Pro Glu Glu Val Ser Gln Glu His Ile Glu Thr Ala
                20                  25                  30 tac cgc atc tgg ctg gag ccc tgc att cgc ggc gtg tgc aga cga aac         383
Tyr Arg Ile Trp Leu Glu Pro Cys Ile Arg Gly Val Cys Arg Arg Asn
            35                  40                  45 tgc aaa gga aat ccg aat tgc ttg gtt ggt att ggt gag cat att tgg         431
Cys Lys Gly Asn Pro Asn Cys Leu Val Gly Ile Gly Glu His Ile Trp
        50                  55                  60 tta gga gaa ata gat gaa aat agt ttt cat aac atc gat gat ccc aac         479
Leu Gly Glu Ile Asp Glu Asn Ser Phe His Asn Ile Asp Asp Pro Asn
65                  70                  75 tgt gag agg aga aaa aag aac tca ttt gtg ggc ctg act aac ctt gga         527
Cys Glu Arg Arg Lys Lys Asn Ser Phe Val Gly Leu Thr Asn Leu Gly
```

```
                    -continued
      80                 85                   90                95 gcc act tgt tat gtc aac aca ttt ctt caa gtg tgg ttt ctc aac ttg      575
Ala Thr Cys Tyr Val Asn Thr Phe Leu Gln Val Trp Phe Leu Asn Leu
                    100                 105                110 gag ctt cgg cag gca ctc tac tta tgt cca agc act tgt agt gac tac      623
Glu Leu Arg Gln Ala Leu Tyr Leu Cys Pro Ser Thr Cys Ser Asp Tyr
                115                 120                 125 atg ctg gga gac ggc atc caa gaa gaa aaa gat tat gag cct caa aca      671
Met Leu Gly Asp Gly Ile Gln Glu Glu Lys Asp Tyr Glu Pro Gln Thr
            130                 135                 140 att tgt gag cat ctc cag tac ttg ttt gcc ttg ttg caa aac agt aat      719
Ile Cys Glu His Leu Gln Tyr Leu Phe Ala Leu Leu Gln Asn Ser Asn
        145                 150                 155 agg cga tac att gat cca tca gga ttt gtt aaa gcc ttg ggc ctg gac      767
Arg Arg Tyr Ile Asp Pro Ser Gly Phe Val Lys Ala Leu Gly Leu Asp
    160                 165                 170                 175 act gga caa cag cag gat gct caa gaa ttt tca aag ctc ttt atg tct      815
Thr Gly Gln Gln Gln Asp Ala Gln Glu Phe Ser Lys Leu Phe Met Ser
                    180                 185                 190 cta ttg gaa gat act ttg tct aaa caa aag aat cca gat gtg cgc aat      863
Leu Leu Glu Asp Thr Leu Ser Lys Gln Lys Asn Pro Asp Val Arg Asn
                195                 200                 205 att gtt caa cag cag ttc tgt gga gaa tat gcc tat gta act gtt tgc      911
Ile Val Gln Gln Gln Phe Cys Gly Glu Tyr Ala Tyr Val Thr Val Cys
            210                 215                 220 aac cag tgt ggc aga gag tct aag ctt ttg tca aaa ttt tat gag ctg      959
Asn Gln Cys Gly Arg Glu Ser Lys Leu Leu Ser Lys Phe Tyr Glu Leu
        225                 230                 235 gag tta aat atc caa ggc cac aaa cag tta aca gat tgt atc tcg gaa     1007
Glu Leu Asn Ile Gln Gly His Lys Gln Leu Thr Asp Cys Ile Ser Glu
240                 245                 250                 255 ttt ttg aag gaa gaa aaa tta gaa gga gac aat cgc tat ttt tgc gag     1055
Phe Leu Lys Glu Glu Lys Leu Glu Gly Asp Asn Arg Tyr Phe Cys Glu
                    260                 265                 270 aac tgt caa agc aaa cag aat gca aca aga aag att cga ctt ctt agc     1103
Asn Cys Gln Ser Lys Gln Asn Ala Thr Arg Lys Ile Arg Leu Leu Ser
                275                 280                 285 ctt cct tgc act ctg aac ttg cag cta atg cgt ttt gtc ttt gac agg     1151
Leu Pro Cys Thr Leu Asn Leu Gln Leu Met Arg Phe Val Phe Asp Arg
            290                 295                 300 caa act gga cat aag aaa aag ctg aat acc tac att ggc ttc tca gaa     1199
Gln Thr Gly His Lys Lys Lys Leu Asn Thr Tyr Ile Gly Phe Ser Glu
        305                 310                 315 att ttg gat atg gag cct tat gtg gaa cat aaa ggt ggg tcc tac gtg     1247
Ile Leu Asp Met Glu Pro Tyr Val Glu His Lys Gly Gly Ser Tyr Val
320                 325                 330                 335 tat gaa ctc agc gca gtc ctc ata cac aga gga gtg agt gct tat tct     1295
Tyr Glu Leu Ser Ala Val Leu Ile His Arg Gly Val Ser Ala Tyr Ser
                    340                 345                 350 ggc cac tac atc gcc cac gtg aaa gat cca cag tct ggt gaa tgg tat     1343
Gly His Tyr Ile Ala His Val Lys Asp Pro Gln Ser Gly Glu Trp Tyr
                355                 360                 365 aag ttt aat gat gaa gac ata gaa aag atg gag ggg aag aaa tta caa     1391
Lys Phe Asn Asp Glu Asp Ile Glu Lys Met Glu Gly Lys Lys Leu Gln
            370                 375                 380 cta ggg att gag gaa gat cta gca gaa cct tct aag tct cag aca cgt     1439
Leu Gly Ile Glu Glu Asp Leu Ala Glu Pro Ser Lys Ser Gln Thr Arg
        385                 390                 395 aaa ccc aag tgt ggc aaa gga act cat tgc tct cga aat gca tat atg     1487
```

```
Lys Pro Lys Cys Gly Lys Gly Thr His Cys Ser Arg Asn Ala Tyr Met
400                 405                 410                 415 ttg gtt tat aga ctg caa act caa gaa aag ccc aac act act gtt caa    1535
Leu Val Tyr Arg Leu Gln Thr Gln Glu Lys Pro Asn Thr Thr Val Gln
                420                 425                 430 gtt cca gcc ttt ctt caa gag ctg gta gat cgg gat aat tcc aaa ttt    1583
Val Pro Ala Phe Leu Gln Glu Leu Val Asp Arg Asp Asn Ser Lys Phe
            435                 440                 445 gag gag tgg tgt att gaa atg gct gag atg cgt aag caa agt gtg gat    1631
Glu Glu Trp Cys Ile Glu Met Ala Glu Met Arg Lys Gln Ser Val Asp
        450                 455                 460 aaa gga aaa gca aaa cac gaa gag gtt aag gag ctg tac caa agg tta    1679
Lys Gly Lys Ala Lys His Glu Glu Val Lys Glu Leu Tyr Gln Arg Leu
    465                 470                 475 cct gct gga gct ggt ctg taagatattc tgggacagca ctgttgccat           1727
Pro Ala Gly Ala Gly Leu
480             485 taagtgcctt gttttttat gttcacaaat gtatatgaag aaactttctc aaacttactc   1787
tttctaataa cccactaaag ccagcttaaa cactctaaaa gtactttgta aaccaacaat  1847
aacttgatgt gtagcattcc atattatttc attacgttgt actcctaaaa atgggaagct  1907
gttaataaat tataacattt aggtcagcac tctgcatcca tgagtattgt agatatttat  1967
attttgtgag atattaactt gtttaagaaa atccgattg gattactatg gaaaaagcaa   2027
cttgcctgtt ctgtttcttt gcatactttg tgacctaaca gttttaacag acattctatt  2087
atatgaatac agttttttg atactattag attaacttga agtttaatac caaatattat   2147
gctaagagta gaaaagcttt ctgctgaccc ctgatttctt agaaatatcc cacataatcc  2207
agcttatccc ttttctgtat atgttttattc aggtttacct gatgtctcaa aatgaaacca 2267 aattaagcct ttttaaaggc tgatgtgcca tttgtattaa gttatctttg tcattttaaa  2327
gacatgaatt ccccaagcct aattcctact taaggaagag agacaattta gtccttactt  2387
tagaaaataa atacttaagc ataaaaaaaa aaaaaaaaa aaaaaaaaa aaaaaaaa      2446
```

<210> SEQ ID NO 41
<211> LENGTH: 485
<212> TYPE: PRT
<213> ORGANISM: Homo sapiens

<400> SEQUENCE: 41

```
Met Ala Pro Arg Leu Gln Leu Glu Lys Ala Ala Trp Arg Trp Ala Glu
1               5                   10                  15

Thr Val Arg Pro Glu Glu Val Ser Gln Glu His Ile Glu Thr Ala Tyr
                20                  25                  30

Arg Ile Trp Leu Glu Pro Cys Ile Arg Gly Val Cys Arg Arg Asn Cys
            35                  40                  45

Lys Gly Asn Pro Asn Cys Leu Val Gly Ile Gly Glu His Ile Trp Leu
        50                  55                  60

Gly Glu Ile Asp Glu Asn Ser Phe His Asn Ile Asp Asp Pro Asn Cys
65                  70                  75                  80

Glu Arg Arg Lys Lys Asn Ser Phe Val Gly Leu Thr Asn Leu Gly Ala
                85                  90                  95

Thr Cys Tyr Val Asn Thr Phe Leu Gln Val Trp Phe Leu Asn Leu Glu
            100                 105                 110

Leu Arg Gln Ala Leu Tyr Leu Cys Pro Ser Thr Cys Ser Asp Tyr Met
        115                 120                 125
```

```
Leu Gly Asp Gly Ile Gln Glu Glu Lys Asp Tyr Glu Pro Gln Thr Ile
            130                 135                 140

Cys Glu His Leu Gln Tyr Leu Phe Ala Leu Leu Gln Asn Ser Asn Arg
145                 150                 155                 160

Arg Tyr Ile Asp Pro Ser Gly Phe Val Lys Ala Leu Gly Leu Asp Thr
                165                 170                 175

Gly Gln Gln Gln Asp Ala Gln Glu Phe Ser Lys Leu Phe Met Ser Leu
            180                 185                 190

Leu Glu Asp Thr Leu Ser Lys Gln Lys Asn Pro Asp Val Arg Asn Ile
            195                 200                 205

Val Gln Gln Gln Phe Cys Gly Glu Tyr Ala Tyr Val Thr Val Cys Asn
210                 215                 220

Gln Cys Gly Arg Glu Ser Lys Leu Leu Ser Lys Phe Tyr Glu Leu Glu
225                 230                 235                 240

Leu Asn Ile Gln Gly His Lys Gln Leu Thr Asp Cys Ile Ser Glu Phe
                245                 250                 255

Leu Lys Glu Glu Lys Leu Glu Gly Asp Asn Arg Tyr Phe Cys Glu Asn
            260                 265                 270

Cys Gln Ser Lys Gln Asn Ala Thr Arg Lys Ile Arg Leu Leu Ser Leu
            275                 280                 285

Pro Cys Thr Leu Asn Leu Gln Leu Met Arg Phe Val Phe Asp Arg Gln
290                 295                 300

Thr Gly His Lys Lys Lys Leu Asn Thr Tyr Ile Gly Phe Ser Glu Ile
305                 310                 315                 320

Leu Asp Met Glu Pro Tyr Val Glu His Lys Gly Gly Ser Tyr Val Tyr
                325                 330                 335

Glu Leu Ser Ala Val Leu Ile His Arg Gly Val Ser Ala Tyr Ser Gly
            340                 345                 350

His Tyr Ile Ala His Val Lys Asp Pro Gln Ser Gly Glu Trp Tyr Lys
            355                 360                 365

Phe Asn Asp Glu Asp Ile Glu Lys Met Glu Gly Lys Lys Leu Gln Leu
370                 375                 380

Gly Ile Glu Glu Asp Leu Ala Glu Pro Ser Lys Ser Gln Thr Arg Lys
385                 390                 395                 400

Pro Lys Cys Gly Lys Gly Thr His Cys Ser Arg Asn Ala Tyr Met Leu
                405                 410                 415

Val Tyr Arg Leu Gln Thr Gln Glu Lys Pro Asn Thr Thr Val Gln Val
            420                 425                 430

Pro Ala Phe Leu Gln Glu Leu Val Asp Arg Asp Asn Ser Lys Phe Glu
            435                 440                 445

Glu Trp Cys Ile Glu Met Ala Glu Met Arg Lys Gln Ser Val Asp Lys
450                 455                 460

Gly Lys Ala Lys His Glu Glu Val Lys Glu Leu Tyr Gln Arg Leu Pro
465                 470                 475                 480

Ala Gly Ala Gly Leu
                485

<210> SEQ ID NO 42
<211> LENGTH: 1455
<212> TYPE: DNA
<213> ORGANISM: Homo sapiens

<400> SEQUENCE: 42
atggccccgc ggctgcagct ggagaaggcg gcctggcgct gggcggagac ggtgcggccc      60
```

-continued

```
gaggaggtgt cgcaggagca catcgagacc gcttaccgca tctggctgga gccctgcatt      120
cgcggcgtgt gcagacgaaa ctgcaaagga atccgaatt gcttggttgg tattggtgag       180
catatttggt taggagaaat agatgaaaat agttttcata acatcgatga tcccaactgt      240
gagaggagaa aaaagaactc atttgtgggc ctgactaacc ttggagccac ttgttatgtc      300
aacacatttc ttcaagtgtg gtttctcaac ttggagcttc ggcaggcact ctacttatgt      360
ccaagcactt gtagtgacta catgctggga gacggcatcc aagaagaaaa agattatgag      420
cctcaaacaa tttgtgagca tctccagtac ttgtttgcct tgttgcaaaa cagtaatagg      480
cgatacattg atccatcagg atttgttaaa gccttgggcc tggacactgg acaacagcag      540
gatgctcaag aattttcaaa gctctttatg tctctattgg aagatacttt gtctaaacaa      600
aagaatccag atgtgcgcaa tattgttcaa cagcagttct gtggagaata tgcctatgta      660
actgtttgca accagtgtgg cagagagtct aagcttttgt caaaattta tgagctggag       720 ttaaatatcc aaggccacaa acagttaaca gattgtatct cggaattttt gaaggaagaa      780
aaattagaag gagacaatcg ctattttgc gagaactgtc aaagcaaaca gaatgcaaca       840
agaaagattc gacttcttag ccttccttgc actctgaact gcagctaat gcgttttgtc       900 tttgacaggc aaactggaca taagaaaaag ctgaatacct acattggctt ctcagaaatt      960
ttggatatgg agcctatgt ggaacataaa ggtgggtcct acgtgtatga actcagcgca       1020
gtcctcatac acagaggagt gagtgcttat tctggccact acatcgccca cgtgaaagat      1080
ccacagtctg gtgaatggta taagtttaat gatgaagaca tagaaaagat ggaggggaag      1140
aaattacaac tagggattga ggaagatcta gcagaacctt ctaagtctca gacacgtaaa      1200
cccaagtgtg gcaaaggaac tcattgctct cgaaatgcat atatgttggt ttatagactg      1260
caaactcaag aaaagcccaa cactactgtt caagttccag cctttcttca agagctggta      1320
gatcgggata attccaaatt tgaggagtgg tgtattgaaa tggctgagat gcgtaagcaa      1380
agtgtggata aggaaaagc aaaacacgaa gaggttaagg agctgtacca aaggttacct      1440
gctggagctg gtctg                                                       1455
```

<210> SEQ ID NO 43
<211> LENGTH: 32
<212> TYPE: PRT
<213> ORGANISM: Artificial Sequence
<220> FEATURE:
<223> OTHER INFORMATION: consensus sequence

<400> SEQUENCE: 43

Thr Gly Leu Ile Asn Leu Gly Asn Thr Cys Tyr Met Asn Ser Val Leu
1               5                   10                  15

Gln Cys Leu Phe Ser Ile Pro Pro Leu Arg Asp Tyr Leu Leu Asp Ile
            20                  25                  30

<210> SEQ ID NO 44
<211> LENGTH: 69
<212> TYPE: PRT
<213> ORGANISM: Artificial Sequence
<220> FEATURE:
<223> OTHER INFORMATION: consensus sequence

<400> SEQUENCE: 44

Gly Pro Gly Lys Tyr Glu Leu Tyr Ala Val Val His Ser Gly Ser
1               5                   10                  15

Ser Leu Ser Gly Gly His Tyr Thr Ala Tyr Val Lys Lys Glu Asn Trp
            20                  25                  30

```
Tyr Lys Phe Asp Asp Asp Lys Val Ser Arg Val Thr Glu Glu Glu Val
            35                  40                  45

Leu Lys Glu Ser Gly Gly Glu Ser Gly Asp Thr Ser Ser Ala Tyr Ile
    50                  55                  60

Leu Phe Tyr Glu Arg
65

<210> SEQ ID NO 45
<211> LENGTH: 19
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 5
<223> OTHER INFORMATION: Xaa = Ser, Ala, or Gly
<220> FEATURE:
<221> NAME/KEY: VARIANT
<222> LOCATION: 6
<223> OTHER INFORMATION: Xaa = Leu, Ile, Val, Met, Phe, or Thr
<220> FEATURE:
<221> NAME/KEY: VARIANT
<222> LOCATION: 2, 4, 7-8, 10, 12-16
<223> OTHER INFORMATION: Xaa = Any Amino Acid

<400> SEQUENCE: 45

Tyr Xaa Leu Xaa Xaa Xaa Xaa Xaa His Xaa Gly Xaa Xaa Xaa Xaa Xaa
1               5                   10                  15

Gly His Tyr
```